US012699092B2

(12) United States Patent
Crowe, Jr.

(10) Patent No.: US 12,699,092 B2
(45) Date of Patent: Aug. 4, 2026

(54) HUMAN ANTIBODIES TO CRIMEAN CONGO HEMORRHAGIC FEVER VIRUS

(71) Applicant: Vanderbilt University, Nashville, TN (US)

(72) Inventor: James E. Crowe, Jr., Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 746 days.

(21) Appl. No.: 17/792,008

(22) PCT Filed: Jan. 11, 2021

(86) PCT No.: PCT/US2021/012901
§ 371 (c)(1),
(2) Date: Jul. 11, 2022

(87) PCT Pub. No.: WO2021/142413
PCT Pub. Date: Jul. 15, 2021

(65) Prior Publication Data
US 2024/0288426 A1 Aug. 29, 2024

Related U.S. Application Data

(60) Provisional application No. 62/960,080, filed on Jan. 12, 2020.

(51) Int. Cl.
*C07K 16/10* (2026.01)
*G01N 33/569* (2006.01)

(52) U.S. Cl.
CPC ....... *G01N 33/56983* (2013.01); *C07K 16/10* (2013.01); *C07K 2317/565* (2013.01); *G01N 2333/175* (2013.01)

(58) Field of Classification Search
None
See application file for complete search history.

(56) References Cited

U.S. PATENT DOCUMENTS

| | | | |
|---|---|---|---|
| 2008/0131912 A1 | 6/2008 | Tu et al. | |
| 2018/0112003 A1 | 4/2018 | Epstein et al. | |
| 2019/0218279 A1 | 7/2019 | Agrawal et al. | |

FOREIGN PATENT DOCUMENTS

| | | | |
|---|---|---|---|
| WO | WO 2005/047328 A2 | 5/2005 | |
| WO | WO 2008/110937 A2 | 9/2008 | |
| WO | WO 2018/075621 A1 | 4/2018 | |

OTHER PUBLICATIONS

Bertolotti-Ciarlet, A. et al., "Cellular Localization and Antigenic Characterization of Crimean-Congo Hemorrhagic Fever Virus Glycoproteins," *Journal of Virology*, 79.10 (2005): 6152-6161.
PCT International Search report and Written Opinion issued in International Patent Application No. PCT/US2021/012901, mailed May 20, 2021.
PCT International Preliminary Report on Patentability issued in International Patent Application No. PCT/US2021/012901, mailed Jul. 21, 2022.
Saijo, M. et al., "Antigen-Capture Enzyme-Linked Immunosorbent Assay for the Diagnosis of Crimean-Congo Hemorrhagic Fever Using a Novel Monoclonal Antibody," *Journal of Medical Virology*, 77 (2005): 83-88.
Canakoglu, Nurettin, et al. "Pseudo-plaque reduction neutralization test (PPRNT) for the measurement of neutralizing antibodies to Crimean-Congo hemorrhagic fever virus." *Virology journal* 10 (2013): 1-7.
Extended European Search Report issued in European Application No. 21738928.7, mailed Apr. 15, 2024.
Fels, J. Maximilian, et al. "Protective neutralizing antibodies from human survivors of Crimean-Congo hemorrhagic fever." *Cell* 184. 13 (2021): 3486-3501.
Golden, Joseph W., et al. "GP38-targeting monoclonal antibodies protect adult mice against lethal Crimean-Congo hemorrhagic fever virus infection." *Science Advances* 5.7 (2019): eaaw9535.
Partial European Search Report issued in European Application No. 21738928.7, mailed Jan. 25, 2024.
Durie, Ian A., et al. "Structural characterization of protective non-neutralizing antibodies targeting Crimean-Congo hemorrhagic fever virus." *Nature Communications* 13.1 (2022); 7298.

*Primary Examiner* — Nicole Kinsey White
(74) *Attorney, Agent, or Firm* — pH IP Law

(57) ABSTRACT

The present disclosure is directed to antibodies binding to and neutralizing Crimean Congo Hemorrhagic Fever Virus and methods for use thereof.

20 Claims, 4 Drawing Sheets

Specification includes a Sequence Listing.

| Antibody | IC50 µg/mL |
|---|---|
| CCHF 23c | <0.2 |
| CCHF 64b | 0.2 |
| CCHF 79a | 0.3 |
| CCHF 55b | 0.9 |
| CCHF 88a | 0.9 |
| CCHF 114c | 1.2 |
| CCHF 95a | 1.4 |
| CCHF 133a | 1.4 |
| CCHF 137b | 2.2 |
| CCHF 59a | 3.1 |
| CCHF 3b | 3.1 |
| CCHF 74a | 3.5 |
| CCHF 2b | 4.4 |
| CCHF 69c | 4.6 |
| CCHF 82c | 5.1 |
| CCHF 141b | 7.8 |
| CCHF 117a | 8.1 |
| CCHF 116c | 13.6 |
| CCHF 65a | 17.9 |
| CCHF 4C | 23.6 |
| CCHF 115c | 34.0 |
| CCHF 62b | 71.1 |
| CCHF 29C | 334.1 |
| CCHF 8b | 445.7 |
| CCHF 86c | 1107.0 |
| CCHF 61 | Non-neut |
| CCHF 105b | Non-neut |
| CCHF 75a | Non-neut |
| CCHF 5A | Non-neut |
| CCHF 14a | Non-neut |
| CCHF 128c | Non-neut |
| CCHF 73c | Non-neut |
| CCHF 40a | Non-neut |
| CCHF 135c | Non-neut |
| CCHF 50b | Non-neut |

FIG. 1C

SEQUENCE LISTING

```
<160> NUMBER OF SEQ ID NOS: 500

<210> SEQ ID NO 1
<211> LENGTH: 357
<212> TYPE: DNA
<213> ORGANISM: Artificial sequence
<220> FEATURE:
<223> OTHER INFORMATION: Synthetic antibody

<400> SEQUENCE: 1
cacgtgcagc tggtggagtc tggggggagcc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagtt ttggtagtaa cactttctac     180
gcagactttg tgaagggccg attcaccatc tccagggaca atgccaagaa gtcactgtat     240
ctgcaaatga gcagcctgag agccgaggac acggccgtgt attactgtgc gagaagcctc     300
cgcggtatag cagtgccgtc ctactggggc cagggaaccc tggtcaccgt ctcctca       357

<210> SEQ ID NO 2
<211> LENGTH: 324
<212> TYPE: DNA
<213> ORGANISM: Artificial sequence
<220> FEATURE:
<223> OTHER INFORMATION: Synthetic antibody

<400> SEQUENCE: 2
gaaatagtga tgacgcagtc tccagccacc ctgtctgtgt ctccagggga aagagtcacc      60
ctctcctgca gggccagtca gagtgttagc agcgacttgg cctggtacca ccagaaacct     120
ggccaggctc ccaggctcct catctacgat gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggcctccttg gacgttcggc     300
caagggacca aggtggaaat caaa                                           324

<210> SEQ ID NO 3
<211> LENGTH: 357
<212> TYPE: DNA
<213> ORGANISM: Artificial sequence
<220> FEATURE:
<223> OTHER INFORMATION: Synthetic antibody

<400> SEQUENCE: 3
cacgtgcagc tggtggagtc tggggggagcc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagtt ttggtagtaa cactttctac     180
gcagactttg tgaagggccg attcaccatc tccagggaca atgccaagaa gtcactgtat     240
ctgcaaatga gcagcctgag agccgaggac acggccgtgt attactgtgc gagaagcctc     300
cgcggtatag cagtgccgtc ctactggggc cagggaaccc tggtcaccgt ctcctca       357

<210> SEQ ID NO 4
<211> LENGTH: 324
```

```
<212> TYPE: DNA
<213> ORGANISM: Artificial sequence
<220> FEATURE:
<223> OTHER INFORMATION: Synthetic antibody

<400> SEQUENCE: 4
gaaatagtga tgacgcagtc tccagccacc ctgtctgtgt ctccagggga aagagtcacc      60
ctctcctgca gggccagtca gagtgttagc agcgacttgg cctggtacca ccagaaacct     120
ggccaggctc ccaggctcct catctacgat gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggcctccttg gacgttcggc     300
caagggacca aggtggaaat caaa                                            324

<210> SEQ ID NO 5
<211> LENGTH: 375
<212> TYPE: DNA
<213> ORGANISM: Artificial sequence
<220> FEATURE:
<223> OTHER INFORMATION: Synthetic antibody

<400> SEQUENCE: 5
cagctgcagc tgttggagtc gggcccagga ctggtgaagc cttcggagac cctgtccctc      60
acctgcactg tctctggtgg ctccatcagc agtaatattt actactgggg ctggatccgc     120
cagcccccag ggaaggggct ggaatggatt gggagtatct attatagtgg gaacacccac     180
tacaacccgt ccctcaagag tcgagtcacc atatccgtag acacgtccaa gaaccagttc     240
tccctgaagc tgagctctct gaccgccgca gactcggctc tttattactg tgcgagccag     300
aaaatggtct atccaataaa acggaacaac tggttcgacc cctggggcca gggaaccctg     360
gtcatcgtct cctca                                                      375

<210> SEQ ID NO 6
<211> LENGTH: 330
<212> TYPE: DNA
<213> ORGANISM: Artificial sequence
<220> FEATURE:
<223> OTHER INFORMATION: Synthetic antibody

<400> SEQUENCE: 6
cagtctgtgc tgactcagtc accctcagcg tctgggaccc ccgggcagag ggtcaccatc      60
tcttgttctg gaagcagctc caacatcgaa agtaatactg taacctggta ccagcagctc     120
ccaggaacgg cccccaaact cctcatctat ggtaataatc agcggccctc aggggtccct     180
gaccgattct ctggctccaa gtctggcacc tcagcctccc tggccatcag tggcctccag     240
tctgaggatg aggctgatta ttactgtgca gcatgggatg acggcctgaa tgggtgggtg     300
ttcggcggag ggaccaagct gaccgtccta                                      330

<210> SEQ ID NO 7
<211> LENGTH: 390
<212> TYPE: DNA
<213> ORGANISM: Artificial sequence
<220> FEATURE:
<223> OTHER INFORMATION: Synthetic antibody

<400> SEQUENCE: 7
gaggtgcacc tggtgcagtc tggagcagag gtgaaaaagc ccggggagtc tctgaagatc      60
tcctgtaagg gttctggata cagctttacc agctactgga tcggctgggt gcgccagatg     120
```

```
cccgggaaag gcctggagtg gatggggatc atctatcctg gtgactctga taccagatac        180
agcccgtcct tccaaggcca ggtcaccatc tcagccgaca agtccatcag caccgcctac        240
ctgcagtgga gcagcctgaa ggcctcggac accgccatgt attactgtgc gcgacatgaa        300
agtgaagctt tttcgatttt tggagtggtt cgatactact actactacat ggacgtctgg        360
ggcaaaggga ccacggtcac cgtctcctca                                          390

<210> SEQ ID NO 8
<211> LENGTH: 324
<212> TYPE: DNA
<213> ORGANISM: Artificial sequence
<220> FEATURE:
<223> OTHER INFORMATION: Synthetic antibody

<400> SEQUENCE: 8
cagtctgccc tgactcagcc tcgctcagtg tccgggtctc ctggacagtc agtcaccatc         60
tcctgcactg gaaccagcag tgatgttggt ggttataact atgtctcctg gtaccaacag        120
cacccagaca aagcccccaa actcatgatt tatgatgtca ctaagcggcc ctcaggggtc        180
cctgatcgct tctctggctc caagtctggc aacacggcct ccctgaccat ctctgggctc        240
caggctgagg atgaggctga ttattactgc tgctcatatg caggcaccgt ggtattcggc        300
ggagggacca agctgaccgt ccta                                               324

<210> SEQ ID NO 9
<211> LENGTH: 366
<212> TYPE: DNA
<213> ORGANISM: Artificial sequence
<220> FEATURE:
<223> OTHER INFORMATION: Synthetic antibody

<400> SEQUENCE: 9
caggtgcagc tgcaggagtc gggcccagga ctggtgaagc cttcggggac cctgtccctc         60
acctgcgctg tctctggtgg ctccatcagc agtagtaagt ggtggagttg ggtccgccag        120
tccccaggga aggggctgga gtggattggc gaaatctatc atagtgggag caccaactac        180
aacccgtccc tcaagagtcg agccaccatt tcagtagaca agtccaagaa ccagttctcc        240
ctgaagctga actctgtgac cgccgcggac acggccgtgt actattgtgc gagagtgggc        300
ttgggctggc acgatggaaa cggtatggac gtctggggcc aagggaccac ggtcaccgtc        360
tcctca                                                                   366

<210> SEQ ID NO 10
<211> LENGTH: 327
<212> TYPE: DNA
<213> ORGANISM: Artificial sequence
<220> FEATURE:
<223> OTHER INFORMATION: Synthetic antibody

<400> SEQUENCE: 10
gaaattgtgt tgacacagtc tccagccacc ctgtctttgt ctccagggga aagagccacc         60
ctctcctgcc gggccagtct caatattggg agctacttag cctggtacca acagaaacct        120
ggccaggctc ccaggctcct catctatgat gcatccaaca gggccactgg catccccgcc        180
aggttcagtg gcagtgggtc tgggacagac ttcactctca ccatcaggag cctagagcct        240
gaagattttg caatttacta ctgtcagcag cgtagcaact ggccccccgg gtacactttt        300
ggccagggga ccaagctgga gatcaga                                            327
```

-continued

```
<210> SEQ ID NO 11
<211> LENGTH: 387
<212> TYPE: DNA
<213> ORGANISM: Artificial sequence
<220> FEATURE:
<223> OTHER INFORMATION: Synthetic antibody

<400> SEQUENCE: 11
caggtgcagc tgcaggagtc gggcccggga ctggtgaagc cttcacagac cctgtccctc      60
acctgcactg tctctggtgg ctccatcagc agtggtgatt attactggag ctggctccgc     120
cagcacccag ggaagggcct ggagtggatt gggtacatct attacagtgg gagcgcctac     180
tccaacccgt ccctcaacag tcgagatatc atttcaatag acacgtctaa gaatcggttc     240
tccctgaaac tgagctctgt gactgccgcg gacacggccg tgtattactg tgcgagattc     300
cggctaggcg atgccccaac cagagatggc tacaatttgc actactttga ctactggggc     360
cagggatccc tggtcaccgt ctcctca                                         387

<210> SEQ ID NO 12
<211> LENGTH: 333
<212> TYPE: DNA
<213> ORGANISM: Artificial sequence
<220> FEATURE:
<223> OTHER INFORMATION: Synthetic antibody

<400> SEQUENCE: 12
cagtctgccc tgactcagcc tgcctccgtg tctgggtctc ctggacagtc gatcaccatc      60
tcctgcactg gaaccagcag tgatgttggg agctataacc ttgtctcctg gtaccaacag     120
cacccaggca aagcccccaa agtcatgatt tatgaggtca gtaagcggcc ctcaggggtt     180
tctaatcgct tctctggctc caagtctggc aacacggcct ccctgacaat ctctgggctc     240
caggctgagg acgaggctga ttattactgc tgctcatatg gaggttttag tacccatgtg     300
gttttcggcg gagggaccag gctgaccgtc cta                                  333

<210> SEQ ID NO 13
<211> LENGTH: 378
<212> TYPE: DNA
<213> ORGANISM: Artificial sequence
<220> FEATURE:
<223> OTHER INFORMATION: Synthetic antibody

<400> SEQUENCE: 13
gaggtgcagc tggtggagtc tgggggaggc ttggtacagc cagggcggtc cctgagactc      60
tcctgtacag gttctggatt cacctttggt gattacgcca tgagttgggc ccgccaggct     120
ccagggaagg ggctggagtg ggtaggattc atcagaagca aaggttacgg tgggacaaca     180
caatacgccg cgtctgtgaa aggcagattc accatctcaa gagatgattc caaaagaatc     240
gcctatttgc aagtgaatag tctgaaaatc gaggacacag ccgtgtattt ctgtactaga     300
gcccactatg attacgtttg ggggaattat tggagctttg cgtactgggg ccagggaacc     360
ctggtcaccg tctcctca                                                   378

<210> SEQ ID NO 14
<211> LENGTH: 330
<212> TYPE: DNA
<213> ORGANISM: Artificial sequence
<220> FEATURE:
<223> OTHER INFORMATION: Synthetic antibody

<400> SEQUENCE: 14
```

```
cagtctgtgc tgacgcagcc gccctcactg tctgcggccc caggacagaa ggtcaccatc      60
tcctgctctg gaagcagctc caacattggg aataattatg tatcctggta ccagcacctc     120
ccaggaacag cccccaaact catcatttat gacgataatc agcgaccctc agggattcct     180
gaccgattct ctggctccaa gtctggcacg tcagccaccc tgggcatcac cggactccag     240
actggggacg aggccgatta ttactgcgga acatgggata gcagcctgag tgtttttgtc     300
ttcggaactg ggaccaaggt caccgtccta                                       330

<210> SEQ ID NO 15
<211> LENGTH: 381
<212> TYPE: DNA
<213> ORGANISM: Artificial sequence
<220> FEATURE:
<223> OTHER INFORMATION: Synthetic antibody

<400> SEQUENCE: 15
caagtgcagc tggtggagtc tgggggaggc gtggtccagc ctgggaggtc cctgagactc      60
tcctgtgcag cgtctggatt caccttcagt acctatggca tgcactgggt ccgccaggct     120
ccaggcaagg ggctggagtg ggtggcagtt atatggtatg atggaagtaa taagtactat     180
gtagactccg tgaagggccg attcaccatc tccagagaca attccaagaa cacgctgtat     240
ctgcaaatga acagcctgag agccgaagac acggctctct attactgtgc gagagacccc     300
gggggtcgta gagatggcta catactaaga cctgatgctt ttgatatctg gggccaaggg     360
acaatggtca ccgtctcttc a                                                381

<210> SEQ ID NO 16
<211> LENGTH: 321
<212> TYPE: DNA
<213> ORGANISM: Artificial sequence
<220> FEATURE:
<223> OTHER INFORMATION: Synthetic antibody

<400> SEQUENCE: 16
gacatccaga tgacccagtc tccttccacc ctgtctgcat ctgtaggaga cagagtcacc      60
atcacttgcc gggccagtca gagtattact agctggttgg cctggtatca gcagaaacca     120
gggaaagccc ctaagctcct gatctataag gcatctagtt tagaaagtgg ggtcccatca     180
aggttcagcg gcagtggatc tgggacagaa ttcactctca ccatcagcag cctgcagcct     240
gatgattttg caacttatta ctgccaacag tataatactt atacgtggac gttcggccaa     300
gggaccaagg tggaaatcaa a                                                321

<210> SEQ ID NO 17
<211> LENGTH: 348
<212> TYPE: DNA
<213> ORGANISM: Artificial sequence
<220> FEATURE:
<223> OTHER INFORMATION: Synthetic antibody

<400> SEQUENCE: 17
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag ggcttgagtg gatgggatgg atcagcgctt acaatggtaa cacaaactat     180
gtacagaagc tccagggcag agtcaccatg accacagaca catccacgag cacagcctac     240
atggagctga ggagcctgag atctgacgac acggccgtgt attactgtgc gaggtccggg     300
ggctacgcaa tattttgggg ccagggaacc ctggtcaccg tctcctca                   348
```

<210> SEQ ID NO 18
<211> LENGTH: 327
<212> TYPE: DNA
<213> ORGANISM: Artificial sequence
<220> FEATURE:
<223> OTHER INFORMATION: Synthetic antibody

<400> SEQUENCE: 18
gaaattgtgt tgacgcagtc tccaggcacc ctgtctttgt ctccagggga aagtgccacc        60
ctctcctgca gggccagtca gagtcttagc agcagctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta gtacacctcc gtacactttt       300
ggccagggga ccaagctgga gatcaaa                                           327

<210> SEQ ID NO 19
<211> LENGTH: 354
<212> TYPE: DNA
<213> ORGANISM: Artificial sequence
<220> FEATURE:
<223> OTHER INFORMATION: Synthetic antibody

<400> SEQUENCE: 19
cagatcacct tgaaggagtc tggtccaacg ctggtgaaac ccacacagac cctcacgctg        60
acctgcacct ctctctgggtt ctcaatcagt agtagtggag tgggtgtggg ctggatccgt       120
cagcccccag gaaaggccct ggagtggctt gcactccttt attgggatga tagtaagcgc       180
tacagcccat ctctgaggag caggctcacc atcaccaagg acacctccaa aaaccaggta       240
gtccttacaa tgaccaacat ggaccctgtg gacacaggca catattactg tgcacacaga       300
cggactacgg tttttgacta ctggggccag ggaaccctgg tcaccgtctc ctca             354

<210> SEQ ID NO 20
<211> LENGTH: 330
<212> TYPE: DNA
<213> ORGANISM: Artificial sequence
<220> FEATURE:
<223> OTHER INFORMATION: Synthetic antibody

<400> SEQUENCE: 20
aattttatgc tgactcagcc ccactctgtg tcggagtctc cggggaagac ggtaaccatc        60
tcctgcaccc gcagcagggg cagcatcgcc agcaactatg tgcagtggta ccagcagcgc       120
ccgggcagtt cccccaccaa tgtgatctat gaggataacc agagaccctc tggggtccct       180
gatcggttct ctggctccat cgacagctcc tccaactctg cctccctcac catctctgga       240
ctgaagactg aggacgaggc tgactactac tgtcagtctt atgatagcta caaccatgtg       300
ttcggcggag ggaccaggct gaccgtccta                                        330

<210> SEQ ID NO 21
<211> LENGTH: 396
<212> TYPE: DNA
<213> ORGANISM: Artificial sequence
<220> FEATURE:
<223> OTHER INFORMATION: Synthetic antibody

<400> SEQUENCE: 21
gaggtgcagc tggtgcagtc tggagcagag gtgaaaaagc ccggggagtc tctgaagatc        60

-continued

```
tcctgtaagg gttctggata caggtttacc aactactgga tcggctgggt gcgccagatg      120
cccgggaaag gcctggagtg gatggggatc atctatcctg gtgactctaa taccagatat      180
agcccgtcct ccaaggcca ggtcaccatc tcagccgaca agtccatcag caccgcctac      240
ttgcagtggg gcagcctgaa ggcctcggac accgccatgt attactgtgc gagacattca      300
gaaactaaag atggctacaa ttgggcccag ggtaatttct actcctacta ctatatggac      360
gtctggggca aagggaccac ggtcaccgtc tcctca                              396
```

<210> SEQ ID NO 22
<211> LENGTH: 324
<212> TYPE: DNA
<213> ORGANISM: Artificial sequence
<220> FEATURE:
<223> OTHER INFORMATION: Synthetic antibody

<400> SEQUENCE: 22

```
gacatccaga tgacccagtc tccatcctcc ctgtctgcat ctgtaggaga cagagtcacc       60
atcacttgcc gggcaagtca gagcattagc agctatttaa attggtatca gcagatacca      120
gggaaagccc ctaaactcct gatctatgct gcatccagtt tgcaaagtgg ggtcccatca      180
aggttcagtg gcagtggatc tgggacagat ttcactctca gcatcagcag tctgcaacct      240
gaagattttg caacttacta ctgtcaacag agttacagta tctcccctct cagtttcggc      300
ggagggacca aggtggagat caaa                                           324
```

<210> SEQ ID NO 23
<211> LENGTH: 375
<212> TYPE: DNA
<213> ORGANISM: Artificial sequence
<220> FEATURE:
<223> OTHER INFORMATION: Synthetic antibody

<400> SEQUENCE: 23

```
caggtgcagc tgcaggagtc gggcccagga ctggtgaagc cttcggagac cctgtccctc       60
acctgcactg tctctggtgg ctccatcaat tattactact ggagctggat ccggcagccc      120
ccagggaagg gactggagtg gattgcatat atctattaca ttgagggcag tgagagcacc      180
aactacaacc cctccctcaa gagtcgagtc accatgtcag tagacacgtc caagaaccag      240
ttgtccctga agctgagctc tgtgaccgct gcggacacgg ccgcgtatta ctgtgcgagg      300
gattcccgtc gaaacagata tagtggctac tactttgact tctggggcca gggaaccctg      360
gtcaccgtct cctca                                                     375
```

<210> SEQ ID NO 24
<211> LENGTH: 321
<212> TYPE: DNA
<213> ORGANISM: Artificial sequence
<220> FEATURE:
<223> OTHER INFORMATION: Synthetic antibody

<400> SEQUENCE: 24

```
gaaatagtga tgacgcagtc tccagtcacc ctgtctgtgt ctccagggga aagagccacc       60
ctctcctgca gggccagtca gagtgttagg agcaacttag cctggtacca gcacaaacct      120
ggccaggctc ccaggctcct cttctatggt gcatccacca gggccactgg tgtcccagcc      180
aggttcagtg gcagtgggtc agggacagag ttcactctca ccatcagcag cctgcagtct      240
gaagattttg cagtttattt ctgtcaccag tataataact ggcctcagac gttcggccaa      300
gggaccaagg tggaaatcaa a                                              321
```

<210> SEQ ID NO 25
<211> LENGTH: 378
<212> TYPE: DNA
<213> ORGANISM: Artificial sequence
<220> FEATURE:
<223> OTHER INFORMATION: Synthetic antibody

<400> SEQUENCE: 25
caggtgcagc tgcaggagtc gggcccagga ctggtgaagc cttcggggac cctgtccctc      60
acctgcgctg tctctggtga ctccatcagc gggagtttct ggtggagttg ggtccgccag     120
cccccaggga aggggctgga gtggcttggg gaaatctatc atagtggcaa cacccactac     180
aacccgtccc tcaagagtcg agtcaccatg tcaagagaca agtctaagaa ccagttctcc     240
ctgaagctaa cctctgtgac cgccgcggac acggccgtct attactgttc gagagtattg     300
ggtctgtacc agctgctagg gagtggttac tacgctatgg acgtctgggg ccaagggacc     360
acggtcaccg tctcctca                                                   378

<210> SEQ ID NO 26
<211> LENGTH: 360
<212> TYPE: DNA
<213> ORGANISM: Artificial sequence
<220> FEATURE:
<223> OTHER INFORMATION: Synthetic antibody

<400> SEQUENCE: 26
caggtccaac tggtacaatc tggggctgag gtgaagaagc ctggggcctc agtgaaggtc      60
tcctgcaagg tttccggata ctccctcact gagttatcca tgcactgggt gcgacagcct     120
cctgcaaaag ggcttgagtg gatgggacgt tttgatcctg agatcgtaa  accaatctac     180 gcacagaggt tccagggcag aatcaccatg accgaggaca catctacaga cacgaccttc     240
atggaactga gcagcctgag atctgaggac acggccctat atttctgtgc aacagatcct     300
ggagcagtgg ctggtttcct gggcttctgg ggccagggaa ccctggtcac cgtctcctcg     360

<210> SEQ ID NO 27
<211> LENGTH: 336
<212> TYPE: DNA
<213> ORGANISM: Artificial sequence
<220> FEATURE:
<223> OTHER INFORMATION: Synthetic antibody

<400> SEQUENCE: 27
gacatcgtga tgacccagtc tccagactcc ctggctgtgt ctctgggcga gagggccacc      60
atcaactgca gtccagcca  gagtgtttta tacaggtcca acaataacaa ctacttagca     120
tggtaccagc agaaagtagg acagcctcct aagctgctca tttactgggc atctatccgg     180
gaatccgggg tccctgaccg attcagtggc agcgggtctg ggacagattt cactctcacc     240
atcagcagcc tgcaggctga agatgtggca gtttattact gtcagcaata ctatggtacc     300
gtcactttcg gccctgggac caaagtggat atcaaa                               336

<210> SEQ ID NO 28
<211> LENGTH: 360
<212> TYPE: DNA
<213> ORGANISM: Artificial sequence
<220> FEATURE:
<223> OTHER INFORMATION: Synthetic antibody

<400> SEQUENCE: 28

-continued
_____ gaggtgcagc tggtggagtc tggggggaggc ttggtacagc cagggcggtc cctgagactc        60
tcctgtacag cttctgggtt cacctttggt gattatgtta tgacctgggt ccgccaggct       120
ccagggaagg ggctggagtg cgtaggtttc atcagaacca aaccttatgg tgggacaaca       180
gaatacgccg cgtctgtgaa aggcagattc accatctcaa gagatgattc caaaagcatc       240
gcctatctgc aaatgaacag cctgaaaacc gacgacacag ccgtgtatta ctgtttagcc       300
ggcactgact ggtcctactt tgactactgg ggccagggaa ccctggtcac cgtctcctca       360

<210> SEQ ID NO 29
<211> LENGTH: 330
<212> TYPE: DNA
<213> ORGANISM: Artificial sequence
<220> FEATURE:
<223> OTHER INFORMATION: Synthetic antibody

<400> SEQUENCE: 29
cagtctgccc tgactcagcc tcgctcagtg tccgggtctc ctggacagtc agtcaccatc        60
tcctgcactg gaaccagcag tgatgttggt ggttataact atgtctcctg gtaccaacgg       120
cacccaggca aagcccccca actcatgatt tatgatgtca ataagcggcc ctcaggggtc       180
cctgatcgct tctctggctc caagtctggc aacacggcct ccctgaccat ctctgggctc       240
caggctgacg atgaggctga ttattactgc tgctcatatg caggcagcta cacttgggtg       300
ttcggcggag ggaccaagct gaccgtccta                                        330

<210> SEQ ID NO 30
<211> LENGTH: 375
<212> TYPE: DNA
<213> ORGANISM: Artificial sequence
<220> FEATURE:
<223> OTHER INFORMATION: Synthetic antibody

<400> SEQUENCE: 30
caggtgcagc tgcaggagtc gggcccagga ctggtgaagc cttcggagac cctgtccctc        60
acctgcactg tctctggtgg ctccatcagt agttactact ggacctggat ccggcagccc       120
ccagggaagg ggctggagtg gattggtcat atgtattaca gtgggagcac caacaacaac       180
ccctccctca agggtcgagt caccgtatca gtggacacgt ccaagaacca gttctccctg       240
aagctgacct ctgtgaccgc tgcggacacg gccgtgtatt actgtgcgag aggggcctac       300
tacggttcgg gtagtttttca ctactactac tacatggacg tctgggggcaa agggaccacg       360 gtcaccgtct cctca                                                        375

<210> SEQ ID NO 31
<211> LENGTH: 321
<212> TYPE: DNA
<213> ORGANISM: Artificial sequence
<220> FEATURE:
<223> OTHER INFORMATION: Synthetic antibody

<400> SEQUENCE: 31
gacatccaga tgacccagtc tccttccacc ctgtctgcat ctgtaggaga cagagtcacc        60
atcacttgcc gggccagtca gagtattagt aactggttgg cctggtatca gcagaaacca       120
gggaaagccc ctaagctcct gatctctaag gcatctagat tagaaggtgg ggtcccatca       180
aggttcagcg gcagtggatc tgggacagag ttcactttca ccatcagcag cctgcagcct       240
gatgattgtg caacttatta ctgccaacaa tataatggtt attcctacac ttttggccag       300
gggaccaagc tggagatcaa a                                                 321

```
<210> SEQ ID NO 32
<211> LENGTH: 378
<212> TYPE: DNA
<213> ORGANISM: Artificial sequence
<220> FEATURE:
<223> OTHER INFORMATION: Synthetic antibody

<400> SEQUENCE: 32
gaggtgcagc tggtggagtc tgggggaggc ctggtcaagc ctgggggggtc cctgagactc      60 tcctgtgcag tctctggatt caccttcagt agctatagca tgaactgggt ccgccaggct     120
ccagggaagg ggctggagtg ggtctcatcc attagtagta gtagtacttt catagactac     180
gcagactcag tgaagggccg attcaccatc tccagagaca cgccaagaa tttactgtat      240 ctgcaaatga acagcctgag agccgaggac acggctgtgt tttactgtgc gagaggcggt     300
aatgactaca gtgactacga aaactactac tactacatgg acgtctgggg caaagggacc     360
acggtcaccg tctcctca                                                    378

<210> SEQ ID NO 33
<211> LENGTH: 321
<212> TYPE: DNA
<213> ORGANISM: Artificial sequence
<220> FEATURE:
<223> OTHER INFORMATION: Synthetic antibody

<400> SEQUENCE: 33
tcctatgagc tgactcagcc accctcagtg tccgtgtccc caggacagac agccagcatc      60
acctgctctg gagatgaatt gggggataaa tatgcttgct ggtatcagaa gaagccaggc     120
cagtcccctg tgctggtcat ctatcaagat aacaagcggc cctcaggat ccctgagcga      180 ttctctggct ccaactctgg gaacacagcc actctgacca tcagcgggac ccaggctatg     240
gatgaggctg actattactg tcaggcgtgg gacagcagca ctgcttatgt cttcggaact     300
gggaccaagg tcaccgtcct a                                                321

<210> SEQ ID NO 34
<211> LENGTH: 363
<212> TYPE: DNA
<213> ORGANISM: Artificial sequence
<220> FEATURE:
<223> OTHER INFORMATION: Synthetic antibody

<400> SEQUENCE: 34
gaagtgcagc tggtggagtc tgggggaggc ttggtacagc ctggcaggtc cctgagactc      60
tcctgtgcag cctctggatt catctttgat gattatgcca tacactgggt ccggcaagct     120
ccagggaagg gcctggagtg ggtctcaggt attacctggg atagtggtag gataggctat     180
gcggactctg tgaagggccg attcaccatc tccagagaca cgccaagaa gtccctgtat      240 ctgcaaatga acagtctgag acctgaggac acggccttgt attactgtgc aaaagatagg     300
ggcccattcg ggtggcttac ccttgactac tggggccagg gaaccctggt catcgtctcc     360
tca                                                                    363

<210> SEQ ID NO 35
<211> LENGTH: 321
<212> TYPE: DNA
<213> ORGANISM: Artificial sequence
<220> FEATURE:
<223> OTHER INFORMATION: Synthetic antibody
```

<400> SEQUENCE: 35
gacatccaga tgacccagtc tccatcctcc ctgtctgcat ctgtaggaga cagagtcacc        60
atcacttgcc gggcaagtca gagcattagg agctatttaa attggtatca gcagaaacca       120
gggaaagccc ctaagctcct gatctatgct ggatccactt tgcaaagtgg ggtcccatca       180
aggttcagtg gcggtggatc tgggacaggt ttcactctca ccatcagcag tctgcaacct       240
gaagattttg caacttacta ctgtcagcag agttccacta ccccgtggac gttcggccaa       300
gggaccaagg tggaattcaa a                                                 321

<210> SEQ ID NO 36
<211> LENGTH: 384
<212> TYPE: DNA
<213> ORGANISM: Artificial sequence
<220> FEATURE:
<223> OTHER INFORMATION: Synthetic antibody

<400> SEQUENCE: 36
gaggtgcagc tggtggagtc tggggggaggc ttggtacagc caggcggtc cctgagactc        60 tcctgtacag catctggatt cacctttggt gattatgctc tgaactgggt ccgccaggct       120
ccagggaagg ggctggagtg ggtaggtttc attagaagca aagcttatgg tgggacaaca       180
gaatacgccg cgtctgtgaa aggcagattc accatctcaa gagatgattc caaaagcatc       240
gcctttctgc aaatgaacag cctgaaaacc gaggacacac ccgtgtatta ctgtactaga       300
gcaactcccg tattactatg gttcgggagc tccgggaact tctttgacta ctggggccag       360
ggaaccctgg tcaccgtctc ctca                                              384

<210> SEQ ID NO 37
<211> LENGTH: 330
<212> TYPE: DNA
<213> ORGANISM: Artificial sequence
<220> FEATURE:
<223> OTHER INFORMATION: Synthetic antibody

<400> SEQUENCE: 37
cagtctgccc tgactcagcc tgcctccgtg tctgggtctc ctggacagtc gatcaccatc        60
tcctgcactg gaaccagcag tgacgttggt ggttataact atgtctcctg gtaccaacaa       120
cacccaggca aagcccccaa actcatgatt tatgatgtca gtaatcggcc ctcagggggtt       180 tctaatcgct tctctggctc caagtctggc aacacggcct ccctgaccat ctctgggctc       240
caggctgagg acgaggctga ttattactgc agctcatata caaccagcaa ctcctatgtc       300
ttcggaactg ggaccaaggt caccgtccta                                        330

<210> SEQ ID NO 38
<211> LENGTH: 357
<212> TYPE: DNA
<213> ORGANISM: Artificial sequence
<220> FEATURE:
<223> OTHER INFORMATION: Synthetic antibody

<400> SEQUENCE: 38
cagctgcagc tgcaggagtc gggcccagga ctggtgaagc cttcggagac cctgtccctc        60
acctgcactg tctctggtga ctccatcaac aataataatt actactgggg ctggatccgc       120
cagcccccag ggaaggggct ggagtggatt gggagtatct attatagtgg gatcacctac       180
tacaacccgt ccctcaagag tcgagtcacc atatccgtgg acacgtccaa gaaccagttc       240
tccctgaagc tgagctctgt gaccgccgca gacacggctg tttattactg tgtgagacac       300
ggtttggacc acaaatttga ctactggggc cagggaaccc tggtcaccgt ctcctca          357

<210> SEQ ID NO 39
<211> LENGTH: 333
<212> TYPE: DNA
<213> ORGANISM: Artificial sequence
<220> FEATURE:
<223> OTHER INFORMATION: Synthetic antibody

<400> SEQUENCE: 39
cagtctgccc tgactcagcc tgcctccgtg tctgggtctc ctggacagtc gatcaccatc          60
tcctgcactg gaaccagcag tgatgttggg acttataacc ttctctcctg gtaccaacag         120
taccccggca aagcccccag gctcgtgatt tatgaggtca gtaagcggcc ctcaggggtt         180
tctattcgct tctctggctc caagtctggc aacacggcct ccctgacaat ctctgggctc         240
caggctgagg acgaggctga ttattactgc tgctcatatg caggtggcag caattcagtg         300
ctattcggcg gggggaccaa gctgaccgtc cta                                        333

<210> SEQ ID NO 40
<211> LENGTH: 345
<212> TYPE: DNA
<213> ORGANISM: Artificial sequence
<220> FEATURE:
<223> OTHER INFORMATION: Synthetic antibody

<400> SEQUENCE: 40
gaggtgcagc tggtggagtc tgggggaggc ttggtacagc ctggggggtc cctgagactc          60
tcctgtgcag cctctggatt cactttcagt agctatagca tgaactgggt ccgccaggct         120
ccagggaagg ggctggagtg cgtttcatac attagtagta gtagtggtgc catatactac         180
gcagactctg tgaagggccg attcaccatc tccagagaca atgccaagaa ctcactgtat         240
ctgcaaatga acagcctgag agccgaggac acggctgtgt attactgtgc gagagggaac         300
ggtgcgacgt actggggcca gggaaccctg gtcaccgtct cctca                          345

<210> SEQ ID NO 41
<211> LENGTH: 321
<212> TYPE: DNA
<213> ORGANISM: Artificial sequence
<220> FEATURE:
<223> OTHER INFORMATION: Synthetic antibody

<400> SEQUENCE: 41
gacatccaga tgacccagtc tccatcctca ctgtctgcat ctgtaggaga cagagtcacc          60
atcacttgtc gggcgagtca ggacattagt agttatttag cctggtttca gcagaaacca         120
gggaaagccc ctaagtccct gatctatgct gcatccagtt tgcaaagtgg ggtcccatca         180
aagttcagcg gcagtggatc tgggacagat ttcactctca ccatcagcag cctgcaacct         240
gaagattttg caacttatta ctgccaacag tataatattt acccgatcac cttcggccaa         300
gggacacgac tggagattaa a                                                     321

<210> SEQ ID NO 42
<211> LENGTH: 360
<212> TYPE: DNA
<213> ORGANISM: Artificial sequence
<220> FEATURE:
<223> OTHER INFORMATION: Synthetic antibody

<400> SEQUENCE: 42

-continued

```
gaggtgcagc tggtgcagtc tggagcagag gtgaaaaagc ccggggagtc tctgaagatc      60
tcctgtaagg gttctggata caggtttacc aactactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccgtcag caccgcctac     240 ctgcagtgga gcagcctgaa ggcctcggac tccgccttgt attactgtgc gagacttccg     300
catccagtga ctggtccct tgactactgg ggccagggaa ccctggtcac cgtctcctca     360
```

<210> SEQ ID NO 43
<211> LENGTH: 330
<212> TYPE: DNA
<213> ORGANISM: Artificial sequence
<220> FEATURE:
<223> OTHER INFORMATION: Synthetic antibody

<400> SEQUENCE: 43

```
cagtctgccc tgactcagcc tgcctccgtg tctgggtctc ctggacagtc gatcaccatc      60
tcctgcactg gaaccagcaa tgatgttggg agttataacc ttgtctcctg gtaccaacat     120
cacccaggca aagcccccaa actcatgatt tatgaggtca gtaagcggcc ctcaggggtt     180
tctaatcgct tctctggctc caagtctggc aacacggcct ccctgacagt ctctgggctc     240
caggctgagg acgaggctga ttattactgc tgctcatatg caggtagtat gacttgggtg     300
ttcggcggag ggaccaagct gaccgtccta                                       330
```

<210> SEQ ID NO 44
<211> LENGTH: 372
<212> TYPE: DNA
<213> ORGANISM: Artificial sequence
<220> FEATURE:
<223> OTHER INFORMATION: Synthetic antibody

<400> SEQUENCE: 44

```
gaggtgcagc tggtggagtc tgggggaggc ctggtcaagc ctggggggtc cctgagactc      60
tcctgtgcag cctctggatt caccttcagg agttatacca tgaactgggt ccgccaggct     120
ccagggaagg ggctggagtg ggtctcgtcc attagtacta gtagtagtta catatactac     180
gcagactctg tgaagggccg attcaccatt tccagagaca cgccaagag ctcactgtat     240 ctgcaaatga acagcctgag agccgaggac acggctgttt attactgtgc gagtttgagg     300
aaagattcgg ggagttttta taatcgagcc ctcgactact ggggccaggg aaccctggtc     360
accgtctcct ca                                                         372
```

<210> SEQ ID NO 45
<211> LENGTH: 330
<212> TYPE: DNA
<213> ORGANISM: Artificial sequence
<220> FEATURE:
<223> OTHER INFORMATION: Synthetic antibody

<400> SEQUENCE: 45

```
cagtctgccc tgactcagcc tgcctccgtg tctgggtctc ctggacagtc gatcaccatc      60
tcctgcactg gaaccagcag tgacgttggt ggttataatt atgtttcctg gtaccaacaa     120
cacccaggca aagcccccaa actcatgatt tatgatgtca gtaatcggcc ctcaggggtt     180
tctaatcgct tctctggctc caagtctggc aacacggcct ccctgaccat ctctgggctc     240
caggctgagg acgaggctga ttattactgc tactcatata cgagcaacag cacttatgtc     300
ttcggaactg ggaccaaggt caccgtccta                                       330
```

<210> SEQ ID NO 46
<211> LENGTH: 387
<212> TYPE: DNA
<213> ORGANISM: Artificial sequence
<220> FEATURE:
<223> OTHER INFORMATION: Synthetic antibody

<400> SEQUENCE: 46
gaagtgcagc tggtggagtc tggggggggc ttggtacagc ctggcaagtc cctgagactc      60
tcctgtgcag cctctggatt cacctttgat gcttatgcca tgcactgggt ccggcaagct     120
ccagggaagg gcctggagtg ggtctcaggt attagttgga atggtggtaa cataggctat     180
gcggactctg tgaagggccg attcaccttc tccagagaca cgccaagaa ctccctgtat     240 ctgcaaatga acagtctgag agctgatgac acggccttgt atttctgtgc aaaagaagat     300
tgtcctagta ccagctgcta tttttgttcgt tggggactaa actggctcga cccctggggc     360
cagggaaccc tggtcaccgt ctcctca                                         387

<210> SEQ ID NO 47
<211> LENGTH: 333
<212> TYPE: DNA
<213> ORGANISM: Artificial sequence
<220> FEATURE:
<223> OTHER INFORMATION: Synthetic antibody

<400> SEQUENCE: 47
cagtctgtgc tgacgcagcc gccctcagtg tctggggccc cagggcagag ggtcaccatc      60
tcctgcactg ggagcagctc caacatcggg gcaggttatg atgtacactg gtaccagcag     120
cttccaggaa cagcccccaa actcctcatc tatgataaca caaatcggcc ctcaggggtc     180
cctgaccgat tctctggctc caagtctggc acctcagcct ccctggccat cactgggctc     240
caggctgagg atgaggctga ttattactgc cagtcctttg acagcagcct gagtaggggg     300
gtattcggcg gagggaccaa gctgaccgtc cta                                  333

<210> SEQ ID NO 48
<211> LENGTH: 372
<212> TYPE: DNA
<213> ORGANISM: Artificial sequence
<220> FEATURE:
<223> OTHER INFORMATION: Synthetic antibody

<400> SEQUENCE: 48
gaggtgcagc tggtggagtc tggggggggc ttggtacagc cagggcggtc cctgagactc      60
tcctgttcag cttctggatt cacctttgct gattatgctg tgagctgggt ccgccaggct     120
ccagggaagg ggctggaatg ggtaggtttc attagaagcg aaacttatgg tgggacaaca     180
gaatacgccg cctctgtgaa aggcagattc accatctcaa gagatgattc aaaagcatc     240 gcctatctgc aaatgcacag cctgaacacc gaggacacac ccgtgtttta ctgtactaga     300
gcccgtcacg acacgcgaag ttgggtgtta agtgaccact ggggccaggg aaccctggtc     360
accgtctcct ca                                                         372

<210> SEQ ID NO 49
<211> LENGTH: 315
<212> TYPE: DNA
<213> ORGANISM: Artificial sequence
<220> FEATURE:
<223> OTHER INFORMATION: Synthetic antibody -continued

```
<400> SEQUENCE: 49
gacgcccaga tgacccagtc tccttccacc ctgtctgcat ctgtaggaga cagagtcacc      60
atcacttgcc gggccagtca gaacattaat agttggttgg cctggtatca gcacaaacca     120
gggaaagccc ctaaactcct gatctataag gcatctagtt tagaaagtga ggtcccatca     180
aggttcagcg gcagtgggtc tgggacagat ttcactctca ccatcagcaa cctgcagcct     240
gatgattttg caacttatta ctgccaacag tataatagtt tccattttgg ccagggggacc    300 aagttggaga tcaaa                                                       315

<210> SEQ ID NO 50
<211> LENGTH: 381
<212> TYPE: DNA
<213> ORGANISM: Artificial sequence
<220> FEATURE:
<223> OTHER INFORMATION: Synthetic antibody

<400> SEQUENCE: 50
cagcttcagc tggtgcagtc tggagttgag gtgaagaagc ctgggggcctc agtgaaggtc      60 tcctgcaagg cttctggtta caccttttacc agctatggta tccactgggt gcgacaggcc     120
cctggacaag ggcttgagtg gatgggatgg atcagcggtt acaatggtaa cacaaactat      180
gcacagaagc tccagggcag agtcaccatg accacagaca catccacgag aacagcctac      240
atggagctga ggagcctgag atctgacgac acggccgtgt attactgtgc gagagatccc      300
tctatgatga cctttgggggg agttatcgtt tctcgctact ttgactactg gggccaggga     360
accctggtca ccgtctcctc a                                                381

<210> SEQ ID NO 51
<211> LENGTH: 327
<212> TYPE: DNA
<213> ORGANISM: Artificial sequence
<220> FEATURE:
<223> OTHER INFORMATION: Synthetic antibody

<400> SEQUENCE: 51
cagtctgtgc tgacgcagcc gccctcagtg tctgggggccc cagggcagag ggtcaccatc      60
tcctgcactg ggagcagctc caacatcggg gcaggttatg atgtacactg gtaccagcaa      120
cttccaggaa cagcccccaa actcctcatt tataataaca gcaatcggcc ctcaggggtc      180
cctgaccgat tctctggctc caagtctggc acctcagcct ccctggccat cactgggctc      240
caggctgagg atgaggctga ttattactgc cagtcctatg acagcagtgt gacggtgttc      300
ggcggaggga ccaaactgac cgtccta                                          327

<210> SEQ ID NO 52
<211> LENGTH: 372
<212> TYPE: DNA
<213> ORGANISM: Artificial sequence
<220> FEATURE:
<223> OTHER INFORMATION: Synthetic antibody

<400> SEQUENCE: 52
cagctgcagc tgcaggagtc gggcccagga ctggtgaagc cttcggagac cctgtccctc      60
acctgcactc tctctggtgg cttcatcaga agtagtagtt actactgggg ctggatccgc     120
cagcccccag ggaaggggct ggagtggatt gggagtatct attatactga gagcacctac     180 tacaaccccgt ccctcaagag tcgagtcacc atatccgtgg acacgtccaa gaaccagttc     240
tccctgaagc tgaactctgt gaccgccgca gacacggcta tattactgtg tgcgagacat     300
```

-continued

```
gattattgga ctggtgcccg ttacagctgg ttcgacccct ggggccaggg aaccctggtc       360
accgtctcct ca                                                            372

<210> SEQ ID NO 53
<211> LENGTH: 336
<212> TYPE: DNA
<213> ORGANISM: Artificial sequence
<220> FEATURE:
<223> OTHER INFORMATION: Synthetic antibody

<400> SEQUENCE: 53
cagtctgtgc tgacgcagcc gccctcagtg tctggggccc cagggcagag ggtcaccatt        60
tcctgcactg ggagcagctc caacatcggg gcaggttatg atgtacactg gtaccagcag       120
cttccaggaa cagcccccaa actcctcatc tatggtaaca gcaatcggcc ctcagggtc        180 cctgaccgat tctctggctc caagtctggc acctctgcct ccctggccat cactgggctc       240
caggctgagg atgaggctga ttattactgc cagtcctatg acaccagcct cagtggttcg       300
ggcgtgttcg gcggagggac caagctgacc gtccta                                 336

<210> SEQ ID NO 54
<211> LENGTH: 381
<212> TYPE: DNA
<213> ORGANISM: Artificial sequence
<220> FEATURE:
<223> OTHER INFORMATION: Synthetic antibody

<400> SEQUENCE: 54
caggtgcagc tggtgcagtc tggggctgag gtgaagaagc ctggggcctc agtgaagctt        60
tcctgcaagg catctggata caccttcacc agctactata tgcactgggt gcgacaggcc       120
cctggacaag ggcttgagtg ggtgggaatt atgaacccca gtggcggtag tacaatgtac       180
gcacagaagt accagggcag agtcaccatg accaggggaca cgtccacgag cacagtctac       240
atggagctga gcagtctgag atccgaggac acggccgtgt attactgtgc gagagagact       300
gtggttcaga gactagtagg gagggactac taccacggta tggacgtctg gggccaaggg       360
accacggtca ccgtctcctc a                                                  381

<210> SEQ ID NO 55
<211> LENGTH: 336
<212> TYPE: DNA
<213> ORGANISM: Artificial sequence
<220> FEATURE:
<223> OTHER INFORMATION: Synthetic antibody

<400> SEQUENCE: 55
gatattgtga tgactcagtc tccactctcc ctgcccgtca ccctggaga gccggcctcc         60 atctcctgca ggtctagtca gagcctcctg catagtaatg gatacaacta tttggattgg       120
tacctgcaga agccagggca gtctccacag ctcctgatct atttcggttc taatcgggcc       180
tccggggtcc ctgacaggtt cagtggcagt ggatcaggca cagattttac actgaagatc       240
agcagagtgg aggctgagga tgttgggggtt tattactgca tgcaagctct acaaactccc       300
ctcactttcg gcggagggac caaggtggag atcaga                                 336

<210> SEQ ID NO 56
<211> LENGTH: 363
<212> TYPE: DNA
<213> ORGANISM: Artificial sequence
<220> FEATURE:
```

-continued

<223> OTHER INFORMATION: Synthetic antibody

<400> SEQUENCE: 56

```
gaagtgcagc tggtggagtc tggggggagtc gtggtgcagc ctggggggtc cctgagactc      60
tcctgtgcag cctctggatt caccttttgat gattatgcca tgcactgggt ccgtcaagct     120
ccggggaaga gtctggagtg ggtctctctt ataagttggg atggtggtag gacatactat     180
gcagactctg tgaagggtcg attcaccatc tccagagaca acagcaaaaa ctccctgtac     240
ttgcaaatga acagtctgag acctgaggac acagccttat attactgtgc aacgggacac     300 cccccccttgg tcctatggtc cctgggctac tggggccagg gaaccctggt caccgtctcc     360
tca                                                                    363
```

<210> SEQ ID NO 57
<211> LENGTH: 321
<212> TYPE: DNA
<213> ORGANISM: Artificial sequence
<220> FEATURE:
<223> OTHER INFORMATION: Synthetic antibody

<400> SEQUENCE: 57

```
gacatccaga tgacccagtc tccatcctcc ctgtctgcat ctgtaggaga cagagtcacc      60
atcacttgcc gggcaagtgc gaacattaac agctatttaa attggtatca gcagaaacca     120
ggaaaagccc ctaaattcct gatctatgct gcatccagtt tgcaaggtgg ggtcccatca     180
aggtttagtg gcagtggatc tgggacagtt ttcactctca ccatcagcag tctgcaacct     240
gaagattttg caacttacta ctgtcaacag agttacacta ccccgatcac cttcggccaa     300
gggacacgac tggagattaa a                                                321
```

<210> SEQ ID NO 58
<211> LENGTH: 387
<212> TYPE: DNA
<213> ORGANISM: Artificial sequence
<220> FEATURE:
<223> OTHER INFORMATION: Synthetic antibody

<400> SEQUENCE: 58

```
caggtgcagc tggtgcagtc tggggctgag gtgaagaagc ctgggtcctc ggtgaaggtc      60
tcctgcaagg cctctggagg caccttcagc acctttgctt tcagctgggt gcgacaggcc     120
cctggacgag gacttgagtg gatgggaggg atcatcccta tctttgatag accagcctac     180
gcacagaggt tcagggcag agtcacaatt accgcggacg agtccacgag cacagcctac     240
gtggagctga gcagcctgag atctgaggac acggccgtgt attactgtgc gagagatcgg     300
aggtataact atgagagtag tgctagtcag aataacagat ggtacttcga tctctggggc     360
cgtggcaccc tggtcactgt ctcctca                                          387
```

<210> SEQ ID NO 59
<211> LENGTH: 339
<212> TYPE: DNA
<213> ORGANISM: Artificial sequence
<220> FEATURE:
<223> OTHER INFORMATION: Synthetic antibody

<400> SEQUENCE: 59

```
gacatcgtga tgacccagtc tccagactcc ctggctgtgt ctctgggcga gagggccacc      60
atcaactgca agtccagcca gagtgtttta tacacctcca acaataagaa ttatttagct     120
tggtatcagc agaaaccagg acagcctcct aagttgctcg tttactgggc atctatccgg     180
```

-continued

```
gaatccggggg tccctgaccg attcagtggc agcgggtctg ggacagattt cactctcacc      240
atcagcagcc tgcaggctga agatgtggcg gtttattact gtcagcaata ttatactact      300
cctctcactt tcggcggagg gaccaaggtg gagatcaaa                              339

<210> SEQ ID NO 60
<211> LENGTH: 372
<212> TYPE: DNA
<213> ORGANISM: Artificial sequence
<220> FEATURE:
<223> OTHER INFORMATION: Synthetic antibody

<400> SEQUENCE: 60
caggtgcagc tggtggagtc tggggggaggc gtggtccagc ctggggggtc cctgagactc       60
tcctgtgcag cgtctggctt caccttcagt aattatggca ttcactgggt ccgccaggct      120
ccaggcaagg ggctggagtg ggtggcattt atacggtatg atggaagtaa tcaaaactat      180
ggagactccg tgaagggccg attcaccatc tccagagaca attccaggaa cacgctgttt      240
ctgcaaatga gcagcctgag agctgaggac acggctgtgt attactgtgc gaaagacttg      300
gctgtactac tgatgtatgg gttcgggggt tttgacgcct ggggccaggg aaccctggtc      360
accgtctcct ca                                                          372

<210> SEQ ID NO 61
<211> LENGTH: 321
<212> TYPE: DNA
<213> ORGANISM: Artificial sequence
<220> FEATURE:
<223> OTHER INFORMATION: Synthetic antibody

<400> SEQUENCE: 61
gacatccagg tgacccagtc tccatcctcc ctgtctgcat ctgtaggaga cagagtctcc       60
atcacttgtc gggcaagtca gagcattagc cactatttaa attggtatca acagaaacca      120
gggaaagccc ctaaactcct gatctatgct gcatccactt tgcaaagtgg ggtcccatca      180
aggttcagtg gcagtggatc tgggacaggt ttcactctca ccatcagcgg tctgcaacct      240
gaggattttg caacttacta ctgtcaacag agttacagta cccccgtgtc gttcggccaa      300
gggaccaagg tggaaatcaa a                                                321

<210> SEQ ID NO 62
<211> LENGTH: 381
<212> TYPE: DNA
<213> ORGANISM: Artificial sequence
<220> FEATURE:
<223> OTHER INFORMATION: Synthetic antibody

<400> SEQUENCE: 62
caggtgcagc tggtgcagtc tggggctgag gtgaagaagc ctgggtcctc ggtgaaggtc       60
tcctgcaagg cctctggagg caccttcaga agctatgcta tcaactgggt gcgacaggcc      120
cctggacaag ggcttgagtg gatgggaggg atcatcccta tctttggtac agcaaactac      180
gcacagaatt tccagggcag agtcacgatt acgcggacg aatccacgag cacagcctac      240
atggagctga gcagcctgag atctgaggac acggccgtgt attactgtgc gaggtatttt      300
ttcaccacac cccattggac cctgcccatt gactacggta tggacgtctg gggccaaggg      360
accacggtca ccgtctcctc a                                                381

<210> SEQ ID NO 63
```

```
<211> LENGTH: 336
<212> TYPE: DNA
<213> ORGANISM: Artificial sequence
<220> FEATURE:
<223> OTHER INFORMATION: Synthetic antibody

<400> SEQUENCE: 63
gatattgtga tgactcagtc tccactctcc ctgcccgtca cccctggaga gccggcctcc      60
atctcctgca ggtctagtca gagcctcctg catagtaatg gatacaactc tttggattgg     120
taccttcaga agccagggca gtctccacag ctcctgatct atttgggttc ttatcgggcc     180 tccgggggtcc ctgacaggtt cagtggcagt ggatcaggca cagattttac actgaaaatt    240
agcagagtgg aggctgagga tgttgggggtt tattactgca tgcaagctct acaaactccg    300 tacactttttg gccaggggac caagctggag atcaaa                               336

<210> SEQ ID NO 64
<211> LENGTH: 357
<212> TYPE: DNA
<213> ORGANISM: Artificial sequence
<220> FEATURE:
<223> OTHER INFORMATION: Synthetic antibody

<400> SEQUENCE: 64
caggtgcagc tgcaggagtc gggcccagga ctggtgaagc cttcggggac cctgtccctc      60
acctgcgctg tctctggtgg ctccatcagc agtagtaact ggtggagttg ggtccgccag     120
cccccaggga aggggctgga gtggattgga caaatctatt atagtgggac caccaactac     180
aacccgtccc tgaagagtcg agtcagcata tcagtggaca agtccaagaa ccagttcgcc     240
ctgaaactga gctctgtgac cgccgcggac acggccgtgt attattgtgc tggtggggacc    300 tactttaggc gctactttga ctactggggc cagggagccc tggtcaccgt ctcccca       357

<210> SEQ ID NO 65
<211> LENGTH: 324
<212> TYPE: DNA
<213> ORGANISM: Artificial sequence
<220> FEATURE:
<223> OTHER INFORMATION: Synthetic antibody

<400> SEQUENCE: 65
gaaatagtga tgacgcagtc tccagccacc ctgtctgtgt ctccagggga aagagccacc      60
ctctcctgca gggccagtca gagtgttagc gacaacttag cctggtacca gcagaaacct     120
ggccaggctc ccaggctcct catctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggcctccgct cactttcggc     300
ggagggacca aggtggagat caaa                                             324

<210> SEQ ID NO 66
<211> LENGTH: 375
<212> TYPE: DNA
<213> ORGANISM: Artificial sequence
<220> FEATURE:
<223> OTHER INFORMATION: Synthetic antibody

<400> SEQUENCE: 66
cagttgcagt tgcaggagtc gggcccagga ctggtgaagc cttcggagac cctgtccctc      60
atttgcactg tctctggtgg ctccatcagc agtagtagtt actactgggg ctggatccgc     120 cagccccccag ggaaggggct ggagtggatt gggagtgtct ctatagtggg aataccctac    180
```

-continued

```
tacaacccgt ccctcaagag tcgagtcacc atctccgtag acacgtccaa gaaccagttc      240
tccctgaacc tgagctctgt gaccgccgca gacacgactg tctactactg tgcgagacac      300
caatatagca gcagctggaa ccgcattgat gcttttgata tttggggcca agggacagtg      360
gtcaccgtct ctgca                                                       375

<210> SEQ ID NO 67
<211> LENGTH: 360
<212> TYPE: DNA
<213> ORGANISM: Artificial sequence
<220> FEATURE:
<223> OTHER INFORMATION: Synthetic antibody

<400> SEQUENCE: 67
gaagtgcagc tggtggagtc tgggggaggc ttgatacagc cagggcggtc cctgagactc       60
tcctgtacaa cttctggatt cacctttggt aactatgtta tgagctgggt ccgccaggct      120
ccagggaagg ggctggagtg ggtaggtttc attagaagca aagcttatgg tgggacaaca      180
gaatacgccg cgtctgtgga aggcagattc agcatctcaa gagatgattc caaaagcatc      240
gcctatctgc acatgaacag cctgaaaacc gaggacacag ccgtatatta ctgtttagcc      300
gccactgtct ggacctactt tgacttctgg ggccagggaa ccctggtcac cgtctcttca      360

<210> SEQ ID NO 68
<211> LENGTH: 330
<212> TYPE: DNA
<213> ORGANISM: Artificial sequence
<220> FEATURE:
<223> OTHER INFORMATION: Synthetic antibody

<400> SEQUENCE: 68
cagtctgccc tgactcagcc tcgctcagtg tccgggtctc ctggacagtc agtcaccatc       60
tcctgcactg gaaccagcag tgatgttggt gcttataact atgtctcctg gtaccaacat      120
cacccaggca aagcccccaa actcatgatt tttgatgtca atagccggcc ctcaggggtc      180
cctgatcgct tctctggctc caagtctggc aacacggcct ccctgaccat ctctgggctc      240
caggctgacg atgaggctga ttattactgc tgctcatatg caggcagttt cacttgggtg      300
ttcggcggag ggaccaagtt gaccgtccta                                       330

<210> SEQ ID NO 69
<211> LENGTH: 354
<212> TYPE: DNA
<213> ORGANISM: Artificial sequence
<220> FEATURE:
<223> OTHER INFORMATION: Synthetic antibody

<400> SEQUENCE: 69
caggttcagc tggtgcagtc tggagctgag gtgaagaagc ctggggcctc agtgaaggtc       60
tcctgcaagg cttctggtta cccctttacc aactatggta tcagctgggt gcgacaggcc      120
cctggacaag ggcttgagtg gatgggatgg atcagcgctt acaatggtaa cacaaactat      180
gcacagaagc tccagggcag agtcaccatg accacagaca catccacgag cacagcctac      240
atggagctga ggagcctgag atctgacgac acggccgtgt attactgtgc gagagattac      300
tatgatagta gtggttccgt ctggggccaa gggaccacgg tcaccgtctc ctca           354

<210> SEQ ID NO 70
<211> LENGTH: 321
<212> TYPE: DNA
```

-continued

```
<213> ORGANISM: Artificial sequence
<220> FEATURE:
<223> OTHER INFORMATION: Synthetic antibody

<400> SEQUENCE: 70
gacatccaga tgacccagtc tccatcctcc ctgtctgcat ctgtaggaga cagagtcacc      60
atcacttgcc gggcaagtca gagcattagc acctatttaa attggtatca gcagaaacca     120
gggaaagccc ctaacctcct gatctatggt gcatccagtt tgcaaagtgg ggtcccatca     180
aggttcagtg gcagtggatc tgggacagat ttcactctca ccatcagcag tctgcaacct     240
gaagattttg caacttacta ctgtcaacag acatacacta cccctcgaac gttcggccaa     300
gggaccaagg tggaaatcaa a                                                321

<210> SEQ ID NO 71
<211> LENGTH: 375
<212> TYPE: DNA
<213> ORGANISM: Artificial sequence
<220> FEATURE:
<223> OTHER INFORMATION: Synthetic antibody

<400> SEQUENCE: 71
caggtccagc ttgtgcagtc tggggctgag gtgaagaagc ctggggcctc agtgaaggtt      60
tcctgcaaga cttctggata caccttcatt agttatacta tgcattgggt gcgccaggcc     120
cccggacaaa ggcttgagtg gatgggatgg atcaacggtg gcaatggtaa cacaaaatat     180
tcgcagaggt tccagggcag agtcaccatt accagggaca catccgcgac cacagtctac     240
atggagttga gcagcctgac atctgaagac acggctctgt attactgtgc gagagtaaaa     300
tcggacaccc ttgattttaa ctggaaccca cgctttgact actggggcca gggaaccctg     360
gtcaccgtct cctca                                                      375

<210> SEQ ID NO 72
<211> LENGTH: 324
<212> TYPE: DNA
<213> ORGANISM: Artificial sequence
<220> FEATURE:
<223> OTHER INFORMATION: Synthetic antibody

<400> SEQUENCE: 72
gaaattgtgt tgacgcagtc tccaggcacc ctgtctctgt ctccggggga aagagccacc      60
ctctcctgca gggccagtca gagtgttagc agcagctatt tggtctggta ccagcagaaa     120
cctggccagg ctcccaggct cctcatctat ggtgcatcca gcagggccac cggcatccca     180
gacaggttca gtggcagtgg gtctgggaca gacttcactc tcaccatcag cagactggag     240
cctgaagact ttgcagtgta ttactgtcag cagtgtggta gctccccgat caccttcggc     300
caagggacac gactggagat taaa                                            324

<210> SEQ ID NO 73
<211> LENGTH: 348
<212> TYPE: DNA
<213> ORGANISM: Artificial sequence
<220> FEATURE:
<223> OTHER INFORMATION: Synthetic antibody

<400> SEQUENCE: 73
caggtgcagc tacaggagtc gggcccagga ctggtgaagc cttcggagac cctgtccctc      60
acctgcgatg tctctggtta ctccatcagc agtggttatt attggggctg gatccggcag     120
cccccaggga aggggctgga gtggattggg agtatctatc atagtgggat catctactac     180
```

-continued

```
aacccgtccc tcaagagtcg agtcaccata tcagtagaca cgtccaagaa ccagttctcc      240
ctgaagctga gctctgtgac cgccgcagac acggccgtgt attactgtgc gagacttcta      300
ccaagcaaca tctactgggg ccagggaatc ctggtcaccg tctcctca                  348

<210> SEQ ID NO 74
<211> LENGTH: 330
<212> TYPE: DNA
<213> ORGANISM: Artificial sequence
<220> FEATURE:
<223> OTHER INFORMATION: Synthetic antibody

<400> SEQUENCE: 74
cagtctgccc tgactcagcc tcgctcagtg tccgggtctc ctggacagtc agtcaccatc       60
tcctgcactg gaaccagcag tgatgttggt agttataact atgtctcctg gtacaaacag      120
cacccaggca agcccccaa actcatgatt tttgatgtca gtaggcggcc ctcaggggtc        180
cctgatcgct tctctggctc caagtctggc aacacggcct ccctgaccat ctctgggctc      240
caggctgagg atgaggctga ttatttctgc tgcttatatg caggcagcta cactttcaaa      300
ttcggcggag ggaccaaggt gaccgtccta                                       330

<210> SEQ ID NO 75
<211> LENGTH: 369
<212> TYPE: DNA
<213> ORGANISM: Artificial sequence
<220> FEATURE:
<223> OTHER INFORMATION: Synthetic antibody

<400> SEQUENCE: 75
gaagtgcagt tggtggagtc tggggggaggc ttggtgcggc ctggcaggtc cctgagactc       60
tcctgtgcag cctctggatt caccttttgat gattatgcca tgcactgggt ccggcaagct      120
ccagggaagg gcctggagtg ggtctcaggt attagttggc atagtggtag cataggctat       180
gcggactctg tgcagggccg attcaccacc tccagagaca cgccaagaa ctccctgtat        240 ctgcaaatgg acagtctccg acctgaggac acggccttct attattgtgc aaaatctccc       300
ttgaaaattt ggcagcacct gactccctat gactactggg gccagggaac cctggtcacc      360
gtctcctca                                                              369

<210> SEQ ID NO 76
<211> LENGTH: 321
<212> TYPE: DNA
<213> ORGANISM: Artificial sequence
<220> FEATURE:
<223> OTHER INFORMATION: Synthetic antibody

<400> SEQUENCE: 76
gaaatagtga tgacgcagtc tccagccacc ctgtctgtgt ctccagggga aagagccacc        60
ctctcctgta gggccagtca gagtgttagc agcaacttag cctggtacca gcagaaacgt      120
ggccaggctc ccaggctcct catgtatggt gcatccacca gggccactgg tatcccagcc      180
aggttcagtg gcagtgggtc tgggacagag ttcactctca ccatcagcag cctgcagtct      240
gaagattttg cagtttatta ctgtcagcag tataataact ggcctccctt tttcggcgga      300
gggaccaagg tggagatcaa a                                                321

<210> SEQ ID NO 77
<211> LENGTH: 390
<212> TYPE: DNA
```

-continued

```
<213> ORGANISM: Artificial sequence
<220> FEATURE:
<223> OTHER INFORMATION: Synthetic antibody

<400> SEQUENCE: 77
caggtgcagc tgcaggagtc gggcccagga ctggtgaagc cttcacagac cctgtccctc      60
acctgcactg tctctgatgg ctccatcagc agtggtgatt actactggag ctgggtccgc     120
cagcccccag ggaagggcct ggagtggatt gggtacatat attacagtgg gagcaccctat    180 tacagcccgt ccctcaagag tcgagttacc atctcagtaa acatgtccaa gaaccagttc     240
tccctgaagc tcagctctgt gactgccgca gacacggccg tgtattactg tgccaccgcc     300
cccgcggtag ggagttacta catgagatgg acgggatacc actactacat ggacgtctgg     360
ggcaaaggga ccacggtcac cgtctcctca                                      390

<210> SEQ ID NO 78
<211> LENGTH: 330
<212> TYPE: DNA
<213> ORGANISM: Artificial sequence
<220> FEATURE:
<223> OTHER INFORMATION: Synthetic antibody

<400> SEQUENCE: 78
cagtctgtgc tgacgcagcc gccctcagtg tctgcggccc caggacagaa ggtgaccatc      60
tcctgctctg gaagcagctc caacattgaa tataattatg tatcctggta ccagcagctc     120
ccaagaacag ccccaaact cctcattat gacaataata agcgaccctc agggattcct         180
gaccgattct ctggctccaa gtctggcacg tcagccaccc tgggcatcac cggactccag      240
actggggacg aggccgatta ttactgcgga acatgggata gtagcctgaa tgcttgggtg      300
ttcggcggag ggaccaagct gaccgtccta                                      330

<210> SEQ ID NO 79
<211> LENGTH: 390
<212> TYPE: DNA
<213> ORGANISM: Artificial sequence
<220> FEATURE:
<223> OTHER INFORMATION: Synthetic antibody

<400> SEQUENCE: 79
caggtgcagc tgcaggagtc gggcccagga ctggtgaagc cttcacagac cctgtccctc      60
acctgcactg tctctgatgg ctccatcagc agtggtgatt actactggag ctgggtccgc     120
cagcccccag ggaagggcct ggagtggatt gggtacatat attacagtgg gagcaccctat    180 tacagcccgt ccctcaagag tcgagttacc atctcagtaa acatgtccaa gaaccagttc     240
tccctgaagc tcagctctgt gactgccgca gacacggccg tgtattactg tgccaccgcc     300
cccgcggtag ggagttacta catgagatgg acgggatacc actactacat ggacgtctgg     360
ggcaaaggga ccacggtcac cgtctcctca                                      390

<210> SEQ ID NO 80
<211> LENGTH: 330
<212> TYPE: DNA
<213> ORGANISM: Artificial sequence
<220> FEATURE:
<223> OTHER INFORMATION: Synthetic antibody

<400> SEQUENCE: 80
cagtctgtgc tgacgcagcc gccctcagtg tctgcggccc caggacagaa ggtgaccatc      60
tcctgctctg gaagcagctc caacattgaa tataattatg tatcctggta ccagcagctc     120
```

```
ccaagaacag cccccaaact cctcatttat gacaataata agcgaccctc agggattcct      180
gaccgattct ctggctccaa gtctggcacg tcagccaccc tgggcatcac cggactccag      240
actggggacg aggccgatta ttactgcgga acatgggata gtagcctgaa tgcttgggtg      300
ttcggcggag ggaccaagct gaccgtccta                                        330
```

```
<210> SEQ ID NO 81
<211> LENGTH: 378
<212> TYPE: DNA
<213> ORGANISM: Artificial sequence
<220> FEATURE:
<223> OTHER INFORMATION: Synthetic antibody

<400> SEQUENCE: 81
caaatgcagc tggtgcagtc tgggcctgag gtgaagaagc ctgggacctc agtgaaggtc       60
ccctgcaagg cttctggact cacctttagt agatctgctg tgcagtgggt gcgacaggct      120
cgtggacaac gccttgagtg gataggatgg atcgttgttg gcagtggtaa cacaaactac      180
gcacagaaat tccaggatag agtcaccatt accagggaca tgtccacaag cacggcctac      240
atggagctga gcagcctgag atccgaggac acggccatat attactgtgc ggcaggtcca      300
ggtgtatggg ctagaactga acgcccgaat gatgcttta atctctgggg ccaagggaca      360
atggtcaccg tctcttca                                                     378
```

```
<210> SEQ ID NO 82
<211> LENGTH: 330
<212> TYPE: DNA
<213> ORGANISM: Artificial sequence
<220> FEATURE:
<223> OTHER INFORMATION: Synthetic antibody

<400> SEQUENCE: 82
cagtctgtgc tgacgcagcc gccctcagtg tctgcggccc caggacagaa ggtcaccatc       60
tcctgctctg gaagcagctc caacattggg aacaattatg tatcctggta ccagcagctc      120
ccaggagcag cccccaaagt cctcatttat gacaataatg agcgaccctc ggggattcct      180
gaccgattct ctggctccaa gtctggcagg tcagccaccc tgggcatcac cggactccag      240
actggggacg aggccgatta tttctgcgga acatgggata gcagcctgag tgcctggatt      300
ttcggcggag ggaccaagct gaccgtccta                                        330
```

```
<210> SEQ ID NO 83
<211> LENGTH: 381
<212> TYPE: DNA
<213> ORGANISM: Artificial sequence
<220> FEATURE:
<223> OTHER INFORMATION: Synthetic antibody

<400> SEQUENCE: 83
gaagtgcagc tgttggagtc tgggggaggc ttggtgcagc ctggggggtc cctgagactc       60
tcctgtgcag cctctggatt cacctttagc agctatgcca tgatctgggt ccgccaggct      120
ccagggaggg ggctggagtg ggtctcaact attactggta gtggtggtag cacacgcttc      180
gcagactcct tgaagggccg cttcgccatc tccagagaca attccaagaa cacgctgtat      240
ctgcaaatga acagcctgag agtcgaggac acggccgtat attactgtgc gaaacgatat      300
tgtagtggta ccacctccca tctttactgc tactacgcca tggacgtctg gggccaaggg      360
acagcggtca ccgtctcctc a                                                 381
```

-continued

```
<210> SEQ ID NO 84
<211> LENGTH: 330
<212> TYPE: DNA
<213> ORGANISM: Artificial sequence
<220> FEATURE:
<223> OTHER INFORMATION: Synthetic antibody

<400> SEQUENCE: 84
cagtctgccc tgactcagcc tgcctccgtg tctgggtctc ctggacagtc gatcaccatc      60
tcctgcactg gaaccagcag tgacgttggt ggttataact atgtctcctg gtaccaacaa     120
cacccaggca aagcccccaa actcatgatt tatgatgtca gtaatcggcc ctcaggggtt     180
tctaatcgct tctctggctc caagtctggc aacacggcct ccctgaccat ctctgggctc     240
caggctgagg acgaggctga ttattactgc agctcatata caagcagcag cactaaactc     300
ttcggaactg ggaccaaggt caccgtccta                                      330

<210> SEQ ID NO 85
<211> LENGTH: 366
<212> TYPE: DNA
<213> ORGANISM: Artificial sequence
<220> FEATURE:
<223> OTHER INFORMATION: Synthetic antibody

<400> SEQUENCE: 85
caggtgcagc tgcaggagtc gggcccagga ctggtgaagc cttcggagac cctgtccctc      60
acctgcgctg tctctgatta ctccatcagc agtggttact actgggctg gatccggcag      120 cccccaggaa aggggctgga gtggattgcg agtatctatc atggtgggag caccgactac     180
aacccgtccc tcaagagtcg agtcaccata tcgctagaca cgtccaagat ccagttctcc     240
ctgaagctga gctctgtgac cgccgcagac acggccgtgt attattgtgc gagtcgtcat     300
gatcgtagtg gttatgacga atacttcgag tactggggcc agggcaccct ggtcaccgtc     360
tcctca                                                                366

<210> SEQ ID NO 86
<211> LENGTH: 321
<212> TYPE: DNA
<213> ORGANISM: Artificial sequence
<220> FEATURE:
<223> OTHER INFORMATION: Synthetic antibody

<400> SEQUENCE: 86
gacatccaga tgacccagtc tccatcctcc ctgtctgctt ctgtgggaga cagagtcacc      60
atcatttgcc gggcgagtca cggcattagc aattctttag cctggtatca gcagaaacca     120
gggaaagccc ctaagctcct gctctatgct gcatccagat tgaaaagtgg ggtcccttcc     180
aggttcagtg gcagtggatc tgggacggat tacactctca ccatcaccag cctgcagcct     240
gaagattttg caacttatta ctgtcaacag tattatagta cgcctctgac tttcggccct     300
gggaccaaag tggatctcaa a                                               321

<210> SEQ ID NO 87
<211> LENGTH: 360
<212> TYPE: DNA
<213> ORGANISM: Artificial sequence
<220> FEATURE:
<223> OTHER INFORMATION: Synthetic antibody

<400> SEQUENCE: 87
gaggaacagc tggtggagtc tggaggaggc ttgattcacc ctggggggtc cctgagactc      60
```

-continued

```
tcctgtgcgg cctctgggtt caccgtcagt agtacctaca tgaattgggt ccgccagtct    120
ccagggaagg ggctggagtg ggtctcactt atttatagcg gtggtagtac atactacgca    180
gactccgtga agggccgatt caccatctcc agagacaatt ccaagaacac ggtgtatctt    240
caaatgaaca gcctgagagc cgaagacacg gccgtgtatt attgtgcgag aattcccctc    300
tccttcggcc caatgtactt tgactattgg ggccagggaa cccgggtcac cgtctcctca    360
```

```
<210> SEQ ID NO 88
<211> LENGTH: 360
<212> TYPE: DNA
<213> ORGANISM: Artificial sequence
<220> FEATURE:
<223> OTHER INFORMATION: Synthetic antibody

<400> SEQUENCE: 88
```

```
gaggaacagc tggtggagtc tggaggaggc ttgattcacc ctggggggtc cctgagactc     60
tcctgtgcgg cctctgggtt caccgtcagt agtacctaca tgaattgggt ccgccagtct    120
ccagggaagg ggctggagtg ggtctcactt atttatagcg gtggtagtac atactacgca    180
gactccgtga agggccgatt caccatctcc agagacaatt ccaagaacac ggtgtatctt    240
caaatgaaca gcctgagagc cgaagacacg gccgtgtatt attgtgcgag aattcccctc    300
tccttcggcc caatgtactt tgactattgg ggccagggaa cccgggtcac cgtctcctca    360
```

```
<210> SEQ ID NO 89
<211> LENGTH: 378
<212> TYPE: DNA
<213> ORGANISM: Artificial sequence
<220> FEATURE:
<223> OTHER INFORMATION: Synthetic antibody

<400> SEQUENCE: 89
```

```
caggtgcagc tggtggagtc tggggggaggc tcggtcaagc ctggagggtc cctgagactc     60
tcctgtgcag cctctggatt caccttcagt gactactaca tgacctggat ccgccaggct    120
ccagggaagg ggctggagtg ggtttcatat attagtagta gtgctactac catctactac    180
gccgactctg tgaagggccg attcaccatc tcccgggaca cgccaagaa cttactgtat    240 ctgcaaatga acagcctgag agccgaggac acggccgtat attactgtgc gagagatcat    300
aggtattgta ctagtaccaa ctgctttgca cactggttcg acccctgggg ccagggaatc    360
ctggtcaccg tctccca                                                   378
```

```
<210> SEQ ID NO 90
<211> LENGTH: 330
<212> TYPE: DNA
<213> ORGANISM: Artificial sequence
<220> FEATURE:
<223> OTHER INFORMATION: Synthetic antibody

<400> SEQUENCE: 90
```

```
cagtctgtgc tgactcagcc accctcagcg tctgggaccc ccgggcagag ggtcaccatc     60
tcttgttctg gaagcagctc caacatcgga agtgacactg taaagtggta ccagcaactc    120
ccaggaacgg cccccagact tctcatctat agtaataatc agcggccctc aggggtccct    180
gaccgattct ctggctccaa gtctggcacc tcagcctccc tggccatcag tgggctccag    240
tctgaggatg aggctgatta ttactgtgca gcatgggatg acagcctgaa tggtccggtg    300
ttcggcggag ggaccaaact gaccgtccta                                     330
```

<210> SEQ ID NO 91
<211> LENGTH: 369
<212> TYPE: DNA
<213> ORGANISM: Artificial sequence
<220> FEATURE:
<223> OTHER INFORMATION: Synthetic antibody

<400> SEQUENCE: 91
caggtgcaac tggtgcagtc tgggggctgag gtgaagaagc ctgggggcctc agtgaaggtt      60 tcctgcaagg catctggata caccttcagc agttactata tacactgggt gcgacaggcc     120
cctggacaag ggcttgagtg gatgggaata atcaacccta gtgttggtgc cacagagtac     180
gcacacattt ccagggcag agtcaccctg accagggaca cgtccacgag tacagtctac     240
atggacttga gcaggcttac atctgacgac acggccgtgt attactgtgc tagatggggg     300
ctcattagtg agagctcacc aaaatacttt gactcctggg gccagggaac cctggtcacc     360
gtctcctca                                                              369

<210> SEQ ID NO 92
<211> LENGTH: 339
<212> TYPE: DNA
<213> ORGANISM: Artificial sequence
<220> FEATURE:
<223> OTHER INFORMATION: Synthetic antibody

<400> SEQUENCE: 92
cagtctgtgc tgacgcagcc gccctcagtg tctggggccc cagggcagag ggtcaccatc      60
tcctgcactg ggagcaactc caacatcggg gcaggttatg atgtacactg gtaccagcag     120
cttccaggaa cagcccccaa actcctcatc tatgataata ccaatcggcc ctcagggggtc     180 cctgaccgat tctctggctc caagtctggc acgtcagcct ccctggccat cactgggctc     240
caggctgagg atgaggctga ttattactgc cagtcctatg acagcagcgt gagtggtttt     300
tacgtgcttt tcggcggagg gaccaagctg accgtccta                            339

<210> SEQ ID NO 93
<211> LENGTH: 411
<212> TYPE: DNA
<213> ORGANISM: Artificial sequence
<220> FEATURE:
<223> OTHER INFORMATION: Synthetic antibody

<400> SEQUENCE: 93
cagatcacct tgaaggagtc tggtccaacg ctggtgaaac ccacacagac cctcaccctg      60
acctgcacct tctctggatt ctcactgagc aatagtggag tgggtgtggg ctggatccgt     120
cagcccccag gaaaggccct ggagtggctt gcactcattt attgggatga tgacaagcgc     180
tacaggccat ctctgaagag caggctcacc atcaccaagg acacctccaa aaaccaggtg     240
gtccttaaaa tgaccaacat ggaccctgtg gacacagcca cctattactg tgcacacagt     300
tatttcgact tttggagtgg ttatttttcg ctggaccgtc gggaccgtcg cgccgggcga     360
cagtcctact ttgactactg gggccaggga accctggtca ccgtctcctc a              411

<210> SEQ ID NO 94
<211> LENGTH: 324
<212> TYPE: DNA
<213> ORGANISM: Artificial sequence
<220> FEATURE:
<223> OTHER INFORMATION: Synthetic antibody

<400> SEQUENCE: 94

-continued

```
cagtctgccc tgactcagcc tgcctccgtg tctgggtctc ctggacagtc gatcaccatc       60
tcctgcactg gaaccaccag tgacgttggt ggttatgact atgtctcgtg gtaccaacaa      120
cacccaggca aagccccaa actcatgatt tttgatgtca atcatcggcc ctcaggggtt       180
tccagccgct tctctggctc caagtctggc aacacggcct ccctgaccat ctctgggctc      240
caggctgaag acgaggctgc ttattactgc tcctcatata caaccggcac cctcttcggc      300
ggagggacca agctgaccgt cctg                                              324

<210> SEQ ID NO 95
<211> LENGTH: 366
<212> TYPE: DNA
<213> ORGANISM: Artificial sequence
<220> FEATURE:
<223> OTHER INFORMATION: Synthetic antibody

<400> SEQUENCE: 95
caggtgctac tgcaggagtc gggcccagga ctggtgaagc cttcggggac cctgtccctc       60
acctgcgctg tctctggtgg ctccatcacc actaataact ggtggagttg ggtccgccag      120
cccccaggga gggggctgga gtggattggg gaaatctttc atggtggaaa aaccaactac      180
aacccgtccc tcaagagtcg agtcaccata tcagtcgaca agtccaagaa ccagttctcc      240
ctgaagctga cctctctgac cgccgcggac acggccgtgt attactgtgc gagagccggg      300
ctatatagca ccaactggtc cccgttcgac ccctggggcc agggaaccct ggtcaccgtc      360
tcctca                                                                  366

<210> SEQ ID NO 96
<211> LENGTH: 324
<212> TYPE: DNA
<213> ORGANISM: Artificial sequence
<220> FEATURE:
<223> OTHER INFORMATION: Synthetic antibody

<400> SEQUENCE: 96
gaagttgtgt tgacgcagtc tccaggcacc ctgtctttgt ctccagggga aagagccacc       60
ctctcctgca gggccagtca gagtgttacc agcagctact tagcctggta ccagcaaaaa      120
cctggccagg ctcccaggct cctcatcttt gatgcatcca gcagggccac tggcatccca      180
gacaggttca gtggcagtgg gtctgggaca gacttcactc tcaccatcag gagactggag      240
cctgaagatt ttgcagtgta ttactgtcag cagtatggtg gctcaccgtg gacgttcggc      300
caagggacca aggtggaaat caaa                                              324

<210> SEQ ID NO 97
<211> LENGTH: 369
<212> TYPE: DNA
<213> ORGANISM: Artificial sequence
<220> FEATURE:
<223> OTHER INFORMATION: Synthetic antibody

<400> SEQUENCE: 97
caggtgcaac tggtgcagtc tggggctgag gtgaagaagc ctggggcctc agtgaaggtt       60
tcctgcaagg catctggata caccttcagc agttactata tacactgggt gcgacaggcc      120
cctggacaag ggcttgagtg gatgggaata atcaacccta gtgttggtgc cacagagtac      180
gcacacattt ccagggcag agtcaccctg accaggggac cgtccacgag tacagtctac        240
atggacttga gcaggcttac atctgacgac acggccgtgt attactgtgc tagatggggg      300
```

-continued

```
ctcattagtg agagctcacc aaaatacttt gactcctggg gccagggaac cctggtcacc      360
gtctcctca                                                              369

<210> SEQ ID NO 98
<211> LENGTH: 321
<212> TYPE: DNA
<213> ORGANISM: Artificial sequence
<220> FEATURE:
<223> OTHER INFORMATION: Synthetic antibody

<400> SEQUENCE: 98
gaaattgtgt tgacacagtc tccagccacc ctgtctttgt ctccagggga aagagccacc       60
ctctcctgca gggccagtca gagtgttagc agctacttag cctggtacca acagagacct      120
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg cagtttatta ctgtcagcag cgtagtaact ggccctacac ttttggccgg      300
gggaccaagc tggagatcaa a                                                321

<210> SEQ ID NO 99
<211> LENGTH: 351
<212> TYPE: DNA
<213> ORGANISM: Artificial sequence
<220> FEATURE:
<223> OTHER INFORMATION: Synthetic antibody

<400> SEQUENCE: 99
caggtgcagc tggtgcagtc tggggctgag gtgaagaagc ctgggtcctc ggtgaaggtc       60
tcctgcaagg cttctggagg caccttcagc agctattcta tcagctggct gcgacaggcc      120
cctggacaag ggcttgagtg gatgggacag atcatcccta tgtttggaac agcaaactac      180
gcacagaagt tccagggcag agtcacgatt accgcggacg aatccacgag cacagcctac      240
atggagctga gcagccttag atctgaggac acggccgtgt attactgtgc gagagaggcc      300
agagccgagg gggacgtctg gggccaaggg accacggtca ccgtctcctc a               351

<210> SEQ ID NO 100
<211> LENGTH: 321
<212> TYPE: DNA
<213> ORGANISM: Artificial sequence
<220> FEATURE:
<223> OTHER INFORMATION: Synthetic antibody

<400> SEQUENCE: 100
gaaattgtgt tgacacagtc tccagccacc ctgtctttgt ctccagggga aagagccacc       60
ctctcctgca gggccagtca gagtgttagc agctacttag cctggtacca acagagacct      120
ggccaggctc ccaggctcct catctatgat gcatccaaca gggccactgg catcccagcc      180
aggttcagtg gcagtgggtc tgggacagac ttcactctca ccatcagcag cctagagcct      240
gaagattttg cagtttatta ctgtcagcag cgtagtaact ggccctacac ttttggccgg      300
gggaccaagc tggagatcaa a                                                321

<210> SEQ ID NO 101
<211> LENGTH: 119
<212> TYPE: PRT
<213> ORGANISM: Artificial sequence
<220> FEATURE:
<223> OTHER INFORMATION: Synthetic antibody

<400> SEQUENCE: 101
```

```
His Val Gln Leu Val Glu Ser Gly Gly Ala Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Phe Gly Ser Asn Thr Phe Tyr Ala Asp Phe Val
    50                  55                  60

Lys Gly Arg Phe Thr Ile Ser Arg Asp Asn Ala Lys Lys Ser Leu Tyr
65                  70                  75                  80

Leu Gln Met Ser Ser Leu Arg Ala Glu Asp Thr Ala Val Tyr Tyr Cys
                85                  90                  95

Ala Arg Ser Leu Arg Gly Ile Ala Val Pro Ser Tyr Trp Gly Gln Gly
            100                 105                 110

Thr Leu Val Thr Val Ser Ser
        115
```

<210> SEQ ID NO 102
<211> LENGTH: 108
<212> TYPE: PRT
<213> ORGANISM: Artificial sequence
<220> FEATURE:
<223> OTHER INFORMATION: Synthetic antibody

<400> SEQUENCE: 102

```
Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Asp
            20                  25                  30

Leu Ala Trp Tyr His Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys
            100                 105
```

<210> SEQ ID NO 103
<211> LENGTH: 119
<212> TYPE: PRT
<213> ORGANISM: Artificial sequence
<220> FEATURE:
<223> OTHER INFORMATION: Synthetic antibody

<400> SEQUENCE: 103

```
His Val Gln Leu Val Glu Ser Gly Gly Ala Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Phe Gly Ser Asn Thr Phe Tyr Ala Asp Phe Val
    50                  55                  60

Lys Gly Arg Phe Thr Ile Ser Arg Asp Asn Ala Lys Lys Ser Leu Tyr
```

-continued

```
65              70              75              80

Leu Gln Met Ser Ser Leu Arg Ala Glu Asp Thr Ala Val Tyr Tyr Cys
                85              90              95

Ala Arg Ser Leu Arg Gly Ile Ala Val Pro Ser Tyr Trp Gly Gln Gly
            100             105             110

Thr Leu Val Thr Val Ser Ser
        115

<210> SEQ ID NO 104
<211> LENGTH: 108
<212> TYPE: PRT
<213> ORGANISM: Artificial sequence
<220> FEATURE:
<223> OTHER INFORMATION: Synthetic antibody

<400> SEQUENCE: 104

Glu Ile Val Met Thr Gln Ser Pro Ala Thr Leu Ser Val Ser Pro Gly
1               5               10              15

Glu Arg Val Thr Leu Ser Cys Arg Ala Ser Gln Ser Val Ser Ser Asp
            20              25              30

Leu Ala Trp Tyr His Gln Lys Pro Gly Gln Ala Pro Arg Leu Leu Ile
        35              40              45

Tyr Asp Ala Ser Thr Arg Ala Thr Gly Ile Pro Ala Arg Phe Ser Gly
    50              55              60

Ser Gly Ser Gly Thr Glu Phe Thr Leu Thr Ile Ser Ser Leu Gln Ser
65              70              75              80

Glu Asp Phe Ala Val Tyr Tyr Cys Gln Gln Tyr Asn Asn Trp Pro Pro
                85              90              95

Trp Thr Phe Gly Gln Gly Thr Lys Val Glu Ile Lys
            100             105

<210> SEQ ID NO 105
<211> LENGTH: 125
<212> TYPE: PRT
<213> ORGANISM: Artificial sequence
<220> FEATURE:
<223> OTHER INFORMATION: Synthetic antibody

<400> SEQUENCE: 105

Gln Leu Gln Leu Leu Glu Ser Gly Pro Gly Leu Val Lys Pro Ser Glu
1               5               10              15

Thr Leu Ser Leu Thr Cys Thr Val Ser Gly Gly Ser Ile Ser Ser Asn
            20              25              30

Ile Tyr Tyr Trp Gly Trp Ile Arg Gln Pro Pro Gly Lys Gly Leu Glu
        35              40              45

Trp Ile Gly Ser Ile Tyr Tyr Ser Gly Asn Thr His Tyr Asn Pro Ser
    50              55              60

Leu Lys Ser Arg Val Thr Ile Ser Val Asp Thr Ser Lys Asn Gln Phe
65              70              75              80

Ser Leu Lys Leu Ser Ser Leu Thr Ala Ala Asp Ser Ala Leu Tyr Tyr
                85              90              95

Cys Ala Ser Gln Lys Met Val Tyr Pro Ile Lys Arg Asn Asn Trp Phe
            100             105             110

Asp Pro Trp Gly Gln Gly Thr Leu Val Ile Val Ser Ser
        115             120             125

<210> SEQ ID NO 106
<211> LENGTH: 110
```

```
<212> TYPE: PRT
<213> ORGANISM: Artificial sequence
<220> FEATURE:
<223> OTHER INFORMATION: Synthetic antibody

<400> SEQUENCE: 106

Gln Ser Val Leu Thr Gln Ser Pro Ser Ala Ser Gly Thr Pro Gly Gln
1               5                   10                  15

Arg Val Thr Ile Ser Cys Ser Gly Ser Ser Ser Asn Ile Glu Ser Asn
            20                  25                  30

Thr Val Thr Trp Tyr Gln Gln Leu Pro Gly Thr Ala Pro Lys Leu Leu
        35                  40                  45

Ile Tyr Gly Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Gly Leu
                85                  90                  95

Asn Gly Trp Val Phe Gly Gly Gly Thr Lys Leu Thr Val Leu
            100                 105                 110

<210> SEQ ID NO 107
<211> LENGTH: 130
<212> TYPE: PRT
<213> ORGANISM: Artificial sequence
<220> FEATURE:
<223> OTHER INFORMATION: Synthetic antibody

<400> SEQUENCE: 107

Glu Val His Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Glu Ser Glu Ala Phe Ser Ile Phe Gly Val Val Arg Tyr
            100                 105                 110

Tyr Tyr Tyr Tyr Met Asp Val Trp Gly Lys Gly Thr Thr Val Thr Val
        115                 120                 125

Ser Ser
    130

<210> SEQ ID NO 108
<211> LENGTH: 108
<212> TYPE: PRT
<213> ORGANISM: Artificial sequence
<220> FEATURE:
<223> OTHER INFORMATION: Synthetic antibody

<400> SEQUENCE: 108

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Gly Tyr
```

```
              20              25              30

Asn Tyr Val Ser Trp Tyr Gln Gln His Pro Asp Lys Ala Pro Lys Leu
          35              40              45

Met Ile Tyr Asp Val Thr Lys Arg Pro Ser Gly Val Pro Asp Arg Phe
      50              55              60

Ser Gly Ser Lys Ser Gly Asn Thr Ala Ser Leu Thr Ile Ser Gly Leu
65              70              75              80

Gln Ala Glu Asp Glu Ala Asp Tyr Tyr Cys Cys Ser Tyr Ala Gly Thr
              85              90              95

Val Val Phe Gly Gly Gly Thr Lys Leu Thr Val Leu
              100             105

<210> SEQ ID NO 109
<211> LENGTH: 122
<212> TYPE: PRT
<213> ORGANISM: Artificial sequence
<220> FEATURE:
<223> OTHER INFORMATION: Synthetic antibody

<400> SEQUENCE: 109

Gln Val Gln Leu Gln Glu Ser Gly Pro Gly Leu Val Lys Pro Ser Gly
1               5               10              15

Thr Leu Ser Leu Thr Cys Ala Val Ser Gly Gly Ser Ile Ser Ser Ser
              20              25              30

Lys Trp Trp Ser Trp Val Arg Gln Ser Pro Gly Lys Gly Leu Glu Trp
          35              40              45

Ile Gly Glu Ile Tyr His Ser Gly Ser Thr Asn Tyr Asn Pro Ser Leu
      50              55              60

Lys Ser Arg Ala Thr Ile Ser Val Asp Lys Ser Lys Asn Gln Phe Ser
65              70              75              80

Leu Lys Leu Asn Ser Val Thr Ala Ala Asp Thr Ala Val Tyr Tyr Cys
              85              90              95

Ala Arg Val Gly Leu Gly Trp His Asp Gly Asn Gly Met Asp Val Trp
              100             105             110

Gly Gln Gly Thr Thr Val Thr Val Ser Ser
          115             120

<210> SEQ ID NO 110
<211> LENGTH: 109
<212> TYPE: PRT
<213> ORGANISM: Artificial sequence
<220> FEATURE:
<223> OTHER INFORMATION: Synthetic antibody

<400> SEQUENCE: 110

Glu Ile Val Leu Thr Gln Ser Pro Ala Thr Leu Ser Leu Ser Pro Gly
1               5               10              15

Glu Arg Ala Thr Leu Ser Cys Arg Ala Ser Leu Asn Ile Gly Ser Tyr
              20              25              30

Leu Ala Trp Tyr Gln Gln Lys Pro Gly Gln Ala Pro Arg Leu Leu Ile
          35              40              45

Tyr Asp Ala Ser Asn Arg Ala Thr Gly Ile Pro Ala Arg Phe Ser Gly
      50              55              60

Ser Gly Ser Gly Thr Asp Phe Thr Leu Thr Ile Arg Ser Leu Glu Pro
65              70              75              80

Glu Asp Phe Ala Ile Tyr Tyr Cys Gln Gln Arg Ser Asn Trp Pro Pro
              85              90              95
```

```
Gly Tyr Thr Phe Gly Gln Gly Thr Lys Leu Glu Ile Arg
            100                 105
```

```
<210> SEQ ID NO 111
<211> LENGTH: 129
<212> TYPE: PRT
<213> ORGANISM: Artificial sequence
<220> FEATURE:
<223> OTHER INFORMATION: Synthetic antibody

<400> SEQUENCE: 111

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Leu Arg Gln His Pro Gly Lys Gly Leu Glu
        35                  40                  45

Trp Ile Gly Tyr Ile Tyr Tyr Ser Gly Ser Ala Tyr Ser Asn Pro Ser
    50                  55                  60

Leu Asn Ser Arg Asp Ile Ile Ser Ile Asp Thr Ser Lys Asn Arg Phe
65                  70                  75                  80

Ser Leu Lys Leu Ser Ser Val Thr Ala Ala Asp Thr Ala Val Tyr Tyr
                85                  90                  95

Cys Ala Arg Phe Arg Leu Gly Asp Ala Pro Thr Arg Asp Gly Tyr Asn
            100                 105                 110

Leu His Tyr Phe Asp Tyr Trp Gly Gln Gly Ser Leu Val Thr Val Ser
        115                 120                 125

Ser
```

```
<210> SEQ ID NO 112
<211> LENGTH: 111
<212> TYPE: PRT
<213> ORGANISM: Artificial sequence
<220> FEATURE:
<223> OTHER INFORMATION: Synthetic antibody

<400> SEQUENCE: 112

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Leu Val Ser Trp Tyr Gln Gln His Pro Gly Lys Ala Pro Lys Val
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Gly Gly Phe
                85                  90                  95

Ser Thr His Val Val Phe Gly Gly Gly Thr Arg Leu Thr Val Leu
            100                 105                 110
```

```
<210> SEQ ID NO 113
<211> LENGTH: 126
<212> TYPE: PRT
<213> ORGANISM: Artificial sequence
<220> FEATURE:
<223> OTHER INFORMATION: Synthetic antibody

<400> SEQUENCE: 113
```

Glu Val Gln Leu Val Glu Ser Gly Gly Gly Leu Val Gln Pro Gly Arg
1               5                   10                  15

Ser Leu Arg Leu Ser Cys Thr Gly Ser Gly Phe Thr Phe Gly Asp Tyr
            20                  25                  30

Ala Met Ser Trp Ala Arg Gln Ala Pro Gly Lys Gly Leu Glu Trp Val
        35                  40                  45

Gly Phe Ile Arg Ser Lys Gly Tyr Gly Gly Thr Thr Gln Tyr Ala Ala
    50                  55                  60

Ser Val Lys Gly Arg Phe Thr Ile Ser Arg Asp Asp Ser Lys Arg Ile
65                  70                  75                  80

Ala Tyr Leu Gln Val Asn Ser Leu Lys Ile Glu Asp Thr Ala Val Tyr
            85                  90                  95

Phe Cys Thr Arg Ala His Tyr Asp Tyr Val Trp Gly Asn Tyr Trp Ser
        100                 105                 110

Phe Ala Tyr Trp Gly Gln Gly Thr Leu Val Thr Val Ser Ser
        115                 120                 125

<210> SEQ ID NO 114
<211> LENGTH: 110
<212> TYPE: PRT
<213> ORGANISM: Artificial sequence
<220> FEATURE:
<223> OTHER INFORMATION: Synthetic antibody

<400> SEQUENCE: 114

Gln Ser Val Leu Thr Gln Pro Pro Ser Leu Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln His Leu Pro Gly Thr Ala Pro Lys Leu Ile
        35                  40                  45

Ile Tyr Asp Asp Asn Gln Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
            85                  90                  95

Ser Val Phe Val Phe Gly Thr Gly Thr Lys Val Thr Val Leu
        100                 105                 110

<210> SEQ ID NO 115
<211> LENGTH: 127
<212> TYPE: PRT
<213> ORGANISM: Artificial sequence
<220> FEATURE:
<223> OTHER INFORMATION: Synthetic antibody

<400> SEQUENCE: 115

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr

```
65                  70                  75                  80

Leu Gln Met Asn Ser Leu Arg Ala Glu Asp Thr Ala Leu Tyr Tyr Cys
                85                  90                  95

Ala Arg Asp Pro Gly Gly Arg Arg Asp Gly Tyr Ile Leu Arg Pro Asp
            100                 105                 110

Ala Phe Asp Ile Trp Gly Gln Gly Thr Met Val Thr Val Ser Ser
            115                 120                 125

<210> SEQ ID NO 116
<211> LENGTH: 107
<212> TYPE: PRT
<213> ORGANISM: Artificial sequence
<220> FEATURE:
<223> OTHER INFORMATION: Synthetic antibody

<400> SEQUENCE: 116

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Thr Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Tyr Thr Trp
                85                  90                  95

Thr Phe Gly Gln Gly Thr Lys Val Glu Ile Lys
            100                 105

<210> SEQ ID NO 117
<211> LENGTH: 116
<212> TYPE: PRT
<213> ORGANISM: Artificial sequence
<220> FEATURE:
<223> OTHER INFORMATION: Synthetic antibody

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Val Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ser Gly Gly Tyr Ala Ile Phe Trp Gly Gln Gly Thr Leu Val
            100                 105                 110

Thr Val Ser Ser
            115

<210> SEQ ID NO 118
<211> LENGTH: 109
```

<212> TYPE: PRT
<213> ORGANISM: Artificial sequence
<220> FEATURE:
<223> OTHER INFORMATION: Synthetic antibody

<400> SEQUENCE: 118

Glu Ile Val Leu Thr Gln Ser Pro Gly Thr Leu Ser Leu Ser Pro Gly
1               5                   10                  15

Glu Ser Ala Thr Leu Ser Cys Arg Ala Ser Gln Ser Leu Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Thr Pro
                85                  90                  95

Pro Tyr Thr Phe Gly Gln Gly Thr Lys Leu Glu Ile Lys
            100                 105

<210> SEQ ID NO 119
<211> LENGTH: 118
<212> TYPE: PRT
<213> ORGANISM: Artificial sequence
<220> FEATURE:
<223> OTHER INFORMATION: Synthetic antibody

<400> SEQUENCE: 119

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Ile Ser Ser Ser
            20                  25                  30

Gly Val Gly Val Gly Trp Ile Arg Gln Pro Pro Gly Lys Ala Leu Glu
        35                  40                  45

Trp Leu Ala Leu Leu Tyr Trp Asp Asp Ser Lys Arg Tyr Ser Pro Ser
    50                  55                  60

Leu Arg Ser Arg Leu Thr Ile Thr Lys Asp Thr Ser Lys Asn Gln Val
65                  70                  75                  80

Val Leu Thr Met Thr Asn Met Asp Pro Val Asp Thr Gly Thr Tyr Tyr
                85                  90                  95

Cys Ala His Arg Arg Thr Thr Val Phe Asp Tyr Trp Gly Gln Gly Thr
            100                 105                 110

Leu Val Thr Val Ser Ser
        115

<210> SEQ ID NO 120
<211> LENGTH: 110
<212> TYPE: PRT
<213> ORGANISM: Artificial sequence
<220> FEATURE:
<223> OTHER INFORMATION: Synthetic antibody

<400> SEQUENCE: 120

Asn Phe Met Leu Thr Gln Pro His Ser Val Ser Glu Ser Pro Gly Lys
1               5                   10                  15

Thr Val Thr Ile Ser Cys Thr Arg Ser Arg Gly Ser Ile Ala Ser Asn
            20                  25                  30

Tyr Val Gln Trp Tyr Gln Gln Arg Pro Gly Ser Ser Pro Thr Asn Val

```
              35                    40                    45

Ile Tyr Glu Asp Asn Gln Arg Pro Ser Gly Val Pro Asp Arg Phe Ser
    50                    55                    60

Gly Ser Ile Asp Ser Ser Ser Asn Ser Ala Ser Leu Thr Ile Ser Gly
65                    70                    75                    80

Leu Lys Thr Glu Asp Glu Ala Asp Tyr Tyr Cys Gln Ser Tyr Asp Ser
                  85                    90                    95

Tyr Asn His Val Phe Gly Gly Gly Thr Arg Leu Thr Val Leu
                  100                   105                   110

<210> SEQ ID NO 121
<211> LENGTH: 132
<212> TYPE: PRT
<213> ORGANISM: Artificial sequence
<220> FEATURE:
<223> OTHER INFORMATION: Synthetic antibody

<400> SEQUENCE: 121

Glu Val Gln Leu Val Gln Ser Gly Ala Glu Val Lys Lys Pro Gly Glu
1                   5                     10                    15

Ser Leu Lys Ile Ser Cys Lys Gly Ser Gly Tyr Arg Phe Thr Asn Tyr
                  20                    25                    30

Trp Ile Gly Trp Val Arg Gln Met Pro Gly Lys Gly Leu Glu Trp Met
              35                    40                    45

Gly Ile Ile Tyr Pro Gly Asp Ser Asn Thr Arg Tyr Ser Pro Ser Phe
    50                    55                    60

Gln Gly Gln Val Thr Ile Ser Ala Asp Lys Ser Ile Ser Thr Ala Tyr
65                    70                    75                    80

Leu Gln Trp Gly Ser Leu Lys Ala Ser Asp Thr Ala Met Tyr Tyr Cys
                  85                    90                    95

Ala Arg His Ser Glu Thr Lys Asp Gly Tyr Asn Trp Ala Gln Gly Asn
                  100                   105                   110

Phe Tyr Ser Tyr Tyr Tyr Met Asp Val Trp Gly Lys Gly Thr Thr Val
              115                   120                   125

Thr Val Ser Ser
    130

<210> SEQ ID NO 122
<211> LENGTH: 108
<212> TYPE: PRT
<213> ORGANISM: Artificial sequence
<220> FEATURE:
<223> OTHER INFORMATION: Synthetic antibody

<400> SEQUENCE: 122

Asp Ile Gln Met Thr Gln Ser Pro Ser Ser Leu Ser Ala Ser Val Gly
1                   5                     10                    15

Asp Arg Val Thr Ile Thr Cys Arg Ala Ser Gln Ser Ile Ser Ser Tyr
                  20                    25                    30

Leu Asn Trp Tyr Gln Gln Ile Pro Gly Lys Ala Pro Lys Leu Leu Ile
              35                    40                    45

Tyr Ala Ala Ser Ser Leu Gln Ser Gly Val Pro Ser Arg Phe Ser Gly
    50                    55                    60

Ser Gly Ser Gly Thr Asp Phe Thr Leu Ser Ile Ser Ser Leu Gln Pro
65                    70                    75                    80

Glu Asp Phe Ala Thr Tyr Tyr Cys Gln Gln Ser Tyr Ser Ile Ser Pro
                  85                    90                    95
```

-continued

```
Leu Ser Phe Gly Gly Gly Thr Lys Val Glu Ile Lys
            100                 105

<210> SEQ ID NO 123
<211> LENGTH: 125
<212> TYPE: PRT
<213> ORGANISM: Artificial sequence
<220> FEATURE:
<223> OTHER INFORMATION: Synthetic antibody

<400> SEQUENCE: 123

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Asn Tyr Tyr
            20                  25                  30

Tyr Trp Ser Trp Ile Arg Gln Pro Pro Gly Lys Gly Leu Glu Trp Ile
        35                  40                  45

Ala Tyr Ile Tyr Tyr Ile Glu Gly Ser Glu Ser Thr Asn Tyr Asn Pro
    50                  55                  60

Ser Leu Lys Ser Arg Val Thr Met Ser Val Asp Thr Ser Lys Asn Gln
65                  70                  75                  80

Leu Ser Leu Lys Leu Ser Ser Val Thr Ala Ala Asp Thr Ala Ala Tyr
            85                  90                  95

Tyr Cys Ala Arg Asp Ser Arg Arg Asn Arg Tyr Ser Gly Tyr Tyr Phe
            100                 105                 110

Asp Phe Trp Gly Gln Gly Thr Leu Val Thr Val Ser Ser
        115                 120                 125

<210> SEQ ID NO 124
<211> LENGTH: 107
<212> TYPE: PRT
<213> ORGANISM: Artificial sequence
<220> FEATURE:
<223> OTHER INFORMATION: Synthetic antibody

<400> SEQUENCE: 124

Glu Ile Val Met Thr Gln Ser Pro Val Thr Leu Ser Val Ser Pro Gly
1               5                   10                  15

Glu Arg Ala Thr Leu Ser Cys Arg Ala Ser Gln Ser Val Arg Ser Asn
            20                  25                  30

Leu Ala Trp Tyr Gln His Lys Pro Gly Gln Ala Pro Arg Leu Leu Phe
        35                  40                  45

Tyr Gly Ala Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys His Gln Tyr Asn Asn Trp Pro Gln
            85                  90                  95

Thr Phe Gly Gln Gly Thr Lys Val Glu Ile Lys
            100                 105

<210> SEQ ID NO 125
<211> LENGTH: 126
<212> TYPE: PRT
<213> ORGANISM: Artificial sequence
<220> FEATURE:
<223> OTHER INFORMATION: Synthetic antibody

<400> SEQUENCE: 125

Gln Val Gln Leu Gln Glu Ser Gly Pro Gly Leu Val Lys Pro Ser Gly
```

-continued

```
1               5                    10                   15

Thr Leu Ser Leu Thr Cys Ala Val Ser Gly Asp Ser Ile Ser Gly Ser
            20                   25                   30

Phe Trp Trp Ser Trp Val Arg Gln Pro Pro Gly Lys Gly Leu Glu Trp
            35                   40                   45

Leu Gly Glu Ile Tyr His Ser Gly Asn Thr His Tyr Asn Pro Ser Leu
        50                   55                   60

Lys Ser Arg Val Thr Met Ser Arg Asp Lys Ser Lys Asn Gln Phe Ser
65                   70                   75                   80

Leu Lys Leu Thr Ser Val Thr Ala Ala Asp Thr Ala Val Tyr Tyr Cys
                85                   90                   95

Ser Arg Val Leu Gly Leu Tyr Gln Leu Leu Gly Ser Gly Tyr Tyr Ala
            100                  105                  110

Met Asp Val Trp Gly Gln Gly Thr Thr Val Thr Val Ser Ser
            115                  120                  125
```

<210> SEQ ID NO 126
<211> LENGTH: 120
<212> TYPE: PRT
<213> ORGANISM: Artificial sequence
<220> FEATURE:
<223> OTHER INFORMATION: Synthetic antibody

<400> SEQUENCE: 126

```
Gln Val Gln Leu Val Gln Ser Gly Ala Glu Val Lys Lys Pro Gly Ala
1               5                    10                   15

Ser Val Lys Val Ser Cys Lys Val Ser Gly Tyr Ser Leu Thr Glu Leu
            20                   25                   30

Ser Met His Trp Val Arg Gln Pro Pro Ala Lys Gly Leu Glu Trp Met
        35                   40                   45

Gly Arg Phe Asp Pro Gly Asp Arg Lys Pro Ile Tyr Ala Gln Arg Phe
    50                   55                   60

Gln Gly Arg Ile Thr Met Thr Glu Asp Thr Ser Thr Asp Thr Thr Phe
65                   70                   75                   80

Met Glu Leu Ser Ser Leu Arg Ser Glu Asp Thr Ala Leu Tyr Phe Cys
                85                   90                   95

Ala Thr Asp Pro Gly Ala Val Ala Gly Phe Leu Gly Phe Trp Gly Gln
            100                  105                  110

Gly Thr Leu Val Thr Val Ser Ser
        115                  120
```

<210> SEQ ID NO 127
<211> LENGTH: 112
<212> TYPE: PRT
<213> ORGANISM: Artificial sequence
<220> FEATURE:
<223> OTHER INFORMATION: Synthetic antibody

<400> SEQUENCE: 127

```
Asp Ile Val Met Thr Gln Ser Pro Asp Ser Leu Ala Val Ser Leu Gly
1               5                    10                   15

Glu Arg Ala Thr Ile Asn Cys Lys Ser Ser Gln Ser Val Leu Tyr Arg
            20                   25                   30

Ser Asn Asn Asn Asn Tyr Leu Ala Trp Tyr Gln Gln Lys Val Gly Gln
        35                   40                   45

Pro Pro Lys Leu Leu Ile Tyr Trp Ala Ser Ile Arg Glu Ser Gly Val
    50                   55                   60
```

Pro Asp Arg Phe Ser Gly Ser Gly Ser Gly Thr Asp Phe Thr Leu Thr
65              70              75              80

Ile Ser Ser Leu Gln Ala Glu Asp Val Ala Val Tyr Tyr Cys Gln Gln
                85              90              95

Tyr Tyr Gly Thr Val Thr Phe Gly Pro Gly Thr Lys Val Asp Ile Lys
            100             105             110

<210> SEQ ID NO 128
<211> LENGTH: 120
<212> TYPE: PRT
<213> ORGANISM: Artificial sequence
<220> FEATURE:
<223> OTHER INFORMATION: Synthetic antibody

<400> SEQUENCE: 128

Glu Val Gln Leu Val Glu Ser Gly Gly Gly Leu Val Gln Pro Gly Arg
1               5               10              15

Ser Leu Arg Leu Ser Cys Thr Ala Ser Gly Phe Thr Phe Gly Asp Tyr
                20              25              30

Val Met Thr Trp Val Arg Gln Ala Pro Gly Lys Gly Leu Glu Cys Val
            35              40              45

Gly Phe Ile Arg Thr Lys Pro Tyr Gly Gly Thr Thr Glu Tyr Ala Ala
        50              55              60

Ser Val Lys Gly Arg Phe Thr Ile Ser Arg Asp Asp Ser Lys Ser Ile
65              70              75              80

Ala Tyr Leu Gln Met Asn Ser Leu Lys Thr Asp Asp Thr Ala Val Tyr
                85              90              95

Tyr Cys Leu Ala Gly Thr Asp Trp Ser Tyr Phe Asp Tyr Trp Gly Gln
            100             105             110

Gly Thr Leu Val Thr Val Ser Ser
        115             120

<210> SEQ ID NO 129
<211> LENGTH: 110
<212> TYPE: PRT
<213> ORGANISM: Artificial sequence
<220> FEATURE:
<223> OTHER INFORMATION: Synthetic antibody

<400> SEQUENCE: 129

Gln Ser Ala Leu Thr Gln Pro Arg Ser Val Ser Gly Ser Pro Gly Gln
1               5               10              15

Ser Val Thr Ile Ser Cys Thr Gly Thr Ser Ser Asp Val Gly Gly Tyr
                20              25              30

Asn Tyr Val Ser Trp Tyr Gln Arg His Pro Gly Lys Ala Pro Gln Leu
            35              40              45

Met Ile Tyr Asp Val Asn Lys Arg Pro Ser Gly Val Pro Asp Arg Phe
        50              55              60

Ser Gly Ser Lys Ser Gly Asn Thr Ala Ser Leu Thr Ile Ser Gly Leu
65              70              75              80

Gln Ala Asp Asp Glu Ala Asp Tyr Tyr Cys Cys Ser Tyr Ala Gly Ser
                85              90              95

Tyr Thr Trp Val Phe Gly Gly Gly Thr Lys Leu Thr Val Leu
            100             105             110

<210> SEQ ID NO 130
<211> LENGTH: 125
<212> TYPE: PRT
<213> ORGANISM: Artificial sequence
<220> FEATURE:
<223> OTHER INFORMATION: Synthetic antibody

<400> SEQUENCE: 130

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Thr Trp Ile Arg Gln Pro Pro Gly Lys Gly Leu Glu Trp Ile
        35                  40                  45

Gly His Met Tyr Tyr Ser Gly Ser Thr Asn Asn Asn Pro Ser Leu Lys
    50                  55                  60

Gly Arg Val Thr Val Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Gly Ala Tyr Tyr Gly Ser Gly Ser Phe His Tyr Tyr Tyr Tyr Met
            100                 105                 110

Asp Val Trp Gly Lys Gly Thr Thr Val Thr Val Ser Ser
        115                 120                 125
```

<210> SEQ ID NO 131
<211> LENGTH: 107
<212> TYPE: PRT
<213> ORGANISM: Artificial sequence
<220> FEATURE:
<223> OTHER INFORMATION: Synthetic antibody

<400> SEQUENCE: 131

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Ser Lys Ala Ser Arg Leu Glu Gly Gly Val Pro Ser Arg Phe Ser Gly
    50                  55                  60

Ser Gly Ser Gly Thr Glu Phe Thr Phe Thr Ile Ser Ser Leu Gln Pro
65                  70                  75                  80

Asp Asp Cys Ala Thr Tyr Tyr Cys Gln Gln Tyr Asn Gly Tyr Ser Tyr
                85                  90                  95

Thr Phe Gly Gln Gly Thr Lys Leu Glu Ile Lys
            100                 105
```

<210> SEQ ID NO 132
<211> LENGTH: 126
<212> TYPE: PRT
<213> ORGANISM: Artificial sequence
<220> FEATURE:
<223> OTHER INFORMATION: Synthetic antibody

<400> SEQUENCE: 132

```
Glu Val Gln Leu Val Glu Ser Gly Gly Gly Leu Val Lys Pro Gly Gly
1               5                   10                  15

Ser Leu Arg Leu Ser Cys Ala Val Ser Gly Phe Thr Phe Ser Ser Tyr
            20                  25                  30

Ser Met Asn Trp Val Arg Gln Ala Pro Gly Lys Gly Leu Glu Trp Val
        35                  40                  45
```

-continued

```
Ser Ser Ile Ser Ser Ser Ser Thr Phe Ile Asp Tyr Ala Asp Ser Val
    50              55              60

Lys Gly Arg Phe Thr Ile Ser Arg Asp Asn Ala Lys Asn Leu Leu Tyr
65              70              75              80

Leu Gln Met Asn Ser Leu Arg Ala Glu Asp Thr Ala Val Phe Tyr Cys
            85              90              95

Ala Arg Gly Gly Asn Asp Tyr Ser Asp Tyr Glu Asn Tyr Tyr Tyr Tyr
            100             105             110

Met Asp Val Trp Gly Lys Gly Thr Thr Val Thr Val Ser Ser
        115             120             125

<210> SEQ ID NO 133
<211> LENGTH: 107
<212> TYPE: PRT
<213> ORGANISM: Artificial sequence
<220> FEATURE:
<223> OTHER INFORMATION: Synthetic antibody

<400> SEQUENCE: 133

Ser Tyr Glu Leu Thr Gln Pro Pro Ser Val Ser Val Ser Pro Gly Gln
1               5               10              15

Thr Ala Ser Ile Thr Cys Ser Gly Asp Glu Leu Gly Asp Lys Tyr Ala
            20              25              30

Cys Trp Tyr Gln Lys Lys Pro Gly Gln Ser Pro Val Leu Val Ile Tyr
        35              40              45

Gln Asp Asn Lys Arg Pro Ser Gly Ile Pro Glu Arg Phe Ser Gly Ser
    50              55              60

Asn Ser Gly Asn Thr Ala Thr Leu Thr Ile Ser Gly Thr Gln Ala Met
65              70              75              80

Asp Glu Ala Asp Tyr Tyr Cys Gln Ala Trp Asp Ser Ser Thr Ala Tyr
            85              90              95

Val Phe Gly Thr Gly Thr Lys Val Thr Val Leu
            100             105

<210> SEQ ID NO 134
<211> LENGTH: 121
<212> TYPE: PRT
<213> ORGANISM: Artificial sequence
<220> FEATURE:
<223> OTHER INFORMATION: Synthetic antibody

<400> SEQUENCE: 134

Glu Val Gln Leu Val Glu Ser Gly Gly Gly Leu Val Gln Pro Gly Arg
1               5               10              15

Ser Leu Arg Leu Ser Cys Ala Ala Ser Gly Phe Ile Phe Asp Asp Tyr
            20              25              30

Ala Ile His Trp Val Arg Gln Ala Pro Gly Lys Gly Leu Glu Trp Val
        35              40              45

Ser Gly Ile Thr Trp Asp Ser Gly Arg Ile Gly Tyr Ala Asp Ser Val
    50              55              60

Lys Gly Arg Phe Thr Ile Ser Arg Asp Asn Ala Lys Lys Ser Leu Tyr
65              70              75              80

Leu Gln Met Asn Ser Leu Arg Pro Glu Asp Thr Ala Leu Tyr Tyr Cys
            85              90              95

Ala Lys Asp Arg Gly Pro Phe Gly Trp Leu Thr Leu Asp Tyr Trp Gly
            100             105             110

Gln Gly Thr Leu Val Ile Val Ser Ser
        115             120
```

```
<210> SEQ ID NO 135
<211> LENGTH: 107
<212> TYPE: PRT
<213> ORGANISM: Artificial sequence
<220> FEATURE:
<223> OTHER INFORMATION: Synthetic antibody

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Lys Ala Pro Lys Leu Leu Ile
        35                  40                  45

Tyr Ala Gly Ser Thr Leu Gln Ser Gly Val Pro Ser Arg Phe Ser Gly
    50                  55                  60

Gly Gly Ser Gly Thr Gly Phe Thr Leu Thr Ile Ser Ser Leu Gln Pro
65                  70                  75                  80

Glu Asp Phe Ala Thr Tyr Tyr Cys Gln Gln Ser Ser Thr Thr Pro Trp
                85                  90                  95

Thr Phe Gly Gln Gly Thr Lys Val Glu Phe Lys
            100                 105

<210> SEQ ID NO 136
<211> LENGTH: 128
<212> TYPE: PRT
<213> ORGANISM: Artificial sequence
<220> FEATURE:
<223> OTHER INFORMATION: Synthetic antibody

<400> SEQUENCE: 136

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Leu Asn Trp Val Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Phe Leu Gln Met Asn Ser Leu Lys Thr Glu Asp Thr Ala Val Tyr
                85                  90                  95

Tyr Cys Thr Arg Ala Thr Pro Val Leu Leu Trp Phe Gly Ser Ser Gly
            100                 105                 110

Asn Phe Phe Asp Tyr Trp Gly Gln Gly Thr Leu Val Thr Val Ser Ser
        115                 120                 125

<210> SEQ ID NO 137
<211> LENGTH: 110
<212> TYPE: PRT
<213> ORGANISM: Artificial sequence
<220> FEATURE:
<223> OTHER INFORMATION: Synthetic antibody

<400> SEQUENCE: 137

Gln Ser Ala Leu Thr Gln Pro Ala Ser Val Ser Gly Ser Pro Gly Gln
1               5                   10                  15
```

-continued

```
Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Asn Ser Tyr Val Phe Gly Thr Gly Thr Lys Val Thr Val Leu
            100                 105                 110
```

<210> SEQ ID NO 138
<211> LENGTH: 119
<212> TYPE: PRT
<213> ORGANISM: Artificial sequence
<220> FEATURE:
<223> OTHER INFORMATION: Synthetic antibody

<400> SEQUENCE: 138

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Asn Asn
            20                  25                  30

Asn Tyr Tyr Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg His Gly Leu Asp His Lys Phe Asp Tyr Trp Gly Gln Gly
            100                 105                 110

Thr Leu Val Thr Val Ser Ser
        115
```

<210> SEQ ID NO 139
<211> LENGTH: 111
<212> TYPE: PRT
<213> ORGANISM: Artificial sequence
<220> FEATURE:
<223> OTHER INFORMATION: Synthetic antibody

<400> SEQUENCE: 139

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Thr Tyr
            20                  25                  30

Asn Leu Leu Ser Trp Tyr Gln Gln Tyr Pro Gly Lys Ala Pro Arg Leu
        35                  40                  45

Val Ile Tyr Glu Val Ser Lys Arg Pro Ser Gly Val Ser Ile Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Gly
                85                  90                  95
```

Ser Asn Ser Val Leu Phe Gly Gly Gly Thr Lys Leu Thr Val Leu
            100                 105                 110

<210> SEQ ID NO 140
<211> LENGTH: 115
<212> TYPE: PRT
<213> ORGANISM: Artificial sequence
<220> FEATURE:
<223> OTHER INFORMATION: Synthetic antibody

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Cys Val
        35                  40                  45

Ser Tyr Ile Ser Ser Ser Ser Gly Ala Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Asn Gly Ala Thr Tyr Trp Gly Gln Gly Thr Leu Val Thr
            100                 105                 110

Val Ser Ser
        115

<210> SEQ ID NO 141
<211> LENGTH: 107
<212> TYPE: PRT
<213> ORGANISM: Artificial sequence
<220> FEATURE:
<223> OTHER INFORMATION: Synthetic antibody

<400> SEQUENCE: 141

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Ile
                85                  90                  95

Thr Phe Gly Gln Gly Thr Arg Leu Glu Ile Lys
            100                 105

<210> SEQ ID NO 142
<211> LENGTH: 120
<212> TYPE: PRT
<213> ORGANISM: Artificial sequence
<220> FEATURE:
<223> OTHER INFORMATION: Synthetic antibody

<400> SEQUENCE: 142

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Val Ser Thr Ala Tyr
65                  70                  75                  80

Leu Gln Trp Ser Ser Leu Lys Ala Ser Asp Ser Ala Leu Tyr Tyr Cys
            85                  90                  95

Ala Arg Leu Pro His Pro Val Thr Gly Pro Leu Asp Tyr Trp Gly Gln
            100                 105                 110

Gly Thr Leu Val Thr Val Ser Ser
        115                 120

<210> SEQ ID NO 143
<211> LENGTH: 110
<212> TYPE: PRT
<213> ORGANISM: Artificial sequence
<220> FEATURE:
<223> OTHER INFORMATION: Synthetic antibody

<400> SEQUENCE: 143

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Ser Tyr
            20                  25                  30

Asn Leu Val Ser Trp Tyr Gln His His Pro Gly Lys Ala Pro Lys Leu
        35                  40                  45

Met Ile Tyr Glu Val Ser Lys Arg Pro Ser Gly Val Ser Asn Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Cys Ser Tyr Ala Gly Ser
            85                  90                  95

Met Thr Trp Val Phe Gly Gly Gly Thr Lys Leu Thr Val Leu
            100                 105                 110

<210> SEQ ID NO 144
<211> LENGTH: 124
<212> TYPE: PRT
<213> ORGANISM: Artificial sequence
<220> FEATURE:
<223> OTHER INFORMATION: Synthetic antibody

<400> SEQUENCE: 144

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Ser Tyr
            20                  25                  30

Thr Met Asn Trp Val Arg Gln Ala Pro Gly Lys Gly Leu Glu Trp Val
        35                  40                  45

Ser Ser Ile Ser Thr Ser Ser Ser Tyr Ile Tyr Tyr Ala Asp Ser Val
    50                  55                  60

Lys Gly Arg Phe Thr Ile Ser Arg Asp Ser Ala Lys Ser Ser Leu Tyr
65                  70                  75                  80

```
Leu Gln Met Asn Ser Leu Arg Ala Glu Asp Thr Ala Val Tyr Tyr Cys
                85                  90                  95

Ala Ser Leu Arg Lys Asp Ser Gly Ser Phe Tyr Asn Arg Ala Leu Asp
               100                 105                 110

Tyr Trp Gly Gln Gly Thr Leu Val Thr Val Ser Ser
       115                 120
```

<210> SEQ ID NO 145
<211> LENGTH: 110
<212> TYPE: PRT
<213> ORGANISM: Artificial sequence
<220> FEATURE:
<223> OTHER INFORMATION: Synthetic antibody

<400> SEQUENCE: 145

```
Gln Ser Ala Leu Thr Gln Pro Ala Ser Val Ser Gly Ser Pro Gly Gln
1                   5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Tyr Ser Tyr Thr Ser Asn
                85                  90                  95

Ser Thr Tyr Val Phe Gly Thr Gly Thr Lys Val Thr Val Leu
               100                 105                 110
```

<210> SEQ ID NO 146
<211> LENGTH: 129
<212> TYPE: PRT
<213> ORGANISM: Artificial sequence
<220> FEATURE:
<223> OTHER INFORMATION: Synthetic antibody

<400> SEQUENCE: 146

```
Glu Val Gln Leu Val Glu Ser Gly Gly Gly Leu Val Gln Pro Gly Lys
1                   5                  10                  15

Ser Leu Arg Leu Ser Cys Ala Ala Ser Gly Phe Thr Phe Asp Ala Tyr
               20                  25                  30

Ala Met His Trp Val Arg Gln Ala Pro Gly Lys Gly Leu Glu Trp Val
        35                  40                  45

Ser Gly Ile Ser Trp Asn Gly Gly Asn Ile Gly Tyr Ala Asp Ser Val
    50                  55                  60

Lys Gly Arg Phe Thr Phe Ser Arg Asp Asn Ala Lys Asn Ser Leu Tyr
65                  70                  75                  80

Leu Gln Met Asn Ser Leu Arg Ala Asp Asp Thr Ala Leu Tyr Phe Cys
                85                  90                  95

Ala Lys Glu Asp Cys Pro Ser Thr Ser Cys Tyr Phe Val Arg Trp Gly
               100                 105                 110

Leu Asn Trp Leu Asp Pro Trp Gly Gln Gly Thr Leu Val Thr Val Ser
        115                 120                 125

Ser
```

<210> SEQ ID NO 147

```
<211> LENGTH: 111
<212> TYPE: PRT
<213> ORGANISM: Artificial sequence
<220> FEATURE:
<223> OTHER INFORMATION: Synthetic antibody

<400> SEQUENCE: 147

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Phe Asp Ser Ser
                85                  90                  95

Leu Ser Arg Gly Val Phe Gly Gly Gly Thr Lys Leu Thr Val Leu
                100                 105                 110

<210> SEQ ID NO 148
<211> LENGTH: 124
<212> TYPE: PRT
<213> ORGANISM: Artificial sequence
<220> FEATURE:
<223> OTHER INFORMATION: Synthetic antibody

<400> SEQUENCE: 148

Glu Val Gln Leu Val Glu Ser Gly Gly Gly Leu Val Gln Pro Gly Arg
1               5                   10                  15

Ser Leu Arg Leu Ser Cys Ser Ala Ser Gly Phe Thr Phe Ala Asp Tyr
            20                  25                  30

Ala Val Ser Trp Val Arg Gln Ala Pro Gly Lys Gly Leu Glu Trp Val
        35                  40                  45

Gly Phe Ile Arg Ser Glu Thr Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met His Ser Leu Asn Thr Glu Asp Thr Ala Val Phe
                85                  90                  95

Tyr Cys Thr Arg Ala Arg His Asp Thr Arg Ser Trp Val Leu Ser Asp
                100                 105                 110

His Trp Gly Gln Gly Thr Leu Val Thr Val Ser Ser
        115                 120

<210> SEQ ID NO 149
<211> LENGTH: 105
<212> TYPE: PRT
<213> ORGANISM: Artificial sequence
<220> FEATURE:
<223> OTHER INFORMATION: Synthetic antibody

<400> SEQUENCE: 149

Asp Ala Gln Met Thr Gln Ser Pro Ser Thr Leu Ser Ala Ser Val Gly
1               5                   10                  15

Asp Arg Val Thr Ile Thr Cys Arg Ala Ser Gln Asn Ile Asn Ser Trp
            20                  25                  30
```

```
Leu Ala Trp Tyr Gln His Lys Pro Gly Lys Ala Pro Lys Leu Leu Ile
        35                  40                  45

Tyr Lys Ala Ser Ser Leu Glu Ser Glu Val Pro Ser Arg Phe Ser Gly
        50                  55                  60

Ser Gly Ser Gly Thr Asp Phe Thr Leu Thr Ile Ser Asn Leu Gln Pro
65                  70                  75                  80

Asp Asp Phe Ala Thr Tyr Tyr Cys Gln Gln Tyr Asn Ser Phe His Phe
                85                  90                  95

Gly Gln Gly Thr Lys Leu Glu Ile Lys
                100                 105
```

<210> SEQ ID NO 150
<211> LENGTH: 127
<212> TYPE: PRT
<213> ORGANISM: Artificial sequence
<220> FEATURE:
<223> OTHER INFORMATION: Synthetic antibody

<400> SEQUENCE: 150

```
Gln Leu Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile His Trp Val Arg Gln Ala Pro Gly Gln Gly Leu Glu Trp Met
        35                  40                  45

Gly Trp Ile Ser Gly Tyr Asn Gly Asn Thr Asn Tyr Ala Gln Lys Leu
        50                  55                  60

Gln Gly Arg Val Thr Met Thr Thr Asp Thr Ser Thr Arg Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Pro Ser Met Met Thr Phe Gly Gly Val Ile Val Ser Arg
                100                 105                 110

Tyr Phe Asp Tyr Trp Gly Gln Gly Thr Leu Val Thr Val Ser Ser
                115                 120                 125
```

<210> SEQ ID NO 151
<211> LENGTH: 109
<212> TYPE: PRT
<213> ORGANISM: Artificial sequence
<220> FEATURE:
<223> OTHER INFORMATION: Synthetic antibody

<400> SEQUENCE: 151

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
        35                  40                  45

Leu Ile Tyr Asn Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Val Thr Val Phe Gly Gly Gly Thr Lys Leu Thr Val Leu
                100                 105
```

-continued

<210> SEQ ID NO 152
<211> LENGTH: 124
<212> TYPE: PRT
<213> ORGANISM: Artificial sequence
<220> FEATURE:
<223> OTHER INFORMATION: Synthetic antibody

<400> SEQUENCE: 152

Gln Leu Gln Leu Gln Glu Ser Gly Pro Gly Leu Val Lys Pro Ser Glu
1               5                   10                  15

Thr Leu Ser Leu Thr Cys Thr Leu Ser Gly Gly Phe Ile Arg Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Thr Glu Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Asn Ser Val Thr Ala Ala Asp Thr Ala Ile Tyr Tyr
                85                  90                  95

Cys Ala Arg His Asp Tyr Trp Thr Gly Ala Arg Tyr Ser Trp Phe Asp
            100                 105                 110

Pro Trp Gly Gln Gly Thr Leu Val Thr Val Ser Ser
        115                 120

<210> SEQ ID NO 153
<211> LENGTH: 112
<212> TYPE: PRT
<213> ORGANISM: Artificial sequence
<220> FEATURE:
<223> OTHER INFORMATION: Synthetic antibody

<400> SEQUENCE: 153

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Thr Ser
                85                  90                  95

Leu Ser Gly Ser Gly Val Phe Gly Gly Gly Thr Lys Leu Thr Val Leu
            100                 105                 110

<210> SEQ ID NO 154
<211> LENGTH: 127
<212> TYPE: PRT
<213> ORGANISM: Artificial sequence
<220> FEATURE:
<223> OTHER INFORMATION: Synthetic antibody

<400> SEQUENCE: 154

Gln Val Gln Leu Val Gln Ser Gly Ala Glu Val Lys Lys Pro Gly Ala
1               5                   10                  15

```
Ser Val Lys Leu Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Val
            35                  40                  45

Gly Ile Met Asn Pro Ser Gly Gly Ser Thr Met Tyr Ala Gln Lys Tyr
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Thr Val Val Gln Arg Leu Val Gly Arg Asp Tyr Tyr His
            100                 105                 110

Gly Met Asp Val Trp Gly Gln Gly Thr Thr Val Thr Val Ser Ser
            115                 120                 125
```

```
<210> SEQ ID NO 155
<211> LENGTH: 112
<212> TYPE: PRT
<213> ORGANISM: Artificial sequence
<220> FEATURE:
<223> OTHER INFORMATION: Synthetic antibody

<400> SEQUENCE: 155

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Phe Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Arg
            100                 105                 110
```

```
<210> SEQ ID NO 156
<211> LENGTH: 121
<212> TYPE: PRT
<213> ORGANISM: Artificial sequence
<220> FEATURE:
<223> OTHER INFORMATION: Synthetic antibody

<400> SEQUENCE: 156

Glu Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Ser Leu Glu Trp Val
            35                  40                  45

Ser Leu Ile Ser Trp Asp Gly Gly Arg Thr Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Pro Glu Asp Thr Ala Leu Tyr Tyr Cys
                85                  90                  95
```

-continued

Ala Thr Gly His Pro Pro Leu Val Leu Trp Ser Leu Gly Tyr Trp Gly
            100                 105                 110

Gln Gly Thr Leu Val Thr Val Ser Ser
        115                 120

<210> SEQ ID NO 157
<211> LENGTH: 107
<212> TYPE: PRT
<213> ORGANISM: Artificial sequence
<220> FEATURE:
<223> OTHER INFORMATION: Synthetic antibody

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Asn Ile Asn Ser Tyr
            20                  25                  30

Leu Asn Trp Tyr Gln Gln Lys Pro Gly Lys Ala Pro Lys Phe Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Val Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Ile
                85                  90                  95

Thr Phe Gly Gln Gly Thr Arg Leu Glu Ile Lys
            100                 105

<210> SEQ ID NO 158
<211> LENGTH: 129
<212> TYPE: PRT
<213> ORGANISM: Artificial sequence
<220> FEATURE:
<223> OTHER INFORMATION: Synthetic antibody

<400> SEQUENCE: 158

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Phe
            20                  25                  30

Ala Phe Ser Trp Val Arg Gln Ala Pro Gly Arg Gly Leu Glu Trp Met
        35                  40                  45

Gly Gly Ile Ile Pro Ile Phe Asp Arg Pro Ala Tyr Ala Gln Arg Phe
    50                  55                  60

Gln Gly Arg Val Thr Ile Thr Ala Asp Glu Ser Thr Ser Thr Ala Tyr
65                  70                  75                  80

Val Glu Leu Ser Ser Leu Arg Ser Glu Asp Thr Ala Val Tyr Tyr Cys
                85                  90                  95

Ala Arg Asp Arg Arg Tyr Asn Tyr Glu Ser Ser Ala Ser Gln Asn Asn
            100                 105                 110

Arg Trp Tyr Phe Asp Leu Trp Gly Arg Gly Thr Leu Val Thr Val Ser
        115                 120                 125

Ser

<210> SEQ ID NO 159
<211> LENGTH: 113
<212> TYPE: PRT
<213> ORGANISM: Artificial sequence

```
<220> FEATURE:
<223> OTHER INFORMATION: Synthetic antibody

<400> SEQUENCE: 159

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Thr
                20                  25                  30

Ser Asn Asn Lys Asn Tyr Leu Ala Trp Tyr Gln Gln Lys Pro Gly Gln
        35                  40                  45

Pro Pro Lys Leu Leu Val Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Leu Thr Phe Gly Gly Gly Thr Lys Val Glu Ile
                100                 105                 110

Lys

<210> SEQ ID NO 160
<211> LENGTH: 124
<212> TYPE: PRT
<213> ORGANISM: Artificial sequence
<220> FEATURE:
<223> OTHER INFORMATION: Synthetic antibody

<400> SEQUENCE: 160

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Tyr
                20                  25                  30

Gly Ile His Trp Val Arg Gln Ala Pro Gly Lys Gly Leu Glu Trp Val
        35                  40                  45

Ala Phe Ile Arg Tyr Asp Gly Ser Asn Gln Asn Tyr Gly Asp Ser Val
    50                  55                  60

Lys Gly Arg Phe Thr Ile Ser Arg Asp Asn Ser Arg Asn Thr Leu Phe
65                  70                  75                  80

Leu Gln Met Ser Ser Leu Arg Ala Glu Asp Thr Ala Val Tyr Tyr Cys
                85                  90                  95

Ala Lys Asp Leu Ala Val Leu Leu Met Tyr Gly Phe Gly Gly Phe Asp
                100                 105                 110

Ala Trp Gly Gln Gly Thr Leu Val Thr Val Ser Ser
        115                 120

<210> SEQ ID NO 161
<211> LENGTH: 107
<212> TYPE: PRT
<213> ORGANISM: Artificial sequence
<220> FEATURE:
<223> OTHER INFORMATION: Synthetic antibody

<400> SEQUENCE: 161

Asp Ile Gln Val Thr Gln Ser Pro Ser Ser Leu Ser Ala Ser Val Gly
1               5                   10                  15

Asp Arg Val Ser Ile Thr Cys Arg Ala Ser Gln Ser Ile Ser His Tyr
                20                  25                  30

Leu Asn Trp Tyr Gln Gln Lys Pro Gly Lys Ala Pro Lys Leu Leu Ile
```

-continued

```
                35                40                45

Tyr Ala Ala Ser Thr Leu Gln Ser Gly Val Pro Ser Arg Phe Ser Gly
        50                55                60

Ser Gly Ser Gly Thr Gly Phe Thr Leu Thr Ile Ser Gly Leu Gln Pro
65                70                75                80

Glu Asp Phe Ala Thr Tyr Tyr Cys Gln Gln Ser Tyr Ser Thr Pro Val
                85                90                95

Ser Phe Gly Gln Gly Thr Lys Val Glu Ile Lys
            100                105

<210> SEQ ID NO 162
<211> LENGTH: 127
<212> TYPE: PRT
<213> ORGANISM: Artificial sequence
<220> FEATURE:
<223> OTHER INFORMATION: Synthetic antibody

<400> SEQUENCE: 162

Gln Val Gln Leu Val Gln Ser Gly Ala Glu Val Lys Lys Pro Gly Ser
1                5                10                15

Ser Val Lys Val Ser Cys Lys Ala Ser Gly Gly Thr Phe Arg Ser Tyr
            20                25                30

Ala Ile Asn Trp Val Arg Gln Ala Pro Gly Gln Gly Leu Glu Trp Met
        35                40                45

Gly Gly Ile Ile Pro Ile Phe Gly Thr Ala Asn Tyr Ala Gln Asn Phe
        50                55                60

Gln Gly Arg Val Thr Ile Ile Ala Asp Glu Ser Thr Ser Thr Ala Tyr
65                70                75                80

Met Glu Leu Ser Ser Leu Arg Ser Glu Asp Thr Ala Val Tyr Tyr Cys
                85                90                95

Ala Arg Tyr Phe Phe Thr Thr Pro His Trp Thr Leu Pro Ile Asp Tyr
            100                105                110

Gly Met Asp Val Trp Gly Gln Gly Thr Thr Val Thr Val Ser Ser
            115                120                125

<210> SEQ ID NO 163
<211> LENGTH: 112
<212> TYPE: PRT
<213> ORGANISM: Artificial sequence
<220> FEATURE:
<223> OTHER INFORMATION: Synthetic antibody

<400> SEQUENCE: 163

Asp Ile Val Met Thr Gln Ser Pro Leu Ser Leu Pro Val Thr Pro Gly
1                5                10                15

Glu Pro Ala Ser Ile Ser Cys Arg Ser Ser Gln Ser Leu Leu His Ser
            20                25                30

Asn Gly Tyr Asn Ser Leu Asp Trp Tyr Leu Gln Lys Pro Gly Gln Ser
        35                40                45

Pro Gln Leu Leu Ile Tyr Leu Gly Ser Tyr Arg Ala Ser Gly Val Pro
        50                55                60

Asp Arg Phe Ser Gly Ser Gly Ser Gly Thr Asp Phe Thr Leu Lys Ile
65                70                75                80

Ser Arg Val Glu Ala Glu Asp Val Gly Val Tyr Tyr Cys Met Gln Ala
                85                90                95

Leu Gln Thr Pro Tyr Thr Phe Gly Gln Gly Thr Lys Leu Glu Ile Lys
            100                105                110
```

<210> SEQ ID NO 164
<211> LENGTH: 119
<212> TYPE: PRT
<213> ORGANISM: Artificial sequence
<220> FEATURE:
<223> OTHER INFORMATION: Synthetic antibody

<400> SEQUENCE: 164

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Gln Ile Tyr Tyr Ser Gly Thr Thr Asn Tyr Asn Pro Ser Leu
    50                  55                  60

Lys Ser Arg Val Ser Ile Ser Val Asp Lys Ser Lys Asn Gln Phe Ala
65                  70                  75                  80

Leu Lys Leu Ser Ser Val Thr Ala Ala Asp Thr Ala Val Tyr Tyr Cys
            85                  90                  95

Ala Gly Gly Thr Tyr Phe Arg Arg Tyr Phe Asp Tyr Trp Gly Gln Gly
            100                 105                 110

Ala Leu Val Thr Val Ser Pro
        115

<210> SEQ ID NO 165
<211> LENGTH: 108
<212> TYPE: PRT
<213> ORGANISM: Artificial sequence
<220> FEATURE:
<223> OTHER INFORMATION: Synthetic antibody

<400> SEQUENCE: 165

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Asp Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
            85                  90                  95

Leu Thr Phe Gly Gly Gly Thr Lys Val Glu Ile Lys
        100                 105

<210> SEQ ID NO 166
<211> LENGTH: 125
<212> TYPE: PRT
<213> ORGANISM: Artificial sequence
<220> FEATURE:
<223> OTHER INFORMATION: Synthetic antibody

<400> SEQUENCE: 166

Gln Leu Gln Leu Gln Glu Ser Gly Pro Gly Leu Val Lys Pro Ser Glu
1               5                   10                  15

Thr Leu Ser Leu Ile Cys Thr Val Ser Gly Gly Ser Ile Ser Ser Ser

```
                20                  25                  30

Ser Tyr Tyr Trp Gly Trp Ile Arg Gln Pro Pro Gly Lys Gly Leu Glu
            35                  40                  45

Trp Ile Gly Ser Val Phe Tyr Ser Gly Asn Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Asn Leu Ser Ser Val Thr Ala Ala Asp Thr Thr Val Tyr Tyr
                85                  90                  95

Cys Ala Arg His Gln Tyr Ser Ser Ser Trp Asn Arg Ile Asp Ala Phe
                100                 105                 110

Asp Ile Trp Gly Gln Gly Thr Val Val Thr Val Ser Ala
                115                 120                 125

<210> SEQ ID NO 167
<211> LENGTH: 120
<212> TYPE: PRT
<213> ORGANISM: Artificial sequence
<220> FEATURE:
<223> OTHER INFORMATION: Synthetic antibody

<400> SEQUENCE: 167

Glu Val Gln Leu Val Glu Ser Gly Gly Gly Leu Ile Gln Pro Gly Arg
1               5                   10                  15

Ser Leu Arg Leu Ser Cys Thr Thr Ser Gly Phe Thr Phe Gly Asn Tyr
            20                  25                  30

Val Met Ser Trp Val Arg Gln Ala Pro Gly Lys Gly Leu Glu Trp Val
            35                  40                  45

Gly Phe Ile Arg Ser Lys Ala Tyr Gly Gly Thr Thr Glu Tyr Ala Ala
        50                  55                  60

Ser Val Glu Gly Arg Phe Ser Ile Ser Arg Asp Asp Ser Lys Ser Ile
65                  70                  75                  80

Ala Tyr Leu His Met Asn Ser Leu Lys Thr Glu Asp Thr Ala Val Tyr
                85                  90                  95

Tyr Cys Leu Ala Ala Thr Val Trp Thr Tyr Phe Asp Phe Trp Gly Gln
            100                 105                 110

Gly Thr Leu Val Thr Val Ser Ser
        115                 120

<210> SEQ ID NO 168
<211> LENGTH: 110
<212> TYPE: PRT
<213> ORGANISM: Artificial sequence
<220> FEATURE:
<223> OTHER INFORMATION: Synthetic antibody

<400> SEQUENCE: 168

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ala Tyr
            20                  25                  30

Asn Tyr Val Ser Trp Tyr Gln His His Pro Gly Lys Ala Pro Lys Leu
            35                  40                  45

Met Ile Phe Asp Val Asn Ser Arg Pro Ser Gly Val Pro Asp Arg Phe
        50                  55                  60

Ser Gly Ser Lys Ser Gly Asn Thr Ala Ser Leu Thr Ile Ser Gly Leu
65                  70                  75                  80
```

-continued

```
Gln Ala Asp Asp Glu Ala Asp Tyr Tyr Cys Cys Ser Tyr Ala Gly Ser
                85                  90                  95

Phe Thr Trp Val Phe Gly Gly Gly Thr Lys Leu Thr Val Leu
            100                 105                 110

<210> SEQ ID NO 169
<211> LENGTH: 118
<212> TYPE: PRT
<213> ORGANISM: Artificial sequence
<220> FEATURE:
<223> OTHER INFORMATION: Synthetic antibody

<400> SEQUENCE: 169

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Tyr Asp Ser Ser Gly Ser Val Trp Gly Gln Gly Thr
            100                 105                 110

Thr Val Thr Val Ser Ser
        115

<210> SEQ ID NO 170
<211> LENGTH: 107
<212> TYPE: PRT
<213> ORGANISM: Artificial sequence
<220> FEATURE:
<223> OTHER INFORMATION: Synthetic antibody

<400> SEQUENCE: 170

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Asn Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Thr Pro Arg
                85                  90                  95

Thr Phe Gly Gln Gly Thr Lys Val Glu Ile Lys
            100                 105

<210> SEQ ID NO 171
<211> LENGTH: 125
<212> TYPE: PRT
<213> ORGANISM: Artificial sequence
<220> FEATURE:
<223> OTHER INFORMATION: Synthetic antibody
```

<400> SEQUENCE: 171

Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Ile Ser Tyr
                20                  25                  30

Thr Met His Trp Val Arg Gln Ala Pro Gly Gln Arg Leu Glu Trp Met
            35                  40                  45

Gly Trp Ile Asn Gly Gly Asn Gly Asn Thr Lys Tyr Ser Gln Arg Phe
        50                  55                  60

Gln Gly Arg Val Thr Ile Thr Arg Asp Thr Ser Ala Thr Thr Val Tyr
65                  70                  75                  80

Met Glu Leu Ser Ser Leu Thr Ser Glu Asp Thr Ala Leu Tyr Tyr Cys
                85                  90                  95

Ala Arg Val Lys Ser Asp Thr Leu Asp Phe Asn Trp Asn Pro Arg Phe
                100                 105                 110

Asp Tyr Trp Gly Gln Gly Thr Leu Val Thr Val Ser Ser
            115                 120                 125

<210> SEQ ID NO 172
<211> LENGTH: 108
<212> TYPE: PRT
<213> ORGANISM: Artificial sequence
<220> FEATURE:
<223> OTHER INFORMATION: Synthetic antibody

<400> SEQUENCE: 172

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Val Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Cys Gly Ser Ser Pro
                85                  90                  95

Ile Thr Phe Gly Gln Gly Thr Arg Leu Glu Ile Lys
                100                 105

<210> SEQ ID NO 173
<211> LENGTH: 116
<212> TYPE: PRT
<213> ORGANISM: Artificial sequence
<220> FEATURE:
<223> OTHER INFORMATION: Synthetic antibody

<400> SEQUENCE: 173

Gln Val Gln Leu Gln Glu Ser Gly Pro Gly Leu Val Lys Pro Ser Glu
1               5                   10                  15

Thr Leu Ser Leu Thr Cys Asp Val Ser Gly Tyr Ser Ile Ser Ser Gly
                20                  25                  30

Tyr Tyr Trp Gly Trp Ile Arg Gln Pro Pro Gly Lys Gly Leu Glu Trp
            35                  40                  45

Ile Gly Ser Ile Tyr His Ser Gly Ile Ile Tyr Tyr Asn Pro Ser Leu
        50                  55                  60

-continued

```
Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Leu Leu Pro Ser Asn Ile Tyr Trp Gly Gln Gly Ile Leu Val
                100                 105                 110

Thr Val Ser Ser
            115

<210> SEQ ID NO 174
<211> LENGTH: 110
<212> TYPE: PRT
<213> ORGANISM: Artificial sequence
<220> FEATURE:
<223> OTHER INFORMATION: Synthetic antibody

<400> SEQUENCE: 174

Gln Ser Ala Leu Thr Gln Pro Arg Ser Val Ser Gly Ser Pro Gly Gln
1               5                   10                  15

Ser Val Thr Ile Ser Cys Thr Gly Thr Ser Ser Asp Val Gly Ser Tyr
                20                  25                  30

Asn Tyr Val Ser Trp Tyr Lys Gln His Pro Gly Lys Ala Pro Lys Leu
            35                  40                  45

Met Ile Phe Asp Val Ser Arg Arg Pro Ser Gly Val Pro Asp Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Phe Cys Cys Leu Tyr Ala Gly Ser
                85                  90                  95

Tyr Thr Phe Lys Phe Gly Gly Gly Thr Lys Val Thr Val Leu
                100                 105                 110

<210> SEQ ID NO 175
<211> LENGTH: 123
<212> TYPE: PRT
<213> ORGANISM: Artificial sequence
<220> FEATURE:
<223> OTHER INFORMATION: Synthetic antibody

<400> SEQUENCE: 175

Glu Val Gln Leu Val Glu Ser Gly Gly Gly Leu Val Arg Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Gly Ile Ser Trp His Ser Gly Ser Ile Gly Tyr Ala Asp Ser Val
            50                  55                  60

Gln Gly Arg Phe Thr Thr Ser Arg Asp Asn Ala Lys Asn Ser Leu Tyr
65                  70                  75                  80

Leu Gln Met Asp Ser Leu Arg Pro Glu Asp Thr Ala Phe Tyr Tyr Cys
                85                  90                  95

Ala Lys Ser Pro Leu Lys Ile Trp Gln His Leu Thr Pro Tyr Asp Tyr
                100                 105                 110

Trp Gly Gln Gly Thr Leu Val Thr Val Ser Ser
            115                 120

<210> SEQ ID NO 176
```

-continued

```
<211> LENGTH: 107
<212> TYPE: PRT
<213> ORGANISM: Artificial sequence
<220> FEATURE:
<223> OTHER INFORMATION: Synthetic antibody

<400> SEQUENCE: 176

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Arg Gly Gln Ala Pro Arg Leu Leu Met
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Phe Phe Gly Gly Gly Thr Lys Val Glu Ile Lys
            100                 105

<210> SEQ ID NO 177
<211> LENGTH: 130
<212> TYPE: PRT
<213> ORGANISM: Artificial sequence
<220> FEATURE:
<223> OTHER INFORMATION: Synthetic antibody

<400> SEQUENCE: 177

Gln Val Gln Leu Gln Glu Ser Gly Pro Gly Leu Val Lys Pro Ser Gln
1               5                   10                  15

Thr Leu Ser Leu Thr Cys Thr Val Ser Asp Gly Ser Ile Ser Ser Gly
            20                  25                  30

Asp Tyr Tyr Trp Ser Trp Val Arg Gln Pro Pro Gly Lys Gly Leu Glu
        35                  40                  45

Trp Ile Gly Tyr Ile Tyr Tyr Ser Gly Ser Thr Tyr Tyr Ser Pro Ser
    50                  55                  60

Leu Lys Ser Arg Val Thr Ile Ser Val Asn Met Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Thr Ala Pro Ala Val Gly Ser Tyr Tyr Met Arg Trp Thr Gly
            100                 105                 110

Tyr His Tyr Tyr Met Asp Val Trp Gly Lys Gly Thr Thr Val Thr Val
        115                 120                 125

Ser Ser
    130

<210> SEQ ID NO 178
<211> LENGTH: 110
<212> TYPE: PRT
<213> ORGANISM: Artificial sequence
<220> FEATURE:
<223> OTHER INFORMATION: Synthetic antibody

<400> SEQUENCE: 178

Gln Ser Val Leu Thr Gln Pro Pro Ser Val Ser Ala Ala Pro Gly Gln
1               5                   10                  15
```

```
Lys Val Thr Ile Ser Cys Ser Gly Ser Ser Ser Asn Ile Glu Tyr Asn
            20                  25                  30

Tyr Val Ser Trp Tyr Gln Gln Leu Pro Arg Thr Ala Pro Lys Leu Leu
            35                  40                  45

Ile Tyr Asp Asn Asn Lys Arg Pro Ser Gly Ile Pro Asp Arg Phe Ser
            50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                    85                  90                  95

Asn Ala Trp Val Phe Gly Gly Gly Thr Lys Leu Thr Val Leu
            100                 105                 110

<210> SEQ ID NO 179
<211> LENGTH: 130
<212> TYPE: PRT
<213> ORGANISM: Artificial sequence
<220> FEATURE:
<223> OTHER INFORMATION: Synthetic antibody

<400> SEQUENCE: 179

Gln Val Gln Leu Gln Glu Ser Gly Pro Gly Leu Val Lys Pro Ser Gln
1               5                   10                  15

Thr Leu Ser Leu Thr Cys Thr Val Ser Asp Gly Ser Ile Ser Ser Gly
            20                  25                  30

Asp Tyr Tyr Trp Ser Trp Val Arg Gln Pro Pro Gly Lys Gly Leu Glu
            35                  40                  45

Trp Ile Gly Tyr Ile Tyr Tyr Ser Gly Ser Thr Tyr Tyr Ser Pro Ser
            50                  55                  60

Leu Lys Ser Arg Val Thr Ile Ser Val Asn Met Ser Lys Asn Gln Phe
65                  70                  75                  80

Ser Leu Lys Leu Ser Ser Val Thr Ala Ala Asp Thr Ala Val Tyr Tyr
                    85                  90                  95

Cys Ala Thr Ala Pro Ala Val Gly Ser Tyr Tyr Met Arg Trp Thr Gly
            100                 105                 110

Tyr His Tyr Tyr Met Asp Val Trp Gly Lys Gly Thr Thr Val Thr Val
            115                 120                 125

Ser Ser
    130

<210> SEQ ID NO 180
<211> LENGTH: 110
<212> TYPE: PRT
<213> ORGANISM: Artificial sequence
<220> FEATURE:
<223> OTHER INFORMATION: Synthetic antibody

<400> SEQUENCE: 180

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Glu Tyr Asn
            20                  25                  30

Tyr Val Ser Trp Tyr Gln Gln Leu Pro Arg Thr Ala Pro Lys Leu Leu
            35                  40                  45

Ile Tyr Asp Asn Asn Lys Arg Pro Ser Gly Ile Pro Asp Arg Phe Ser
            50                  55                  60

Gly Ser Lys Ser Gly Thr Ser Ala Thr Leu Gly Ile Thr Gly Leu Gln
65                  70                  75                  80
```

-continued

Thr Gly Asp Glu Ala Asp Tyr Tyr Cys Gly Thr Trp Asp Ser Ser Leu
                85                  90                  95

Asn Ala Trp Val Phe Gly Gly Gly Thr Lys Leu Thr Val Leu
            100                 105                 110

<210> SEQ ID NO 181
<211> LENGTH: 126
<212> TYPE: PRT
<213> ORGANISM: Artificial sequence
<220> FEATURE:
<223> OTHER INFORMATION: Synthetic antibody

<400> SEQUENCE: 181

Gln Met Gln Leu Val Gln Ser Gly Pro Glu Val Lys Lys Pro Gly Thr
1               5                   10                  15

Ser Val Lys Val Pro Cys Lys Ala Ser Gly Leu Thr Phe Ser Arg Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Asp Arg Val Thr Ile Thr Arg Asp Met Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Ala Gly Pro Gly Val Trp Ala Arg Thr Glu Arg Pro Asn Asp Ala
            100                 105                 110

Phe Asn Leu Trp Gly Gln Gly Thr Met Val Thr Val Ser Ser
            115                 120                 125

<210> SEQ ID NO 182
<211> LENGTH: 110
<212> TYPE: PRT
<213> ORGANISM: Artificial sequence
<220> FEATURE:
<223> OTHER INFORMATION: Synthetic antibody

<400> SEQUENCE: 182

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Ala Ala Pro Lys Val Leu
        35                  40                  45

Ile Tyr Asp Asn Asn Glu Arg Pro Ser Gly Ile Pro Asp Arg Phe Ser
    50                  55                  60

Gly Ser Lys Ser Gly Arg Ser Ala Thr Leu Gly Ile Thr Gly Leu Gln
65                  70                  75                  80

Thr Gly Asp Glu Ala Asp Tyr Phe Cys Gly Thr Trp Asp Ser Ser Leu
                85                  90                  95

Ser Ala Trp Ile Phe Gly Gly Gly Thr Lys Leu Thr Val Leu
            100                 105                 110

<210> SEQ ID NO 183
<211> LENGTH: 127
<212> TYPE: PRT
<213> ORGANISM: Artificial sequence
<220> FEATURE:
<223> OTHER INFORMATION: Synthetic antibody

<400> SEQUENCE: 183

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ile Trp Val Arg Gln Ala Pro Gly Arg Gly Leu Glu Trp Val
        35                  40                  45

Ser Thr Ile Thr Gly Ser Gly Gly Ser Thr Arg Phe Ala Asp Ser Leu
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Arg Tyr Cys Ser Gly Thr Thr Ser His Leu Tyr Cys Tyr Tyr
            100                 105                 110

Ala Met Asp Val Trp Gly Gln Gly Thr Ala Val Thr Val Ser Ser
            115                 120                 125
```

<210> SEQ ID NO 184
<211> LENGTH: 110
<212> TYPE: PRT
<213> ORGANISM: Artificial sequence
<220> FEATURE:
<223> OTHER INFORMATION: Synthetic antibody

<400> SEQUENCE: 184

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Lys Leu Phe Gly Thr Gly Thr Lys Val Thr Val Leu
            100                 105                 110
```

<210> SEQ ID NO 185
<211> LENGTH: 122
<212> TYPE: PRT
<213> ORGANISM: Artificial sequence
<220> FEATURE:
<223> OTHER INFORMATION: Synthetic antibody

<400> SEQUENCE: 185

```
Gln Val Gln Leu Gln Glu Ser Gly Pro Gly Leu Val Lys Pro Ser Glu
1               5                   10                  15

Thr Leu Ser Leu Thr Cys Ala Val Ser Asp Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Ala Ser Ile Tyr His Gly Gly Ser Thr Asp Tyr Asn Pro Ser Leu
    50                  55                  60
```

Lys Ser Arg Val Thr Ile Ser Leu Asp Thr Ser Lys Ile Gln Phe Ser
65                  70                  75                  80

Leu Lys Leu Ser Ser Val Thr Ala Ala Asp Thr Ala Val Tyr Tyr Cys
                85                  90                  95

Ala Ser Arg His Asp Arg Ser Gly Tyr Asp Glu Tyr Phe Glu Tyr Trp
            100                 105                 110

Gly Gln Gly Thr Leu Val Thr Val Ser Ser
        115                 120

<210> SEQ ID NO 186
<211> LENGTH: 107
<212> TYPE: PRT
<213> ORGANISM: Artificial sequence
<220> FEATURE:
<223> OTHER INFORMATION: Synthetic antibody

<400> SEQUENCE: 186

Asp Ile Gln Met Thr Gln Ser Pro Ser Ser Leu Ser Ala Ser Val Gly
1                   5                   10                  15

Asp Arg Val Thr Ile Ile Cys Arg Ala Ser His Gly Ile Ser Asn Ser
                20                  25                  30

Leu Ala Trp Tyr Gln Gln Lys Pro Gly Lys Ala Pro Lys Leu Leu Leu
            35                  40                  45

Tyr Ala Ala Ser Arg Leu Lys Ser Gly Val Pro Ser Arg Phe Ser Gly
        50                  55                  60

Ser Gly Ser Gly Thr Asp Tyr Thr Leu Thr Ile Thr Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Pro Gly Thr Lys Val Asp Leu Lys
            100                 105

<210> SEQ ID NO 187
<211> LENGTH: 120
<212> TYPE: PRT
<213> ORGANISM: Artificial sequence
<220> FEATURE:
<223> OTHER INFORMATION: Synthetic antibody

<400> SEQUENCE: 187

Glu Glu Gln Leu Val Glu Ser Gly Gly Gly Leu Ile His Pro Gly Gly
1                   5                   10                  15

Ser Leu Arg Leu Ser Cys Ala Ala Ser Gly Phe Thr Val Ser Ser Thr
            20                  25                  30

Tyr Met Asn Trp Val Arg Gln Ser Pro Gly Lys Gly Leu Glu Trp Val
        35                  40                  45

Ser Leu Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ile Pro Leu Ser Phe Gly Pro Met Tyr Phe Asp Tyr Trp Gly Gln
            100                 105                 110

Gly Thr Arg Val Thr Val Ser Ser
        115                 120

<210> SEQ ID NO 188
<211> LENGTH: 120
<212> TYPE: PRT
<213> ORGANISM: Artificial sequence
<220> FEATURE:
<223> OTHER INFORMATION: Synthetic antibody

<400> SEQUENCE: 188

Glu Glu Gln Leu Val Glu Ser Gly Gly Gly Leu Ile His Pro Gly Gly
1               5                   10                  15

Ser Leu Arg Leu Ser Cys Ala Ala Ser Gly Phe Thr Val Ser Ser Thr
            20                  25                  30

Tyr Met Asn Trp Val Arg Gln Ser Pro Gly Lys Gly Leu Glu Trp Val
        35                  40                  45

Ser Leu Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Ile Pro Leu Ser Phe Gly Pro Met Tyr Phe Asp Tyr Trp Gly Gln
            100                 105                 110

Gly Thr Arg Val Thr Val Ser Ser
            115                 120

<210> SEQ ID NO 189
<211> LENGTH: 126
<212> TYPE: PRT
<213> ORGANISM: Artificial sequence
<220> FEATURE:
<223> OTHER INFORMATION: Synthetic antibody

<400> SEQUENCE: 189

Gln Val Gln Leu Val Glu Ser Gly Gly Gly Ser Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Thr Trp Ile Arg Gln Ala Pro Gly Lys Gly Leu Glu Trp Val
        35                  40                  45

Ser Tyr Ile Ser Ser Ser Ala Thr Thr Ile Tyr Tyr Ala Asp Ser Val
    50                  55                  60

Lys Gly Arg Phe Thr Ile Ser Arg Asp Asn Ala Lys Asn Leu Leu Tyr
65                  70                  75                  80

Leu Gln Met Asn Ser Leu Arg Ala Glu Asp Thr Ala Val Tyr Tyr Cys
                85                  90                  95

Ala Arg Asp His Arg Tyr Cys Thr Ser Thr Asn Cys Phe Ala His Trp
            100                 105                 110

Phe Asp Pro Trp Gly Gln Gly Ile Leu Val Thr Val Ser Pro
            115                 120                 125

<210> SEQ ID NO 190
<211> LENGTH: 110
<212> TYPE: PRT
<213> ORGANISM: Artificial sequence
<220> FEATURE:
<223> OTHER INFORMATION: Synthetic antibody

<400> SEQUENCE: 190

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asp
              20                  25                  30

Thr Val Lys Trp Tyr Gln Gln Leu Pro Gly Thr Ala Pro Arg Leu Leu
              35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                    85                  90                  95

Asn Gly Pro Val Phe Gly Gly Gly Thr Lys Leu Thr Val Leu
              100                 105                 110

<210> SEQ ID NO 191
<211> LENGTH: 123
<212> TYPE: PRT
<213> ORGANISM: Artificial sequence
<220> FEATURE:
<223> OTHER INFORMATION: Synthetic antibody

<400> SEQUENCE: 191

Gln Val Gln Leu Val Gln Ser Gly Ala Glu Val Lys Lys Pro Gly Ala
1                   5                   10                  15

Ser Val Lys Val Ser Cys Lys Ala Ser Gly Tyr Thr Phe Ser Ser Tyr
              20                  25                  30

Tyr Ile His Trp Val Arg Gln Ala Pro Gly Gln Gly Leu Glu Trp Met
        35                  40                  45

Gly Ile Ile Asn Pro Ser Val Gly Ala Thr Glu Tyr Ala His Ile Phe
        50                  55                  60

Gln Gly Arg Val Thr Leu Thr Arg Asp Thr Ser Thr Ser Thr Val Tyr
65                  70                  75                  80

Met Asp Leu Ser Arg Leu Thr Ser Asp Asp Thr Ala Val Tyr Tyr Cys
                    85                  90                  95

Ala Arg Trp Gly Leu Ile Ser Glu Ser Ser Pro Lys Tyr Phe Asp Ser
              100                 105                 110

Trp Gly Gln Gly Thr Leu Val Thr Val Ser Ser
              115                 120

<210> SEQ ID NO 192
<211> LENGTH: 113
<212> TYPE: PRT
<213> ORGANISM: Artificial sequence
<220> FEATURE:
<223> OTHER INFORMATION: Synthetic antibody

<400> SEQUENCE: 192

Gln Ser Val Leu Thr Gln Pro Pro Ser Val Ser Gly Ala Pro Gly Gln
1                   5                   10                  15

Arg Val Thr Ile Ser Cys Thr Gly Ser Asn Ser Asn Ile Gly Ala Gly
              20                  25                  30

Tyr Asp Val His Trp Tyr Gln Gln Leu Pro Gly Thr Ala Pro Lys Leu
        35                  40                  45

Leu Ile Tyr Asp Asn Thr Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser

-continued

```
                    85              90              95

Val Ser Gly Phe Tyr Val Leu Phe Gly Gly Gly Thr Lys Leu Thr Val
            100             105             110

Leu

<210> SEQ ID NO 193
<211> LENGTH: 137
<212> TYPE: PRT
<213> ORGANISM: Artificial sequence
<220> FEATURE:
<223> OTHER INFORMATION: Synthetic antibody

<400> SEQUENCE: 193

Gln Ile Thr Leu Lys Glu Ser Gly Pro Thr Leu Val Lys Pro Thr Gln
1               5               10              15

Thr Leu Thr Leu Thr Cys Thr Phe Ser Gly Phe Ser Leu Ser Asn Ser
            20              25              30

Gly Val Gly Val Gly Trp Ile Arg Gln Pro Pro Gly Lys Ala Leu Glu
        35              40              45

Trp Leu Ala Leu Ile Tyr Trp Asp Asp Asp Lys Arg Tyr Arg Pro Ser
    50              55              60

Leu Lys Ser Arg Leu Thr Ile Thr Lys Asp Thr Ser Lys Asn Gln Val
65              70              75              80

Val Leu Lys Met Thr Asn Met Asp Pro Val Asp Thr Ala Thr Tyr Tyr
                85              90              95

Cys Ala His Ser Tyr Phe Asp Phe Trp Ser Gly Tyr Phe Ser Leu Asp
            100             105             110

Arg Arg Asp Arg Arg Ala Gly Arg Gln Ser Tyr Phe Asp Tyr Trp Gly
        115             120             125

Gln Gly Thr Leu Val Thr Val Ser Ser
    130             135

<210> SEQ ID NO 194
<211> LENGTH: 108
<212> TYPE: PRT
<213> ORGANISM: Artificial sequence
<220> FEATURE:
<223> OTHER INFORMATION: Synthetic antibody

<400> SEQUENCE: 194

Gln Ser Ala Leu Thr Gln Pro Ala Ser Val Ser Gly Ser Pro Gly Gln
1               5               10              15

Ser Ile Thr Ile Ser Cys Thr Gly Thr Thr Ser Asp Val Gly Gly Tyr
            20              25              30

Asp Tyr Val Ser Trp Tyr Gln Gln His Pro Gly Lys Ala Pro Lys Leu
        35              40              45

Met Ile Phe Asp Val Asn His Arg Pro Ser Gly Val Ser Ser Arg Phe
    50              55              60

Ser Gly Ser Lys Ser Gly Asn Thr Ala Ser Leu Thr Ile Ser Gly Leu
65              70              75              80

Gln Ala Glu Asp Glu Ala Ala Tyr Tyr Cys Ser Ser Tyr Thr Thr Gly
                85              90              95

Thr Leu Phe Gly Gly Gly Thr Lys Leu Thr Val Leu
            100             105

<210> SEQ ID NO 195
<211> LENGTH: 122
<212> TYPE: PRT
```

-continued

<213> ORGANISM: Artificial sequence
<220> FEATURE:
<223> OTHER INFORMATION: Synthetic antibody

<400> SEQUENCE: 195

```
Gln Val Leu Leu Gln Glu Ser Gly Pro Gly Leu Val Lys Pro Ser Gly
1               5                   10                  15

Thr Leu Ser Leu Thr Cys Ala Val Ser Gly Gly Ser Ile Thr Thr Asn
            20                  25                  30

Asn Trp Trp Ser Trp Val Arg Gln Pro Pro Gly Arg Gly Leu Glu Trp
        35                  40                  45

Ile Gly Glu Ile Phe His Gly Gly Lys Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Thr Ser Leu Thr Ala Ala Asp Thr Ala Val Tyr Tyr Cys
            85                  90                  95

Ala Arg Ala Gly Leu Tyr Ser Thr Asn Trp Ser Pro Phe Asp Pro Trp
        100                 105                 110

Gly Gln Gly Thr Leu Val Thr Val Ser Ser
        115                 120
```

<210> SEQ ID NO 196
<211> LENGTH: 108
<212> TYPE: PRT
<213> ORGANISM: Artificial sequence
<220> FEATURE:
<223> OTHER INFORMATION: Synthetic antibody

<400> SEQUENCE: 196

```
Glu Val Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Tyr Leu Ala Trp Tyr Gln Gln Lys Pro Gly Gln Ala Pro Arg Leu Leu
        35                  40                  45

Ile Phe Asp Ala Ser Ser Arg Ala Thr Gly Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Val Tyr Tyr Cys Gln Gln Tyr Gly Gly Ser Pro
            85                  90                  95

Trp Thr Phe Gly Gln Gly Thr Lys Val Glu Ile Lys
        100                 105
```

<210> SEQ ID NO 197
<211> LENGTH: 123
<212> TYPE: PRT
<213> ORGANISM: Artificial sequence
<220> FEATURE:
<223> OTHER INFORMATION: Synthetic antibody

<400> SEQUENCE: 197

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Tyr Ile His Trp Val Arg Gln Ala Pro Gly Gln Gly Leu Glu Trp Met
        35                  40                  45
```

Gly Ile Ile Asn Pro Ser Val Gly Ala Thr Glu Tyr Ala His Ile Phe
    50                  55                  60

Gln Gly Arg Val Thr Leu Thr Arg Asp Thr Ser Thr Ser Thr Val Tyr
65                  70                  75                  80

Met Asp Leu Ser Arg Leu Thr Ser Asp Asp Thr Ala Val Tyr Tyr Cys
                85                  90                  95

Ala Arg Trp Gly Leu Ile Ser Glu Ser Ser Pro Lys Tyr Phe Asp Ser
                100                 105                 110

Trp Gly Gln Gly Thr Leu Val Thr Val Ser Ser
        115                 120

<210> SEQ ID NO 198
<211> LENGTH: 107
<212> TYPE: PRT
<213> ORGANISM: Artificial sequence
<220> FEATURE:
<223> OTHER INFORMATION: Synthetic antibody

<400> SEQUENCE: 198

Glu Ile Val Leu Thr Gln Ser Pro Ala Thr Leu Ser Leu Ser Pro Gly
1                   5                   10                  15

Glu Arg Ala Thr Leu Ser Cys Arg Ala Ser Gln Ser Val Ser Ser Tyr
                20                  25                  30

Leu Ala Trp Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Thr Phe Gly Arg Gly Thr Lys Leu Glu Ile Lys
                100                 105

<210> SEQ ID NO 199
<211> LENGTH: 117
<212> TYPE: PRT
<213> ORGANISM: Artificial sequence
<220> FEATURE:
<223> OTHER INFORMATION: Synthetic antibody

<400> SEQUENCE: 199

Gln Val Gln Leu Val Gln Ser Gly Ala Glu Val Lys Lys Pro Gly Ser
1                   5                   10                  15

Ser Val Lys Val Ser Cys Lys Ala Ser Gly Gly Thr Phe Ser Ser Tyr
                20                  25                  30

Ser Ile Ser Trp Leu Arg Gln Ala Pro Gly Gln Gly Leu Glu Trp Met
        35                  40                  45

Gly Gln Ile Ile Pro Met Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Arg Ala Glu Gly Asp Val Trp Gly Gln Gly Thr Thr
                100                 105                 110

Val Thr Val Ser Ser

115

```
<210> SEQ ID NO 200
<211> LENGTH: 107
<212> TYPE: PRT
<213> ORGANISM: Artificial sequence
<220> FEATURE:
<223> OTHER INFORMATION: Synthetic antibody

<400> SEQUENCE: 200

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Tyr
                85                  90                  95

Thr Phe Gly Arg Gly Thr Lys Leu Glu Ile Lys
            100                 105

<210> SEQ ID NO 201
<211> LENGTH: 8
<212> TYPE: PRT
<213> ORGANISM: Artificial sequence
<220> FEATURE:
<223> OTHER INFORMATION: Synthetic antibody

<400> SEQUENCE: 201

Gly Phe Thr Phe Ser Asp Tyr Tyr
1               5

<210> SEQ ID NO 202
<211> LENGTH: 8
<212> TYPE: PRT
<213> ORGANISM: Artificial sequence
<220> FEATURE:
<223> OTHER INFORMATION: Synthetic antibody

<400> SEQUENCE: 202

Ile Ser Ser Phe Gly Ser Asn Thr
1               5

<210> SEQ ID NO 203
<211> LENGTH: 12
<212> TYPE: PRT
<213> ORGANISM: Artificial sequence
<220> FEATURE:
<223> OTHER INFORMATION: Synthetic antibody

<400> SEQUENCE: 203

Ala Arg Ser Leu Arg Gly Ile Ala Val Pro Ser Tyr
1               5                   10

<210> SEQ ID NO 204
<211> LENGTH: 8
<212> TYPE: PRT
<213> ORGANISM: Artificial sequence
<220> FEATURE:
<223> OTHER INFORMATION: Synthetic antibody
```

<400> SEQUENCE: 204

Gly Phe Thr Phe Ser Asp Tyr Tyr
1               5

<210> SEQ ID NO 205
<211> LENGTH: 8
<212> TYPE: PRT
<213> ORGANISM: Artificial sequence
<220> FEATURE:
<223> OTHER INFORMATION: Synthetic antibody

<400> SEQUENCE: 205

Ile Ser Ser Phe Gly Ser Asn Thr
1               5

<210> SEQ ID NO 206
<211> LENGTH: 12
<212> TYPE: PRT
<213> ORGANISM: Artificial sequence
<220> FEATURE:
<223> OTHER INFORMATION: Synthetic antibody

<400> SEQUENCE: 206

Ala Arg Ser Leu Arg Gly Ile Ala Val Pro Ser Tyr
1               5                   10

<210> SEQ ID NO 207
<211> LENGTH: 10
<212> TYPE: PRT
<213> ORGANISM: Artificial sequence
<220> FEATURE:
<223> OTHER INFORMATION: Synthetic antibody

<400> SEQUENCE: 207

Gly Gly Ser Ile Ser Ser Asn Ile Tyr Tyr
1               5                   10

<210> SEQ ID NO 208
<211> LENGTH: 7
<212> TYPE: PRT
<213> ORGANISM: Artificial sequence
<220> FEATURE:
<223> OTHER INFORMATION: Synthetic antibody

<400> SEQUENCE: 208

Ile Tyr Tyr Ser Gly Asn Thr
1               5

<210> SEQ ID NO 209
<211> LENGTH: 17
<212> TYPE: PRT
<213> ORGANISM: Artificial sequence
<220> FEATURE:
<223> OTHER INFORMATION: Synthetic antibody

<400> SEQUENCE: 209

Ala Ser Gln Lys Met Val Tyr Pro Ile Lys Arg Asn Asn Trp Phe Asp
1               5                   10                  15

Pro

<210> SEQ ID NO 210
<211> LENGTH: 8
<212> TYPE: PRT
<213> ORGANISM: Artificial sequence
<220> FEATURE:

<223> OTHER INFORMATION: Synthetic antibody

<400> SEQUENCE: 210

Gly Tyr Ser Phe Thr Ser Tyr Trp
1               5

<210> SEQ ID NO 211
<211> LENGTH: 8
<212> TYPE: PRT
<213> ORGANISM: Artificial sequence
<220> FEATURE:
<223> OTHER INFORMATION: Synthetic antibody

<400> SEQUENCE: 211

Ile Tyr Pro Gly Asp Ser Asp Thr
1               5

<210> SEQ ID NO 212
<211> LENGTH: 23
<212> TYPE: PRT
<213> ORGANISM: Artificial sequence
<220> FEATURE:
<223> OTHER INFORMATION: Synthetic antibody

<400> SEQUENCE: 212

Ala Arg His Glu Ser Glu Ala Phe Ser Ile Phe Gly Val Val Arg Tyr
1               5                   10                  15

Tyr Tyr Tyr Tyr Met Asp Val
            20

<210> SEQ ID NO 213
<211> LENGTH: 9
<212> TYPE: PRT
<213> ORGANISM: Artificial sequence
<220> FEATURE:
<223> OTHER INFORMATION: Synthetic antibody

<400> SEQUENCE: 213

Gly Gly Ser Ile Ser Ser Ser Lys Trp
1               5

<210> SEQ ID NO 214
<211> LENGTH: 7
<212> TYPE: PRT
<213> ORGANISM: Artificial sequence
<220> FEATURE:
<223> OTHER INFORMATION: Synthetic antibody

<400> SEQUENCE: 214

Ile Tyr His Ser Gly Ser Thr
1               5

<210> SEQ ID NO 215
<211> LENGTH: 15
<212> TYPE: PRT
<213> ORGANISM: Artificial sequence
<220> FEATURE:
<223> OTHER INFORMATION: Synthetic antibody

<400> SEQUENCE: 215

Ala Arg Val Gly Leu Gly Trp His Asp Gly Asn Gly Met Asp Val
1               5                   10                  15

<210> SEQ ID NO 216
<211> LENGTH: 10
<212> TYPE: PRT

<213> ORGANISM: Artificial sequence
<220> FEATURE:
<223> OTHER INFORMATION: Synthetic antibody

<400> SEQUENCE: 216

Gly Gly Ser Ile Ser Ser Gly Asp Tyr Tyr
1               5                   10

<210> SEQ ID NO 217
<211> LENGTH: 7
<212> TYPE: PRT
<213> ORGANISM: Artificial sequence
<220> FEATURE:
<223> OTHER INFORMATION: Synthetic antibody

<400> SEQUENCE: 217

Ile Tyr Tyr Ser Gly Ser Ala
1               5

<210> SEQ ID NO 218
<211> LENGTH: 21
<212> TYPE: PRT
<213> ORGANISM: Artificial sequence
<220> FEATURE:
<223> OTHER INFORMATION: Synthetic antibody

<400> SEQUENCE: 218

Ala Arg Phe Arg Leu Gly Asp Ala Pro Thr Arg Asp Gly Tyr Asn Leu
1               5                   10                  15

His Tyr Phe Asp Tyr
            20

<210> SEQ ID NO 219
<211> LENGTH: 8
<212> TYPE: PRT
<213> ORGANISM: Artificial sequence
<220> FEATURE:
<223> OTHER INFORMATION: Synthetic antibody

<400> SEQUENCE: 219

Gly Phe Thr Phe Gly Asp Tyr Ala
1               5

<210> SEQ ID NO 220
<211> LENGTH: 10
<212> TYPE: PRT
<213> ORGANISM: Artificial sequence
<220> FEATURE:
<223> OTHER INFORMATION: Synthetic antibody

<400> SEQUENCE: 220

Ile Arg Ser Lys Gly Tyr Gly Gly Thr Thr
1               5                   10

<210> SEQ ID NO 221
<211> LENGTH: 17
<212> TYPE: PRT
<213> ORGANISM: Artificial sequence
<220> FEATURE:
<223> OTHER INFORMATION: Synthetic antibody

<400> SEQUENCE: 221

Thr Arg Ala His Tyr Asp Tyr Val Trp Gly Asn Tyr Trp Ser Phe Ala
1               5                   10                  15

Tyr

-continued

```
<210> SEQ ID NO 222
<211> LENGTH: 8
<212> TYPE: PRT
<213> ORGANISM: Artificial sequence
<220> FEATURE:
<223> OTHER INFORMATION: Synthetic antibody

<400> SEQUENCE: 222

Gly Phe Thr Phe Ser Thr Tyr Gly
1               5

<210> SEQ ID NO 223
<211> LENGTH: 8
<212> TYPE: PRT
<213> ORGANISM: Artificial sequence
<220> FEATURE:
<223> OTHER INFORMATION: Synthetic antibody

<400> SEQUENCE: 223

Ile Trp Tyr Asp Gly Ser Asn Lys
1               5

<210> SEQ ID NO 224
<211> LENGTH: 20
<212> TYPE: PRT
<213> ORGANISM: Artificial sequence
<220> FEATURE:
<223> OTHER INFORMATION: Synthetic antibody

<400> SEQUENCE: 224

Ala Arg Asp Pro Gly Gly Arg Arg Asp Gly Tyr Ile Leu Arg Pro Asp
1               5                   10                  15

Ala Phe Asp Ile
            20

<210> SEQ ID NO 225
<211> LENGTH: 8
<212> TYPE: PRT
<213> ORGANISM: Artificial sequence
<220> FEATURE:
<223> OTHER INFORMATION: Synthetic antibody

<400> SEQUENCE: 225

Gly Tyr Thr Phe Thr Ser Tyr Gly
1               5

<210> SEQ ID NO 226
<211> LENGTH: 8
<212> TYPE: PRT
<213> ORGANISM: Artificial sequence
<220> FEATURE:
<223> OTHER INFORMATION: Synthetic antibody

<400> SEQUENCE: 226

Ile Ser Ala Tyr Asn Gly Asn Thr
1               5

<210> SEQ ID NO 227
<211> LENGTH: 9
<212> TYPE: PRT
<213> ORGANISM: Artificial sequence
<220> FEATURE:
<223> OTHER INFORMATION: Synthetic antibody

<400> SEQUENCE: 227

Ala Arg Ser Gly Gly Tyr Ala Ile Phe
```

1               5

<210> SEQ ID NO 228
<211> LENGTH: 10
<212> TYPE: PRT
<213> ORGANISM: Artificial sequence
<220> FEATURE:
<223> OTHER INFORMATION: Synthetic antibody

<400> SEQUENCE: 228

Gly Phe Ser Ile Ser Ser Ser Gly Val Gly
1               5                   10

<210> SEQ ID NO 229
<211> LENGTH: 7
<212> TYPE: PRT
<213> ORGANISM: Artificial sequence
<220> FEATURE:
<223> OTHER INFORMATION: Synthetic antibody

<400> SEQUENCE: 229

Leu Tyr Trp Asp Asp Ser Lys
1               5

<210> SEQ ID NO 230
<211> LENGTH: 10
<212> TYPE: PRT
<213> ORGANISM: Artificial sequence
<220> FEATURE:
<223> OTHER INFORMATION: Synthetic antibody

<400> SEQUENCE: 230

Ala His Arg Arg Thr Thr Val Phe Asp Tyr
1               5                   10

<210> SEQ ID NO 231
<211> LENGTH: 8
<212> TYPE: PRT
<213> ORGANISM: Artificial sequence
<220> FEATURE:
<223> OTHER INFORMATION: Synthetic antibody

<400> SEQUENCE: 231

Gly Tyr Arg Phe Thr Asn Tyr Trp
1               5

<210> SEQ ID NO 232
<211> LENGTH: 8
<212> TYPE: PRT
<213> ORGANISM: Artificial sequence
<220> FEATURE:
<223> OTHER INFORMATION: Synthetic antibody

<400> SEQUENCE: 232

Ile Tyr Pro Gly Asp Ser Asn Thr
1               5

<210> SEQ ID NO 233
<211> LENGTH: 25
<212> TYPE: PRT
<213> ORGANISM: Artificial sequence
<220> FEATURE:
<223> OTHER INFORMATION: Synthetic antibody

<400> SEQUENCE: 233

Ala Arg His Ser Glu Thr Lys Asp Gly Tyr Asn Trp Ala Gln Gly Asn
1               5                   10                  15

```
Phe Tyr Ser Tyr Tyr Tyr Met Asp Val
            20                  25

<210> SEQ ID NO 234
<211> LENGTH: 8
<212> TYPE: PRT
<213> ORGANISM: Artificial sequence
<220> FEATURE:
<223> OTHER INFORMATION: Synthetic antibody

<400> SEQUENCE: 234

Gly Gly Ser Ile Asn Tyr Tyr Tyr
1               5

<210> SEQ ID NO 235
<211> LENGTH: 10
<212> TYPE: PRT
<213> ORGANISM: Artificial sequence
<220> FEATURE:
<223> OTHER INFORMATION: Synthetic antibody

<400> SEQUENCE: 235

Ile Tyr Tyr Ile Glu Gly Ser Glu Ser Thr
1               5                   10

<210> SEQ ID NO 236
<211> LENGTH: 16
<212> TYPE: PRT
<213> ORGANISM: Artificial sequence
<220> FEATURE:
<223> OTHER INFORMATION: Synthetic antibody

<400> SEQUENCE: 236

Ala Arg Asp Ser Arg Arg Asn Arg Tyr Ser Gly Tyr Tyr Phe Asp Phe
1               5                   10                  15

<210> SEQ ID NO 237
<211> LENGTH: 9
<212> TYPE: PRT
<213> ORGANISM: Artificial sequence
<220> FEATURE:
<223> OTHER INFORMATION: Synthetic antibody

<400> SEQUENCE: 237

Gly Asp Ser Ile Ser Gly Ser Phe Trp
1               5

<210> SEQ ID NO 238
<211> LENGTH: 7
<212> TYPE: PRT
<213> ORGANISM: Artificial sequence
<220> FEATURE:
<223> OTHER INFORMATION: Synthetic antibody

<400> SEQUENCE: 238

Ile Tyr His Ser Gly Asn Thr
1               5

<210> SEQ ID NO 239
<211> LENGTH: 19
<212> TYPE: PRT
<213> ORGANISM: Artificial sequence
<220> FEATURE:
<223> OTHER INFORMATION: Synthetic antibody

<400> SEQUENCE: 239
```

-continued

Ser Arg Val Leu Gly Leu Tyr Gln Leu Leu Gly Ser Gly Tyr Tyr Ala
1               5                   10                  15

Met Asp Val

<210> SEQ ID NO 240
<211> LENGTH: 8
<212> TYPE: PRT
<213> ORGANISM: Artificial sequence
<220> FEATURE:
<223> OTHER INFORMATION: Synthetic antibody

<400> SEQUENCE: 240

Gly Tyr Ser Leu Thr Glu Leu Ser
1               5

<210> SEQ ID NO 241
<211> LENGTH: 8
<212> TYPE: PRT
<213> ORGANISM: Artificial sequence
<220> FEATURE:
<223> OTHER INFORMATION: Synthetic antibody

<400> SEQUENCE: 241

Phe Asp Pro Gly Asp Arg Lys Pro
1               5

<210> SEQ ID NO 242
<211> LENGTH: 13
<212> TYPE: PRT
<213> ORGANISM: Artificial sequence
<220> FEATURE:
<223> OTHER INFORMATION: Synthetic antibody

<400> SEQUENCE: 242

Ala Thr Asp Pro Gly Ala Val Ala Gly Phe Leu Gly Phe
1               5                   10

<210> SEQ ID NO 243
<211> LENGTH: 8
<212> TYPE: PRT
<213> ORGANISM: Artificial sequence
<220> FEATURE:
<223> OTHER INFORMATION: Synthetic antibody

<400> SEQUENCE: 243

Gly Phe Thr Phe Gly Asp Tyr Val
1               5

<210> SEQ ID NO 244
<211> LENGTH: 10
<212> TYPE: PRT
<213> ORGANISM: Artificial sequence
<220> FEATURE:
<223> OTHER INFORMATION: Synthetic antibody

<400> SEQUENCE: 244

Ile Arg Thr Lys Pro Tyr Gly Gly Thr Thr
1               5                   10

<210> SEQ ID NO 245
<211> LENGTH: 11
<212> TYPE: PRT
<213> ORGANISM: Artificial sequence
<220> FEATURE:
<223> OTHER INFORMATION: Synthetic antibody

<400> SEQUENCE: 245

Leu Ala Gly Thr Asp Trp Ser Tyr Phe Asp Tyr
1               5                   10

<210> SEQ ID NO 246
<211> LENGTH: 8
<212> TYPE: PRT
<213> ORGANISM: Artificial sequence
<220> FEATURE:
<223> OTHER INFORMATION: Synthetic antibody

<400> SEQUENCE: 246

Gly Gly Ser Ile Ser Ser Tyr Tyr
1               5

<210> SEQ ID NO 247
<211> LENGTH: 7
<212> TYPE: PRT
<213> ORGANISM: Artificial sequence
<220> FEATURE:
<223> OTHER INFORMATION: Synthetic antibody

<400> SEQUENCE: 247

Met Tyr Tyr Ser Gly Ser Thr
1               5

<210> SEQ ID NO 248
<211> LENGTH: 19
<212> TYPE: PRT
<213> ORGANISM: Artificial sequence
<220> FEATURE:
<223> OTHER INFORMATION: Synthetic antibody

<400> SEQUENCE: 248

Ala Arg Gly Ala Tyr Tyr Gly Ser Gly Ser Phe His Tyr Tyr Tyr Tyr
1               5                   10                  15

Met Asp Val

<210> SEQ ID NO 249
<211> LENGTH: 8
<212> TYPE: PRT
<213> ORGANISM: Artificial sequence
<220> FEATURE:
<223> OTHER INFORMATION: Synthetic antibody

<400> SEQUENCE: 249

Gly Phe Thr Phe Ser Ser Tyr Ser
1               5

<210> SEQ ID NO 250
<211> LENGTH: 8
<212> TYPE: PRT
<213> ORGANISM: Artificial sequence
<220> FEATURE:
<223> OTHER INFORMATION: Synthetic antibody

<400> SEQUENCE: 250

Ile Ser Ser Ser Ser Thr Phe Ile
1               5

<210> SEQ ID NO 251
<211> LENGTH: 19
<212> TYPE: PRT
<213> ORGANISM: Artificial sequence
<220> FEATURE:
<223> OTHER INFORMATION: Synthetic antibody -continued

```
<400> SEQUENCE: 251

Ala Arg Gly Gly Asn Asp Tyr Ser Asp Tyr Glu Asn Tyr Tyr Tyr Tyr
1               5                   10                  15

Met Asp Val

<210> SEQ ID NO 252
<211> LENGTH: 8
<212> TYPE: PRT
<213> ORGANISM: Artificial sequence
<220> FEATURE:
<223> OTHER INFORMATION: Synthetic antibody

<400> SEQUENCE: 252

Gly Phe Ile Phe Asp Asp Tyr Ala
1               5

<210> SEQ ID NO 253
<211> LENGTH: 8
<212> TYPE: PRT
<213> ORGANISM: Artificial sequence
<220> FEATURE:
<223> OTHER INFORMATION: Synthetic antibody

<400> SEQUENCE: 253

Ile Thr Trp Asp Ser Gly Arg Ile
1               5

<210> SEQ ID NO 254
<211> LENGTH: 14
<212> TYPE: PRT
<213> ORGANISM: Artificial sequence
<220> FEATURE:
<223> OTHER INFORMATION: Synthetic antibody

<400> SEQUENCE: 254

Ala Lys Asp Arg Gly Pro Phe Gly Trp Leu Thr Leu Asp Tyr
1               5                   10

<210> SEQ ID NO 255
<211> LENGTH: 8
<212> TYPE: PRT
<213> ORGANISM: Artificial sequence
<220> FEATURE:
<223> OTHER INFORMATION: Synthetic antibody

<400> SEQUENCE: 255

Gly Phe Thr Phe Gly Asp Tyr Ala
1               5

<210> SEQ ID NO 256
<211> LENGTH: 10
<212> TYPE: PRT
<213> ORGANISM: Artificial sequence
<220> FEATURE:
<223> OTHER INFORMATION: Synthetic antibody

<400> SEQUENCE: 256

Ile Arg Ser Lys Ala Tyr Gly Gly Thr Thr
1               5                   10

<210> SEQ ID NO 257
<211> LENGTH: 19
<212> TYPE: PRT
<213> ORGANISM: Artificial sequence
<220> FEATURE:
<223> OTHER INFORMATION: Synthetic antibody
```

<400> SEQUENCE: 257

Thr Arg Ala Thr Pro Val Leu Leu Trp Phe Gly Ser Ser Gly Asn Phe
1               5                   10                  15

Phe Asp Tyr

<210> SEQ ID NO 258
<211> LENGTH: 10
<212> TYPE: PRT
<213> ORGANISM: Artificial sequence
<220> FEATURE:
<223> OTHER INFORMATION: Synthetic antibody

<400> SEQUENCE: 258

Gly Asp Ser Ile Asn Asn Asn Asn Tyr Tyr
1               5                   10

<210> SEQ ID NO 259
<211> LENGTH: 7
<212> TYPE: PRT
<213> ORGANISM: Artificial sequence
<220> FEATURE:
<223> OTHER INFORMATION: Synthetic antibody

<400> SEQUENCE: 259

Ile Tyr Tyr Ser Gly Ile Thr
1               5

<210> SEQ ID NO 260
<211> LENGTH: 11
<212> TYPE: PRT
<213> ORGANISM: Artificial sequence
<220> FEATURE:
<223> OTHER INFORMATION: Synthetic antibody

<400> SEQUENCE: 260

Val Arg His Gly Leu Asp His Lys Phe Asp Tyr
1               5                   10

<210> SEQ ID NO 261
<211> LENGTH: 8
<212> TYPE: PRT
<213> ORGANISM: Artificial sequence
<220> FEATURE:
<223> OTHER INFORMATION: Synthetic antibody

<400> SEQUENCE: 261

Gly Phe Thr Phe Ser Ser Tyr Ser
1               5

<210> SEQ ID NO 262
<211> LENGTH: 8
<212> TYPE: PRT
<213> ORGANISM: Artificial sequence
<220> FEATURE:
<223> OTHER INFORMATION: Synthetic antibody

<400> SEQUENCE: 262

Ile Ser Ser Ser Ser Gly Ala Ile
1               5

<210> SEQ ID NO 263
<211> LENGTH: 8
<212> TYPE: PRT
<213> ORGANISM: Artificial sequence
<220> FEATURE:

<223> OTHER INFORMATION: Synthetic antibody

<400> SEQUENCE: 263

Ala Arg Gly Asn Gly Ala Thr Tyr
1               5

<210> SEQ ID NO 264
<211> LENGTH: 8
<212> TYPE: PRT
<213> ORGANISM: Artificial sequence
<220> FEATURE:
<223> OTHER INFORMATION: Synthetic antibody

<400> SEQUENCE: 264

Gly Tyr Arg Phe Thr Asn Tyr Trp
1               5

<210> SEQ ID NO 265
<211> LENGTH: 8
<212> TYPE: PRT
<213> ORGANISM: Artificial sequence
<220> FEATURE:
<223> OTHER INFORMATION: Synthetic antibody

<400> SEQUENCE: 265

Ile Tyr Pro Gly Asp Ser Asp Thr
1               5

<210> SEQ ID NO 266
<211> LENGTH: 13
<212> TYPE: PRT
<213> ORGANISM: Artificial sequence
<220> FEATURE:
<223> OTHER INFORMATION: Synthetic antibody

<400> SEQUENCE: 266

Ala Arg Leu Pro His Pro Val Thr Gly Pro Leu Asp Tyr
1               5                   10

<210> SEQ ID NO 267
<211> LENGTH: 8
<212> TYPE: PRT
<213> ORGANISM: Artificial sequence
<220> FEATURE:
<223> OTHER INFORMATION: Synthetic antibody

<400> SEQUENCE: 267

Gly Phe Thr Phe Arg Ser Tyr Thr
1               5

<210> SEQ ID NO 268
<211> LENGTH: 8
<212> TYPE: PRT
<213> ORGANISM: Artificial sequence
<220> FEATURE:
<223> OTHER INFORMATION: Synthetic antibody

<400> SEQUENCE: 268

Ile Ser Thr Ser Ser Ser Tyr Ile
1               5

<210> SEQ ID NO 269
<211> LENGTH: 17
<212> TYPE: PRT
<213> ORGANISM: Artificial sequence
<220> FEATURE:
<223> OTHER INFORMATION: Synthetic antibody

<400> SEQUENCE: 269

Ala Ser Leu Arg Lys Asp Ser Gly Ser Phe Tyr Asn Arg Ala Leu Asp
1               5                   10                  15

Tyr

<210> SEQ ID NO 270
<211> LENGTH: 8
<212> TYPE: PRT
<213> ORGANISM: Artificial sequence
<220> FEATURE:
<223> OTHER INFORMATION: Synthetic antibody

<400> SEQUENCE: 270

Gly Phe Thr Phe Asp Ala Tyr Ala
1               5

<210> SEQ ID NO 271
<211> LENGTH: 8
<212> TYPE: PRT
<213> ORGANISM: Artificial sequence
<220> FEATURE:
<223> OTHER INFORMATION: Synthetic antibody

<400> SEQUENCE: 271

Ile Ser Trp Asn Gly Gly Asn Ile
1               5

<210> SEQ ID NO 272
<211> LENGTH: 22
<212> TYPE: PRT
<213> ORGANISM: Artificial sequence
<220> FEATURE:
<223> OTHER INFORMATION: Synthetic antibody

<400> SEQUENCE: 272

Ala Lys Glu Asp Cys Pro Ser Thr Ser Cys Tyr Phe Val Arg Trp Gly
1               5                   10                  15

Leu Asn Trp Leu Asp Pro
            20

<210> SEQ ID NO 273
<211> LENGTH: 8
<212> TYPE: PRT
<213> ORGANISM: Artificial sequence
<220> FEATURE:
<223> OTHER INFORMATION: Synthetic antibody

<400> SEQUENCE: 273

Gly Phe Thr Phe Ala Asp Tyr Ala
1               5

<210> SEQ ID NO 274
<211> LENGTH: 10
<212> TYPE: PRT
<213> ORGANISM: Artificial sequence
<220> FEATURE:
<223> OTHER INFORMATION: Synthetic antibody

<400> SEQUENCE: 274

Ile Arg Ser Glu Thr Tyr Gly Gly Thr Thr
1               5                   10

<210> SEQ ID NO 275
<211> LENGTH: 15

```
<212> TYPE: PRT
<213> ORGANISM: Artificial sequence
<220> FEATURE:
<223> OTHER INFORMATION: Synthetic antibody

<400> SEQUENCE: 275

Thr Arg Ala Arg His Asp Thr Arg Ser Trp Val Leu Ser Asp His
1               5                   10                  15

<210> SEQ ID NO 276
<211> LENGTH: 8
<212> TYPE: PRT
<213> ORGANISM: Artificial sequence
<220> FEATURE:
<223> OTHER INFORMATION: Synthetic antibody

<400> SEQUENCE: 276

Gly Tyr Thr Phe Thr Ser Tyr Gly
1               5

<210> SEQ ID NO 277
<211> LENGTH: 8
<212> TYPE: PRT
<213> ORGANISM: Artificial sequence
<220> FEATURE:
<223> OTHER INFORMATION: Synthetic antibody

<400> SEQUENCE: 277

Ile Ser Gly Tyr Asn Gly Asn Thr
1               5

<210> SEQ ID NO 278
<211> LENGTH: 20
<212> TYPE: PRT
<213> ORGANISM: Artificial sequence
<220> FEATURE:
<223> OTHER INFORMATION: Synthetic antibody

<400> SEQUENCE: 278

Ala Arg Asp Pro Ser Met Met Thr Phe Gly Gly Val Ile Val Ser Arg
1               5                   10                  15

Tyr Phe Asp Tyr
            20

<210> SEQ ID NO 279
<211> LENGTH: 10
<212> TYPE: PRT
<213> ORGANISM: Artificial sequence
<220> FEATURE:
<223> OTHER INFORMATION: Synthetic antibody

<400> SEQUENCE: 279

Gly Gly Phe Ile Arg Ser Ser Ser Tyr Tyr
1               5                   10

<210> SEQ ID NO 280
<211> LENGTH: 7
<212> TYPE: PRT
<213> ORGANISM: Artificial sequence
<220> FEATURE:
<223> OTHER INFORMATION: Synthetic antibody

<400> SEQUENCE: 280

Ile Tyr Tyr Thr Glu Ser Thr
1               5
```

```
<210> SEQ ID NO 281
<211> LENGTH: 16
<212> TYPE: PRT
<213> ORGANISM: Artificial sequence
<220> FEATURE:
<223> OTHER INFORMATION: Synthetic antibody

<400> SEQUENCE: 281

Ala Arg His Asp Tyr Trp Thr Gly Ala Arg Tyr Ser Trp Phe Asp Pro
1               5                   10                  15

<210> SEQ ID NO 282
<211> LENGTH: 8
<212> TYPE: PRT
<213> ORGANISM: Artificial sequence
<220> FEATURE:
<223> OTHER INFORMATION: Synthetic antibody

<400> SEQUENCE: 282

Gly Tyr Thr Phe Thr Ser Tyr Tyr
1               5

<210> SEQ ID NO 283
<211> LENGTH: 8
<212> TYPE: PRT
<213> ORGANISM: Artificial sequence
<220> FEATURE:
<223> OTHER INFORMATION: Synthetic antibody

<400> SEQUENCE: 283

Met Asn Pro Ser Gly Gly Ser Thr
1               5

<210> SEQ ID NO 284
<211> LENGTH: 20
<212> TYPE: PRT
<213> ORGANISM: Artificial sequence
<220> FEATURE:
<223> OTHER INFORMATION: Synthetic antibody

<400> SEQUENCE: 284

Ala Arg Glu Thr Val Val Gln Arg Leu Val Gly Arg Asp Tyr Tyr His
1               5                   10                  15

Gly Met Asp Val
            20

<210> SEQ ID NO 285
<211> LENGTH: 8
<212> TYPE: PRT
<213> ORGANISM: Artificial sequence
<220> FEATURE:
<223> OTHER INFORMATION: Synthetic antibody

<400> SEQUENCE: 285

Gly Phe Thr Phe Asp Asp Tyr Ala
1               5

<210> SEQ ID NO 286
<211> LENGTH: 8
<212> TYPE: PRT
<213> ORGANISM: Artificial sequence
<220> FEATURE:
<223> OTHER INFORMATION: Synthetic antibody

<400> SEQUENCE: 286

Ile Ser Trp Asp Gly Gly Arg Thr
1               5
```

<210> SEQ ID NO 287
<211> LENGTH: 14
<212> TYPE: PRT
<213> ORGANISM: Artificial sequence
<220> FEATURE:
<223> OTHER INFORMATION: Synthetic antibody

<400> SEQUENCE: 287

Ala Thr Gly His Pro Pro Leu Val Leu Trp Ser Leu Gly Tyr
1               5                   10

<210> SEQ ID NO 288
<211> LENGTH: 8
<212> TYPE: PRT
<213> ORGANISM: Artificial sequence
<220> FEATURE:
<223> OTHER INFORMATION: Synthetic antibody

<400> SEQUENCE: 288

Gly Gly Thr Phe Ser Thr Phe Ala
1               5

<210> SEQ ID NO 289
<211> LENGTH: 8
<212> TYPE: PRT
<213> ORGANISM: Artificial sequence
<220> FEATURE:
<223> OTHER INFORMATION: Synthetic antibody

<400> SEQUENCE: 289

Ile Ile Pro Ile Phe Asp Arg Pro
1               5

<210> SEQ ID NO 290
<211> LENGTH: 22
<212> TYPE: PRT
<213> ORGANISM: Artificial sequence
<220> FEATURE:
<223> OTHER INFORMATION: Synthetic antibody

<400> SEQUENCE: 290

Ala Arg Asp Arg Arg Tyr Asn Tyr Glu Ser Ser Ala Ser Gln Asn Asn
1               5                   10                  15

Arg Trp Tyr Phe Asp Leu
            20

<210> SEQ ID NO 291
<211> LENGTH: 8
<212> TYPE: PRT
<213> ORGANISM: Artificial sequence
<220> FEATURE:
<223> OTHER INFORMATION: Synthetic antibody

<400> SEQUENCE: 291

Gly Phe Thr Phe Ser Asn Tyr Gly
1               5

<210> SEQ ID NO 292
<211> LENGTH: 8
<212> TYPE: PRT
<213> ORGANISM: Artificial sequence
<220> FEATURE:
<223> OTHER INFORMATION: Synthetic antibody

<400> SEQUENCE: 292

```
Ile Arg Tyr Asp Gly Ser Asn Gln
1               5

<210> SEQ ID NO 293
<211> LENGTH: 17
<212> TYPE: PRT
<213> ORGANISM: Artificial sequence
<220> FEATURE:
<223> OTHER INFORMATION: Synthetic antibody

<400> SEQUENCE: 293

Ala Lys Asp Leu Ala Val Leu Leu Met Tyr Gly Phe Gly Gly Phe Asp
1               5                   10                  15

Ala

<210> SEQ ID NO 294
<211> LENGTH: 8
<212> TYPE: PRT
<213> ORGANISM: Artificial sequence
<220> FEATURE:
<223> OTHER INFORMATION: Synthetic antibody

<400> SEQUENCE: 294

Gly Gly Thr Phe Arg Ser Tyr Ala
1               5

<210> SEQ ID NO 295
<211> LENGTH: 8
<212> TYPE: PRT
<213> ORGANISM: Artificial sequence
<220> FEATURE:
<223> OTHER INFORMATION: Synthetic antibody

<400> SEQUENCE: 295

Ile Ile Pro Ile Phe Gly Thr Ala
1               5

<210> SEQ ID NO 296
<211> LENGTH: 20
<212> TYPE: PRT
<213> ORGANISM: Artificial sequence
<220> FEATURE:
<223> OTHER INFORMATION: Synthetic antibody

<400> SEQUENCE: 296

Ala Arg Tyr Phe Phe Thr Thr Pro His Trp Thr Leu Pro Ile Asp Tyr
1               5                   10                  15

Gly Met Asp Val
            20

<210> SEQ ID NO 297
<211> LENGTH: 9
<212> TYPE: PRT
<213> ORGANISM: Artificial sequence
<220> FEATURE:
<223> OTHER INFORMATION: Synthetic antibody

<400> SEQUENCE: 297

Gly Gly Ser Ile Ser Ser Ser Asn Trp
1               5

<210> SEQ ID NO 298
<211> LENGTH: 7
<212> TYPE: PRT
<213> ORGANISM: Artificial sequence
<220> FEATURE:
```

<223> OTHER INFORMATION: Synthetic antibody

<400> SEQUENCE: 298

Ile Tyr Tyr Ser Gly Thr Thr
1               5

<210> SEQ ID NO 299
<211> LENGTH: 12
<212> TYPE: PRT
<213> ORGANISM: Artificial sequence
<220> FEATURE:
<223> OTHER INFORMATION: Synthetic antibody

<400> SEQUENCE: 299

Ala Gly Gly Thr Tyr Phe Arg Arg Tyr Phe Asp Tyr
1               5                   10

<210> SEQ ID NO 300
<211> LENGTH: 10
<212> TYPE: PRT
<213> ORGANISM: Artificial sequence
<220> FEATURE:
<223> OTHER INFORMATION: Synthetic antibody

<400> SEQUENCE: 300

Gly Gly Ser Ile Ser Ser Ser Ser Tyr Tyr
1               5                   10

<210> SEQ ID NO 301
<211> LENGTH: 7
<212> TYPE: PRT
<213> ORGANISM: Artificial sequence
<220> FEATURE:
<223> OTHER INFORMATION: Synthetic antibody

<400> SEQUENCE: 301

Val Phe Tyr Ser Gly Asn Thr
1               5

<210> SEQ ID NO 302
<211> LENGTH: 17
<212> TYPE: PRT
<213> ORGANISM: Artificial sequence
<220> FEATURE:
<223> OTHER INFORMATION: Synthetic antibody

<400> SEQUENCE: 302

Ala Arg His Gln Tyr Ser Ser Ser Trp Asn Arg Ile Asp Ala Phe Asp
1               5                   10                  15

Ile

<210> SEQ ID NO 303
<211> LENGTH: 8
<212> TYPE: PRT
<213> ORGANISM: Artificial sequence
<220> FEATURE:
<223> OTHER INFORMATION: Synthetic antibody

<400> SEQUENCE: 303

Gly Phe Thr Phe Gly Asn Tyr Val
1               5

<210> SEQ ID NO 304
<211> LENGTH: 10
<212> TYPE: PRT
<213> ORGANISM: Artificial sequence
<220> FEATURE:
<223> OTHER INFORMATION: Synthetic antibody

<400> SEQUENCE: 304

Ile Arg Ser Lys Ala Tyr Gly Gly Thr Thr
1               5                   10

<210> SEQ ID NO 305
<211> LENGTH: 11
<212> TYPE: PRT
<213> ORGANISM: Artificial sequence
<220> FEATURE:
<223> OTHER INFORMATION: Synthetic antibody

<400> SEQUENCE: 305

Leu Ala Ala Thr Val Trp Thr Tyr Phe Asp Phe
1               5                   10

<210> SEQ ID NO 306
<211> LENGTH: 8
<212> TYPE: PRT
<213> ORGANISM: Artificial sequence
<220> FEATURE:
<223> OTHER INFORMATION: Synthetic antibody

<400> SEQUENCE: 306

Gly Tyr Pro Phe Thr Asn Tyr Gly
1               5

<210> SEQ ID NO 307
<211> LENGTH: 8
<212> TYPE: PRT
<213> ORGANISM: Artificial sequence
<220> FEATURE:
<223> OTHER INFORMATION: Synthetic antibody

<400> SEQUENCE: 307

Ile Ser Ala Tyr Asn Gly Asn Thr
1               5

<210> SEQ ID NO 308
<211> LENGTH: 11
<212> TYPE: PRT
<213> ORGANISM: Artificial sequence
<220> FEATURE:
<223> OTHER INFORMATION: Synthetic antibody

<400> SEQUENCE: 308

Ala Arg Asp Tyr Tyr Asp Ser Ser Gly Ser Val
1               5                   10

<210> SEQ ID NO 309
<211> LENGTH: 8
<212> TYPE: PRT
<213> ORGANISM: Artificial sequence
<220> FEATURE:
<223> OTHER INFORMATION: Synthetic antibody

<400> SEQUENCE: 309

Gly Tyr Thr Phe Ile Ser Tyr Thr
1               5

<210> SEQ ID NO 310
<211> LENGTH: 8
<212> TYPE: PRT
<213> ORGANISM: Artificial sequence
<220> FEATURE:

<223> OTHER INFORMATION: Synthetic antibody

<400> SEQUENCE: 310

Ile Asn Gly Gly Asn Gly Asn Thr
1               5

<210> SEQ ID NO 311
<211> LENGTH: 18
<212> TYPE: PRT
<213> ORGANISM: Artificial sequence
<220> FEATURE:
<223> OTHER INFORMATION: Synthetic antibody

<400> SEQUENCE: 311

Ala Arg Val Lys Ser Asp Thr Leu Asp Phe Asn Trp Asn Pro Arg Phe
1               5                   10                  15

Asp Tyr

<210> SEQ ID NO 312
<211> LENGTH: 9
<212> TYPE: PRT
<213> ORGANISM: Artificial sequence
<220> FEATURE:
<223> OTHER INFORMATION: Synthetic antibody

<400> SEQUENCE: 312

Gly Tyr Ser Ile Ser Ser Gly Tyr Tyr
1               5

<210> SEQ ID NO 313
<211> LENGTH: 7
<212> TYPE: PRT
<213> ORGANISM: Artificial sequence
<220> FEATURE:
<223> OTHER INFORMATION: Synthetic antibody

<400> SEQUENCE: 313

Ile Tyr His Ser Gly Ile Ile
1               5

<210> SEQ ID NO 314
<211> LENGTH: 9
<212> TYPE: PRT
<213> ORGANISM: Artificial sequence
<220> FEATURE:
<223> OTHER INFORMATION: Synthetic antibody

<400> SEQUENCE: 314

Ala Arg Leu Leu Pro Ser Asn Ile Tyr
1               5

<210> SEQ ID NO 315
<211> LENGTH: 8
<212> TYPE: PRT
<213> ORGANISM: Artificial sequence
<220> FEATURE:
<223> OTHER INFORMATION: Synthetic antibody

<400> SEQUENCE: 315

Gly Phe Thr Phe Asp Asp Tyr Ala
1               5

<210> SEQ ID NO 316
<211> LENGTH: 8
<212> TYPE: PRT
<213> ORGANISM: Artificial sequence -continued

```
<220> FEATURE:
<223> OTHER INFORMATION: Synthetic antibody

<400> SEQUENCE: 316

Ile Ser Trp His Ser Gly Ser Ile
1               5

<210> SEQ ID NO 317
<211> LENGTH: 16
<212> TYPE: PRT
<213> ORGANISM: Artificial sequence
<220> FEATURE:
<223> OTHER INFORMATION: Synthetic antibody

<400> SEQUENCE: 317

Ala Lys Ser Pro Leu Lys Ile Trp Gln His Leu Thr Pro Tyr Asp Tyr
1               5                   10                  15

<210> SEQ ID NO 318
<211> LENGTH: 10
<212> TYPE: PRT
<213> ORGANISM: Artificial sequence
<220> FEATURE:
<223> OTHER INFORMATION: Synthetic antibody

<400> SEQUENCE: 318

Asp Gly Ser Ile Ser Ser Gly Asp Tyr Tyr
1               5                   10

<210> SEQ ID NO 319
<211> LENGTH: 7
<212> TYPE: PRT
<213> ORGANISM: Artificial sequence
<220> FEATURE:
<223> OTHER INFORMATION: Synthetic antibody

<400> SEQUENCE: 319

Ile Tyr Tyr Ser Gly Ser Thr
1               5

<210> SEQ ID NO 320
<211> LENGTH: 22
<212> TYPE: PRT
<213> ORGANISM: Artificial sequence
<220> FEATURE:
<223> OTHER INFORMATION: Synthetic antibody

<400> SEQUENCE: 320

Ala Thr Ala Pro Ala Val Gly Ser Tyr Tyr Met Arg Trp Thr Gly Tyr
1               5                   10                  15

His Tyr Tyr Met Asp Val
            20

<210> SEQ ID NO 321
<211> LENGTH: 10
<212> TYPE: PRT
<213> ORGANISM: Artificial sequence
<220> FEATURE:
<223> OTHER INFORMATION: Synthetic antibody

<400> SEQUENCE: 321

Asp Gly Ser Ile Ser Ser Gly Asp Tyr Tyr
1               5                   10

<210> SEQ ID NO 322
<211> LENGTH: 7
```

```
<212> TYPE: PRT
<213> ORGANISM: Artificial sequence
<220> FEATURE:
<223> OTHER INFORMATION: Synthetic antibody

<400> SEQUENCE: 322

Ile Tyr Tyr Ser Gly Ser Thr
1               5

<210> SEQ ID NO 323
<211> LENGTH: 22
<212> TYPE: PRT
<213> ORGANISM: Artificial sequence
<220> FEATURE:
<223> OTHER INFORMATION: Synthetic antibody

<400> SEQUENCE: 323

Ala Thr Ala Pro Ala Val Gly Ser Tyr Tyr Met Arg Trp Thr Gly Tyr
1               5                   10                  15

His Tyr Tyr Met Asp Val
            20

<210> SEQ ID NO 324
<211> LENGTH: 8
<212> TYPE: PRT
<213> ORGANISM: Artificial sequence
<220> FEATURE:
<223> OTHER INFORMATION: Synthetic antibody

<400> SEQUENCE: 324

Gly Leu Thr Phe Ser Arg Ser Ala
1               5

<210> SEQ ID NO 325
<211> LENGTH: 8
<212> TYPE: PRT
<213> ORGANISM: Artificial sequence
<220> FEATURE:
<223> OTHER INFORMATION: Synthetic antibody

<400> SEQUENCE: 325

Ile Val Val Gly Ser Gly Asn Thr
1               5

<210> SEQ ID NO 326
<211> LENGTH: 19
<212> TYPE: PRT
<213> ORGANISM: Artificial sequence
<220> FEATURE:
<223> OTHER INFORMATION: Synthetic antibody

<400> SEQUENCE: 326

Ala Ala Gly Pro Gly Val Trp Ala Arg Thr Glu Arg Pro Asn Asp Ala
1               5                   10                  15

Phe Asn Leu

<210> SEQ ID NO 327
<211> LENGTH: 8
<212> TYPE: PRT
<213> ORGANISM: Artificial sequence
<220> FEATURE:
<223> OTHER INFORMATION: Synthetic antibody

<400> SEQUENCE: 327

Gly Phe Thr Phe Ser Ser Tyr Ala
1               5
```

<210> SEQ ID NO 328
<211> LENGTH: 8
<212> TYPE: PRT
<213> ORGANISM: Artificial sequence
<220> FEATURE:
<223> OTHER INFORMATION: Synthetic antibody

<400> SEQUENCE: 328

Ile Thr Gly Ser Gly Gly Ser Thr
1               5

<210> SEQ ID NO 329
<211> LENGTH: 20
<212> TYPE: PRT
<213> ORGANISM: Artificial sequence
<220> FEATURE:
<223> OTHER INFORMATION: Synthetic antibody

<400> SEQUENCE: 329

Ala Lys Arg Tyr Cys Ser Gly Thr Thr Ser His Leu Tyr Cys Tyr Tyr
1               5                   10                  15

Ala Met Asp Val
            20

<210> SEQ ID NO 330
<211> LENGTH: 9
<212> TYPE: PRT
<213> ORGANISM: Artificial sequence
<220> FEATURE:
<223> OTHER INFORMATION: Synthetic antibody

<400> SEQUENCE: 330

Asp Tyr Ser Ile Ser Ser Gly Tyr Tyr
1               5

<210> SEQ ID NO 331
<211> LENGTH: 7
<212> TYPE: PRT
<213> ORGANISM: Artificial sequence
<220> FEATURE:
<223> OTHER INFORMATION: Synthetic antibody

<400> SEQUENCE: 331

Ile Tyr His Gly Gly Ser Thr
1               5

<210> SEQ ID NO 332
<211> LENGTH: 15
<212> TYPE: PRT
<213> ORGANISM: Artificial sequence
<220> FEATURE:
<223> OTHER INFORMATION: Synthetic antibody

<400> SEQUENCE: 332

Ala Ser Arg His Asp Arg Ser Gly Tyr Asp Glu Tyr Phe Glu Tyr
1               5                   10                  15

<210> SEQ ID NO 333
<211> LENGTH: 8
<212> TYPE: PRT
<213> ORGANISM: Artificial sequence
<220> FEATURE:
<223> OTHER INFORMATION: Synthetic antibody

<400> SEQUENCE: 333

Gly Phe Thr Val Ser Ser Thr Tyr
1               5

<210> SEQ ID NO 334
<211> LENGTH: 7
<212> TYPE: PRT
<213> ORGANISM: Artificial sequence
<220> FEATURE:
<223> OTHER INFORMATION: Synthetic antibody

<400> SEQUENCE: 334

Ile Tyr Ser Gly Gly Ser Thr
1               5

<210> SEQ ID NO 335
<211> LENGTH: 14
<212> TYPE: PRT
<213> ORGANISM: Artificial sequence
<220> FEATURE:
<223> OTHER INFORMATION: Synthetic antibody

<400> SEQUENCE: 335

Ala Arg Ile Pro Leu Ser Phe Gly Pro Met Tyr Phe Asp Tyr
1               5                   10

<210> SEQ ID NO 336
<211> LENGTH: 8
<212> TYPE: PRT
<213> ORGANISM: Artificial sequence
<220> FEATURE:
<223> OTHER INFORMATION: Synthetic antibody

<400> SEQUENCE: 336

Gly Phe Thr Val Ser Ser Thr Tyr
1               5

<210> SEQ ID NO 337
<211> LENGTH: 7
<212> TYPE: PRT
<213> ORGANISM: Artificial sequence
<220> FEATURE:
<223> OTHER INFORMATION: Synthetic antibody

<400> SEQUENCE: 337

Ile Tyr Ser Gly Gly Ser Thr
1               5

<210> SEQ ID NO 338
<211> LENGTH: 14
<212> TYPE: PRT
<213> ORGANISM: Artificial sequence
<220> FEATURE:
<223> OTHER INFORMATION: Synthetic antibody

<400> SEQUENCE: 338

Ala Arg Ile Pro Leu Ser Phe Gly Pro Met Tyr Phe Asp Tyr
1               5                   10

<210> SEQ ID NO 339
<211> LENGTH: 8
<212> TYPE: PRT
<213> ORGANISM: Artificial sequence
<220> FEATURE:
<223> OTHER INFORMATION: Synthetic antibody

<400> SEQUENCE: 339

Gly Phe Thr Phe Ser Asp Tyr Tyr

-continued 1               5

<210> SEQ ID NO 340
<211> LENGTH: 8
<212> TYPE: PRT
<213> ORGANISM: Artificial sequence
<220> FEATURE:
<223> OTHER INFORMATION: Synthetic antibody

<400> SEQUENCE: 340

Ile Ser Ser Ser Ala Thr Thr Ile
1               5

<210> SEQ ID NO 341
<211> LENGTH: 19
<212> TYPE: PRT
<213> ORGANISM: Artificial sequence
<220> FEATURE:
<223> OTHER INFORMATION: Synthetic antibody

<400> SEQUENCE: 341

Ala Arg Asp His Arg Tyr Cys Thr Ser Thr Asn Cys Phe Ala His Trp
1               5                   10                  15

Phe Asp Pro

<210> SEQ ID NO 342
<211> LENGTH: 8
<212> TYPE: PRT
<213> ORGANISM: Artificial sequence
<220> FEATURE:
<223> OTHER INFORMATION: Synthetic antibody

<400> SEQUENCE: 342

Gly Tyr Thr Phe Ser Ser Tyr Tyr
1               5

<210> SEQ ID NO 343
<211> LENGTH: 8
<212> TYPE: PRT
<213> ORGANISM: Artificial sequence
<220> FEATURE:
<223> OTHER INFORMATION: Synthetic antibody

<400> SEQUENCE: 343

Ile Asn Pro Ser Val Gly Ala Thr
1               5

<210> SEQ ID NO 344
<211> LENGTH: 16
<212> TYPE: PRT
<213> ORGANISM: Artificial sequence
<220> FEATURE:
<223> OTHER INFORMATION: Synthetic antibody

<400> SEQUENCE: 344

Ala Arg Trp Gly Leu Ile Ser Glu Ser Ser Pro Lys Tyr Phe Asp Ser
1               5                   10                  15

<210> SEQ ID NO 345
<211> LENGTH: 10
<212> TYPE: PRT
<213> ORGANISM: Artificial sequence
<220> FEATURE:
<223> OTHER INFORMATION: Synthetic antibody

<400> SEQUENCE: 345

```
Gly Phe Ser Leu Ser Asn Ser Gly Val Gly
1               5                   10

<210> SEQ ID NO 346
<211> LENGTH: 7
<212> TYPE: PRT
<213> ORGANISM: Artificial sequence
<220> FEATURE:
<223> OTHER INFORMATION: Synthetic antibody

<400> SEQUENCE: 346

Ile Tyr Trp Asp Asp Asp Lys
1               5

<210> SEQ ID NO 347
<211> LENGTH: 29
<212> TYPE: PRT
<213> ORGANISM: Artificial sequence
<220> FEATURE:
<223> OTHER INFORMATION: Synthetic antibody

<400> SEQUENCE: 347

Ala His Ser Tyr Phe Asp Phe Trp Ser Gly Tyr Phe Ser Leu Asp Arg
1               5                   10                  15

Arg Asp Arg Arg Ala Gly Arg Gln Ser Tyr Phe Asp Tyr
            20                  25

<210> SEQ ID NO 348
<211> LENGTH: 9
<212> TYPE: PRT
<213> ORGANISM: Artificial sequence
<220> FEATURE:
<223> OTHER INFORMATION: Synthetic antibody

<400> SEQUENCE: 348

Gly Gly Ser Ile Thr Thr Asn Asn Trp
1               5

<210> SEQ ID NO 349
<211> LENGTH: 7
<212> TYPE: PRT
<213> ORGANISM: Artificial sequence
<220> FEATURE:
<223> OTHER INFORMATION: Synthetic antibody

<400> SEQUENCE: 349

Ile Phe His Gly Gly Lys Thr
1               5

<210> SEQ ID NO 350
<211> LENGTH: 15
<212> TYPE: PRT
<213> ORGANISM: Artificial sequence
<220> FEATURE:
<223> OTHER INFORMATION: Synthetic antibody

<400> SEQUENCE: 350

Ala Arg Ala Gly Leu Tyr Ser Thr Asn Trp Ser Pro Phe Asp Pro
1               5                   10                  15

<210> SEQ ID NO 351
<211> LENGTH: 8
<212> TYPE: PRT
<213> ORGANISM: Artificial sequence
<220> FEATURE:
<223> OTHER INFORMATION: Synthetic antibody
```

```
<400> SEQUENCE: 351

Gly Tyr Thr Phe Ser Ser Tyr Tyr
1               5

<210> SEQ ID NO 352
<211> LENGTH: 8
<212> TYPE: PRT
<213> ORGANISM: Artificial sequence
<220> FEATURE:
<223> OTHER INFORMATION: Synthetic antibody

<400> SEQUENCE: 352

Ile Asn Pro Ser Val Gly Ala Thr
1               5

<210> SEQ ID NO 353
<211> LENGTH: 16
<212> TYPE: PRT
<213> ORGANISM: Artificial sequence
<220> FEATURE:
<223> OTHER INFORMATION: Synthetic antibody

<400> SEQUENCE: 353

Ala Arg Trp Gly Leu Ile Ser Glu Ser Ser Pro Lys Tyr Phe Asp Ser
1               5                   10                  15

<210> SEQ ID NO 354
<211> LENGTH: 8
<212> TYPE: PRT
<213> ORGANISM: Artificial sequence
<220> FEATURE:
<223> OTHER INFORMATION: Synthetic antibody

<400> SEQUENCE: 354

Gly Gly Thr Phe Ser Ser Tyr Ser
1               5

<210> SEQ ID NO 355
<211> LENGTH: 8
<212> TYPE: PRT
<213> ORGANISM: Artificial sequence
<220> FEATURE:
<223> OTHER INFORMATION: Synthetic antibody

<400> SEQUENCE: 355

Ile Ile Pro Met Phe Gly Thr Ala
1               5

<210> SEQ ID NO 356
<211> LENGTH: 10
<212> TYPE: PRT
<213> ORGANISM: Artificial sequence
<220> FEATURE:
<223> OTHER INFORMATION: Synthetic antibody

<400> SEQUENCE: 356

Ala Arg Glu Ala Arg Ala Glu Gly Asp Val
1               5                   10

<210> SEQ ID NO 357
<211> LENGTH: 6
<212> TYPE: PRT
<213> ORGANISM: Artificial sequence
<220> FEATURE:
<223> OTHER INFORMATION: Synthetic antibody

<400> SEQUENCE: 357
```

Gln Ser Val Ser Ser Asp
1               5

<210> SEQ ID NO 358
<211> LENGTH: 3
<212> TYPE: PRT
<213> ORGANISM: Artificial sequence
<220> FEATURE:
<223> OTHER INFORMATION: Synthetic antibody

<400> SEQUENCE: 358

Asp Ala Ser
1

<210> SEQ ID NO 359
<211> LENGTH: 10
<212> TYPE: PRT
<213> ORGANISM: Artificial sequence
<220> FEATURE:
<223> OTHER INFORMATION: Synthetic antibody

<400> SEQUENCE: 359

Gln Gln Tyr Asn Asn Trp Pro Pro Trp Thr
1               5                   10

<210> SEQ ID NO 360
<211> LENGTH: 6
<212> TYPE: PRT
<213> ORGANISM: Artificial sequence
<220> FEATURE:
<223> OTHER INFORMATION: Synthetic antibody

<400> SEQUENCE: 360

Gln Ser Val Ser Ser Asp
1               5

<210> SEQ ID NO 361
<211> LENGTH: 3
<212> TYPE: PRT
<213> ORGANISM: Artificial sequence
<220> FEATURE:
<223> OTHER INFORMATION: Synthetic antibody

<400> SEQUENCE: 361

Asp Ala Ser
1

<210> SEQ ID NO 362
<211> LENGTH: 10
<212> TYPE: PRT
<213> ORGANISM: Artificial sequence
<220> FEATURE:
<223> OTHER INFORMATION: Synthetic antibody

<400> SEQUENCE: 362

Gln Gln Tyr Asn Asn Trp Pro Pro Trp Thr
1               5                   10

<210> SEQ ID NO 363
<211> LENGTH: 8
<212> TYPE: PRT
<213> ORGANISM: Artificial sequence
<220> FEATURE:
<223> OTHER INFORMATION: Synthetic antibody

<400> SEQUENCE: 363

```
Ser Ser Asn Ile Glu Ser Asn Thr
1               5

<210> SEQ ID NO 364
<211> LENGTH: 3
<212> TYPE: PRT
<213> ORGANISM: Artificial sequence
<220> FEATURE:
<223> OTHER INFORMATION: Synthetic antibody

<400> SEQUENCE: 364

Gly Asn Asn
1

<210> SEQ ID NO 365
<211> LENGTH: 11
<212> TYPE: PRT
<213> ORGANISM: Artificial sequence
<220> FEATURE:
<223> OTHER INFORMATION: Synthetic antibody

<400> SEQUENCE: 365

Ala Ala Trp Asp Asp Gly Leu Asn Gly Trp Val
1               5                   10

<210> SEQ ID NO 366
<211> LENGTH: 9
<212> TYPE: PRT
<213> ORGANISM: Artificial sequence
<220> FEATURE:
<223> OTHER INFORMATION: Synthetic antibody

<400> SEQUENCE: 366

Ser Ser Asp Val Gly Gly Tyr Asn Tyr
1               5

<210> SEQ ID NO 367
<211> LENGTH: 3
<212> TYPE: PRT
<213> ORGANISM: Artificial sequence
<220> FEATURE:
<223> OTHER INFORMATION: Synthetic antibody

<400> SEQUENCE: 367

Asp Val Thr
1

<210> SEQ ID NO 368
<211> LENGTH: 8
<212> TYPE: PRT
<213> ORGANISM: Artificial sequence
<220> FEATURE:
<223> OTHER INFORMATION: Synthetic antibody

<400> SEQUENCE: 368

Cys Ser Tyr Ala Gly Thr Val Val
1               5

<210> SEQ ID NO 369
<211> LENGTH: 6
<212> TYPE: PRT
<213> ORGANISM: Artificial sequence
<220> FEATURE:
<223> OTHER INFORMATION: Synthetic antibody

<400> SEQUENCE: 369

Leu Asn Ile Gly Ser Tyr
```

-continued

```
1               5

<210> SEQ ID NO 370
<211> LENGTH: 3
<212> TYPE: PRT
<213> ORGANISM: Artificial sequence
<220> FEATURE:
<223> OTHER INFORMATION: Synthetic antibody

<400> SEQUENCE: 370

Asp Ala Ser
1

<210> SEQ ID NO 371
<211> LENGTH: 11
<212> TYPE: PRT
<213> ORGANISM: Artificial sequence
<220> FEATURE:
<223> OTHER INFORMATION: Synthetic antibody

<400> SEQUENCE: 371

Gln Gln Arg Ser Asn Trp Pro Pro Gly Tyr Thr
1               5                   10

<210> SEQ ID NO 372
<211> LENGTH: 9
<212> TYPE: PRT
<213> ORGANISM: Artificial sequence
<220> FEATURE:
<223> OTHER INFORMATION: Synthetic antibody

<400> SEQUENCE: 372

Ser Ser Asp Val Gly Ser Tyr Asn Leu
1               5

<210> SEQ ID NO 373
<211> LENGTH: 3
<212> TYPE: PRT
<213> ORGANISM: Artificial sequence
<220> FEATURE:
<223> OTHER INFORMATION: Synthetic antibody

<400> SEQUENCE: 373

Glu Val Ser
1

<210> SEQ ID NO 374
<211> LENGTH: 11
<212> TYPE: PRT
<213> ORGANISM: Artificial sequence
<220> FEATURE:
<223> OTHER INFORMATION: Synthetic antibody

<400> SEQUENCE: 374

Cys Ser Tyr Gly Gly Phe Ser Thr His Val Val
1               5                   10

<210> SEQ ID NO 375
<211> LENGTH: 8
<212> TYPE: PRT
<213> ORGANISM: Artificial sequence
<220> FEATURE:
<223> OTHER INFORMATION: Synthetic antibody

<400> SEQUENCE: 375

Ser Ser Asn Ile Gly Asn Asn Tyr
1               5
```

-continued

```
<210> SEQ ID NO 376
<211> LENGTH: 3
<212> TYPE: PRT
<213> ORGANISM: Artificial sequence
<220> FEATURE:
<223> OTHER INFORMATION: Synthetic antibody

<400> SEQUENCE: 376

Asp Asp Asn
1

<210> SEQ ID NO 377
<211> LENGTH: 11
<212> TYPE: PRT
<213> ORGANISM: Artificial sequence
<220> FEATURE:
<223> OTHER INFORMATION: Synthetic antibody

<400> SEQUENCE: 377

Gly Thr Trp Asp Ser Ser Leu Ser Val Phe Val
1               5                   10

<210> SEQ ID NO 378
<211> LENGTH: 6
<212> TYPE: PRT
<213> ORGANISM: Artificial sequence
<220> FEATURE:
<223> OTHER INFORMATION: Synthetic antibody

<400> SEQUENCE: 378

Gln Ser Ile Thr Ser Trp
1               5

<210> SEQ ID NO 379
<211> LENGTH: 3
<212> TYPE: PRT
<213> ORGANISM: Artificial sequence
<220> FEATURE:
<223> OTHER INFORMATION: Synthetic antibody

<400> SEQUENCE: 379

Lys Ala Ser
1

<210> SEQ ID NO 380
<211> LENGTH: 9
<212> TYPE: PRT
<213> ORGANISM: Artificial sequence
<220> FEATURE:
<223> OTHER INFORMATION: Synthetic antibody

<400> SEQUENCE: 380

Gln Gln Tyr Asn Thr Tyr Thr Trp Thr
1               5

<210> SEQ ID NO 381
<211> LENGTH: 7
<212> TYPE: PRT
<213> ORGANISM: Artificial sequence
<220> FEATURE:
<223> OTHER INFORMATION: Synthetic antibody

<400> SEQUENCE: 381

Gln Ser Leu Ser Ser Ser Tyr
1               5
```

```
<210> SEQ ID NO 382
<211> LENGTH: 3
<212> TYPE: PRT
<213> ORGANISM: Artificial sequence
<220> FEATURE:
<223> OTHER INFORMATION: Synthetic antibody

<400> SEQUENCE: 382

Gly Ala Ser
1

<210> SEQ ID NO 383
<211> LENGTH: 10
<212> TYPE: PRT
<213> ORGANISM: Artificial sequence
<220> FEATURE:
<223> OTHER INFORMATION: Synthetic antibody

<400> SEQUENCE: 383

Gln Gln Tyr Gly Ser Thr Pro Pro Tyr Thr
1               5                   10

<210> SEQ ID NO 384
<211> LENGTH: 8
<212> TYPE: PRT
<213> ORGANISM: Artificial sequence
<220> FEATURE:
<223> OTHER INFORMATION: Synthetic antibody

<400> SEQUENCE: 384

Arg Gly Ser Ile Ala Ser Asn Tyr
1               5

<210> SEQ ID NO 385
<211> LENGTH: 3
<212> TYPE: PRT
<213> ORGANISM: Artificial sequence
<220> FEATURE:
<223> OTHER INFORMATION: Synthetic antibody

<400> SEQUENCE: 385

Glu Asp Asn
1

<210> SEQ ID NO 386
<211> LENGTH: 9
<212> TYPE: PRT
<213> ORGANISM: Artificial sequence
<220> FEATURE:
<223> OTHER INFORMATION: Synthetic antibody

<400> SEQUENCE: 386

Gln Ser Tyr Asp Ser Tyr Asn His Val
1               5

<210> SEQ ID NO 387
<211> LENGTH: 6
<212> TYPE: PRT
<213> ORGANISM: Artificial sequence
<220> FEATURE:
<223> OTHER INFORMATION: Synthetic antibody

<400> SEQUENCE: 387

Gln Ser Ile Ser Ser Tyr
1               5
```

-continued

<210> SEQ ID NO 388
<211> LENGTH: 3
<212> TYPE: PRT
<213> ORGANISM: Artificial sequence
<220> FEATURE:
<223> OTHER INFORMATION: Synthetic antibody

<400> SEQUENCE: 388

Ala Ala Ser
1

<210> SEQ ID NO 389
<211> LENGTH: 10
<212> TYPE: PRT
<213> ORGANISM: Artificial sequence
<220> FEATURE:
<223> OTHER INFORMATION: Synthetic antibody

<400> SEQUENCE: 389

Gln Gln Ser Tyr Ser Ile Ser Pro Leu Ser
1               5                   10

<210> SEQ ID NO 390
<211> LENGTH: 6
<212> TYPE: PRT
<213> ORGANISM: Artificial sequence
<220> FEATURE:
<223> OTHER INFORMATION: Synthetic antibody

<400> SEQUENCE: 390

Gln Ser Val Arg Ser Asn
1               5

<210> SEQ ID NO 391
<211> LENGTH: 3
<212> TYPE: PRT
<213> ORGANISM: Artificial sequence
<220> FEATURE:
<223> OTHER INFORMATION: Synthetic antibody

<400> SEQUENCE: 391

Gly Ala Ser
1

<210> SEQ ID NO 392
<211> LENGTH: 9
<212> TYPE: PRT
<213> ORGANISM: Artificial sequence
<220> FEATURE:
<223> OTHER INFORMATION: Synthetic antibody

<400> SEQUENCE: 392

His Gln Tyr Asn Asn Trp Pro Gln Thr
1               5

<210> SEQ ID NO 393
<211> LENGTH: 12
<212> TYPE: PRT
<213> ORGANISM: Artificial sequence
<220> FEATURE:
<223> OTHER INFORMATION: Synthetic antibody

<400> SEQUENCE: 393

Gln Ser Val Leu Tyr Arg Ser Asn Asn Asn Asn Tyr
1               5                   10

<210> SEQ ID NO 394

```
<211> LENGTH: 3
<212> TYPE: PRT
<213> ORGANISM: Artificial sequence
<220> FEATURE:
<223> OTHER INFORMATION: Synthetic antibody

<400> SEQUENCE: 394

Trp Ala Ser
1

<210> SEQ ID NO 395
<211> LENGTH: 8
<212> TYPE: PRT
<213> ORGANISM: Artificial sequence
<220> FEATURE:
<223> OTHER INFORMATION: Synthetic antibody

<400> SEQUENCE: 395

Gln Gln Tyr Tyr Gly Thr Val Thr
1               5

<210> SEQ ID NO 396
<211> LENGTH: 9
<212> TYPE: PRT
<213> ORGANISM: Artificial sequence
<220> FEATURE:
<223> OTHER INFORMATION: Synthetic antibody

<400> SEQUENCE: 396

Ser Ser Asp Val Gly Gly Tyr Asn Tyr
1               5

<210> SEQ ID NO 397
<211> LENGTH: 3
<212> TYPE: PRT
<213> ORGANISM: Artificial sequence
<220> FEATURE:
<223> OTHER INFORMATION: Synthetic antibody

<400> SEQUENCE: 397

Asp Val Asn
1

<210> SEQ ID NO 398
<211> LENGTH: 10
<212> TYPE: PRT
<213> ORGANISM: Artificial sequence
<220> FEATURE:
<223> OTHER INFORMATION: Synthetic antibody

<400> SEQUENCE: 398

Cys Ser Tyr Ala Gly Ser Tyr Thr Trp Val
1               5                   10

<210> SEQ ID NO 399
<211> LENGTH: 6
<212> TYPE: PRT
<213> ORGANISM: Artificial sequence
<220> FEATURE:
<223> OTHER INFORMATION: Synthetic antibody

<400> SEQUENCE: 399

Gln Ser Ile Ser Asn Trp
1               5

<210> SEQ ID NO 400
<211> LENGTH: 3
```

```
<212> TYPE: PRT
<213> ORGANISM: Artificial sequence
<220> FEATURE:
<223> OTHER INFORMATION: Synthetic antibody

<400> SEQUENCE: 400

Lys Ala Ser
1

<210> SEQ ID NO 401
<211> LENGTH: 9
<212> TYPE: PRT
<213> ORGANISM: Artificial sequence
<220> FEATURE:
<223> OTHER INFORMATION: Synthetic antibody

<400> SEQUENCE: 401

Gln Gln Tyr Asn Gly Tyr Ser Tyr Thr
1               5

<210> SEQ ID NO 402
<211> LENGTH: 6
<212> TYPE: PRT
<213> ORGANISM: Artificial sequence
<220> FEATURE:
<223> OTHER INFORMATION: Synthetic antibody

<400> SEQUENCE: 402

Glu Leu Gly Asp Lys Tyr
1               5

<210> SEQ ID NO 403
<211> LENGTH: 3
<212> TYPE: PRT
<213> ORGANISM: Artificial sequence
<220> FEATURE:
<223> OTHER INFORMATION: Synthetic antibody

<400> SEQUENCE: 403

Gln Asp Asn
1

<210> SEQ ID NO 404
<211> LENGTH: 10
<212> TYPE: PRT
<213> ORGANISM: Artificial sequence
<220> FEATURE:
<223> OTHER INFORMATION: Synthetic antibody

<400> SEQUENCE: 404

Gln Ala Trp Asp Ser Ser Thr Ala Tyr Val
1               5                   10

<210> SEQ ID NO 405
<211> LENGTH: 6
<212> TYPE: PRT
<213> ORGANISM: Artificial sequence
<220> FEATURE:
<223> OTHER INFORMATION: Synthetic antibody

<400> SEQUENCE: 405

Gln Ser Ile Arg Ser Tyr
1               5

<210> SEQ ID NO 406
<211> LENGTH: 3
<212> TYPE: PRT
```

<213> ORGANISM: Artificial sequence
<220> FEATURE:
<223> OTHER INFORMATION: Synthetic antibody

<400> SEQUENCE: 406

Ala Gly Ser
1

<210> SEQ ID NO 407
<211> LENGTH: 9
<212> TYPE: PRT
<213> ORGANISM: Artificial sequence
<220> FEATURE:
<223> OTHER INFORMATION: Synthetic antibody

<400> SEQUENCE: 407

Gln Gln Ser Ser Thr Thr Pro Trp Thr
1               5

<210> SEQ ID NO 408
<211> LENGTH: 9
<212> TYPE: PRT
<213> ORGANISM: Artificial sequence
<220> FEATURE:
<223> OTHER INFORMATION: Synthetic antibody

<400> SEQUENCE: 408

Ser Ser Asp Val Gly Gly Tyr Asn Tyr
1               5

<210> SEQ ID NO 409
<211> LENGTH: 3
<212> TYPE: PRT
<213> ORGANISM: Artificial sequence
<220> FEATURE:
<223> OTHER INFORMATION: Synthetic antibody

<400> SEQUENCE: 409

Asp Val Ser
1

<210> SEQ ID NO 410
<211> LENGTH: 10
<212> TYPE: PRT
<213> ORGANISM: Artificial sequence
<220> FEATURE:
<223> OTHER INFORMATION: Synthetic antibody

<400> SEQUENCE: 410

Ser Ser Tyr Thr Thr Ser Asn Ser Tyr Val
1               5                   10

<210> SEQ ID NO 411
<211> LENGTH: 9
<212> TYPE: PRT
<213> ORGANISM: Artificial sequence
<220> FEATURE:
<223> OTHER INFORMATION: Synthetic antibody

<400> SEQUENCE: 411

Ser Ser Asp Val Gly Thr Tyr Asn Leu
1               5

<210> SEQ ID NO 412
<211> LENGTH: 3
<212> TYPE: PRT
<213> ORGANISM: Artificial sequence -continued

```
<220> FEATURE:
<223> OTHER INFORMATION: Synthetic antibody

<400> SEQUENCE: 412

Glu Val Ser
1

<210> SEQ ID NO 413
<211> LENGTH: 11
<212> TYPE: PRT
<213> ORGANISM: Artificial sequence
<220> FEATURE:
<223> OTHER INFORMATION: Synthetic antibody

<400> SEQUENCE: 413

Cys Ser Tyr Ala Gly Gly Ser Asn Ser Val Leu
1               5                   10

<210> SEQ ID NO 414
<211> LENGTH: 6
<212> TYPE: PRT
<213> ORGANISM: Artificial sequence
<220> FEATURE:
<223> OTHER INFORMATION: Synthetic antibody

<400> SEQUENCE: 414

Gln Asp Ile Ser Ser Tyr
1               5

<210> SEQ ID NO 415
<211> LENGTH: 3
<212> TYPE: PRT
<213> ORGANISM: Artificial sequence
<220> FEATURE:
<223> OTHER INFORMATION: Synthetic antibody

<400> SEQUENCE: 415

Ala Ala Ser
1

<210> SEQ ID NO 416
<211> LENGTH: 9
<212> TYPE: PRT
<213> ORGANISM: Artificial sequence
<220> FEATURE:
<223> OTHER INFORMATION: Synthetic antibody

<400> SEQUENCE: 416

Gln Gln Tyr Asn Ile Tyr Pro Ile Thr
1               5

<210> SEQ ID NO 417
<211> LENGTH: 9
<212> TYPE: PRT
<213> ORGANISM: Artificial sequence
<220> FEATURE:
<223> OTHER INFORMATION: Synthetic antibody

<400> SEQUENCE: 417

Ser Asn Asp Val Gly Ser Tyr Asn Leu
1               5

<210> SEQ ID NO 418
<211> LENGTH: 3
<212> TYPE: PRT
<213> ORGANISM: Artificial sequence
<220> FEATURE:
```

<223> OTHER INFORMATION: Synthetic antibody

<400> SEQUENCE: 418

Glu Val Ser
1

<210> SEQ ID NO 419
<211> LENGTH: 10
<212> TYPE: PRT
<213> ORGANISM: Artificial sequence
<220> FEATURE:
<223> OTHER INFORMATION: Synthetic antibody

<400> SEQUENCE: 419

Cys Ser Tyr Ala Gly Ser Met Thr Trp Val
1               5                   10

<210> SEQ ID NO 420
<211> LENGTH: 9
<212> TYPE: PRT
<213> ORGANISM: Artificial sequence
<220> FEATURE:
<223> OTHER INFORMATION: Synthetic antibody

<400> SEQUENCE: 420

Ser Ser Asp Val Gly Gly Tyr Asn Tyr
1               5

<210> SEQ ID NO 421
<211> LENGTH: 3
<212> TYPE: PRT
<213> ORGANISM: Artificial sequence
<220> FEATURE:
<223> OTHER INFORMATION: Synthetic antibody

<400> SEQUENCE: 421

Asp Val Ser
1

<210> SEQ ID NO 422
<211> LENGTH: 10
<212> TYPE: PRT
<213> ORGANISM: Artificial sequence
<220> FEATURE:
<223> OTHER INFORMATION: Synthetic antibody

<400> SEQUENCE: 422

Tyr Ser Tyr Thr Ser Asn Ser Thr Tyr Val
1               5                   10

<210> SEQ ID NO 423
<211> LENGTH: 9
<212> TYPE: PRT
<213> ORGANISM: Artificial sequence
<220> FEATURE:
<223> OTHER INFORMATION: Synthetic antibody

<400> SEQUENCE: 423

Ser Ser Asn Ile Gly Ala Gly Tyr Asp
1               5

<210> SEQ ID NO 424
<211> LENGTH: 3
<212> TYPE: PRT
<213> ORGANISM: Artificial sequence
<220> FEATURE:
<223> OTHER INFORMATION: Synthetic antibody

```
<400> SEQUENCE: 424

Asp Asn Asn
1

<210> SEQ ID NO 425
<211> LENGTH: 11
<212> TYPE: PRT
<213> ORGANISM: Artificial sequence
<220> FEATURE:
<223> OTHER INFORMATION: Synthetic antibody

<400> SEQUENCE: 425

Gln Ser Phe Asp Ser Ser Leu Ser Arg Gly Val
1               5                   10

<210> SEQ ID NO 426
<211> LENGTH: 6
<212> TYPE: PRT
<213> ORGANISM: Artificial sequence
<220> FEATURE:
<223> OTHER INFORMATION: Synthetic antibody

<400> SEQUENCE: 426

Gln Asn Ile Asn Ser Trp
1               5

<210> SEQ ID NO 427
<211> LENGTH: 3
<212> TYPE: PRT
<213> ORGANISM: Artificial sequence
<220> FEATURE:
<223> OTHER INFORMATION: Synthetic antibody

<400> SEQUENCE: 427

Lys Ala Ser
1

<210> SEQ ID NO 428
<211> LENGTH: 7
<212> TYPE: PRT
<213> ORGANISM: Artificial sequence
<220> FEATURE:
<223> OTHER INFORMATION: Synthetic antibody

<400> SEQUENCE: 428

Gln Gln Tyr Asn Ser Phe His
1               5

<210> SEQ ID NO 429
<211> LENGTH: 9
<212> TYPE: PRT
<213> ORGANISM: Artificial sequence
<220> FEATURE:
<223> OTHER INFORMATION: Synthetic antibody

<400> SEQUENCE: 429

Ser Ser Asn Ile Gly Ala Gly Tyr Asp
1               5

<210> SEQ ID NO 430
<211> LENGTH: 3
<212> TYPE: PRT
<213> ORGANISM: Artificial sequence
<220> FEATURE:
<223> OTHER INFORMATION: Synthetic antibody
```

```
<400> SEQUENCE: 430

Asn Asn Ser
1

<210> SEQ ID NO 431
<211> LENGTH: 9
<212> TYPE: PRT
<213> ORGANISM: Artificial sequence
<220> FEATURE:
<223> OTHER INFORMATION: Synthetic antibody

<400> SEQUENCE: 431

Gln Ser Tyr Asp Ser Ser Val Thr Val
1               5

<210> SEQ ID NO 432
<211> LENGTH: 9
<212> TYPE: PRT
<213> ORGANISM: Artificial sequence
<220> FEATURE:
<223> OTHER INFORMATION: Synthetic antibody

<400> SEQUENCE: 432

Ser Ser Asn Ile Gly Ala Gly Tyr Asp
1               5

<210> SEQ ID NO 433
<211> LENGTH: 3
<212> TYPE: PRT
<213> ORGANISM: Artificial sequence
<220> FEATURE:
<223> OTHER INFORMATION: Synthetic antibody

<400> SEQUENCE: 433

Gly Asn Ser
1

<210> SEQ ID NO 434
<211> LENGTH: 12
<212> TYPE: PRT
<213> ORGANISM: Artificial sequence
<220> FEATURE:
<223> OTHER INFORMATION: Synthetic antibody

<400> SEQUENCE: 434

Gln Ser Tyr Asp Thr Ser Leu Ser Gly Ser Gly Val
1               5                   10

<210> SEQ ID NO 435
<211> LENGTH: 11
<212> TYPE: PRT
<213> ORGANISM: Artificial sequence
<220> FEATURE:
<223> OTHER INFORMATION: Synthetic antibody

<400> SEQUENCE: 435

Gln Ser Leu Leu His Ser Asn Gly Tyr Asn Tyr
1               5                   10

<210> SEQ ID NO 436
<211> LENGTH: 3
<212> TYPE: PRT
<213> ORGANISM: Artificial sequence
<220> FEATURE:
<223> OTHER INFORMATION: Synthetic antibody

<400> SEQUENCE: 436
```

-continued

```
Phe Gly Ser
1

<210> SEQ ID NO 437
<211> LENGTH: 9
<212> TYPE: PRT
<213> ORGANISM: Artificial sequence
<220> FEATURE:
<223> OTHER INFORMATION: Synthetic antibody

<400> SEQUENCE: 437

Met Gln Ala Leu Gln Thr Pro Leu Thr
1               5

<210> SEQ ID NO 438
<211> LENGTH: 6
<212> TYPE: PRT
<213> ORGANISM: Artificial sequence
<220> FEATURE:
<223> OTHER INFORMATION: Synthetic antibody

<400> SEQUENCE: 438

Ala Asn Ile Asn Ser Tyr
1               5

<210> SEQ ID NO 439
<211> LENGTH: 3
<212> TYPE: PRT
<213> ORGANISM: Artificial sequence
<220> FEATURE:
<223> OTHER INFORMATION: Synthetic antibody

<400> SEQUENCE: 439

Ala Ala Ser
1

<210> SEQ ID NO 440
<211> LENGTH: 9
<212> TYPE: PRT
<213> ORGANISM: Artificial sequence
<220> FEATURE:
<223> OTHER INFORMATION: Synthetic antibody

<400> SEQUENCE: 440

Gln Gln Ser Tyr Thr Thr Pro Ile Thr
1               5

<210> SEQ ID NO 441
<211> LENGTH: 12
<212> TYPE: PRT
<213> ORGANISM: Artificial sequence
<220> FEATURE:
<223> OTHER INFORMATION: Synthetic antibody

<400> SEQUENCE: 441

Gln Ser Val Leu Tyr Thr Ser Asn Asn Lys Asn Tyr
1               5                   10

<210> SEQ ID NO 442
<211> LENGTH: 3
<212> TYPE: PRT
<213> ORGANISM: Artificial sequence
<220> FEATURE:
<223> OTHER INFORMATION: Synthetic antibody

<400> SEQUENCE: 442
```

Trp Ala Ser
1

<210> SEQ ID NO 443
<211> LENGTH: 9
<212> TYPE: PRT
<213> ORGANISM: Artificial sequence
<220> FEATURE:
<223> OTHER INFORMATION: Synthetic antibody

<400> SEQUENCE: 443

Gln Gln Tyr Tyr Thr Thr Pro Leu Thr
1               5

<210> SEQ ID NO 444
<211> LENGTH: 6
<212> TYPE: PRT
<213> ORGANISM: Artificial sequence
<220> FEATURE:
<223> OTHER INFORMATION: Synthetic antibody

<400> SEQUENCE: 444

Gln Ser Ile Ser His Tyr
1               5

<210> SEQ ID NO 445
<211> LENGTH: 3
<212> TYPE: PRT
<213> ORGANISM: Artificial sequence
<220> FEATURE:
<223> OTHER INFORMATION: Synthetic antibody

<400> SEQUENCE: 445

Ala Ala Ser
1

<210> SEQ ID NO 446
<211> LENGTH: 9
<212> TYPE: PRT
<213> ORGANISM: Artificial sequence
<220> FEATURE:
<223> OTHER INFORMATION: Synthetic antibody

<400> SEQUENCE: 446

Gln Gln Ser Tyr Ser Thr Pro Val Ser
1               5

<210> SEQ ID NO 447
<211> LENGTH: 11
<212> TYPE: PRT
<213> ORGANISM: Artificial sequence
<220> FEATURE:
<223> OTHER INFORMATION: Synthetic antibody

<400> SEQUENCE: 447

Gln Ser Leu Leu His Ser Asn Gly Tyr Asn Ser
1               5                   10

<210> SEQ ID NO 448
<211> LENGTH: 3
<212> TYPE: PRT
<213> ORGANISM: Artificial sequence
<220> FEATURE:
<223> OTHER INFORMATION: Synthetic antibody

<400> SEQUENCE: 448

Leu Gly Ser

-continued

1

<210> SEQ ID NO 449
<211> LENGTH: 9
<212> TYPE: PRT
<213> ORGANISM: Artificial sequence
<220> FEATURE:
<223> OTHER INFORMATION: Synthetic antibody

<400> SEQUENCE: 449

Met Gln Ala Leu Gln Thr Pro Tyr Thr
1               5

<210> SEQ ID NO 450
<211> LENGTH: 6
<212> TYPE: PRT
<213> ORGANISM: Artificial sequence
<220> FEATURE:
<223> OTHER INFORMATION: Synthetic antibody

<400> SEQUENCE: 450

Gln Ser Val Ser Asp Asn
1               5

<210> SEQ ID NO 451
<211> LENGTH: 3
<212> TYPE: PRT
<213> ORGANISM: Artificial sequence
<220> FEATURE:
<223> OTHER INFORMATION: Synthetic antibody

<400> SEQUENCE: 451

Gly Ala Ser
1

<210> SEQ ID NO 452
<211> LENGTH: 10
<212> TYPE: PRT
<213> ORGANISM: Artificial sequence
<220> FEATURE:
<223> OTHER INFORMATION: Synthetic antibody

<400> SEQUENCE: 452

Gln Gln Tyr Asn Asn Trp Pro Pro Leu Thr
1               5                   10

<210> SEQ ID NO 453
<211> LENGTH: 9
<212> TYPE: PRT
<213> ORGANISM: Artificial sequence
<220> FEATURE:
<223> OTHER INFORMATION: Synthetic antibody

<400> SEQUENCE: 453

Ser Ser Asp Val Gly Ala Tyr Asn Tyr
1               5

<210> SEQ ID NO 454
<211> LENGTH: 3
<212> TYPE: PRT
<213> ORGANISM: Artificial sequence
<220> FEATURE:
<223> OTHER INFORMATION: Synthetic antibody

<400> SEQUENCE: 454

Asp Val Asn
1

<210> SEQ ID NO 455
<211> LENGTH: 10
<212> TYPE: PRT
<213> ORGANISM: Artificial sequence
<220> FEATURE:
<223> OTHER INFORMATION: Synthetic antibody

<400> SEQUENCE: 455

Cys Ser Tyr Ala Gly Ser Phe Thr Trp Val
1               5                   10

<210> SEQ ID NO 456
<211> LENGTH: 6
<212> TYPE: PRT
<213> ORGANISM: Artificial sequence
<220> FEATURE:
<223> OTHER INFORMATION: Synthetic antibody

<400> SEQUENCE: 456

Gln Ser Ile Ser Thr Tyr
1               5

<210> SEQ ID NO 457
<211> LENGTH: 3
<212> TYPE: PRT
<213> ORGANISM: Artificial sequence
<220> FEATURE:
<223> OTHER INFORMATION: Synthetic antibody

<400> SEQUENCE: 457

Gly Ala Ser
1

<210> SEQ ID NO 458
<211> LENGTH: 9
<212> TYPE: PRT
<213> ORGANISM: Artificial sequence
<220> FEATURE:
<223> OTHER INFORMATION: Synthetic antibody

<400> SEQUENCE: 458

Gln Gln Thr Tyr Thr Thr Pro Arg Thr
1               5

<210> SEQ ID NO 459
<211> LENGTH: 7
<212> TYPE: PRT
<213> ORGANISM: Artificial sequence
<220> FEATURE:
<223> OTHER INFORMATION: Synthetic antibody

<400> SEQUENCE: 459

Gln Ser Val Ser Ser Ser Tyr
1               5

<210> SEQ ID NO 460
<211> LENGTH: 3
<212> TYPE: PRT
<213> ORGANISM: Artificial sequence
<220> FEATURE:
<223> OTHER INFORMATION: Synthetic antibody

<400> SEQUENCE: 460

Gly Ala Ser
1

```
<210> SEQ ID NO 461
<211> LENGTH: 9
<212> TYPE: PRT
<213> ORGANISM: Artificial sequence
<220> FEATURE:
<223> OTHER INFORMATION: Synthetic antibody

<400> SEQUENCE: 461

Gln Gln Cys Gly Ser Ser Pro Ile Thr
1               5

<210> SEQ ID NO 462
<211> LENGTH: 9
<212> TYPE: PRT
<213> ORGANISM: Artificial sequence
<220> FEATURE:
<223> OTHER INFORMATION: Synthetic antibody

<400> SEQUENCE: 462

Ser Ser Asp Val Gly Ser Tyr Asn Tyr
1               5

<210> SEQ ID NO 463
<211> LENGTH: 3
<212> TYPE: PRT
<213> ORGANISM: Artificial sequence
<220> FEATURE:
<223> OTHER INFORMATION: Synthetic antibody

<400> SEQUENCE: 463

Asp Val Ser
1

<210> SEQ ID NO 464
<211> LENGTH: 10
<212> TYPE: PRT
<213> ORGANISM: Artificial sequence
<220> FEATURE:
<223> OTHER INFORMATION: Synthetic antibody

<400> SEQUENCE: 464

Cys Leu Tyr Ala Gly Ser Tyr Thr Phe Lys
1               5                   10

<210> SEQ ID NO 465
<211> LENGTH: 6
<212> TYPE: PRT
<213> ORGANISM: Artificial sequence
<220> FEATURE:
<223> OTHER INFORMATION: Synthetic antibody

<400> SEQUENCE: 465

Gln Ser Val Ser Ser Asn
1               5

<210> SEQ ID NO 466
<211> LENGTH: 3
<212> TYPE: PRT
<213> ORGANISM: Artificial sequence
<220> FEATURE:
<223> OTHER INFORMATION: Synthetic antibody

<400> SEQUENCE: 466

Gly Ala Ser
1
```

-continued

```
<210> SEQ ID NO 467
<211> LENGTH: 9
<212> TYPE: PRT
<213> ORGANISM: Artificial sequence
<220> FEATURE:
<223> OTHER INFORMATION: Synthetic antibody

<400> SEQUENCE: 467

Gln Gln Tyr Asn Asn Trp Pro Pro Phe
1               5

<210> SEQ ID NO 468
<211> LENGTH: 8
<212> TYPE: PRT
<213> ORGANISM: Artificial sequence
<220> FEATURE:
<223> OTHER INFORMATION: Synthetic antibody

<400> SEQUENCE: 468

Ser Ser Asn Ile Glu Tyr Asn Tyr
1               5

<210> SEQ ID NO 469
<211> LENGTH: 3
<212> TYPE: PRT
<213> ORGANISM: Artificial sequence
<220> FEATURE:
<223> OTHER INFORMATION: Synthetic antibody

<400> SEQUENCE: 469

Asp Asn Asn
1

<210> SEQ ID NO 470
<211> LENGTH: 11
<212> TYPE: PRT
<213> ORGANISM: Artificial sequence
<220> FEATURE:
<223> OTHER INFORMATION: Synthetic antibody

<400> SEQUENCE: 470

Gly Thr Trp Asp Ser Ser Leu Asn Ala Trp Val
1               5                   10

<210> SEQ ID NO 471
<211> LENGTH: 8
<212> TYPE: PRT
<213> ORGANISM: Artificial sequence
<220> FEATURE:
<223> OTHER INFORMATION: Synthetic antibody

<400> SEQUENCE: 471

Ser Ser Asn Ile Glu Tyr Asn Tyr
1               5

<210> SEQ ID NO 472
<211> LENGTH: 3
<212> TYPE: PRT
<213> ORGANISM: Artificial sequence
<220> FEATURE:
<223> OTHER INFORMATION: Synthetic antibody

<400> SEQUENCE: 472

Asp Asn Asn
1

<210> SEQ ID NO 473
```

```
<211> LENGTH: 11
<212> TYPE: PRT
<213> ORGANISM: Artificial sequence
<220> FEATURE:
<223> OTHER INFORMATION: Synthetic antibody

<400> SEQUENCE: 473

Gly Thr Trp Asp Ser Ser Leu Asn Ala Trp Val
1               5                   10

<210> SEQ ID NO 474
<211> LENGTH: 8
<212> TYPE: PRT
<213> ORGANISM: Artificial sequence
<220> FEATURE:
<223> OTHER INFORMATION: Synthetic antibody

<400> SEQUENCE: 474

Ser Ser Asn Ile Gly Asn Asn Tyr
1               5

<210> SEQ ID NO 475
<211> LENGTH: 3
<212> TYPE: PRT
<213> ORGANISM: Artificial sequence
<220> FEATURE:
<223> OTHER INFORMATION: Synthetic antibody

<400> SEQUENCE: 475

Asp Asn Asn
1

<210> SEQ ID NO 476
<211> LENGTH: 11
<212> TYPE: PRT
<213> ORGANISM: Artificial sequence
<220> FEATURE:
<223> OTHER INFORMATION: Synthetic antibody

<400> SEQUENCE: 476

Gly Thr Trp Asp Ser Ser Leu Ser Ala Trp Ile
1               5                   10

<210> SEQ ID NO 477
<211> LENGTH: 9
<212> TYPE: PRT
<213> ORGANISM: Artificial sequence
<220> FEATURE:
<223> OTHER INFORMATION: Synthetic antibody

<400> SEQUENCE: 477

Ser Ser Asp Val Gly Gly Tyr Asn Tyr
1               5

<210> SEQ ID NO 478
<211> LENGTH: 3
<212> TYPE: PRT
<213> ORGANISM: Artificial sequence
<220> FEATURE:
<223> OTHER INFORMATION: Synthetic antibody

<400> SEQUENCE: 478

Asp Val Ser
1

<210> SEQ ID NO 479
<211> LENGTH: 10
```

```
<212> TYPE: PRT
<213> ORGANISM: Artificial sequence
<220> FEATURE:
<223> OTHER INFORMATION: Synthetic antibody

<400> SEQUENCE: 479

Ser Ser Tyr Thr Ser Ser Ser Thr Lys Leu
1               5                   10

<210> SEQ ID NO 480
<211> LENGTH: 6
<212> TYPE: PRT
<213> ORGANISM: Artificial sequence
<220> FEATURE:
<223> OTHER INFORMATION: Synthetic antibody

<400> SEQUENCE: 480

His Gly Ile Ser Asn Ser
1               5

<210> SEQ ID NO 481
<211> LENGTH: 3
<212> TYPE: PRT
<213> ORGANISM: Artificial sequence
<220> FEATURE:
<223> OTHER INFORMATION: Synthetic antibody

<400> SEQUENCE: 481

Ala Ala Ser
1

<210> SEQ ID NO 482
<211> LENGTH: 9
<212> TYPE: PRT
<213> ORGANISM: Artificial sequence
<220> FEATURE:
<223> OTHER INFORMATION: Synthetic antibody

<400> SEQUENCE: 482

Gln Gln Tyr Tyr Ser Thr Pro Leu Thr
1               5

<210> SEQ ID NO 483
<211> LENGTH: 8
<212> TYPE: PRT
<213> ORGANISM: Artificial sequence
<220> FEATURE:
<223> OTHER INFORMATION: Synthetic antibody

<400> SEQUENCE: 483

Ser Ser Asn Ile Gly Ser Asp Thr
1               5

<210> SEQ ID NO 484
<211> LENGTH: 3
<212> TYPE: PRT
<213> ORGANISM: Artificial sequence
<220> FEATURE:
<223> OTHER INFORMATION: Synthetic antibody

<400> SEQUENCE: 484

Ser Asn Asn
1

<210> SEQ ID NO 485
<211> LENGTH: 11
<212> TYPE: PRT
```

<213> ORGANISM: Artificial sequence
<220> FEATURE:
<223> OTHER INFORMATION: Synthetic antibody

<400> SEQUENCE: 485

Ala Ala Trp Asp Asp Ser Leu Asn Gly Pro Val
1               5                   10

<210> SEQ ID NO 486
<211> LENGTH: 9
<212> TYPE: PRT
<213> ORGANISM: Artificial sequence
<220> FEATURE:
<223> OTHER INFORMATION: Synthetic antibody

<400> SEQUENCE: 486

Asn Ser Asn Ile Gly Ala Gly Tyr Asp
1               5

<210> SEQ ID NO 487
<211> LENGTH: 3
<212> TYPE: PRT
<213> ORGANISM: Artificial sequence
<220> FEATURE:
<223> OTHER INFORMATION: Synthetic antibody

<400> SEQUENCE: 487

Asp Asn Thr
1

<210> SEQ ID NO 488
<211> LENGTH: 13
<212> TYPE: PRT
<213> ORGANISM: Artificial sequence
<220> FEATURE:
<223> OTHER INFORMATION: Synthetic antibody

<400> SEQUENCE: 488

Gln Ser Tyr Asp Ser Ser Val Ser Gly Phe Tyr Val Leu
1               5                   10

<210> SEQ ID NO 489
<211> LENGTH: 9
<212> TYPE: PRT
<213> ORGANISM: Artificial sequence
<220> FEATURE:
<223> OTHER INFORMATION: Synthetic antibody

<400> SEQUENCE: 489

Thr Ser Asp Val Gly Gly Tyr Asp Tyr
1               5

<210> SEQ ID NO 490
<211> LENGTH: 3
<212> TYPE: PRT
<213> ORGANISM: Artificial sequence
<220> FEATURE:
<223> OTHER INFORMATION: Synthetic antibody

<400> SEQUENCE: 490

Asp Val Asn
1

<210> SEQ ID NO 491
<211> LENGTH: 8
<212> TYPE: PRT
<213> ORGANISM: Artificial sequence

```
<220> FEATURE:
<223> OTHER INFORMATION: Synthetic antibody

<400> SEQUENCE: 491

Ser Ser Tyr Thr Thr Gly Thr Leu
1               5

<210> SEQ ID NO 492
<211> LENGTH: 7
<212> TYPE: PRT
<213> ORGANISM: Artificial sequence
<220> FEATURE:
<223> OTHER INFORMATION: Synthetic antibody

<400> SEQUENCE: 492

Gln Ser Val Thr Ser Ser Tyr
1               5

<210> SEQ ID NO 493
<211> LENGTH: 3
<212> TYPE: PRT
<213> ORGANISM: Artificial sequence
<220> FEATURE:
<223> OTHER INFORMATION: Synthetic antibody

<400> SEQUENCE: 493

Asp Ala Ser
1

<210> SEQ ID NO 494
<211> LENGTH: 9
<212> TYPE: PRT
<213> ORGANISM: Artificial sequence
<220> FEATURE:
<223> OTHER INFORMATION: Synthetic antibody

<400> SEQUENCE: 494

Gln Gln Tyr Gly Gly Ser Pro Trp Thr
1               5

<210> SEQ ID NO 495
<211> LENGTH: 6
<212> TYPE: PRT
<213> ORGANISM: Artificial sequence
<220> FEATURE:
<223> OTHER INFORMATION: Synthetic antibody

<400> SEQUENCE: 495

Gln Ser Val Ser Ser Tyr
1               5

<210> SEQ ID NO 496
<211> LENGTH: 3
<212> TYPE: PRT
<213> ORGANISM: Artificial sequence
<220> FEATURE:
<223> OTHER INFORMATION: Synthetic antibody

<400> SEQUENCE: 496

Asp Ala Ser
1

<210> SEQ ID NO 497
<211> LENGTH: 9
<212> TYPE: PRT
<213> ORGANISM: Artificial sequence
<220> FEATURE:
```

-continued

```
<223> OTHER INFORMATION: Synthetic antibody

<400> SEQUENCE: 497

Gln Gln Arg Ser Asn Trp Pro Tyr Thr
1               5

<210> SEQ ID NO 498
<211> LENGTH: 6
<212> TYPE: PRT
<213> ORGANISM: Artificial sequence
<220> FEATURE:
<223> OTHER INFORMATION: Synthetic antibody

<400> SEQUENCE: 498

Gln Ser Val Ser Ser Tyr
1               5

<210> SEQ ID NO 499
<211> LENGTH: 3
<212> TYPE: PRT
<213> ORGANISM: Artificial sequence
<220> FEATURE:
<223> OTHER INFORMATION: Synthetic antibody

<400> SEQUENCE: 499

Asp Ala Ser
1

<210> SEQ ID NO 500
<211> LENGTH: 9
<212> TYPE: PRT
<213> ORGANISM: Artificial sequence
<220> FEATURE:
<223> OTHER INFORMATION: Synthetic antibody

<400> SEQUENCE: 500

Gln Gln Arg Ser Asn Trp Pro Tyr Thr
1               5
```

HUMAN ANTIBODIES TO CRIMEAN CONGO HEMORRHAGIC FEVER VIRUS

PRIORITY CLAIM

This application is a national phase application under 35 U.S.C. § 371 of International Application No. PCT/US2021/012720, filed Jan. 11, 2021, which claims benefit of priority to U.S. Provisional Application Ser. No. 62/960,080, filed on Jan. 12, 2020, the entire contents of which are hereby incorporated by reference.

BACKGROUND

1. Field of the Disclosure

The present disclosure relates generally to the fields of medicine, infectious disease, and immunology. More particular, the disclosure relates to human antibodies binding to Crimean Congo Hemorrhagic Fever Virus.

2. Background

Bunyavirales is an order of negative-sense single-stranded RNA viruses. It is the only order in the class Ellioviricetes. It was formerly known as Bunyaviridae family of viruses. The name Bunyavirales derives from Bunyamwera, where the original type species Bunyamwera orthobunyavirus was first discovered.

In 2017, the ICTV reclassified the family Bunyaviridae as Bunyavirales, a taxonomic shift from a family of viruses to an order of viruses. The body made these decisions in a 2016 convening in Budapest. Primary reasons for this alteration revolve around these observations: approximately half of viruses in the former Bunyaviridae were at the time unassigned to a genus; novel viruses discovered that were characteristic of and clustered around Bunyaviridae based on phylogenetic analyses had bi-segmented genomes (as opposed to Bunyaviridae's tri-segmentation); and plant viruses also lacking tri-segmentation were previously known to be "bunya-like" yet were not properly assigned to the family Bunyaviridae based upon the past taxonomic classifications. All five genera formerly in the family Bunyaviridae (Hantavirus, Nairovirus, Orthobunyavirus, Phlebovirus, Tospovirus) are now novel viral families, some of which have been combined. These new families include: Hantaviridae, Feraviridae, Fimoviridae, Jonviridae, Nairoviridae, Peribunyaviridae, Phasmaviridae, Phenuiviridae, and Tospoviridae.

This order of viruses belong to the fifth group of the Baltimore classification, the so-called negative-sense single stranded ribonucleic acid (−)ssRNA. They are enveloped RNA viruses. Though generally found in arthropods or rodents, certain viruses in this order occasionally infect humans. Some of them also infect plants.

A majority of bunyaviruses are vector-borne. With the exception of Hantaviruses and Arenaviruses, all viruses in the Bunyavirales order are transmitted by arthropods (mosquitos, tick, or sandfly). Hantaviruses are transmitted through contact with deer mice feces. Incidence of infection is closely linked to vector activity, for example, mosquito-borne viruses are more common in the summer. Human infections with certain members of Bunyavirales, such as Crimean Congo Hemorrhagic Fever Virus, are associated with significant levels of morbidity and mortality. They are also the cause of severe fever with thrombocytopenia syndrome. As such, there is a considerable need for reagents to diagnose such infections as well as treat and prevent them.

SUMMARY

Thus, in accordance with the present disclosure, a method of detecting a Crimean Congo Hemorrhagic Fever Virus infection in a subject comprising (a) contacting a sample from said subject with an antibody or antibody fragment having clone-paired heavy and light chain CDR sequences from Tables 3 and 4, respectively; and (b) detecting Crimean Congo Hemorrhagic Fever Virus in said sample by binding of said antibody or antibody fragment to a Crimean Congo Hemorrhagic Fever Virus antigen in said sample. The sample may be a body fluid, such as blood, sputum, tears, saliva, mucous or serum, semen, cervical or vaginal secretions, amniotic fluid, placental tissues, urine, exudate, transudate, tissue scrapings or feces. Detection may comprise ELISA, RIA, lateral flow assay or western blot. The method may further comprise performing steps (a) and (b) a second time and determining a change in Crimean Congo Hemorrhagic Fever Virus antigen levels as compared to the first assay.

The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment.

In another embodiment, there is provided a method of treating a subject infected with Crimean Congo Hemorrhagic Fever Virus or reducing the likelihood of infection of a subject at risk of contracting Crimean Congo Hemorrhagic Fever Virus, comprising delivering to said subject an antibody or antibody fragment having clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment.

In yet another embodiment, there is provided a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody, or is bispecific antibody, or wherein said antibody or antibody fragment further comprises a cell penetrating peptide and/or is an intrabody.

The monoclonal antibody or antibody fragment may further comprise a domain that facilitates transfer across the blood brain barrier by binding to a transport molecule, thereby facilitating transport into the brain. The transport molecule may be transferrin receptor, heparin-binding EGF, a scavenger receptor AI or BI, EGF receptor, tumor necrosis factor, insulin or insulin-like growth factor receptor, apolipoprotein E receptor 2, leptin receptor, melanotransferrin receptor, or LDL receptor. The domain may be a peptide or an scFv (single chain fragment variable) antibody, Fab fragment, F(ab')$_2$ fragment, Fv fragment, single domain antibody (nanobody) or wherein said domain is a distinct binding specificity as part of a chimeric or bispecific antibody structure. These may further comprise a domain that facilitates transfer across a mucosal surface, such as the respiratory tract barrier, by binding to a transport molecule, thereby facilitating transport across the mucosal surface.

In still yet another embodiment, there is provided a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody, or is bispecific antibody, or wherein said antibody or antibody fragment further comprises a cell penetrating peptide and/or is an intrabody.

In a further embodiment, there is provided a vaccine formulation comprising one or more antibodies or antibody fragments characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, F(ab')$_2$ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody, or is bispecific antibody, or wherein said antibody or antibody fragment further comprises a cell penetrating peptide and/or is an intrabody.

In yet a further embodiment there is provided a vaccine formulation comprising one or more expression vectors encoding a first antibody or antibody fragment as defined above. The expression vector(s) may be Sindbis virus or VEE vector(s). The vaccine may be formulated for delivery by needle injection, jet injection, or electroporation. The vaccine formulation may further comprise one or more expression vectors encoding for a second antibody or antibody fragment, such as a distinct antibody or antibody fragment as described herein.

In still yet a further embodiment, there is provided a method of protecting the health of a placenta and/or fetus of a pregnant a subject infected with or at risk of infection with a Crimean Congo Hemorrhagic Fever Virus comprising delivering to said subject an antibody or antibody fragment having clone-paired heavy and light chain CDR sequences from Tables 3 and 4, respectively.

The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2.

The antibody may be a chimeric antibody or a bispecific antibody, or wherein the antibody fragment is a recombinant scFv (single chain fragment variable) antibody, Fab fragment, F(ab')₂ fragment, or Fv fragment. The antibody may be an IgG, or a recombinant IgG antibody or antibody fragment comprising an Fc portion mutated to alter (eliminate or enhance) FcR interactions, to increase half-life and/or increase therapeutic efficacy, such as a LALA, LALA PG, N297, GASD/ALIE, DHS, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody, or is bispecific antibody, or wherein said antibody or antibody fragment further comprises a cell penetrating peptide and/or is an intrabody.

The antibody or antibody fragment may be administered prior to infection or after infection. The subject may be a pregnant female, a sexually active female, or a female undergoing fertility treatments. Delivering may comprise antibody or antibody fragment administration, or genetic delivery with an RNA or DNA sequence or vector encoding the antibody or antibody fragment. The antibody or antibody fragment may increase the size of the placenta as compared to an untreated control. The antibody or antibody fragment may reduce viral load and/or pathology of the fetus as compared to an untreated control.

In an additional embodiment, there is provided a method of determining the antigenic integrity, correct conformation and/or correct sequence of a Crimean Congo Hemorrhagic Fever Virus antigen comprising (a) contacting a sample comprising said antigen with a first antibody or antibody fragment having clone-paired heavy and light chain CDR sequences from Tables 3 and 4, respectively; and (b) determining antigenic integrity, correct conformation and/or correct sequence of said antigen by detectable binding of said first antibody or antibody fragment to said antigen. The sample may comprise recombinantly produced antigen, or a vaccine formulation or vaccine production batch. Detection may comprise ELISA, RIA, western blot, a biosensor using surface plasmon resonance or biolayer interferometry, or flow cytometric staining.

The first antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The first antibody fragment may be a recombinant scFv (single chain fragment variable) antibody, Fab fragment, F(ab')₂ fragment, or Fv fragment. The method may further comprise performing steps (a) and (b) a second time to determine the antigenic stability of the antigen over time.

The method may further comprise (c) contacting a sample comprising said antigen with a second antibody or antibody fragment having clone-paired heavy and light chain CDR sequences from Tables 3 and 4, respectively; and (d) determining antigenic integrity of said antigen by detectable binding of said second antibody or antibody fragment to said antigen. The second antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, F(ab')2 fragment, or Fv fragment. The method may further comprise performing steps (c) and (d) a second time to determine the antigenic stability of the antigen over time.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIGS. 1A-C. Human monoclonal antibodies against Crimean-Congo hemorrhagic fever virus were isolated through a human B cell hybridoma process by screening cell line supernatants for binding to the full-length M-segment of Ibar10200 strain of CCHFV transiently expressed on the surface 293F cells. Purified monoclonal antibodies also were tested in BSL-4 conditions in a standard neutralization assay with CCHF strain Ibar10200 WT beginning at 100 µg/mL. Data was analyzed in Prism 8, using a three-parameter nonlinear fit of duplicate data.

DESCRIPTION OF ILLUSTRATIVE EMBODIMENTS

Figure 1A:
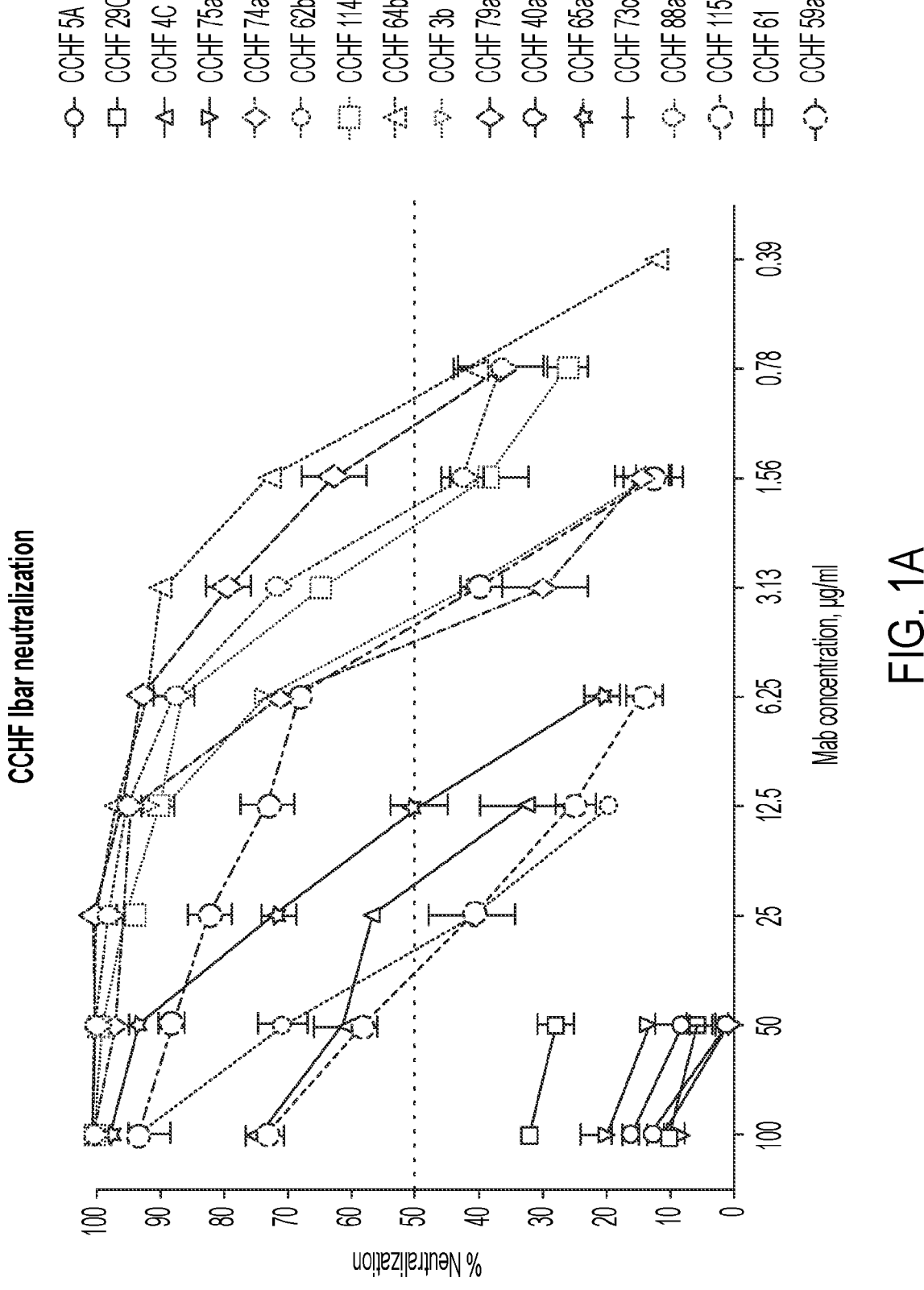
Figure 1B:
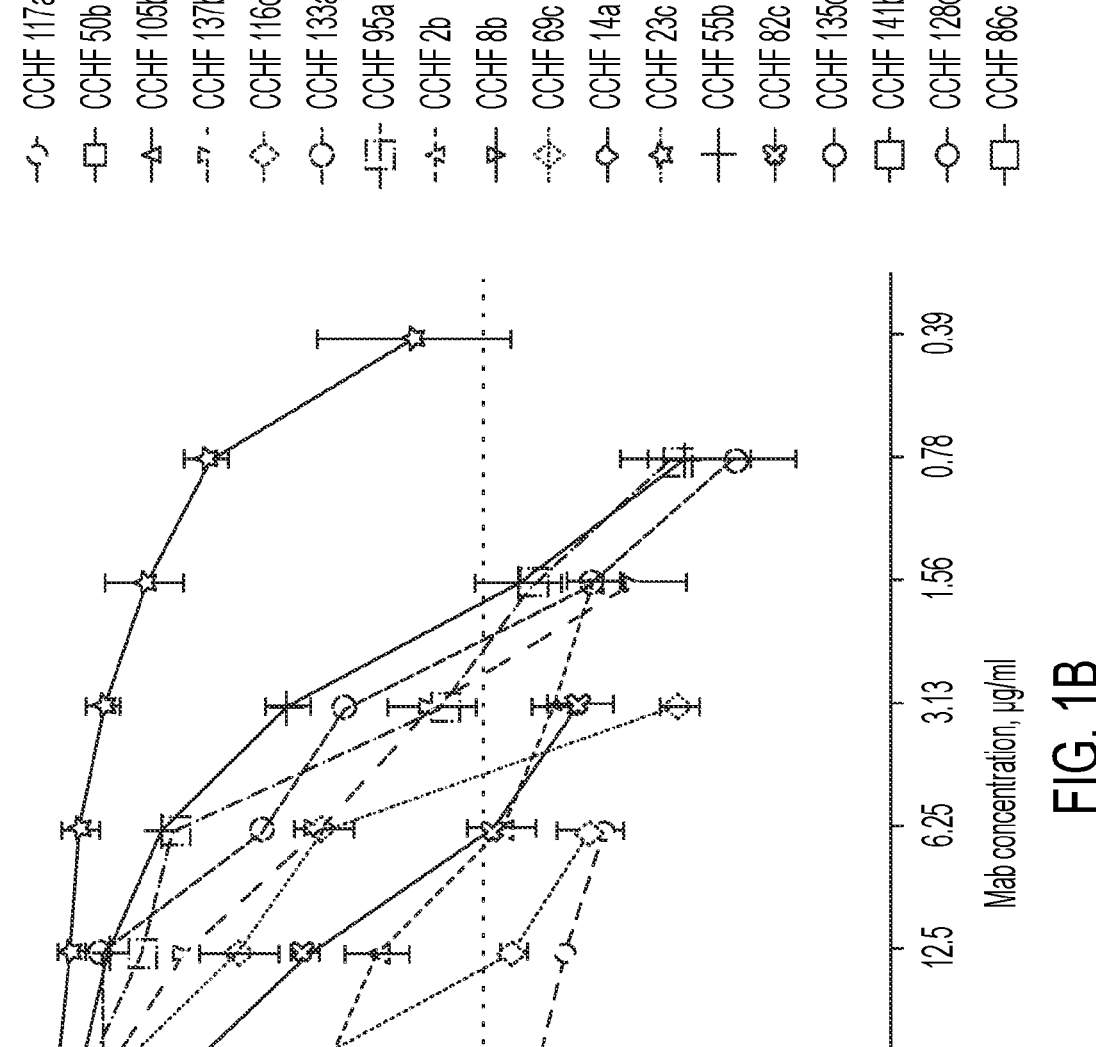
Figure 2:
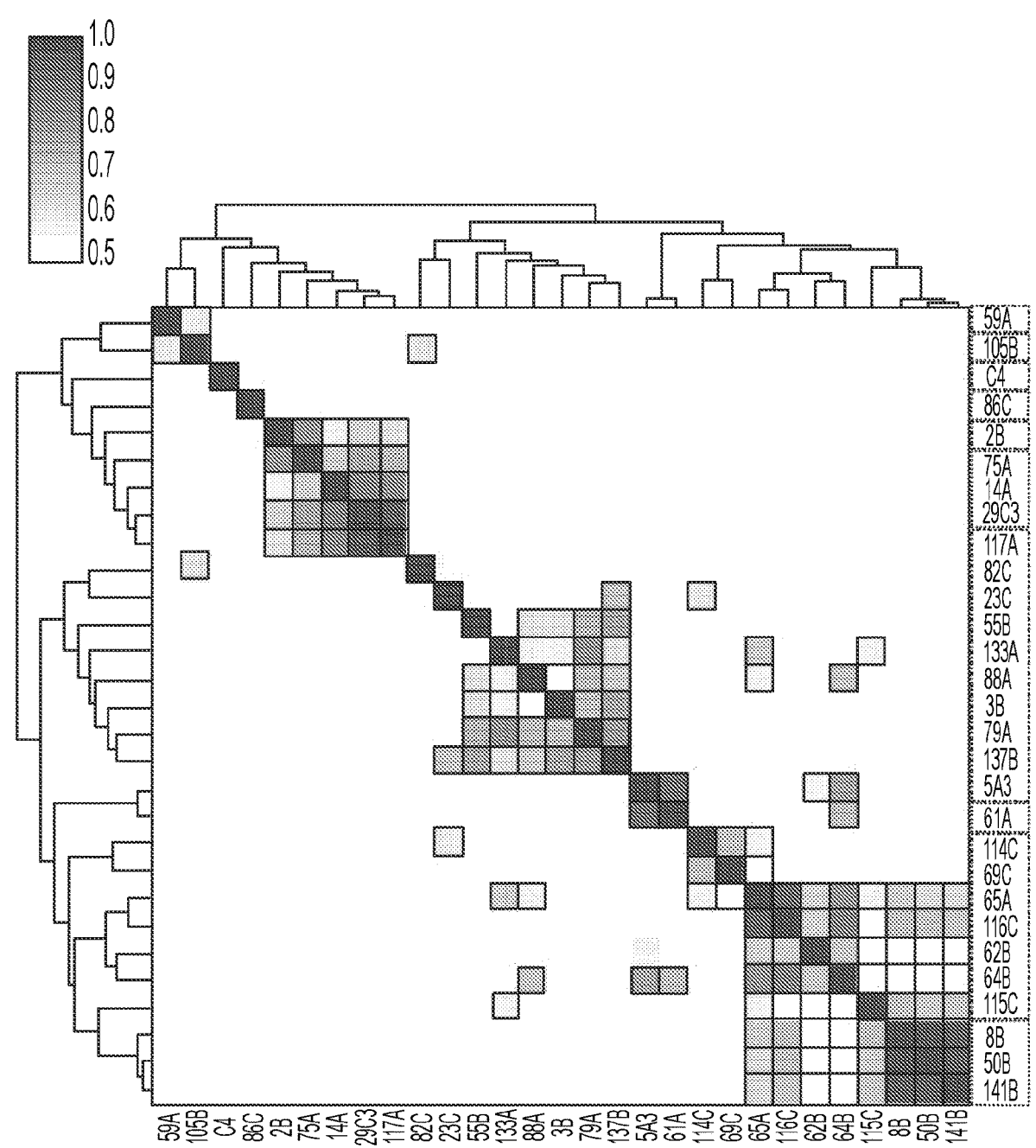
FIG. 2. Data from competition-binding assay using cell-displayed Gc/Gn. Numbers indicate the percentage binding of second mAb labeled with Alexa Fluor 647 in the presence of the first mAb at saturating concentrations compared to binding of un-competed second mAb (representing maximal signal). Assay was performed in biological and technical triplicate and analyzed using a Pearson correlation. Neutralizing mAbs are boxed in green, and non-neutralizing mAbs are highlighted in blue.

As discussed above, there remains a need for reagents to diagnose and treat Crimean Congo Hemorrhagic Fever Virus infections. Described below are human monoclonal antibodies produced from a CCHFV survivor. These neutralizing antibodies recognize two major competition groups and a number of minor groups. These and other aspects of the disclosure are described in detail below.

I. CRIMEAN CONGO HEMORRHAGIC FEVER VIRUS

The Crimean-Congo hemorrhagic fever orthonairovirus (CCHFV) is a member of the genus Orthonairovirus, family Nairoviridae of RNA viruses. The virions are 80-120 nanometers (nm) in diameter and are pleomorphic. There are no host ribosomes within the virion. Each virion contains three copies of the genome. The envelope is single layered and is formed from a lipid bilayer 5 nm thick. It has no protrusions. The envelope proteins form small projections ~5-10 nm long. The nucleocapsids are filamentous and circular with a length of 200-3,000 nm. The virus might enter a cell using the cell surface protein nucleolin.

The genome is circular, negative sense RNA in three parts—Small (S), Medium (M) and Large (L). The L segment is 11-14.4 kilobases in length while the M and S segments are 4.4-6.3 and 1.7-2.1 kilobases long respectively. The L segment encodes the RNA polymerase, the M segment encodes the envelope glycoproteins (Gc and Gn), and the S segment encodes the nucleocapsid protein. The mutation rates for the three parts of the genome were estimated to be: $1.09 \times 10^{-4}$, $1.52 \times 10^{-4}$ and $0.58 \times 10^{-4}$ substitutions/site/year for the S, M, and L segments respectively.

CCHFV is the most genetically diverse of the arboviruses: Its nucleotide sequences frequently differ between different strains, ranging from a 20% variability for the viral S segment to 31% for the M segment. Viruses with diverse sequences can be found within the same geographic area; closely related viruses have been isolated from widely separated regions, suggesting that viral dispersion has occurred possibly by ticks carried on migratory birds or through international livestock trade. Reassortment among genome segments during coinfection of ticks or vertebrates seems likely to have played a role in generating diversity in this virus.

Based on the sequence data, seven genotypes of CCHFV have been recognized: Africa 1 (Senegal), Africa 2 (Democratic Republic of the Congo and South Africa), Africa 3 (southern and western Africa), Europe 1 (Albania, Bulgaria, Kosovo, Russia and Turkey), Europe 2 (Greece), Asia 1 (the Middle East, Iran and Pakistan) and Asia 2 (China, Kazakhstan, Tajikistan and Uzbekistan).

Ticks are both "environmental reservoir" and vector for the virus, carrying it from wild animals to domestic animals and humans. Tick species identified as infected with the virus include *Argas reflexus, Hyalomma anatolicum, Hyalomma detritum, Hyalomma marginatum marginatum* and *Rhipicephalus sanguineus*. At least 31 different species of ticks from the genera *Haemaphysalis* and *Hyalomma* in southeastern Iran have been found to carry the virus.

Wild animals and small mammals, particularly European hare, Middle-African hedgehogs and multimammate rats are the "amplifying hosts" of the virus. Birds are generally resistant to CCHF, with the exception of ostriches. Domestic animals like sheep, goats and cattle can develop high titers of virus in their blood but tend not to fall ill.

The "sporadic infection" of humans is usually caused by a *Hyalomma* tick bite. Animals can transmit the virus to humans, but this would usually be as part of a disease cluster. When clusters of illness occur, it is typically after people treat, butcher or eat infected livestock, particularly ruminants and ostriches. Outbreaks have occurred in abattoirs and other places where workers have been exposed to infected human or animal blood and fomites. Humans can infect humans and outbreaks also occur in clinical facilities through infected blood and unclean medical instruments.

Crimean-Congo hemorrhagic fever (CCHF) is a significant disease with a wide range of symptoms including fever, muscle pains, headache, vomiting, diarrhea, and bleeding into the skin. Onset of symptoms is less than two weeks following exposure. Complications may include liver failure. In those who survive, recovery generally occurs around two weeks after onset.

The CCHF virus is typically spread by tick bites or contact with livestock carrying the disease. Those affected are often farmers or work in slaughterhouses. The virus can also spread between people via body fluids. Diagnosis is by detecting antibodies, the virus's RNA, or the virus itself. It is a type of viral hemorrhagic fever. Prevention involves avoiding tick bites. A vaccine is not commercially available. Treatment is typically with supportive care. The medication ribavirin may also help.

CCHF occurs in Africa, the Balkans, the Middle East, and Asia. Often it occurs in outbreaks. In 2013 Iran, Russia, Turkey, and Uzbekistan documented more than fifty cases. The risk of death among those affected is between 10 and 40%. It was first detected in the 1940s.

The illness in humans is a severe form of hemorrhagic fever. Typically, after a 1-3 day incubation period following a tick bite or 5-6 days after exposure to infected blood or tissues, flu-like symptoms appear, which may resolve after one week. In up to 75% of cases, signs of bleeding can appear within 3-5 days of the onset of illness in case of bad containment of the first symptoms: mood instability, agitation, mental confusion and throat petechiae; and soon after nosebleeds, vomiting, and black stools. The liver becomes swollen and painful. Disseminated intravascular coagulation may occur, as well as acute kidney failure, shock, and sometimes acute respiratory distress syndrome. People usually begin to recover 9-10 days after first symptoms appear. Up to 30% of infected people die by the end of the second week of illness.

Where mammalian tick infection is common, agricultural regulations require de-ticking farm animals before transportation or delivery for slaughter. Personal tick avoidance measures are recommended, such as use of insect repellents, adequate clothing, and body inspection for adherent ticks. When feverish patients with evidence of bleeding require resuscitation or intensive care, body substance isolation precautions should be taken.

CCHD occurs most frequently among agricultural workers, following the bite of an infected tick, and to a lesser extent among slaughterhouse workers exposed to the blood and tissues of infected livestock, and medical personnel through contact with the body fluids of infected persons.[10]

As of 2013, the northern limit of CCHF has been 50 degrees northern latitude, north of which the *Hyalomma* ticks have not been found. Per a WHO map from 2008, *Hyalomma* ticks occurred south of this latitude across all of the Eurasian continent and Africa, sparing only the islands of Sri Lanka, Indonesia and Japan. Serological or virological evidence of CCHF was widespread in Asia, Eastern Europe, the Middle East (except Israel, Lebanon and Jordan), central Africa, Western Africa, South Africa and Madagascar.

In 2008, more than 50 cases/year were reported from only 4 countries: Turkey, Iran, Russia and Uzbekistan. 5-49 cases/year were present in South Africa, Central Asia including Pakistan and Afghanistan (but sparing Turkmenistan), in the Middle East only the UAE and the Balkan countries limited to Romania, Bulgaria, Serbia, Montenegro and Kosovo-Albania.

A 2014 map by the CDC shows endemic areas largely unchanged in Africa and the Middle East, but different for the Balkan, including all countries of the former Yugoslavia, and also Greece, but no longer Romania. India's Northwestern regions of Rajastan and Gujarat saw their first cases.[

From 1995 to 2013, 228 cases of CCHF were reported in the Republic of Kosovo, with a case-fatality rate of 25.5%. Between 2002-2008 the Ministry of Health of Turkey reported 3,128 CCHF cases, with a 5% death rate. In July 2005, authorities reported 41 cases of CCHF in central Turkey's Yozgat Province, with one death. As of August 2008, a total of 50 deaths were reported for the year thus far in various cities in Turkey due to CCHF. Other outbreaks occurred in 2010 and 2016 (Pakistan), 2011, 2013 and 2015 (India), 2012 (Afghanistan), 2013 (Uganda), 2014 (Kazakhstan), and 2016 (Spain).

II. MONOCLONAL ANTIBODIES AND PRODUCTION THEREOF

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the $C_L$ is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest,* 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., *Sequences of Proteins of Immunological Interest,* 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. *Nucl. Acids Res.* 27:209-212 (1999), Ruiz, M. et al. *Nucl. Acids Res.* 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. *J. Mol. Biol.* 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., *Nature,* 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., *Nature,* 352:624-628 (1991) and Marks et al., *J. Mol. Biol.,* 222: 581-597 (1991), for example.

A. General Methods

It will be understood that monoclonal antibodies binding to bunyaviruses will have several applications. These include the production of diagnostic kits for use in detecting and diagnosing Crimean Congo Hemorrhagic Fever Virus infection, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., *Antibodies: A Laboratory Manual,* Cold Spring Harbor Laboratory, 1988; U.S. Pat. No. 4,196,265).

The methods for generating monoclonal antibodies (mAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobenzoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce Crimean Congo Hemorrhagic Fever Virus-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, or herpesvirus, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the mAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective medium are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas then are diluted serially or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector.

Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to Which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke, *Methods Mol. Biol.* 248: 443-63, 2004), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer, *Prot. Sci.* 9: 487-496, 2000). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267: 252-259; Engen and Smith (2001) *Anal. Chem.* 73: 256A-265A. When the antibody neutralizes Crimean Congo Hemorrhagic Fever Virus, antibody escape mutant variant organisms can be isolated by propagating Crimean Congo Hemorrhagic Fever Virus in vitro or in animal models in the presence of high concentrations of the antibody. Sequence analysis of the Crimean Congo Hemorrhagic Fever Virus gene encoding the antigen targeted by the antibody, reveals the nutation(s) conferring antibody escape, indicating residues in the epitope or that affect the stricture of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP; is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the sane epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody hinds to A different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-Crimean Congo Hemorrhagic Fever antibody, the above-described binding methodology is performed in two orientations: In a first orientation, the reference antibody is allowed to bind to the Crimean Congo Hemorrhagic Fever Virus antigen under saturating conditions followed by assessment of binding of the test antibody to the Crimean Congo Hemorrhagic Fever Virus antigen. In a second orientation, the test antibody is allowed to bind to the Crimean Congo Hemorrhagic Fever Virus antigen under saturating conditions followed by assessment of binding of the reference antibody to the Crimean Congo Hemorrhagic Fever Virus antigen. If, in both orientations, only the first (saturating) antibody is capable of binding to the Crimean Congo Hemorrhagic Fever Virus, then it is concluded that the test antibody and the reference antibody compete for binding to the Crimean Congo Hemorrhagic Fever Virus. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et, al., *Cancer Res.* 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J. (1990) Unified Approach to Alignment and Phylogeny pp. 626-645

*Methods in Enzymology* vol. 183, Academic Press, Inc., San Diego, Calif.; Higgins, D. G. and Sharp, P. M. (1989) *CABIOS* 5:151-153; Myers, E. W. and Muller W. (1988) *CABIOS* 4:11-17; Robinson, E. D. (1971) *Comb. Theor* 11:105; Santou, N. Nes, M. (1987) *Mol. Biol. Evol.* 4:406-425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726-730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) *J. Mol. Biol.* 48:443, by the search for similarity methods of Pearson and Lipman (1988) *Proc. Natl. Acad. Sci. USA* 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) *Nucl. Acids Res.* 25:3389-3402 and Altschul et al. (1990) J. *Mol. Biol.* 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) *Proc. Natl. Acad. Sci. USA* 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that specifically binds to an antigen, but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) *"Lack of Fucose on Human IgG N-Linked Oligosaccharide Improves Binding to Human Fcgamma RIII and Antibody-Dependent Cellular Toxicity,"* J. Biol. Chem. 277(30): 26733-26740; Davies J. et al. (2001) *"Expression of GnTIII in a Recombinant Anti-CD20 CHO Production Cell Line: Expression of Antibodies with Altered Glycoforms Leads to an Increase in ADCC through Higher Affinity for FC Gamma RIII,"* Biotechnology & Bioengineering 74(4): 288-294). Methods of altering carbohydrate contents are known to those skilled in the art, see, e.g., Wallick, S. C. et al. (1988) *"Glycosylation of a VH Residue of a Monoclonal Antibody Against Alpha (1-6) Dextran Increases Its Affinity for Antigen,"* J. Exp. Med. 168(3): 1099-1109; Tao, M. H. et al. (1989) *"Studies of Aglycosylated Chimeric Mouse-Hu-*

*man IgG. Role of Carbohydrate in the Structure and Effector Functions Mediated by the Human IgG Constant Region,"* J. Immunol. 143(8): 2595-2601; Routledge, E. G. et al. (1995) *"The Effect of Aglycosylation on the Immunogenicity of a Humanized Therapeutic CD3 Monoclonal Antibody,"* Transplantation 60(8):847-53; Elliott, S. et al. (2003) *"Enhancement of Therapeutic Protein In Vivo Activities Through Glycoengineering,"* Nature Biotechnol. 21:414-21; Shields, R. L. et al. (2002) *"Lack of Fucose on Human IgG N-Linked Oligosaccharide Improves Binding to Human Fcgamma RIII and Antibody-Dependent Cellular Toxicity,"* J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as E. coli, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as Crimean Congo Hemorrhagic Fever Virus replicons based on VEE virus or Sindbis virus also are contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. F(ab') antibody derivatives are monovalent, while F(ab')$_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to IgG$_1$ can increase antibody dependent cell cytotoxicity, switching to class A can improve tissue distribution, and switching to class M can improve valency.

Alternatively or additionally, it may be useful to combine amino acid modifications with one or more further amino acid modifications that alter C1q binding and/or the complement dependent cytotoxicity (CDC) function of the Fc region of an IL-23p19 binding molecule. The binding polypeptide of particular interest may be one that binds to C1q and displays complement dependent cytotoxicity. Polypeptides with pre-existing C1q binding activity, optionally further having the ability to mediate CDC may be modified such that one or both of these activities are enhanced. Amino acid modifications that alter C1q and/or modify its complement dependent cytotoxicity function are described, for example, in WO/0042072, which is hereby incorporated by reference.

One can design an Fc region of an antibody with altered effector function, e.g., by modifying C1q binding and/or FcγR binding and thereby changing CDC activity and/or ADCC activity. "Effector functions" are responsible for activating or diminishing a biological activity (e.g., in a subject). Examples of effector functions include, but are not limited to: C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc. Such effector functions may require the Fc region to be combined with a binding domain (e.g., an antibody variable domain) and can be assessed using various assays (e.g., Fc binding assays, ADCC assays, CDC assays, etc.).

For example, one can generate a variant Fc region of an antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities may be increased, and, optionally, also the other activity reduced (e.g., to generate an Fc region variant with improved ADCC activity, but reduced CDC activity and vice versa).

FcRn binding. Fc mutations can also be introduced and engineered to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, (J. Biol. Chem. 276:6591-6604). A number of methods are known that can result in increased half-life (Kuo and Aveson, (2011)), including amino acid modifications may be generated through techniques including alanine scanning mutagenesis, random mutagenesis and screening to assess the binding to the neonatal Fc receptor (FcRn) and/or the in vivo behavior. Computational strategies followed by mutagenesis may also be used to select one of amino acid mutations to mutate.

The present disclosure therefore provides a variant of an antigen binding protein with optimized binding to FcRn. In a particular embodiment, the said variant of an antigen binding protein comprises at least one amino acid modification in the Fc region of said antigen binding protein, wherein said modification is selected from the group consisting of 226, 227, 228, 230, 231, 233, 234, 239, 241, 243, 246, 250, 252, 256, 259, 264, 265, 267, 269, 270, 276, 284, 285, 288, 289, 290, 291, 292, 294, 297, 298, 299, 301, 302, 303, 305, 307, 308, 309, 311, 315, 317, 320, 322, 325, 327, 330, 332, 334, 335, 338, 340, 342, 343, 345, 347, 350, 352, 354, 355, 356, 359, 360, 361, 362, 369, 370, 371, 375, 378, 380, 382, 384, 385, 386, 387, 389, 390, 392, 393, 394, 395, 396, 397, 398, 399, 400, 401403, 404, 408, 411, 412, 414, 415, 416, 418, 419, 420, 421, 422, 424, 426, 428, 433, 434, 438, 439, 440, 443, 444, 445, 446 and 447 of the Fc region as compared to said parent polypeptide, wherein the numbering of the amino acids in the Fc region is that of the EU index in Kabat. In a further aspect of the disclosure the modifications are M252Y/S254T/T256E.

Additionally, various publications describe methods for obtaining physiologically active molecules whose half-lives are modified, see for example Kontermann (2009) either by introducing an FcRn-binding polypeptide into the molecules or by fusing the molecules with antibodies whose FcRn-binding affinities are preserved but affinities for other Fc receptors have been greatly reduced or fusing with FcRn binding domains of antibodies.

Derivatized antibodies may be used to alter the half-lives (e.g., serum half-lives) of parental antibodies in a mammal, particularly a human. Such alterations may result in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present disclosure or fragments thereof in a mammal, preferably a human, results in a higher serum titer of said antibodies or antibody fragments in the mammal, and thus reduces the frequency of the administration of said antibodies or antibody fragments and/or reduces the concentration of said antibodies or antibody fragments to be administered. Antibodies or fragments thereof having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor.

Beltramello et al. (2010) previously reported the modification of neutralizing mAbs, due to their tendency to enhance dengue virus infection, by generating in which leucine residues at positions 1.3 and 1.2 of CH2 domain (according to the IMGT unique numbering for C-domain) were substituted with alanine residues. This modification, also known as "LALA" mutation, abolishes antibody binding to FcγRI, FcγRII and FcγRIIIa, as described by Hessell et al. (2007). The variant and unmodified recombinant mAbs were compared for their capacity to neutralize and enhance infection by the four dengue virus serotypes. LALA variants retained the same neutralizing activity as unmodified mAb but were completely devoid of enhancing activity. LALA or LALA PG mutations of this nature are therefore contemplated in the context of the presently disclosed antibodies.

Altered glycosylation. A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1 \times 10^{-8}$ M or less and from Fc gamma RIII with a Kd of $1 \times 10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of monoclonal antibody protein sequence liabilities. It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.*, 22 (10), 1302-1306, 2004; Chennamsetty et al., *PNAS,* 106 (29), 11937-11942, 2009; Voynov et al., *Biocon. Chem.,* 21(2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability. Antibodies can be engineered for enhanced biophysical properties. One can use elevated temperature to unfold antibodies to determine relative stability, using average apparent melting temperatures. Differential Scanning Calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 µg/mL.

Solubility. One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

Blood brain barrier. The blood brain barrier regulates the traverse of blood-circulating substances into the brain with selectivity. This barrier may reduce the entry of antibodies into the central nervous system necessary for diagnosis or therapy of central nervous system infection with Crimean Congo Hemorrhagic Fever Virus. It may be possible to exploit the naturally occurring cellular trafficking systems and the receptor-mediated transfer machinery to move antibodies across the blood brain barrier safely to tissue site where the antibodies will be most effective. There have been a large number of studies of molecules that mediate active transport into the brain, including at least 20 receptors, including transferrin receptor, heparin-binding EGF, scavenger receptors AI, BI, EGF receptor, tumor necrosis factor, insulin and insulin-like growth factor receptors, apolipoprotein E receptor 2, leptin receptor, melanotransferrin receptor, or LDL receptors (Preston et al., *Adv. Pharmacol.* 71: 147-163, 2014). Here, the inventors propose to use one or more of these active transport systems to deliver a Crimean Congo Hemorrhagic Fever Virus inhibiting antibody by making a chimeric or bispecific molecule that targets a transporting receptor and possesses a separate domain that targets a Crimean Congo Hemorrhagic Fever Virus protein.

D. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1,054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido)

ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full-length antibodies or antibody fragments (e.g., F(ab')2 bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full-length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., J. Exp. Med., 175: 217-225 (1992) describe the production of a humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., *Nat. Biotechnol.* 16, 677-681 (1998). doi:10.1038/nbt0798-677pmid: 9661204). For example, bispecific antibodies have been produced using leucine zippers (Kostelny et al., *J. Immunol.*, 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA,* 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.,* 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., *FEBS Letters.* 2005; 579: 3264; Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., *J. Immunol.* 147: 60, 1991; Xu et al., *Science,* 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-$(X1)_n$-VD2-$(X2)_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a $C_L$ domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises (a) a first Fab molecule which specifically binds to a first antigen (b) a second Fab molecule which specifically binds to a second antigen, and wherein the variable domains VL and VH of the Fab light chain and the Fab heavy chain are replaced by each other, wherein the first antigen is an activating T cell antigen and the second antigen is a target cell antigen, or the first antigen is a target cell antigen and the second antigen is an activating T cell antigen; and wherein i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

F. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain. A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from IgG1. Alternatives include the $CH_2CH_3$ region of immunoglobulin and portions of CD3. For most scFv based constructs, the IgG1 hinge suffices. However, the best spacer often has to be determined empirically.

Transmembrane domain. The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain. This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3ξ-chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

G. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs viral replication. Due to this targeting, ideally the drug has lower side effects and gives a wider therapeutic window than other agents.

A stable link between the antibody and cytotoxic/antiviral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker.

The availability of better and more stable linkers has changed the function of the chemical bond. The type of linker, cleavable or noncleavable, lends specific properties to the cytotoxic (anti-cancer) drug. For example, a noncleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/antiviral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

H. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/antiviral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

I. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

J. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF CRIMEAN CONGO HEMORRHAGIC FEVER VIRUS INFECTION

A. Formulation and Administration

The present disclosure provides pharmaceutical compositions comprising anti-Crimean Congo Hemorrhagic Fever Virus antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of Crimean Congo Hemorrhagic Fever Virus infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, by nebulizer, or via intrarectal or vaginal delivery. Pharmaceutically acceptable salts include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

B. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example, the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

C. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine[211], [14]carbon, [51]chromium, [36]chlorine, [57]cobalt, [58]cobalt, copper[67], [152]Eu, gallium[67], [3]hydrogen, iodine[123], iodine[125], iodine[131], indium[111], [59]iron, [32]phosphorus, rhenium[186], rhenium[188], [75]selenium, [35]sulphur, technicium[99m] and/or yttrium[90]. [125]I is often being preferred for use in certain embodiments, and technicium[99m] and/or indium[111] are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium[99m] by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies also may be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting Crimean Congo Hemorrhagic Fever Virus and its associated antigens. While such methods can be applied in a traditional sense, another use will be in quality control and monitoring of vaccine and other virus stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of Crimean Congo Hemorrhagic Fever Virus in a subject. A wide variety of assay formats are contemplated, but specifically those that would be used to detect Crimean Congo Hemorrhagic Fever Virus in a fluid obtained from a subject, such as saliva, blood, plasma, sputum, semen or urine. In particular, semen has been demonstrated as a viable sample for detecting viruses (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of Crimean Congo Hemorrhagic Fever Virus antibodies directed to specific parasite epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing Crimean Congo Hemorrhagic Fever Virus and contacting the sample with a first antibody in accordance with the present disclosure, as the case may be, under conditions effective to allow the formation of immunocomplexes.

These methods include methods for purifying Crimean Congo Hemorrhagic Fever Virus or related antigens from a sample. The antibody will preferably be linked to a solid support, such as in the form of a column matrix, and the sample suspected of containing the Crimean Congo Hemorrhagic Fever Virus or antigenic component will be applied to the immobilized antibody. The unwanted components will be washed from the column, leaving the Crimean Congo Hemorrhagic Fever Virus antigen immunocomplexed to the immobilized antibody, which is then collected by removing the organism or antigen from the column.

The immunobinding methods also include methods for detecting and quantifying the amount of Crimean Congo Hemorrhagic Fever Virus or related components in a sample and the detection and quantification of any immune complexes formed during the binding process. Here, one would obtain a sample suspected of containing Crimean Congo Hemorrhagic Fever Virus or its antigens and contact the sample with an antibody that binds Crimean Congo Hemorrhagic Fever Virus or components thereof, followed by detecting and quantifying the amount of immune complexes formed under the specific conditions. In terms of antigen detection, the biological sample analyzed may be any sample that is suspected of containing Crimean Congo Hemorrhagic Fever Virus or Crimean Congo Hemorrhagic Fever Virus antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to Crimean Congo Hemorrhagic Fever Virus or Crimean Congo Hemorrhagic Fever Virus antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histo-enzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the Crimean Congo Hemorrhagic Fever Virus or Crimean Congo Hemorrhagic Fever Virus antigen is added to the wells. After binding and washing to remove non-specifically bound immune complexes, the bound antigen may be detected. Detection may be achieved by the addition of another anti-Crimean Congo Hemorrhagic Fever Virus antibody that is linked to a detectable label. This type of ELISA is a simple "sandwich ELISA." Detection may also be achieved by the addition of a second anti-Crimean Congo Hemorrhagic Fever Virus antibody, followed by the addition of a third antibody that has binding affinity for the second antibody, with the third antibody being linked to a detectable label.

In another exemplary ELISA, the samples suspected of containing the Crimean Congo Hemorrhagic Fever Virus or Crimean Congo Hemorrhagic Fever Virus antigen are immobilized onto the well surface and then contacted with the anti-Crimean Congo Hemorrhagic Fever Virus antibodies of the disclosure. After binding and washing to remove non-specifically bound immune complexes, the bound anti-Crimean Congo Hemorrhagic Fever Virus antibodies are detected. Where the initial anti-Crimean Congo Hemorrhagic Fever Virus antibodies are linked to a detectable label, the immune complexes may be detected directly. Again, the immune complexes may be detected using a second antibody that has binding affinity for the first anti-Crimean Congo Hemorrhagic Fever Virus antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C. or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzothiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of Crimean Congo Hemorrhagic Fever Virus antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled Crimean Congo Hemorrhagic Fever Virus monoclonal antibodies to determine the amount of Crimean Congo Hemorrhagic Fever Virus antibodies in a sample. The basic format would include contacting a known amount of Crimean Congo Hemorrhagic Fever Virus monoclonal antibody (linked to a detectable label) with Crimean Congo Hemorrhagic Fever Virus antigen or particle. The Crimean Congo Hemorrhagic Fever Virus antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically, there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect Crimean Congo Hemorrhagic Fever Virus or Crimean Congo Hemorrhagic Fever Virus antigens, the antibodies may be included in the kit. The immunodetection kits will thus comprise, in suitable container means, a first antibody that binds to Crimean Congo Hemorrhagic Fever Virus or Crimean Congo Hemorrhagic Fever Virus antigen, and optionally an immunodetection reagent.

In certain embodiments, the Crimean Congo Hemorrhagic Fever Virus antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the Crimean Congo Hemorrhagic Fever Virus or Crimean Congo Hemorrhagic Fever Virus antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of a viral antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically correct and intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

Antibodies and fragments thereof as described in the present disclosure may also be used in a kit for monitoring the efficacy of vaccination procedures by detecting the presence of protective Crimean Congo Hemorrhagic Fever Virus antibodies. Antibodies, antibody fragment, or variants and derivatives thereof, as described in the present disclosure may also be used in a kit for monitoring vaccine manufacture with the desired immunogenicity.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

This panel of human monoclonal antibodies was isolated from a human donor that been naturally infected with CCHFV. This panel was isolated using the hybridoma process and screening by binding to cell expressing the CCHFV Ibar10200 strain full length M-segment. The panel has displayed neutralization. Various competition groups are represented by these mAbs. Prophylaxis and therapeutic evaluation is underway.

TABLE 1

NUCLEOTIDE SEQUENCES FOR ANTIBODY VARIABLE REGIONS

| Clone | SEQ ID NO: | Chain | Variable Sequence Region |
|---|---|---|---|
| CCHFV-104A | 1 | heavy | CACGTGCAGCTGGTGGAGTCTGGGGGAGCCTTGGTCAAGCCTGGAGGGTCCCTGAGACTCTCCTGTGCAGCCTCTGG ATTCACCTTCAGTGACTACTACATGAGCTGGATCCGCCAGGCTCCAGGGAAGGGGCTGGAGTGGGTTTCATACATTAG TAGTTTTGGTAGTAACACTTTCTACGCAGACTTTGTGAAGGGCCGATTCACCATCTCCAGGGACAATGCCAAGAAGTCA CTGTATCTGCAAATGAGCAGCCTGAGAGCCGAGGACACGGCCGTGTATTACTGTGCGAGAAGCCTCCGCGGTATAGC AGTGCCGTCCTACTGGGGCCAGGGAACCCTGGTCACCGTCTCCTCA |
|  | 2 | light | GAAATAGTGATGACGCAGTCTCCAGCCACCCTGTCTGTGTCTCCAGGGGAAAGAGTCACCCTCTCCTGCAGGGCCAGT CAGAGTGTTAGCAGCGACTTGGCCTGGTACCACCAGAAACCTGGCCAGGCTCCCAGGCTCCTCATCTACGATGCATCC ACCAGGGCCACTGGTATCCCAGCCAGGTTCAGTGGCAGTGGGTCTGGGACAGAGTTCACTCTCACCATCAGCAGCCTG CAGTCTGAAGATTTTGCAGTTTATTACTGTCAGCAGTATAATAACTGGCCTCCTTGGACGTTCGGCCAAGGGACCAAGG TGGAAATCAAA |
| CCHFV-104B | 3 | heavy | CACGTGCAGCTGGTGGAGTCTGGGGGAGCCTTGGTCAAGCCTGGAGGGTCCCTGAGACTCTCCTGTGCAGCCTCTGG ATTCACCTTCAGTGACTACTACATGAGCTGGATCCGCCAGGCTCCAGGGAAGGGGCTGGAGTGGGTTTCATACATTAG TAGTTTTGGTAGTAACACTTTCTACGCAGACTTTGTGAAGGGCCGATTCACCATCTCCAGGGACAATGCCAAGAAGTCA CTGTATCTGCAAATGAGCAGCCTGAGAGCCGAGGACACGGCCGTGTATTACTGTGCGAGAAGCCTCCGCGGTATAGC AGTGCCGTCCTACTGGGGCCAGGGAACCCTGGTCACCGTCTCCTCA |
|  | 4 | light | GAAATAGTGATGACGCAGTCTCCAGCCACCCTGTCTGTGTCTCCAGGGGAAAGAGTCACCCTCTCCTGCAGGGCCAGT CAGAGTGTTAGCAGCGACTTGGCCTGGTACCACCAGAAACCTGGCCAGGCTCCCAGGCTCCTCATCTACGATGCATCC ACCAGGGCCACTGGTATCCCAGCCAGGTTCAGTGGCAGTGGGTCTGGGACAGAGTTCACTCTCACCATCAGCAGCCTG CAGTCTGAAGATTTTGCAGTTTATTACTGTCAGCAGTATAATAACTGGCCTCCTTGGACGTTCGGCCAAGGGACCAAGG TGGAAATCAAA |
| CCHFV-105B | 5 | heavy | CAGCTGCAGCTGTTGGAGTCGGGCCCAGGACTGGTGAAGCCTTCGGAGACCCTGTCCCTCACCTGCACTGTCTCTGGT GGCTCCATCAGCAGTAATATTTACTACTGGGGCTGGATCCGCCAGCCCCCAGGGAAGGGGCTGGAATGGATTGGGAG TATCTATTATAGTGGGAACACCCACTACAACCCGTCCCTCAAGAGTCGAGTCACCATATCCGTAGACACGTCCAAGAAC CAGTTCTCCCTGAAGCTGAGCTCTGTGACCGCCGCAGACTCGGCTCTTTATTACTGTGCGAGCCAGAAAATGGTCTATC CAATAAAACGGAACAACTGGTTCGACCCCTGGGGCCAGGGAACCCTGGTCATCGTCTCCTCA |
|  | 6 | light | CAGTCTGTGCTGACTCAGTCACCCTCAGCGTCTGGGACCCCCGGGCAGAGGGTCACCATCTCTTGTTCTGGAAGCAGC TCCAACATCGAAAGTAATACTGTAACCTGGTACCAGCAGCTCCCAGGAACGGCCCCCAAACTCCTCATCTATGGTAATA ATCAGCGGCCCTCAGGGGTCCCTGACCGATTCTCTGGCTCCAAGTCTGGCACCTCAGCCTCCCTGGCCATCAGTGGCCT CCAGTCTGAGGATGAGGCTGATTATTACTGTGCAGCATGGGATGACGGCCTGAATGGGTGGGTGTTCGGCGGAGGG ACCAAGCTGACCGTCCTA |

TABLE 1-continued

NUCLEOTIDE SEQUENCES FOR ANTIBODY VARIABLE REGIONS

| Clone | SEQ ID NO: | Chain | Variable Sequence Region |
|-------|------------|-------|--------------------------|
| CCHFV-106A | 7 | heavy | GAGGTGCACCTGGTGCAGTCTGGAGCAGAGGTGAAAAAGCCCGGGGAGTCTCTGAAGATCTCCTGTAAGGGTTCTGG ATACAGCTTTACCAGCTACTGGATCGGCTGGGTGCGCCAGATGCCCGGGAAAGGCCTGGAGTGGATGGGGATCATCT ATCCTGGTGACTCTGATACCAGATACAGCCCGTCCTTCCAAGGCCAGGTCACCATCTCAGCCGACAAGTCCATCAGCAC CGCCTACCTGCAGTGGAGCAGCCTGAAGGCCTCGGACACCGCCATGTATTACTGTGCGCGACATGAAAGTGAAGCTTT TTCGATTTTTGGAGTGGTTCGATACTACTACTACTACATGGACGTCTGGGGCAAAGGGACCACGGTCACCGTCTCCTCA |
| | 8 | light | CAGTCTGCCCTGACTCAGCCTCGCTCAGTGTCCGGGTCTCCTGGACAGTCAGTCACCATCTCCTGCACTGGAACCAGCA GTGATGTTGGTGGTTATAACTATGTCTCCTGGTACCAACAGCACCCAGACAAAGCCCCCAAACTCATGATTTATGATGT CACTAAGCGGCCCTCAGGGGTCCCTGATCGCTTCTCTGGCTCCAAGTCTGGCAACACGGCCTCCCTGACCATCTCTGGG CTCCAGGCTGAGGATGAGGCTGATTATTACTGCTGCTCATATGCAGGCACCGTGGTATTCGGCGGAGGGACCAAGCT GACCGTCCTA |
| CCHFV-108A | 9 | heavy | CAGGTGCAGCTGCAGGAGTCGGGCCCAGGACTGGTGAAGCCTTCGGGGACCCTGTCCCTCACCTGCGCTGTCTCTGGT GGCTCCATCAGCAGTAGTAAGTGGTGGAGTTGGGTCCGCCAGTCCCCAGGGAAGGGGCTGGAGTGGATTGGCGAAA TCTATCATAGTGGGAGCACCAACTACAACCCGTCCCTCAAGAGTCGAGCCACCATTTCAGTAGACAAGTCCAAGAACC AGTTCTCCCTGAAGCTGAACTCTGTGACCGCCGCGGACACGGCCGTGTACTATTGTGCGAGTGGGCTTGGGCTGGC ACGATGGAAACGGTATGGACGTCTGGGGCCAAGGGACCACGGTCACCGTCTCCTCA |
| | 10 | light | GAAATTGTGTTGACACAGTCTCCAGCCACCCTGTCTTTGTCTCCAGGGGAAAGAGCCACCCTCTCCTGCCGGGCCAGTC TCAATATTGGGGAGCTACTTAGCCTGGTACCAACAGAAACCTGGCCAGGCTCCCAGGCTCCTCATCTATGATGCATCCAA CAGGGCCACTGGCATCCCCGCCAGGTTCAGTGGCAGTGGGTCTGGGACAGACTTCACTCTCACCATCAGGAGCCTAGA GCCTGAAGATTTTGCAATTTACTACTGTCAGCAGCGTAGCAACTGGCCCCCGGGGTACACTTTTGGCCAGGGGACCAA GCTGGAGATCAGA |
| CCHFV-114C | 11 | heavy | CAGGTGCAGCTGCAGGAGTCGGGCCCGGGACTGGTGAAGCCTTCACAGACCCTGTCCCTCACCTGCACTGTCTCTGGT GGCTCCATCAGCAGTGGTGATTATTACTGGAGCTGGCTCCGCCAGCACCCAGGGAAGGGGCTGGAGTGGATTGGGTA CATCTATTACAGTGGGAGCGCCTACTCCAACCCGTCCCTCAACAGTCGAGATATCATTTCAATAGACACGTCTAAGAAT CGGTTCTCCCTGAAACTGAGCTCTGTGACTGCCGCGGACACGGCCGTGTATTACTGTGCGAGATTCCGGCTAGGCGAT GCCCCAACCAGAGATGGCTACAATTTGCACTACTTTGACTACTGGGGCCAGGGATCCCTGGTCACCGTCTCCTCA |
| | 12 | light | CAGTCTGCCCTGACTCAGCCTGCCTCCGTGTCTGGGTCTCCTGGACAGTCGATCACCATCTCCTGCACTGGAACCAGCA GTGATGTTGGGAGCTATAACCTTGTCTCCTGGTACCAACAGCACCCAGGCAAAGCCCCCAAAGTCATGATTTATGAGG TCAGTAAGCGGCCCTCAGGGGTTTCTAATCGCTTCTCTGGCTCCAAGTCTGGCAACACGGCCTCCCTGACAATCTCTGG GCTCCAGGCTGAGGACGAGGCTGATTATTACTGCTGCTCATATGGAGGTTTTAGTACCCATGTGGTTTTCGGCGGAGG GACCAGGCTGACCGTCCTA |
| CCHFV-115C | 13 | heavy | GAGGTGCAGCTGGTGGAGTCTGGGGGAGGCTTGGTACAGCCAGGGCGGTCCCTGAGACTCTCCTGTACAGGTTCTGG ATTCACCTTTGGTGATTACGCCATGAGTTGGGTCCGCCAGGCTCCAGGGAAGGGGCTGGAGTGGGTAGGATTCATCA GAAGCAAAGGTTACGGTGGGACAACACAATACGCCGCGTCTGTGAAAGGCAGATTCACCATCTCAAGAGATGATTCC AAAAGAATCGCCTATTTGCAAGTGAATAGTCTGAAAATCGAGGACACAGCCGTGTATTCTGTACTAGAGCCCACTAT GATTACGTTTGGGGGAATTATTGGAGCTTTGCGTACTGGGGCCAGGGAACCCTGGTCACCGTCTCCTCA |
| | 14 | light | CAGTCTGTGCTGACGCAGCCGCCCTCACTGTCTGCGGCCCCAGGACAGAAGGTCACCATCTCCTGCTCTGGAAGCAGC TCCAACATTGGGAATAATTATGTATCCTGGTACCAGCACCTCCCAGGAACAGCCCCCAAACTCATCATTTATGACGATA ATCAGCGACCCTCAGGGATTCCTGACCGATTCTCTGGCTCCAAGTCTGGCACGTCAGCCACCCTGGGCATCACCGGACT CCAGACTGGGGACGAGGCCGATTATTACTGCGGAACATGGGATAGCAGCCTGAGTGTTTTTGTCTTCGGAACTGGGA CCAAGGTCACCGTCCTA |
| CCHFV-116C | 15 | heavy | CAAGTGCAGCTGGTGGAGTCTGGGGGAGGCGTGGTCCAGCCTGGGAGGTCCCTGAGACTCTCCTGTGCAGCGTCTGG ATTCACCTTCAGTACCTATGGCATGCACTGGGTCCGCCAGGCTCCAGGCAAGGGGCTGGAGTGGGTGGCAGTTATATG GTATGATGGAAGTAATAAGTACTATGTAGACTCCGTGAAGGGCCGATTCACCATCTCCAGAGACAATTCCAAGAACAC GCTGTATCTGCAAATGAACAGCCTGAGAGCCGAAGACACGGCTCTCTATTACTGTGCGAGAGACCCCGGGGGTCGTA GAGATGGCTACATACTAAGACCTGATGCTTTTGATATCTGGGGCCAAGGGACAATGGTCACCGTCTCTTCA |
| | 16 | light | GACATCCAGATGACCCAGTCTCCTTCCACCCTGTCTGCATCTGTAGGAGACAGAGTCACCATCACTTGCCGGGCCAGTC AGAGTATTACTAGCTGGTTGGCCTGGTATCAGCAGAAACCAGGGAAAGCCCCTAAGCTCCTGATCTATAAGGCATCTA GTTTAGAAAGTGGGGTCCCATCAAGGTTCAGCGGCAGTGGATCTGGGACAGAATTCACTCTCACCATCAGCAGCCTGC AGCCTGATGATTTTGCAACTTATTACTGCCAACAGTATAATACTTATACGTGGACGTTCGGCCAAGGGACCAAGGTGG AAATCAAA |
| CCHFV-117A | 17 | heavy | CAGGTTCAGCTGGTGCAGTCTGGAGCTGAGGTGAAGAAGCCTGGGGCCTCAGTGAAGGTCTCCTGCAAGGCTTCTGG TTACACCTTTACCAGCTATGGTATCAGCTGGGTGCGACAGGCCCCTGGACAAGGGCTTGAGTGGATGGGATGGATCA GCGCTTACAATGGTAACACAAACTATGTACAGAAGCTCCAGGGCAGAGTCACCATGACCACAGACACATCCACGAGCA CAGCCTACATGGAGCTGAGGAGCCTGAGATCTGACGACACGGCCGTGTATTACTGTGCGAGGTCCGGGGGCTACGCA ATATTTTGGGGCCAGGGAACCCTGGTCACCGTCTCCTCA |
| | 18 | light | GAAATTGTGTTGACGCAGTCTCCAGGCACCCTGTCTTTGTCTCCAGGGGAAAGTGCCACCCTCTCCTGCAGGGCCAGTC AGAGTCTTAGCAGCAGCTACTTAGCCTGGTACCAGCAGAAACCTGGCCAGGCTCCCAGGCTCCTCATCTATGGTGCAT CCAGCAGGGCCACTGGCATCCCAGACAGGTTCAGTGGCAGTGGGTCTGGGACAGACTTCACTCTCACCATCAGCAGAC TGGAGCCTGAAGATTTTGCAGTGTATTACTGTCAGCAGTATGGTAGTACACCTCCGTACACTTTTGGCCAGGGGACCA AGCTGGAGATCAAA |
| CCHFV-128C | 19 | heavy | CAGATCACCTTGAAGGAGTCTGGTCCAACGCTGGTGAAACCCACACAGACCCTCACGCTGACCTGCACCTTCTCTGGGT TCTCAATCAGTAGTAGTGAGTGGGTGTGGGCTGGATCCGTCAGCCCCCAGGAAAGGCCCTGGAGTGGCTTGCACTC CTTTATTGGGATGATAGTAAGCGCTACAGCCCATCTCTGAGGAGCAGGCTCACCATCACCAAGGACACCTCCAAAAAC CAGGTAGTCCTTACAATGACCAACATGGACCCTGTGGACACAGGCACATATTACTGTGCACACAGACGGACTACGGTT TTTGACTACTGGGGCCAGGGAACCCTGGTCACCGTCTCCTCA |
| | 20 | light | AATTTTATGCTGACTCAGCCCCACTCTGTGTCGGAGTCTCCGGGGAAGACGGTAACCATCTCCTGCACCCGCAGCAGG GGCAGCATCGCCAGCAACTATGTGCAGTGGTACCAGCAGCGCCCGGGCAGTTCCCCCACCAATGTGATCTATGAGGAT |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | AACCAGAGACCCTCTGGGGTCCCTGATCGGTTCTCTGGCTCCATCGACAGCTCCTCCAACTCTGCCTCCCTCACCATCTC<br>TGGACTGAAGACTGAGGACGAGGCTGACTACTACTGTCAGTCTTATGATAGCTACAACCATGTGTTCGGCGGAGGGA<br>CCAGGCTGACCGTCCTA |
| CCHFV-131A | 21 | heavy | GAGGTGCAGCTGGTGCAGTCTGGAGCAGAGGTGAAAAAGCCCGGGGAGTCTCTGAAGATCTCCTGTAAGGGTTCTG<br>GATACAGGTTTACCAACTACTGGATCGGCTGGGTGCGCCAGATGCCCGGGAAAGGCCTGGAGTGGATGGGGATCATC<br>TATCCTGGTGACTCTAATACCAGATATAGCCGTCCTTCCAAGGCCAGGTCACCATCTCAGCCGACAAGTCCATCAGCA<br>CCGCCTACTTGCAGTGGGGCAGCCTGAAGGCCTCGGACACCGCCATGTATTACTGTGCGAGACATTCAGAAACTAAAG<br>ATGGCTACAATTGGGCCCAGGGTAATTTCTACTCCTACTACTATATGGACGTCTGGGGCAAAGGGACCACGGTCACCG<br>TCTCCTCA |
| | 22 | light | GACATCCAGATGACCCAGTCTCCATCCTCCCTGTCTGCATCTGTAGGAGACAGAGTCACCATCACTTGCCGGGCAAGTC<br>AGAGCATTAGCAGCTATTTAAATTGGTATCAGCAGATACCAGGGAAAGCCCCTAAACTCCTGATCTATGCTGCATCCAG<br>TTTGCAAAGTGGGGTCCCATCAAGGTTCAGTGGCAGTGGATCTGGGACAGATTTCACTCTCAGCATCAGCAGTCTGCA<br>ACCTGAAGATTTTGCAACTTACTACTGTCAACAGAGTTACAGTATCTCCCCTCTCAGTTTCGGCGGAGGGACCAAGGTG<br>GAGATCAAA |
| CCHFV-132A | 23 | heavy | CAGGTGCAGCTGCAGGAGTCGGGCCCAGGACTGGTGAAGCCTTCGGAGACCCTGTCCCTCACCTGCACTGTCTCTGGT<br>GGCTCCATCAATTATTACTACTGGAGCTGGATCCGGCAGCCCCCAGGGAAGGGACTGGAGTGGATTGCATATATCTAT<br>TACATTGAGGGCAGTGAGAGCACCAACTACAACCCTCCCTCAAGAGTCGAGTCACCATGTCAGTAGACACGTCCAAG<br>AACCAGTTGTCCCTGAAGCTGAGCTCTGTGACCGCTGCGGACACGGCCGCGTATTACTGTGCGAGGGATTCCCGTCGA<br>AACAGATATAGTGGCTACTACTTTGACTTCTGGGGCCAGGGAACCCTGGTCACCGTCTCCTCA |
| | 24 | light | GAAATAGTGATGACGCAGTCTCCAGTCACCCTGTCTGTGTCTCCAGGGGAAAGAGCCACCCTCTCCTGCAGGGCCAGT<br>CAGAGTGTTAGGAGCAACTTAGCCTGGTACCAGCACAAACCTGGCCAGGCTCCCAGGCTCCTCTTCTATGGTGCATCC<br>ACCAGGGCCACTGGTGTCCCAGCCAGGTTCAGTGGCAGTGGGTCAGGGACAGAGTTCACTCTCACCATCAGCAGCCT<br>GCAGTCTGAAGATTTTGCAGTTTATTTCTGTCACCAGTATAATAACTGGCCTCAGACGTTCGGCCAAGGGACCAAGGTG<br>GAAATCAAA |
| CCHFV-133A | 25 | heavy | CAGGTGCAGCTGCAGGAGTCGGGCCCAGGACTGGTGAAGCCTTCGGGGACCCTGTCCCTCACCTGCGCTGTCTCTGGT<br>GACTCCATCAGCGGGAGTTTCTGGTGGAGTTGGGTCCGCCAGCCCCCAGGGAAGGGGCTGGAGTGGCTTGGGGAAA<br>TCTATCATAGTGGCAACACCCACTACAACCCGTCCCTCAAGAGTCGAGTCACCATGTCAAGAGACAAGTCTAAGAACCA<br>GTTCTCCCTGAAGCTAACCTCTGTGACCGCCGCGGACACGGCCGTCTATTACTGTTGGAGAGTATTGGGTCGTACCAG<br>CTGCTAGGGAGTGGTTACTACGCTATGGACGTCTGGGGCCAAGGGACCACGGTCACCGTCTCCTCA |
| | 26 | light | CAGGTCCAACTGGTACAATCTGGGGCTGAGGTGAAGAAGCCTGGGGCCTCAGTGAAGGTCTCCTGCAAGGTTTCCGG<br>ATACTCCCTCACTGAGTTATCCATGCACTGGGTGCGACAGCCTCCTGCAAAAGGGCTTGAGTGGATGGGACGTTTTGA<br>TCCTGGAGATCGTAAACCAATCTACGCACAGAGGTTCCAGGGCAGAATCACCATGACCGAGGACACATCTACAGACAC<br>GACCTTCATGGAACTGAGCAGCCTGAGATCTGAGGACACGGCCCTATATTTCTGTGCAACAGATCCTGGAGCAGTGGC<br>TGGTTTCCTGGGCTTCTGGGGCCAGGGAACCCTGGTCACCGTCTCCTCG |
| CCHFV-135C | 27 | heavy | GACATCGTGATGACCCAGTCTCCAGACTCCCTGGCTGTGTCTCTGGGCGAGAGGGCCACCATCAACTGCAAGTCCAGC<br>CAGAGTGTTTTATACAGGTCCAACAATAACAACTACTTAGCATGGTACCAGCAGAAAGTAGGACAGCCTCCTAAGCTG<br>CTCATTTACTGGGCATCTATCCGGGAATCCGGGGTCCCTGACCGATTCAGTGGCAGCGGGTCTGGGACAGATTTCACT<br>CTCACCATCAGCAGCCTGCAGGCTGAAGATGTGGCAGTTTATTACTGTCAGCAATACTATGGTACCGTCACTTTCGGCC<br>CTGGGACCAAAGTGGATATCAAA |
| | 28 | light | GAGGTGCAGCTGGTGGAGTCTGGGGGAGGCTTGGTACAGCCAGGGCGGTCCCTGAGACTCTCCTGTACAGCTTCTGG<br>GTTCACCTTTGGTGATTATGTTATGACCTGGGTCCGCCAGGCTCCAGGGAAGGGGCTGGAGTGCGTAGGTTTCATCAG<br>AACCAAACCTTATGGTGGGACAACAGAATACGCCGCGTCTGTGAAAGGCAGATTCACCATCTCAAGAGATGATTCCAA<br>AAGCATCGCCTATCTGCAAATGAACAGCCTGAAAACCGACGACACAGCCGTGTATTACTGTTTAGCCGGCACTGACTG<br>GTCCTACTTTGACTACTGGGGCCAGGGAACCCTGGTCACCGTCTCCTCA |
| CCHFV-137B | 29 | heavy | CAGTCTGCCCTGACTCAGCCTCGCTCAGTGTCCGGGTCTCCTGGACAGTCAGTCACCATCTCCTGCACTGGAACCAGCA<br>GTGATGTTGGTGGTTATAACTATGTCTCCTGGTACCAACGGCACCCAGGCAAAGCCCCCCAACTCATGATTTATGATGT<br>CAATAAGCGGCCCTCAGGGGTCCCTGATCGCTTCTCTGGCTCCAAGTCTGGCAACACGGCCTCCCTGACCATCTCTGGG<br>CTCCAGGCTGACGATGAGGCTGATTATTACTGCTGCTCATATGCAGGCAGCTACACTTGGGTGTTCGGCGGAGGGACC<br>AAGCTGACCGTCCTA |
| | 30 | light | CAGGTGCAGCTGCAGGAGTCGGGCCCAGGACTGGTGAAGCCTTCGGAGACCCTGTCCCTCACCTGCACTGTCTCTGGT<br>GGCTCCATCAGTAGTTACTACTGGACCTGGATCCGGCAGCCCCCAGGGAAGGGGCTGGAGTGGATTGGTCATATGTA<br>TTACAGTGGGAGCACCAACAACAACCCCTCCCTCAAGGGTCGAGTCACCGTATCAGTGGACACGTCCAAGAACCAGTT<br>CTCCCTGAAGCTGACCTCTGTGACCGCTGCGGACACGGCCGTGTATTACTGTGCGAGAGGGCCTACTACGGTTCGGG<br>TAGTTTTCACTACTACTACTACATGGACGTCTGGGGCAAAGGGACCACGGTCACCGTCTCCTCA |
| CCHFV-144B | 31 | heavy | GACATCCAGATGACCCAGTCTCCTTCCACCCTGTCTGCATCTGTAGGAGACAGAGTCACCATCACTTGCCGGGCCAGTC<br>AGAGTATTAGTAACTGGTTGGCCTGGTATCAGCAGAAACCAGGGAAAGCCCCTAAGCTCCTGATCTCTAAGGCATCTA<br>GATTAGAAGGTGGGGTCCCATCAAGGTTCAGCGGCAGTGGATCTGGGACAGAGTTCACTTTCACCATCAGCAGCCTGC<br>AGCCTGATGATTGTGCAACTTATTACTGCCAACAATATAATGGTTATTCCTACACTTTTGGCCAGGGGACCAAGCTGGA<br>GATCAAA |
| | 32 | light | GAGGTGCAGCTGGTGGAGTCTGGGGGAGGCCTGGTCAAGCCTGGGGGGTCCCTGAGACTCTCCTGTGCAGTCTCTGG<br>ATTCACCTTCAGTAGCTATAGCATGAACTGGGTCCGCCAGGCTCCAGGGAAGGGGCTGGAGTGGGTCTCATCCATTAG<br>TAGTAGTAGTACTTTCATAGACTACGCAGACTCAGTGAAGGGCCGATTCACCATCTCCAGAGACAACGCCAAGAATTT<br>ACTGTATCTGCAAATGAACAGCCTGAGAGCCGAGGACACGGCTGTGTTTTACTGTGCGAGAGGCGGTAATGACTACA<br>GTGACTACGAAAACTACTACTACTACATGGACGTCTGGGGCAAAGGGACCACGGTCACCGTCTCCTCA |
| CCHFV-14A | 33 | heavy | TCCTATGAGCTGACTCAGCCACCCTCAGTGTCCGTGTCCCCAGGACAGACAGCCAGCATCACCTGCTCTGGAGATGAAT<br>TGGGGGATAAATATGCTTGCTGGTATCAGAAGAAGCCAGGCCAGTCCCCTGTGCTGGTCATCTATCAAGATAACAAGC<br>GGCCCTCAGGGATCCCTGAGCGATTCTCTGGCTCCAACTCTGGGAACACAGCCACTCTGACCATCAGCGGGACCCAGG |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | | | CTATGGATGAGGCTGACTATTACTGTCAGGCGTGGGACAGCAGCACTGCTTATGTCTTCGGAACTGGGACCAAGGTCA<br>CCGTCCTA |
| | 34 | light | GAAGTGCAGCTGGTGGAGTCTGGGGGAGGCTTGGTACAGCCTGGCAGGTCCCTGAGACTCTCCTGTGCAGCCTCTGG<br>ATTCATCTTTGATGATTATGCCATACACTGGGTCCGGCAAGCTCCAGGGAAGGGCCTGGAGTGGGTCTCAGGTATTAC<br>CTGGGATAGTGGTAGGATAGGCTATGCGGACTCTGTGAAGGGCCGATTCACCATCTCCAGAGACAACGCCAAGAAGT<br>CCCTGTATCTGCAAATGAACAGTCTGAGACCTGAGGACACGGCCTTGTATTACTGTGCAAAAGATAGGGGCCCATTCG<br>GGTGGCTTACCCTTGACTACTGGGGCCAGGGAACCCTGGTCATCGTCTCCTCA |
| CCHFV-19C | 35 | heavy | GACATCCAGATGACCCAGTCTCCATCCTCCCTGTCTGCATCTGTAGGAGACAGAGTCACCATCACTTGCCGGGCAAGTC<br>AGAGCATTAGGAGCTATTTAAATTGGTATCAGCAGAAACCAGGGAAAGCCCCTAAGCTCCTGATCTATGCTGGATCCA<br>CTTTGCAAAGTGGGGTCCCATCAAGGTTCAGTGGCGGTGGATCTGGGACAGGTTTCACTCTCACCATCAGCAGTCTGC<br>AACCTGAAGATTTTGCAACTTACTACTGTCAGCAGAGTTCCACTACCCCGTGGACGTTCGGCCAAGGGACCAAGGTGG<br>AATTCAAA |
| | 36 | light | GAGGTGCAGCTGGTGGAGTCTGGGGGAGGCTTGGTACAGCCAGGGCGGTCCCTGAGACTCTCCTGTACAGCATCTGG<br>ATTCACCTTTGGTGATTATGCTCTGAACTGGGTCCGCCAGGCTCCAGGGAAGGGGCTGGAGTGGGTAGGTTTCATTAG<br>AAGCAAAGCTTATGGTGGGACAACAGAATACGCCGCGTCTGTGAAAGGCAGATTCACCATCTCAAGAGATGATTCCAA<br>AAGCATCGCCTTTCTGCAAATGAACAGCTGAAAACCGAGGACACAGCCGTGTATTACTGTACTAGAGCAACTCCCGT<br>ATTACTATGGTTCGGGAGCTCCGGGAACTTCTTTGACTACTGGGGCCAGGGAACCCTGGTCACCGTCTCCTCA |
| CCHFV-21B | 37 | heavy | CAGTCTGCCCTGACTCAGCCTGCCTCCGTGTCTGGGTCTCCTGGACAGTCGATCACCATCTCCTGCACTGGAACCAGCA<br>GTGACGTTGGTGGTTATAACTATGTCTCCTGGTACCAACAACACCCAGGCAAAGCCCCCAAACTCATGATTTATGATGT<br>CAGTAATCGGCCCTCAGGGGTTTCTAATCGCTTCTCTGGCTCCAAGTCTGGCAACACGGCCTCCCTGACCATCTCTGGG<br>CTCCAGGCTGAGGACGAGGCTGATTATTACTGCAGCTCATATACAACCAGCAACTCCTATGTCTTCGGAACTGGGACC<br>AAGGTCACCGTCCTA |
| | 38 | light | CAGCTGCAGCTGCAGGAGTCGGGCCCAGGACTGGTGAAGCCTTCGGAGACCCTGTCCCTCACCTGCACTGTCTCTGGT<br>GACTCCATCAACAATAATAATTACTACTGGGGCTGGATCCGCCAGCCCCCAGGGAAGGGGCTGGAGTGGATTGGGAG<br>TATCTATTATAGTGGGGATCACCTACTACAACCCGTCCCTCAAGAGTCGAGTCACCATATCCGTGGACAGTCCAAGAAC<br>CAGTTCTCCCTGAAGCTGAGCTCTGTGACCGCCGCAGACACGGCTGTTTATTACTGTGTGAGACACGGTTTGGACCACA<br>AATTTGACTACTGGGGCCAGGGAACCCTGGTCACCGTCTCCTCA |
| CCHFV-23C | 39 | heavy | CAGTCTGCCCTGACTCAGCCTGCCTCCGTGTCTGGGTCTCCTGGACAGTCGATCACCATCTCCTGCACTGGAACCAGCA<br>GTGATGTTGGGACTTATAACCTTCTCTCCTGGTACCAACAGTACCCCGGCAAAGCCCCCAGGTCGTGATTTATGAGGT<br>CAGTAAGCGGCCCTCAGGGGTTTCTATTCGCTTCTCTGGCTCCAAGTCTGGCAACACGGCCTCCCTGACAATCTCTGGG<br>CTCCAGGCTGAGGACGAGGCTGATTATTACTGCTGCTCATATGCAGGTGGCAGCAATTCAGTGCTATTCGGCGGGGG<br>GACCAAGCTGACCGTCCTA |
| | 40 | light | GAGGTGCAGCTGGTGGAGTCTGGGGGAGGCTTGGTACAGCCTGGGGGGTCCCTGAGACTCTCCTGTGCAGCCTCTGG<br>ATTCACTTTCAGTAGCTATAGCATGAACTGGGTCCGCCAGGCTCCAGGGAAGGGGCTGGAGTGCGTTTCATACATTAG<br>TAGTAGTAGTGGTGCCATATACTACGCAGACTCTGTGAAGGGCCGATTCACCATCTCCAGAGACAATGCCAAGAACTC<br>ACTGTATCTGCAAATGAACAGCCTGAGAGCCGAGGACACGGCTGTGTATTACTGTGCGAGAGGGAACGGTGCGACGT<br>ACTGGGGCCAGGGAACCCTGGTCACCGTCTCCTCA |
| CCHFV-29C | 41 | heavy | GACATCCAGATGACCCAGTCTCCATCCTCACTGTCTGCATCTGTAGGAGACAGAGTCACCATCACTTGTCGGGCGAGTC<br>AGGACATTAGTAGTTATTTAGCCTGGTTTCAGCAGAAACCAGGGAAAGCCCCTAAGTCCCTGATCTATGCTGCATCCAG<br>TTTGCAAAGTGGGGTCCCATCAAAGTTCAGCGGCAGTGGATCTGGGACAGATTTCACTCTCACCATCAGCAGCCTGCA<br>ACCTGAAGATTTTGCAACTTATTACTGCCAACAGTATAATATTTACCCGATCACCTTCGGCCAAGGGACACGACTGGAG<br>ATTAAA |
| | 42 | light | GAGGTGCAGCTGGTGCAGTCTGGAGCAGAGGTGAAAAAGCCCGGGGAGTCTCTGAAGATCTCCTGTAAGGGTTCTG<br>GATACAGGTTTACCAACTACTGGATCGGCTGGGTGCGCCAGATGCCCGGGAAAGGCCTGGAGTGGATGGGGATCATC<br>TATCCTGGTGACTCTGATACCAGATACAGCCCGTCCTTCCAAGGCCAGGTCACCATCTCAGCCGACAAGTCCGTCAGCA<br>CCGCCTACCTGCAGTGGAGCAGCCTGAAGGCCTCGGACTCCGCCTTGTATTACTGTGCGAGACTTCCGCATCCAGTGA<br>CTGGTCCCCTTGACTACTGGGGCCAGGGAACCCTGGTCACCGTCTCCTCA |
| CCHFV-2B | 43 | heavy | CAGTCTGCCCTGACTCAGCCTGCCTCCGTGTCTGGGTCTCCTGGACAGTCGATCACCATCTCCTGCACTGGAACCAGCA<br>ATGATGTTGGGAGTTATAACCTTGTCTCCTGGTACCAACATCACCCAGGCAAAGCCCCCAAACTCATGATTTATGAGGT<br>CAGTAAGCGGCCCTCAGGGGTTTCTAATCGCTTCTCTGGCTCCAAGTCTGGCAACACGGCCTCCCTGACAGTCTCTGGG<br>CTCCAGGCTGAGGACGAGGCTGATTATTACTGCTGCTCATATGCAGGTAGTATGACTTGGGTGTTCGGCGGAGGGACC<br>AAGCTGACCGTCCTA |
| | 44 | light | GAGGTGCAGCTGGTGGAGTCTGGGGGAGGCCTGGTCAAGCCTGGGGGGTCCCTGAGACTCTCCTGTGCAGCCTCTGG<br>ATTCACCTTCAGGAGTTATACCATGAACTGGGTCCGCCAGGCTCCAGGGAAGGGGCTGGAGTGGGTCTCGTCCATTAG<br>TACTAGTAGTAGTTACATATACTACGCAGACTCTGTGAAGGGCCGATTCACCATTTCCAGAGACAGCGCCAAGAGCTC<br>ACTGTATCTGCAAATGAACAGCCTGAGAGCCGAGGACACGGCTGTGTATTACTGTGCGAGTTTGAGGAAAGATTCGG<br>GGAGTTTTTATAATCGAGCCCTCGACTACTGGGGCCAGGGAACCCTGGTCACCGTCTCCTCA |
| CCHFV-3B | 45 | heavy | CAGTCTGCCCTGACTCAGCCTGCCTCCGTGTCTGGGTCTCCTGGACAGTCGATCACCATCTCCTGCACTGGAACCAGCA<br>GTGACGTTGGTGGTTATAATTATGTTTCCTGGTACCAACAACACCCAGGCAAAGCCCCCAAACTCATGATTTATGATGT<br>CAGTAATCGGCCCTCAGGGGTTTCTAATCGCTTCTCTGGCTCCAAGTCTGGCAACACGGCCTCCCTGACCATCTCTGGG<br>CTCCAGGCTGAGGACGAGGCTGATTATTACTGCTACTCATATACGAGCAACAGCACTTATGTCTTCGGAACTGGGACC<br>AAGGTCACCGTCCTA |
| | 46 | light | GAAGTGCAGCTGGTGGAGTCTGGGGGAGGCTTGGTACAGCCTGGCAAGTCCCTGAGACTCTCCTGTGCAGCCTCTGG<br>ATTCACCTTTGATGCTTATGCCATGCACTGGGTCCGGCAAGCTCCAGGGAAGGGGCTGGAGTGGGTCTCAGGTATTAG<br>TTGGAATGGTGGTAACATAGGCTATGCGGACTCTGTGAAGGGCCGATTCACCTTCTCCAGAGACAACGCCAAGAACTC<br>CCTGTATCTGCAAATGAACAGTCTGAGAGCTGATGACACGGCCTTGTATTTCTGTGCAAAAGAAGATTGTCCTAGTACC<br>AGCTGCTATTTTGTTCGTTGGGGACTAAACTGGCTCGACCCCTGGGGCCAGGGAACCCTGGTCACCGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| CCHFV-40A | 47 | heavy | CAGTCTGTGCTGACGCAGCCGCCCTCAGTGTCTGGGGCCCCAGGGCAGAGGGTCACCATCTCCTGCACTGGGAGCAG CTCCAACATCGGGGCAGGTTATGATGTACAACTGGTACCAGCAGCTTCCAGGAACAGCCCCCAAACTCCTCATCTATGAT AACAACAATCGGCCCTCAGGGGTCCCTGACCGATTCTCTGGCTCCAAGTCTGGCACCTCAGCCTCCCTGGCCATCACTG GGCTCCAGGCTGAGGATGAGGCTGATTATTACTGCCAGTCCTTTGACAGCAGCCTGAGTAGGGGGGTATTCGGCGGA GGGACCAAGCTGACCGTCCTA |
| | 48 | light | GAGGTGCAGCTGGTGGAGTCTGGGGGAGGCTTGGTACAGCCAGGGCGGTCCCTGAGACTCTCCTGTTCAGCTTCTGG ATTCACCTTTGCTGATTATGCTGTGAGCTGGGTCCGCCAGGCTCCAGGGAAGGGGCTGGAATGGGTAGGTTTCATTAG AAGCGAAACTTATGGTGGGACAACAGAATACGCCGCCTCTGTGAAAGGCAGATTCACCATCTCAAGAGATGATTCCAA AAGCATCGCCTATCTGCAAATGCACAGCCTGACACCGAGGACACAGCCGTGTTTTACTGTACTAGAGCCCGTCACGA CACGCGAAGTTGGGTGTTAAGTGACCACTGGGGCCAGGGAACCCTGGTCACCGTCTCCTCA |
| CCHFV-4C | 49 | heavy | GACGCCCAGATGACCCAGTCTCCTTCCACCCTGTCTGCATCTGTAGGAGACAGAGTCACCATCACTTGCCGGGCCAGTC AGAACATTAATAGTTGGTTGGCCTGGTATCAGCACAAACCAGGGAAAGCCCCTAAACTCCTGATCTATAAGGCATCTA GTTTAGAAAGTGAGGTCCCATCAAGGTTCAGCGGCAGTGGGTCTGGGACAGATTTCACTCTCACCATCAGCAACCTGC AGCCTGATGATTTTGCAACTTATTACTGCCAACAGTATAATAGTTTCCATTTTGGCCAGGGGACCAAGTTGGAGATCAA A |
| | 50 | light | CAGCTTCAGCTGGTGCAGTCTGGAGTTGAGGTGAAGAAGCCTGGGGCCTCAGTGAAGGTCTCCTGCAAGGCTTCTGG TTACACCTTTACCAGCTATGGTATCCACTGGGTGCGACAGGCCCCTGGACAAGGGCTTGAGTGGATGGGATGGATCAG CGGTTACAATGGTAACACAAACTATGCACAGAAGCTCCAGGGCAGAGTCACCATGACCACAGACACATCCACGAGAA CAGCCTACATGGAGCTGAGGAGCCTGAGATCTGACGACACGGCCGTGTATTACTGTGCGAGAGATCCCTCTATGATGA CCTTTGGGGGAGTTATCGTTTCTCGCTACTTTGACTACTGGGGCCAGGGAACCCTGGTCACCGTCTCCTCA |
| CCHFV-50B | 51 | heavy | CAGTCTGTGCTGACGCAGCCGCCCTCAGTGTCTGGGGCCCCAGGGCAGAGGGTCACCATCTCCTGCACTGGGAGCAG CTCCAACATCGGGGCAGGTTATGATGTACACTGGTACCAGCAACTTCCAGGAACAGCCCCCAAACTCCTCATTTATAAT AACAGCAATCGGCCCTCAGGGGTCCCTGACCGATTCTCTGGCTCCAAGTCTGGCACCTCAGCCTCCCTGGCCATCACTG GGCTCCAGGCTGAGGATGAGGCTGATTATTACTGCCAGTCCTATGACAGCAGTGTGACGGTGTTCGGCGGAGGGACC AAACTGACCGTCCTA |
| | 52 | light | CAGCTGCAGCTGCAGGAGTCGGGCCCAGGACTGGTGAAGCCTTCGGAGACCCTGTCCCTCACCTGCACTCTCTCTGGT GGCTTCATCAGAAGTAGTAGTTACTACTGGGGCTGGATCCGCCAGCCCCCAGGGAAGGGGCTGGAGTGGATTGGGA GTATCTATTATACTGAGAGCACCTACTACAACCCGTCCCTCAAGAGTCGAGTCACCATATCCGTGGACACGTCCAAGAA CCAGTTCTCCCTGAAGCTGAACTCTGTGACCGCCGCAGACACGGCTATATATTACTGTGCGAGACATGATTATTGGACT GGTGCCCGTTACAGCTGGTTCGACCCCTGGGGCCAGGGAACCCTGGTCACCGTCTCCTCA |
| CCHFV-55B | 53 | heavy | CAGTCTGTGCTGACGCAGCCGCCCTCAGTGTCTGGGGCCCCAGGGCAGAGGGTCACCATTTCCTGCACTGGGAGCAG CTCCAACATCGGGGCAGGTTATGATGTACACTGGTACCAGCAGCTTCCAGGAACAGCCCCCAAACTCCTCATCTATGGT AACAGCAATCGGCCCTCAGGGGTCCCTGACCGATTCTCTGGCTCCAAGTCTGGCACCTCTGCCTCCCTGGCCATCACTG GGCTCCAGGCTGAGGATGAGGCTGATTATTACTGCCAGTCCTATGACACCAGCCTCAGTGGTTCGGGCGTGTTCGGCG GAGGGACCAAGCTGACCGTCCTA |
| | 54 | light | CAGGTGCAGCTGGTGCAGTCTGGGGCTGAGGTGAAGAAGCCTGGGGCCTCAGTGAAGCTTTCCTGCAAGGCATCTGG ATACACCTTCACCAGCTACTATATGCACTGGGTGCGACAGGCCCCTGGACAAGGGCTTGAGTGGATGGGTGGGAATTATGAA CCCCAGTGGCGGTAGTACAATGTACGCACAGAAGTACCAGGGCAGAGTCACCATGACCAGGGACACGTCCACGAGCA CAGTCTACATGGAGCTGAGCAGTCTGAGATCCGAGGACACGGCCGTGTATTACTGTGCGAGAGAGACTGTGGTTCAG AGACTAGTAGGGAGGGACTACTACCACGGTATGGACGTCTGGGGCCAAGGGACCACGGTCACCGTCTCCTCA |
| CCHFV-59A | 55 | heavy | GATATTGTGATGACTCAGTCTCCACTCTCCCTGCCCGTCACCCCTGGAGAGCCGGCCTCCATCTCCTGCAGGTCTAGTCA GAGCCTCCTGCATAGTAATGGATACAACTATTTGGATTGGTACCTGCAGAAGCCAGGGCAGTCTCCACAGCTCCTGAT CTATTTCGGTTCTAATCGGGCCTCCGGGGTCCCTGACAGGTTCAGTGGCAGTGGATCAGGCACAGATTTTACACTGAA GATCAGCAGAGTGGAGGCTGAGGATGTTGGGGTTTATTACTGCATGCAAGCTCTACAAACTCCCCTCACTTTCGGCGG AGGGACCAAGGTGGAGATCAGA |
| | 56 | light | GAAGTGCAGCTGGTGGAGTCTGGGGGAGTCGTGGTGCAGCCTGGGGGGTCCCTGAGACTCTCCTGTGCAGCCTCTGG ATTCACCTTTGATGATTATGCCATGCACTGGGTCCGTCAAGCTCCGGGGAAGAGTCTGGAGTGGGTCTCTCTTATAAGT TGGGATGGTGGTAGCACATCATATGCAGACTCTGTGAAGGGCCGATTCACCATCTCCAGAGACAACAGCAAAAACTCC CTGTACTTGCAAATGAACAGTCTGAGACCTGAGGACACAGCCTTATATTACTGTGCAACGGGACACCCCCCCCTTGGTCC TATGGTCCCTGGGCTACTGGGGCCAGGGAACCCTGGTCACCGTCTCCTCA |
| CCHFV-5A | 57 | heavy | GACATCCAGATGACCCAGTCTCCATCCTCCCTGTCTGCATCTGTAGGAGACAGAGTCACCATCACTTGCCGGGCAAGTG CGAACATTAACAGCTATTTAAATTGGTATCAGCAGAAACCAGGAAAAGCCCCTAAATTCCTGATCTATGCTGCATCCAG TTTGCAAGGTGGGGTCCCATCAAGGTTTAGTGGCAGTGGATCTGGGACAGTTTTCACTCTCACCATCAGCAGTCTGCA ACCTGAAGATTTTGCAACTTACTACTGTCAACAGAGTTACACTACCCCGATCACCTTCGGCCAAGGGACACGACTGGAG ATTAAA |
| | 58 | light | CAGGTGCAGCTGGTGCAGTCTGGGGCTGAGGTGAAGAAGCCTGGGTCCTCGGTGAAGGTCTCCTGCAAGGCCTCTGG AGGCACCTTCAGCACCTTTGCTTTCAGCTGGGTGCGACAGGCCCCTGGACGAGGACTTGAGTGGATGGGAGGGATCA TCCCTATCTTTGATACAGCCTACGCACAGAGGTTTCAGGGCAGAGTCACAATTACCGCGGACGAGTCCACGAGCA CAGCCTACGTGGAGCTGAGCAGCCTGAGATCTGAGGACACGGCCGTGTATTACTGTGCGAGAGATCGGAGGTATAAC TATGAGAGTAGTGCTAGTCAGAATAACAGATGGTACTTCGATCTCTGGGGCCGTGGCACCCTGGTCACTGTCTCCTCA |
| CCHFV-61 | 59 | heavy | GACATCGTGATGACCCAGTCTCCAGACTCCCTGGCTGTGTCTCTGGGCGAGAGGGCCACCATCAACTGCAAGTCCAGC CAGAGTGTTTTATACACCTCCAACAATAAGAATTATTTAGCTTGGTATCAGCAGAAACCAGGACAGCCTCCTAAGTTGC TCGTTTACTGGGCATCTATCCGGGAATCCGGGGTCCCTGACCGATTCAGTGGCAGCGGGTCTGGGACAGATTTCACTC TCACCATCAGCAGCCTGCAGGCTGAAGATGTGGCGGTTTATTACTGTCAGCAATATTATACTACTCCTCACTTTCGGC GGAGGGACCAAGGTGGAGATCAAA |
| | 60 | light | CAGGTGCAGCTGGTGGAGTCTGGGGGAGGCGTGGTCCAGCCTGGGGGGTCCCTGAGACTCTCCTGTGCAGCGTCTG GCTTCACCTTCAGTAATTATGGCATTCACTGGGTCCGCCAGGCTCCAGGCAAGGGGCTGGAGTGGGTGGCATTTATAC GGTATGATGGAAGTAATCAAAACTATGGAGACTCCGTGAAGGGCCGATTCACCATCTCCAGAGACAATTCCAGGAACA |

TABLE 1-continued

NUCLEOTIDE SEQUENCES FOR ANTIBODY VARIABLE REGIONS

| Clone | SEQ ID NO: | Chain | Variable Sequence Region |
|-------|-----------|-------|--------------------------|
|  |  |  | CGCTGTTTCTGCAAATGAGCAGCCTGAGAGCTGAGGACACGGCTGTGTATTACTGTGCGAAAGACTTGGCTGTACTAC TGATGTATGGGTTCGGGGGTTTTGACGCCTGGGGCCAGGGAACCCTGGTCACCGTCTCCTCA |
| CCHFV-62B | 61 | heavy | GACATCCAGGTGACCCAGTCTCCATCCTCCCTGTCTGCATCTGTAGGAGACAGAGTCTCCATCACTTGTCGGGCAAGTC AGAGCATTAGCCACTATTTAAATTGGTATCAACAGAAACCAGGGAAAGCCCCTAAACTCCTGATCTATGCTGCATCCAC TTTGCAAAGTGGGGTCCCATCAAGGTTCAGTGGCAGTGGATCTGGGACAGGTTTCACTCTCACCATCAGCGGTCTGCA ACCTGAGGATTTTGCAACTTACTACTGTCAACAGAGTTACAGTACCCCCGTGTCGTTCGGCCAAGGGACCAAGGTGGA AATCAAA |
|  | 62 | light | CAGGTGCAGCTGGTGCAGTCTGGGGCTGAGGTGAAGAAGCCTGGGTCCTCGGTGAAGGTCTCCTGCAAGGCCTCTGG AGGCACCTTCAGAAGCTATGCTATCAACTGGGTGCGACAGGCCCCTGGACAAGGGCTTGAGTGGATGGGAGGGATCA TCCCTATCTTTGGTACAGCAAACTACGCACAGAATTTCCAGGGCAGAGTCACGATTATCGCGGACGAATCCACGAGCA CAGCCTACATGGAGCTGAGCAGCCTGAGATCTGAGGACACGGCCGTGTATTACTGTGCGAGGTATTTTTTCACCACAC CCCATTGGACCCTGCCCATTGACTACGGTATGGACGTCTGGGGCCAAGGGACCACGGTCACCGTCTCCTCA |
| CCHFV-64B | 63 | heavy | GATATTGTGATGACTCAGTCTCCACTCTCCCTGCCCGTCACCCCTGGAGAGCCGGCCTCCATCTCCTGCAGGTCTAGTCA GAGCCTCCTGCATAGTAATGGATACAACTCTTTGGATTGGTACCTTCAGAAGCCAGGGCAGTCTCCACAGCTCCTGATC TATTTGGGTTCTTATCGGGCCTCCGGGGTCCCTGACAGGTTCAGTGGCAGTGGATCAGGCACAGATTTTACACTGAAA ATTAGCAGAGTGGAGGCTGAGGATGTTGGGGTTTATTACTGCATGCAAGCTCTACAAACTCCGTACACTTTTGGCCAG GGGACCAAGCTGGAGATCAAA |
|  | 64 | light | CAGGTGCAGCTGCAGGAGTCGGGCCCAGGACTGGTGAAGCCTTCGGGGACCCTGTCCCTCACCTGCGCTGTCTCTGGT GGCTCCATCAGCAGTAGTAACTGGTGGAGTTGGGTCCGCCAGCCCCCAGGGAAGGGGCTGGAGTGGATTGGACAAA TCTATTATAGTGGGACCACCAACTACAACCCGTCCCTGAAGAGTCGAGTCAGCATATCAGTGGACAAGTCCAAGAACC AGTTCGCCCTGAAACTGAGCTCTGTGACCGCCGCGGACACGGCCGTGTATTATTGTGCTGGTGGGACCTACTTTAGGC GCTACTTTGACTACTGGGGCCAGGGGAGCCCTGGTCACCGTCTCCCCA |
| CCHFV-65A | 65 | heavy | GAAATAGTGATGACGCAGTCTCCAGCCACCCTGTCTGTGTCTCCAGGGGAAAGAGCCACCCTCTCCTGCAGGGCCAGT CAGAGTGTTAGCGACAACTTAGCCTGGTACCAGCAGAAACCTGGCCAGGCTCCCAGGCTCCTCATCTATGGTGCATCC ACCAGGGCCACTGGTATCCCAGCCAGGTTCAGTGGCAGTGGGTCTGGGACAGAGTTCACTCTCACCATCAGCAGCCTG CAGTCTGAAGATTTTGCAGTTTATTACTGTCAGCAGTATAATAACTGGCCTCCGCTCACTTTCGGCGGAGGGACCAAGG TGGAGATCAAA |
|  | 66 | light | CAGTTGCAGTTGCAGGAGTCGGGCCCAGGACTGGTGAAGCCTTCGGAGACCCTGTCCCTCATTTGCACTGTCTCTGGT GGCTCCATCAGCAGTAGTAGTTACTACTGGGGCTGGATCCGCCAGCCCCCAGGGAAGGGGCTGGAGTGGATTGGA GTGTCTTCTATAGTGGGAATACCTACTACAACCCGTCCCTCAAGAGTCGAGTCACCATCTCCGTAGACACGTCCAAGAA CCAGTTCTCCCTGAACCTGAGCTCTGTGACCGCCGCAGACACGACTGTCTACTACTGTGCGAGACACCAATATAGCAGC AGCTGGAACCGCATTGATGCTTTTGATATTTGGGGCCAAGGGACAGTGGTCACCGTCTCTGCA |
| CCHFV-71C | 67 | heavy | GAAGTGCAGCTGGTGGAGTCTGGGGGAGGCTTGATACAGCCAGGGCGGTCCCTGAGACTCTCCTGTACAACTTCTGG ATTCACCTTTGGTAACTATGTTATGAGCTGGGTCCGCCAGGCTCCAGGGAAGGGGCTGGAGTGGGTAGGTTTCATTAG AAGCAAAGCTTATGGTGGGACAACAGAATACGCCGCGTCTGTGAAGGCAGATTCAGCATCTCAAGAGATGATTCCA AAAGCATCGCCTATCTGCACATGAACAGCCTGAAAACCGAGGACACAGCCGTATATTACTGTTTAGCCGCCACTGTCTG GACCTACTTTGACTTCTGGGGCCAGGGAACCCTGGTCACCGTCTCTTCA |
|  | 68 | light | CAGTCTGCCCTGACTCAGCCTCGCTCAGTGTCCGGGTCTCCTGGACAGTCAGTCACCATCTCCTGCACTGGAACCAGCA GTGATGTTGGTGCTTATAACTATGTCTCCTGGTACCAACATCACCCAGGCAAAGCCCCCAAACTCATGATTTTTGATGTC AATAGCCGGCCCTCAGGGGTCCCTGATCGCTTCTCTGGCTCCAAGTCTGGCAACACGGCCTCCCTGACCATCTCTGGGC TCCAGGCTGACGATGAGGCTGATTATTACTGCTGCTCATATGCAGGCAGTTTCACTTGGGTGTTCGGCGGAGGGACCA AGTTGACCGTCCTA |
| CCHFV-72B | 69 | heavy | CAGGTTCAGCTGGTGCAGTCTGGAGCTGAGGTGAAGAAGCCTGGGGCCTCAGTGAAGGTCTCCTGCAAGGCTTCTGG TTACCCCTTTACCAACTATGGTATCAGCTGGGTGCGACAGGCCCCTGGACAAGGGCTTGAGTGGATGGGATGGATCAG CGCTTACAATGGTAACACAAACTATGCACAGAAGCTCCAGGGCAGAGTCACCATGACCACAGACACATCCACGAGCAC AGCCTACATGGAGCTGAGGAGCCTGAGATCTGACGACACGGCCGTGTATTACTGTGCGAGAGATTACTATGATAGTA GTGGTTCCGTCTGGGGCCAAGGGACCACGGTCACCGTCTCCTCA |
|  | 70 | light | GACATCCAGATGACCCAGTCTCCATCCTCCCTGTCTGCATCTGTAGGAGACAGAGTCACCATCACTTGCCGGGCAAGTC AGAGCATTAGCACCTATTTAAATTGGTATCAGCAGAAACCAGGGAAAGCCCCTAACCTCCTGATCTATGGTGCATCCAG TTTGCAAAGTGGGGTCCCATCAAGGTTCAGTGGCAGTGGATCTGGGACAGATTTCACTCTCACCATCAGCAGTCTGCA ACCTGAAGATTTTGCAACTTACTACTGTCAACAGACATACACTACCCCTCGAACGTTCGGCCAAGGGACCAAGGTGGA AATCAAA |
| CCHFV-73C | 71 | heavy | CAGGTCCAGCTTGTGCAGTCTGGGGCTGAGGTGAAGAAGCCTGGGGCCTCAGTGAAGGTTTCCTGCAAGACTTCTGG ATACACCTTCATTAGTTATACTATGCATTGGGTGCGCCAGGCCCCCGGACAAAGGCTTGAGTGGATGGGATGGATCAA CGGTGGCAATGGTAACACAAAATATTCGCAGAGGTTCAGGGCAGGTCACCATTACCAGGGACACATCCGCGACCA CAGTCTACATGGAGTTGAGCAGCCTGACATCTGAAGACACGGCTCTGTATTACTGTGCGAGAGTAAAATCGGACACCC TTGATTTTAACTGGAACCACGCTTTGACTACTGGGGCCAGGGAACCCTGGTCACCGTCTCCTCA |
|  | 72 | light | GAAATTGTGTTGACGCAGTCTCCAGGCACCCTGTCTCTGTCTCCGGGGGAAAGAGCCACCCTCTCCTGCAGGGCCAGT CAGAGTGTTAGCAGCAGCTATTTGGTCTGGTACCAGCAGAAACCTGGCCAGGCTCCCAGGCTCCTCATCTATGGTGCA TCCAGCAGGGCCACCGGCATCCCAGACAGGTTCAGTGGCAGTGGGTCTGGGACAGACTTCACTCTCACCATCAGCAGA CTGGAGCCTGAAGACTTTGCAGTGTATTACTGTCAGCAGTGTGGTAGCTCCCCGATCACCTTCGGCCAAGGGACACGA CTGGAGATTAAA |
| CCHFV-74A | 73 | heavy | CAGGTGCAGCTACAGGAGTCGGGCCCAGGACTGGTGAAGCCTTCGGAGACCCTGTCCCTCACCTGCGATGTCTCTGGT TACTCCATCAGCAGTGGTTATTATTGGGGCTGGATCCGGCAGCCCCCAGGGAAGGGGCTGGAGTGGATTGGGAGTAT CTATCATAGTGGGATCATCTACTACAACCCGTCCCTCAAGAGTCGAGTCACCATATCAGTAGACACGTCCAAGAACCAG TTCTCCCTGAAGCTGAGCTCTGTGACCGCCGCAGACACGGCCGTGTATTACTGTGCGAGACTTCTACCAAGCAACATCT ACTGGGGCCAGGGAATCCTGGTCACCGTCTCCTCA |

TABLE 1-continued

NUCLEOTIDE SEQUENCES FOR ANTIBODY VARIABLE REGIONS

| Clone | SEQ ID NO: | Chain | Variable Sequence Region |
|---|---|---|---|
| | 74 | light | CAGTCTGCCCTGACTCAGCCTCGCTCAGTGTCCGGGTCTCCTGGACAGTCAGTCACCATCTCCTGCACTGGAACCAGCA GTGATGTTGGTAGTTATAACTATGTCTCCTGGTACAAACAGCACCCAGGCAAAGCCCCCAAACTCATGATTTTTGATGT CAGTAGGCGGCCCTCAGGGGTCCCTGATCGCTTCTCTGGCTCCAAGTCTGGCAACACGGCCTCCCTGACCATCTCTGGG CTCCAGGCTGAGGATGAGGCTGATTATTTCTGCTGCTTATATGCAGGCAGCTACACTTTCAAATTCGGCGGAGGGACC AAGGTGACCGTCCTA |
| CCHFV-75A | 75 | heavy | GAAGTGCAGTTGGTGGAGTCTGGGGGAGGCTTGGTGCGGCCTGGCAGGTCCCTGAGACTCTCCTGTGCAGCCTCTGG ATTCACCTTTGATGATTATGCCATGCACTGGGTCCGGCAAGCTCCAGGGAAGGGCCTGGAGTGGGTCTCAGGTATTAG TTGGCATAGTGGTAGCATAGGCTATGCGGACTCTGTGCAGGGCCGATTCACCACCTCCAGAGACAACGCCAAGAACTC CCTGTATCTGCAAATGGACAGTCTCCGACCTGAGGACACGGCCTTCTATTATTGTGCAAAATCTCCCTTGAAAATTTGG CAGCACCTGACTCCCTATGACTACTGGGGCCAGGGAACCCTGGTCACCGTCTCCTCA |
| | 76 | light | GAAATAGTGATGACGCAGTCTCCAGCCACCCTGTCTGTGTCTCCAGGGGAAAGAGCCACCCTCTCCTGTAGGGCCAGT CAGAGTGTTAGCAGCAACTTAGCTGGTACCAGCAGAAACGTGGCCAGGCTCCCAGGCTCCTCATGTATGGTGCATCC ACCAGGGCCACTGGTATCCCAGCCAGGTTCAGTGGCAGTGGGTCTGGGACAGAGTTCACTCTCACCATCAGCAGCCTG CAGTCTGAAGATTTTGCAGTTTATTACTGTCAGCAGTATAATAACTGGCCTCCCTTTTTCGGCGGAGGGACCAAGGTGG AGATCAAA |
| CCHFV-77A | 77 | heavy | CAGGTGCAGCTGCAGGAGTCGGGCCCAGGACTGGTGAAGCCTTCACAGACCCTGTCCCTCACCTGCACTGTCTCTGAT GGCTCCATCAGCAGTGGTGATTACTACTGGAGCTGGGTCCGCCAGCCCCCAGGGAAGGGGCTGGAGTGGATTGGGTA CATATATTACAGTGGGAGCACCTATTACAGCCCGTCCCTCAAGAGTCGAGTTACCATCTCAGTAAACATGTCCAAGAAC CAGTTCTCCCTGAAGCTCAGCTCTGTGACTGCCGCAGACACGGCCGTGTATTACTGTGCCACCGCCCCGCGGTAGGG AGTTACTACATGAGATGGACGGGATACCACTACTACATGGACGTCTGGGGCAAAGGGACCACGGTCACCGTCTCCTCA |
| | 78 | light | CAGTCTGTGCTGACGCAGCCGCCCTCAGTGTCTGCGGCCCCAGGACAGAAGGTGACCATCTCCTGCTCTGGAAGCAGC TCCAACATTGAATATAATTATGTATCCTGGTACCAGCAGCTCCCAAGAACAGCCCCCAAACTCCTCATTTATGACAATAA TAAGCGACCCTCAGGGATTCCTGACCGATTCTCTGGCTCCAAGTCTGGCACGTCAGCCACCCTGGGCATCACCGGACTC CAGACTGGGGACGAGGCCGATTATTACTGCGGAACATGGGATAGTAGCCTGAATGCTTGGGTGTTCGGCGGAGGGA CCAAGCTGACCGTCCTA |
| CCHFV-77B | 79 | heavy | CAGGTGCAGCTGCAGGAGTCGGGCCCAGGACTGGTGAAGCCTTCACAGACCCTGTCCCTCACCTGCACTGTCTCTGAT GGCTCCATCAGCAGTGGTGATTACTACTGGAGCTGGGTCCGCCAGCCCCCAGGGAAGGGGCTGGAGTGGATTGGGTA CATATATTACAGTGGGAGCACCTATTACAGCCCGTCCCTCAAGAGTCGAGTTACCATCTCAGTAAACATGTCCAAGAAC CAGTTCTCCCTGAAGCTCAGCTCTGTGACTGCCGCAGACACGGCCGTGTATTACTGTGCCACCGCCCCGCGGTAGGG AGTTACTACATGAGATGGACGGGATACCACTACTACATGGACGTCTGGGGCAAAGGGACCACGGTCACCGTCTCCTCA |
| | 80 | light | CAGTCTGTGCTGACGCAGCCGCCCTCAGTGTCTGCGGCCCCAGGACAGAAGGTGACCATCTCCTGCTCTGGAAGCAGC TCCAACATTGAATATAATTATGTATCCTGGTACCAGCAGCTCCCAAGAACAGCCCCCAAACTCCTCATTTATGACAATAA TAAGCGACCCTCAGGGATTCCTGACCGATTCTCTGGCTCCAAGTCTGGCACGTCAGCCACCCTGGGCATCACCGGACTC CAGACTGGGGACGAGGCCGATTATTACTGCGGAACATGGGATAGTAGCCTGAATGCTTGGGTGTTCGGCGGAGGGA CCAAGCTGACCGTCCTA |
| CCHFV-79A | 81 | heavy | CAAATGCAGCTGGTGCAGTCTGGGCCTGAGGTGAAGAAGCCTGGGACCTCAGTGAAGGTCCCCTGCAAGGCTTCTGG ACTCACCTTTAGTAGATCTGCTGTGCAGTGGGTGCGACAGGCTCGTGGACAACGCCTTGAGTGGATAGGATGGATCGT TGTTGGCAGTGGTAACACAAACTACGCACAGAAATTCCAGGATAGAGTCACCATTACCAGGGACATGTCCACAAGCAC GGCCTACATGGAGCTGAGCAGCCTGAGATCCGAGGACACGGCCATATATTACTGTGCGGCAGGTCCAGGTGTATGGG CTAGAACTGAACGCCCGAATGATGCTTTTAATCTCTGGGGCCAAGGGACAATGGTCACCGTCTCTTCA |
| | 82 | light | CAGTCTGTGCTGACGCAGCCGCCCTCAGTGTCTGCGGCCCCAGGACAGAAGGTCACCATCTCCTGCTCTGGAAGCAGC TCCAACATTGGGAACAATTATGTATCCTGGTACCAGCAGCTCCCAGGAGCAGCCCCCAAAGTCCTCATTTATGACAATA ATGAGCGACCCTCGGGGATTCCTGACCGATTCTCTGGCTCCAAGTCTGGCAGGTCAGCCACCCTGGGCATCACCGGAC TCCAGACTGGGGACGAGGCCGATTATTTCTGCGGAACATGGGATAGCAGCCTGAGTGCCTGGATTTTCGGCGGAGGG ACCAAGCTGACCGTCCTA |
| CCHFV-7C | 83 | heavy | GAAGTGCAGCTGTTGGAGTCTGGGGGAGGCTTGGTGCAGCCTGGGGGGTCCCTGAGACTCTCCTGTGCAGCCTCTGG ATTCACCTTTAGCAGCTATGCCATGAGCTGGGTCCGCCAGGCTCCAGGGAAGGGGCTGGAGTGGGTCTCAACTATTAC TGGTAGTGGTGGTAGCACACGCTTCGCAGACTCCTTGAAGGGCCGCTTCGCCATCTCCAGAGACAATTCCAAGAACAC GCTGTATCTGCAAATGAACAGCCTGAGAGTCGAGGACACGGCCGTATATTACTGTGCGAAACGATATTGTAGTGGTAC CACCTCCATCTTTACTGCTACTACGCCATGGACGTCTGGGGCCAAGGGACAGCGGTCACCGTCTCCTCA |
| | 84 | light | CAGTCTGCCCTGACTCAGCCTGCCTCCGTGTCTGGGTCTCCTGGACAGTCGATCACCATCTCCTGCACTGGAACCAGCA GTGACGTTGGTGGTTATAACTATGTCTCCTGGTACCAACAACACCCAGGCAAAGCCCCCAAACTCATGATTTATGATGT CAGTAATCGGCCCTCAGGGGTTTCTAATCGCTTCTCTGGCTCCAAGTCTGGCAACACGGCCTCCCTGACCATCTCTGGG CTCCAGGCTGAGGACGAGGCTGATTATTACTGCAGCTCATATACAAGCAGCAGCACTAAACTCTTCGGAACTGGGACC AAGGTCACCGTCCTA |
| CCHFV-82C | 85 | heavy | CAGGTGCAGCTGCAGGAGTCGGGCCCAGGACTGGTGAAGCCTTCGGAGACCCTGTCCCTCACCTGCGCTGTCTCTGAT TACTCCATCAGCAGTGGTTACTACTGGGGCTGGATCCGGCAGCCCCCAGGGAAGGGGCTGGAGTGGATTGCGAGTAT CTATCATGGTGGGAGCACCGACTACAACCCGTCCCTCAAGAGTCGAGTCACCATATCGCTAGACACGTCCAAGATCCA GTTCTCCCTGAAGCTGAGCTCTGTGACCGCCGCAGACACGGCCGTGTATTATTGTGCGAGTCGTCATGATCGTAGTGG TTATGACGAATACTTCGAGTACTGGGGCCAGGGCACCCTGGTCACCGTCTCCTCA |
| | 86 | light | GACATCCAGATGACCCAGTCTCCATCCTCCCTGTCTGCTTCTGTGGGAGACAGAGTCACCATCATTTGCCGGGCGAGTC ACGGCATTAGCAATTCTTTAGCCTGGTATCAGCAGAAACAGGGAAAGCCCCTAAGCTCCTGCTCTATGCTGCATCCAG ATTGAAAAGTGGGGTCCCTTCCAGGTTCAGTGGCAGTGGATCTGGGACGGATTACACTCTCACCATCACCAGCCTGCA GCCTGAAGATTTTGCAACTTATTACTGTCAACAGTATTATAGTACGCCTCTGACTTTCGGCCCTGGGACCAAAGTGGAT CTCAAA |
| CCHFV-83A | 87 | heavy | GAGGAACAGCTGGTGGAGTCTGGAGGAGGCTTGATTCACCCTGGGGGGTCCCTGAGACTCTCCTGTGCGGCCTCTGG GTTCACCGTCAGTAGTACCTACATGAATTGGGTCCGCCAGTCTCCAGGGAAGGGGCTGGAGTGGGTCTCACTTATTTA |

TABLE 1-continued

NUCLEOTIDE SEQUENCES FOR ANTIBODY VARIABLE REGIONS

| Clone | SEQ ID NO: | Chain | Variable Sequence Region |
|-------|------------|-------|--------------------------|
| | 88 | light | TAGCGGTGGTAGTACATACTACGCAGACTCCGTGAAGGGCCGATTCACCATCTCCAGAGACAATTCCAAGAACACGGT GTATCTTCAAATGAACAGCCTGAGAGCCGAAGACACGGCCGTGTATTATTGTGCGAGAATTCCCCTCTCCTTCGGCCCA ATGTACTTTGACTATTGGGGCCAGGGAACCCGGGTCACCGTCTCCTCA GAGGAACAGCTGGTGGAGTCTGGAGGAGGCTTGATTCACCCTGGGGGGTCCCTGAGACTCTCCTGTGCGGCCTCTGG GTTCACCGTCAGTAGTACCTACATGAATTGGGTCCGCCAGTCTCCAGGGAAGGGGCTGGAGTGGGTCTCACTTATTTA TAGCGGTGGTAGTACATACTACGCAGACTCCGTGAAGGGCCGATTCACCATCTCCAGAGACAATTCCAAGAACACGGT GTATCTTCAAATGAACAGCCTGAGAGCCGAAGACACGGCCGTGTATTATTGTGCGAGAATTCCCCTCTCCTTCGGCCCA ATGTACTTTGACTATTGGGGCCAGGGAACCCGGGTCACCGTCTCCTCA |
| CCHFV-86C | 89 | heavy | CAGGTGCAGCTGGTGGAGTCTGGGGGAGGCTCGGTCAAGCCTGGAGGGTCCCTGAGACTCTCCTGTGCAGCCTCTGG ATTCACCTTCAGTGACTACTACATGACCTGGATCCGCCAGGCTCCAGGGAAGGGGCTGGAGTGGGTTTCATATATTAG TAGTAGTGCTACTACCATCTACTACGCCGACTCTGTGAAGGGCCGATTCACCATCTCCCGGGACAACGCCAAGAACTTA CTGTATCTGCAAATGAACAGCCTGAGAGCCGAGGACACGGCCGTATATTACTGTGCGAGAGATCATAGGTATTGTACT AGTACCAACTGCTTTGCACACTGGTTCGACCCCTGGGGCCAGGGAATCCTGGTCACCGTCTCCCCA |
| | 90 | light | CAGTCTGTGCTGACTCAGCCACCCTCAGCGTCTGGGACCCCCGGGCAGAGGGTCACCATCTCTTGTTCTGGAAGCAGC TCCAACATCGGAAGTGACACTGTAAAGTGGTACCAGCAACTCCCAGGAACGGCCCCCAGACTTCTCATCTATAGTAATA ATCAGCGGCCCTCAGGGGTCCCTGACCGATTCTCTGGCTCCAAGTCTGGCACCTCAGCCTCCCTGGCCATCAGTGGGCT CCAGTCTGAGGATGAGGCTGATTATTACTGTGCAGCATGGGATGACAGCCTGAATGGTCCGGTGTTCGGCGGAGGGA CCAAACTGACCGTCCTA |
| CCHFV-88A | 91 | heavy | CAGGTGCAACTGGTGCAGTCTGGGGCTGAGGTGAAGAAGCCTGGGGCCTCAGTGAAGGTTTCCTGCAAGGCATCTGG ATACACCTTCAGCAGTTACTATATACACTGGGTGCGACAGGCCCCTGGACAAGGGCTTGAGTGGATGGGAATAATCAA CCCTAGTGTTGGTGCCACAGAGTACGCACACATTTTCCAGGGCAGAGTCACCCTGACCAGGGACACGTCCACGAGTAC AGTCTACATGGACTTGAGCAGGCTTACATCTGACGACACGGCCGTGTATTACTGTGCTAGATGGGGGCTCATTAGTGA GAGCTCACCAAAATACTTTGACTCCTGGGGCCAGGGAACCCTGGTCACCGTCTCCTCA |
| | 92 | light | CAGTCTGTGCTGACGCAGCCGCCCTCAGTGTCTGGGGCCCCAGGGCAGAGGGTCACCATCTCCTGCACTGGGAGCAA CTCCAACATCGGGGCAGGTTATGATGTACACTGGTACCAGCAGCTTCCAGGAACAGCCCCCAAACTCCTCATCTATGAT AATACCAATCGGCCCTCAGGGGTCCCTGACCGATTCTCTGGCTCCAAGTCTGGCACGTCAGCCTCCCTGGCCATCACTG GGCTCCAGGCTGAGGATGAGGCTGATTATTACTGCCAGTCCTATGACAGCAGCGTGAGTGGTTTTTACGTGCTTTTCG GCGGAGGGACCAAGCTGACCGTCCTA |
| CCHFV-8B | 93 | heavy | CAGATCACCTTGAAGGAGTCTGGTCCAACGCTGGTGAAACCCACACAGACCCTCACCCTGACCTGCACCTTCTCTGGAT TCTCACTGAGCAATAGTGGAGTGGGTGTGGGCTGGATCCGTCAGCCCCCAGGAAAGGCCCTGGAGTGGCTTGCACTC ATTTATTGGGATGATGACAAGCGCTACAGGCCATCTCTGAAGAGCAGGCTCACCATCACCAAGGACACCTCCAAAAAC CAGGTGGTCCTTAAAAATGACCAACATGGACCCTGTGGACACAGCCACCTATTACTGTGCACACAGTTATTTCGACTTTT GGAGTGGTTATTTTTCGCTGGACCGTCGGGACCGTCGCGCCGGGCGACAGTCCTACTTTGACTACTGGGGCCAGGGA ACCCTGGTCACCGTCTCCTCA |
| | 94 | light | CAGTCTGCCCTGACTCAGCCTCGCCTCCGTGTCTGGGTCTCCTGGACAGTCGATCACCATCTCCTGCACTGGAACCACCA GTGACGTTGGTGGTTATGACTATGTCTCGTGGTACCAACAACACCCAGGCAAAGCCCCCAAACTCATGATTTTTGATGT CAATCATCGGCCCTCAGGGGTTTCCAGCCGCTTCTCTGGCTCCAAGTCTGGCAACACGGCCTCCCTGACCATCTCTGGG CTCCAGGCTGAAGACGAGGCTGCTTATTACTGCTCCTCATATACAACCGGCACCCTCTTCGGCGGAGGGACCAAGCTG ACCGTCCTG |
| CCHFV-95A | 95 | heavy | CAGGTGCTACTGCAGGAGTCGGGGCCCAGGACTGGTGAAGCCTTCGGGGACCCTGTCCCTCACCTGCGCTGTCTCTGGT GGCTCCATCACCACTAATAACTGGTGGAGTTGGGTCCGCCAGCCCCCAGGGAGGGGGCTGGAGTGGATTGGGGAAAT CTTTCATGGTGGAAAAACCAACTACAACCCGTCCCTCAAGAGTCGAGTCACCATATCAGTCGACAAGTCCAAGAACCA GTTCTCCCTGAAGCTGACCTCTCTGACCGCCGCGGACACGGCCGTGTATTACTGTGCGAGAGCCGGGCTATATAGCAC CAACTGGTCCCCGTTCGACCCCTGGGGCCAGGGAACCCTGGTCACCGTCTCCTCA |
| | 96 | light | GAAGTTGTGTTGACGCAGTCTCCAGGCACCCTGTCTTTGTCTCCAGGGGAAAGAGCCACCCTCTCCTGCAGGGCCAGT CAGAGTGTTACCAGCAGCTACTTAGCCTGGTACCAGCAAAAACCTGGCCAGGCTCCCAGGCTCCTCATCTTTGATGCAT CCAGCAGGGCCACTGGCATCCCAGCCAGGTTCAGTGGCAGTGGGTCTGGGACAGACTTCACTCTCACCATCAGGAGA CTGGAGCCTGAAGATTTTGCAGTGTATTACTGTCAGCAGTATGGTGGCTCACCGTGGACGTTCGGCCAAGGGACCAAG GTGGAAATCAAA |
| CCHFV-IgG-BA | 97 | heavy | CAGGTGCAACTGGTGCAGTCTGGGGCTGAGGTGAAGAAGCCTGGGGCCTCAGTGAAGGTTTCCTGCAAGGCATCTGG ATACACCTTCAGCAGTTACTATATACACTGGGTGCGACAGGCCCCTGGACAAGGGCTTGAGTGGATGGGAATAATCAA CCCTAGTGTTGGTGCCACAGAGTACGCACACATTTTCCAGGGCAGAGTCACCCTGACCAGGGACACGTCCACGAGTAC AGTCTACATGGACTTGAGCAGGCTTACATCTGACGACACGGCCGTGTATTACTGTGCTAGATGGGGGCTCATTAGTGA GAGCTCACCAAAATACTTTGACTCCTGGGGCCAGGGAACCCTGGTCACCGTCTCCTCA |
| | 98 | light | GAAATTGTGTTGACACAGTCTCCAGCCACCCTGTCTTTGTCTCCAGGGGAAAGAGCCACCCTCTCCTGCAGGGCCAGTC AGAGTGTTAGCAGCTACTTAGCCTGGTACCAACAGAGACCTGGCCAGGCTCCCAGGCTCCTCATCTATGATGCATCCA ACAGGGCCACTGGCATCCCAGCCAGGTTCAGTGGCAGTGGGTCTGGGACAGACTTCACTCTCACCATCAGCAGCCTAG AGCCTGAAGATTTTGCAGTTTATTACTGTCAGCAGCGTAGTAACTGGCCCTACACTTTTGGCCGGGGGACCAAGCTGG AGATCAAA |
| CCHFV-IgG-BB | 99 | heavy | CAGGTGCAGCTGGTGCAGTCTGGGGCTGAGGTGAAGAAGCCTGGGTCCTCGGTGAAGGTCTCCTGCAAGGCTTCTGG AGGCACCTTCAGCAGCTATTCTATCAGCTGGCTGCGACAGGCCCCTGGACAAGGGCTTGAGTGGATGGGACAGATCA TCCCTATGTTTGGAACAGCAAACTACGCACAGAAGTTCCAGGGCAGAGTCACGATTACCGCGGACGAATCCACGAGCA CAGCCTACATGGAGCTGAGCAGCCTTAGATCTGAGGACACGGCCGTGTATTACTGTGCGAGAGAGGCCAGAGCCGAG GGGGACGTCTGGGGCCAAGGGACCACGGTCACCGTCTCCTCA |

TABLE 1-continued

---

NUCLEOTIDE SEQUENCES FOR ANTIBODY VARIABLE REGIONS

| Clone | SEQ ID NO: | Chain | Variable Sequence Region |
|---|---|---|---|
| | 100 | light | GAAATTGTGTTGACACAGTCTCCAGCCACCCTGTCTTTGTCTCCAGGGGAAAGAGCCACCCTCTCCTGCAGGGCCAGTC AGAGTGTTAGCAGCTACTTAGCCTGGTACCAACAGAGACCTGGCCAGGCTCCCAGGCTCCTCATCTATGATGCATCCA ACAGGGCCACTGGCATCCCAGCCAGGTTCAGTGGCAGTGGGTCTGGGACAGACTTCACTCTCACCATCAGCAGCCTAG AGCCTGAAGATTTTGCAGTTTATTACTGTCAGCAGCGTAGTAACTGGCCCTACACTTTTGGCCGGGGGACCAAGCTGG AGATCAAA |

---

TABLE 2

---

PROTEIN SEQUENCES FOR ANTIBODY VARIABLE REGIONS

| Clone | SEQ ID NO: | Chain | Variable Sequence |
|---|---|---|---|
| CCHFV-104A | 101 | heavy | HVQLVESGGALVKPGGSLRLSCAASGFTFSDYYMSWIRQAPGKGLEWVS YISSFGSNTFYADFVKGRFTISRDNAKKSLYLQMSSLRAEDTAVYYCARSLR GIAVPSYWGQGTLVTVSS |
| | 102 | light | EIVMTQSPATLSVSPGERVTLSCRASQSVSSDLAWYHQKPGQAPRLLIYDA STRATGIPARFSGSGSGTEFTLTISSLQSEDFAVYYCQQYNNWPPWTFGQ GTKVEIK |
| CCHFV-104B | 103 | heavy | HVQLVESGGALVKPGGSLRLSCAASGFTFSDYYMSWIRQAPGKGLEWVS YISSFGSNTFYADFVKGRFTISRDNAKKSLYLQMSSLRAEDTAVYYCARSLR GIAVPSYWGQGTLVTVSS |
| | 104 | light | EIVMTQSPATLSVSPGERVTLSCRASQSVSSDLAWYHQKPGQAPRLLIYDA STRATGIPARFSGSGSGTEFTLTISSLQSEDFAVYYCQQYNNWPPWTFGQ GTKVEIK |
| CCHFV-105B | 105 | heavy | QLQLLESGPGLVKPSETLSLTCTVSGGSISSNIYYWGWIRQPPGKGLEWIG SIYYSGNTHYNPSLKSRVTISVDTSKNQFSLKLSSLTAADSALYYCASQKMV YPIKRNNWFDPWGQGTLVIVSS |
| | 106 | light | QSVLTQSPSASGTPGQRVTISCSGSSSNIESNTVTWYQQLPGTAPKLLIYG NNQRPSGVPDRFSGSKSGTSASLAISGLQSEDEADYYCAAWDDGLNGWV FGGGTKLTVL |
| CCHFV-106A | 107 | heavy | EVHLVQSGAEVKKPGESLKISCKGSGYSFTSYWIGWVRQMPGKGLEWM GIIYPGDSDTRYSPSFQGQVTISADKSISTAYLQWSSLKASDTAMYYCARHE SEAFSIFGVVRYYYYMDVWGKGTTVTVSS |
| | 108 | light | QSALTQPRSVSGSPGQSVTISCTGTSSDVGGYNYVSWYQQHPDKAPKLM IYDVTKRPSGVPDRFSGSKSGNTASLTISGLQAEDEADYYCCSYAGTVVFG GGTKLTVL |
| CCHFV-108A | 109 | heavy | QVQLQESGPGLVKPSGTLSLTCAVSGGSISSSKWWSWVRQSPGKGLEWI GEIYHSGSTNYNPSLKSRATISVDKSKNQFSLKLNSVTAADTAVYYCARVGL GWHDGNGMDVWGQGTTVTVSS |
| | 110 | light | EIVLTQSPATLSLSPGERATLSCRASLNIGSYLAWYQQKPGQAPRLLIYDAS NRATGIPARFSGSGSGTDFTLTIRSLEPEDFAIYYCQQRSNWPPGYTFGQG TKLEIR |
| CCHFV-114C | 111 | heavy | QVQLQESGPGLVKPSQTLSLTCTVSGGSISSGDYYWSWLRQHPGKGLEWI GYIYYSGSAYSNPSLNSRDIISIDTSKNRFSLKLSSVTAADTAVYYCARFRLGD APTRDGYNLHYFDYWGQGSLVTVSS |
| | 112 | light | QSALTQPASVSGSPGQSITISCTGTSSDVGSYNLVSWYQQHPGKAPKVMI YEVSKRPSGVSNRFSGSKSGNTASLTISGLQAEDEADYYCCSYGGFSTHVV FGGGTRLTVL |
| CCHFV-115C | 113 | heavy | EVQLVESGGGLVQPGRSLRLSCTGSGFTFGDYAMSWARQAPGKGLEWV GFIRSKGYGGTTQYAASVKGRFTISRDDSKRIAYLQVNSLKIEDTAVYFCTR AHYDYVWGNYWSFAYWGQGTLVTVSS |
| | 114 | light | QSVLTQPPSLSAAPGQKVTISCSGSSSNIGNNYVSWYQHLPGTAPKLIIYD DNQRPSGIPDRFSGSKSGTSATLGITGLQTGDEADYYCGTWDSSLSVFVFG TGTKVTVL |
| CCHFV-116C | 115 | heavy | QVQLVESGGGVVQPGRSLRLSCAASGFTFSTYGMHWVRQAPGKGLEWV AVIWYDGSNKYYVDSVKGRFTISRDNSKNTLYLQMNSLRAEDTALYYCAR DPGGRRDGYILRPDAFDIWGQGTMVTVSS |
| | 116 | light | DIQMTQSPSTLSASVGDRVTITCRASQSITSWLAWYQQKPGKAPKLLIYKA SSLESGVPSRFSGSGSGTEFTLTISSLQPDDFATYYCQQYNTYTWTFGQGT KVEIK |

TABLE 2-continued

PROTEIN SEQUENCES FOR ANTIBODY VARIABLE REGIONS

| Clone | SEQ ID NO: | Chain | Variable Sequence |
|---|---|---|---|
| CCHFV-117A | 117 | heavy | QVQLVQSGAEVKKPGASVKVSCKASGYTFTSYGISWVRQAPGQGLEWM GWISAYNGNTNYVQKLQGRVTMTTDTSTSTAYMELRSLRSDDTAVYYCA RSGGYAIFWGQGTLVTVSS |
| | 118 | light | EIVLTQSPGTLSLSPGESATLSCRASQSLSSSYLAWYQQKPGQAPRLLIYGA SSRATGIPDRFSGSGSGTDFTLTISRLEPEDFAVYYCQQYGSTPPYTFGQGT KLEIK |
| CCHFV-128C | 119 | heavy | QITLKESGPTLVKPTQTLTLTCTFSGFSISSSGVGVGWIRQPPGKALEWLAL LYWDDSKRYSPSLRSRLTITKDTSKNQVVLTMTNMDPVDTGTYYCAHRRT TVFDYWGQGTLVTVSS |
| | 120 | light | NFMLTQPHSVSESPGKTVTISCTRSRGSIASNYVQWYQQRPGSSPTNVIYE DNQRPSGVPDRFSGSIDSSSNSASLTISGLKTEDEADYYCQSYDSYNHVFG GGTRLTVL |
| CCHFV-131A | 121 | heavy | EVQLVQSGAEVKKPGESLKISCKGSGYRFTNYWIGWVRQMPGKGLEWM GIIYPGDSNTRYSPSFQGQVTISADKSISTAYLQWGSLKASDTAMYYCARH SETKDGYNWAQGNFYSYYYMDVWGKGTTVTVSS |
| | 122 | light | DIQMTQSPSSLSASVGDRVTITCRASQSISSYLNWYQQIPGKAPKLLIYAAS SLQSGVPSRFSGSGSGTDFTLSISSLQPEDFATYYCQQSYSISPLSFGGGTKV EIK |
| CCHFV-132A | 123 | heavy | QVQLQESGPGLVKPSETLSLTCTVSGGSINYYYWSWIRQPPGKGLEWIAYI YYIEGSESTNYNPSLKSRVTMSVDTSKNQLSLKLSSVTAADTAAYYCARDSR RNRYSGYYFDFWGQGTLVTVSS |
| | 124 | light | EIVMTQSPVTLSVSPGERATLSCRASQSVRSNLAWYQHKPGQAPRLLFYG ASTRATGVPARFSGSGSGTEFTLTISSLQSEDFAVYFCHQYNNWPQTFGQ GTKVEIK |
| CCHFV-133A | 125 | heavy | QVQLQESGPGLVKPSGTLSLTCAVSGDSISGSFWWSWVRQPPGKGLEWL GEIYHSGNTHYNPSLKSRVTMSRDKSKNQFSLKLTSVTAADTAVYYCSRVL GLYQLLGSGYYAMDVWGQGTTVTVSS |
| | 126 | light | QVQLVQSGAEVKKPGASVKVSCKVSGYSLTELSMHWVRQPPAKGLEWM GRFDPGDRKPIYAQRFQGRITMTEDTSTDTTFMELSSLRSEDTALYFCATD PGAVAGFLGFWGQGTLVTVSS |
| CCHFV-135C | 127 | heavy | DIVMTQSPDSLAVSLGERATINCKSSQSVLYRSNNNNYLAWYQQKVGQP PKLLIYWASIRESGVPDRFSGSGSGTDFTLTISSLQAEDVAVYYCQQYYGTV TFGPGTKVDIK |
| | 128 | light | EVQLVESGGGLVQPGRSLRLSCTASGFTFGDYVMTWVRQAPGKGLECVG FIRTKPYGGTTEYAASVKGRFTISRDDSKSIAYLQMNSLKTDDTAVYYCLAG TDWSYFDYWGQGTLVTVSS |
| CCHFV-137B | 129 | heavy | QSALTQPRSVSGSPGQSVTISCTGTSSDVGGYNYVSWYQRHPGKAPQLM IYDVNKRPSGVPDRFSGSKSGNTASLTISGLQADDEADYYCCSYAGSYTWV FGGGTKLTVL |
| | 130 | light | QVQLQESGPGLVKPSETLSLTCTVSGGSISSYYWTWIRQPPGKGLEWIGH MYYSGSTNNNPSLKGRVTVSVDTSKNQFSLKLTSVTAADTAVYYCARGAY YGSGSFHYYYMDVWGKGTTVTVSS |
| CCHFV-144B | 131 | heavy | DIQMTQSPSTLSASVGDRVTITCRASQSISNWLAWYQQKPGKAPKLLISKA SRLEGGVPSRFSGSGSGTEFTFTISSLQPDDCATYYCQQYNGYSYTFGQGT KLEIK |
| | 132 | light | EVQLVESGGGLVKPGGSLRLSCAVSGFTFSSYSMNWVRQAPGKGLEWVS SISSSSTFIDYADSVKGRFTISRDNAKNLLYLQMNSLRAEDTAVFYCARGGN DYSDYENYYYMDVWGKGTTVTVSS |
| CCHFV-14A | 133 | heavy | SYELTQPPSVSVSPGQTASITCSGDELGDKYACWYQKKPGQSPVLVIYQD NKRPSGIPERFSGSNSGNTATLTISGTQAMDEADYYCQAWDSSTAYVFGT GTKVTVL |
| | 134 | light | EVQLVESGGGLVQPGRSLRLSCAASGFIFDDYAIHWVRQAPGKGLEWVS GITWDSGRIGYADSVKGRFTISRDNAKKSLYLQMNSLRPEDTALYYCAKDR GPFGWLTLDYWGQGTLVIVSS |
| CCHFV-19C | 135 | heavy | DIQMTQSPSSLSASVGDRVTITCRASQSIRSYLNWYQQKPGKAPKLLIYAG STLQSGVPSRFSGGGSGTGFTLTISSLQPEDFATYYCQQSSTTPWTFGQGT KVEFK |
| | 136 | light | EVQLVESGGGLVQPGRSLRLSCTASGFTFGDYALNWVRQAPGKGLEWV GFIRSKAYGGTTEYAASVKGRFTISRDDSKSIAFLQMNSLKTEDTAVYYCTR ATPVLLWFGSSGNFFDYWGQGTLVTVSS |
| CCHFV-21B | 137 | heavy | QSALTQPASVSGSPGQSITISCTGTSSDVGGYNYVSWYQQHPGKAPKLMI YDVSNRPSGVSNRFSGSKSGNTASLTISGLQAEDEADYYCSSYTTSNSYVF GTGTKVTVL |

TABLE 2-continued

PROTEIN SEQUENCES FOR ANTIBODY VARIABLE REGIONS

| Clone | SEQ ID NO: | Chain | Variable Sequence |
|---|---|---|---|
| | 138 | light | QLQLQESGPGLVKPSETLSLTCTVSGDSINNNNYYWGWIRQPPGKGLEWI GSIYYSGITYYNPSLKSRVTISVDTSKNQFSLKLSSVTAADTAVYYCVRHGLD HKFDYWGQGTLVTVSS |
| CCHFV-23C | 139 | heavy | QSALTQPASVSGSPGQSITISCTGTSSDVGTYNLLSWYQQYPGKAPRLVIYE VSKRPSGVSIRFSGSKSGNTASLTISGLQAEDEADYYCCSYAGGSNSVLFGG GTKLTVL |
| | 140 | light | EVQLVESGGGLVQPGGSLRLSCAASGFTFSSYSMNWVRQAPGKGLECVS YISSSSGAIYYADSVKGRFTISRDNAKNSLYLQMNSLRAEDTAVYYCARGN GATYWGQGTLVTVSS |
| CCHFV-29C | 141 | heavy | DIQMTQSPSSLSASVGDRVTITCRASQDISSYLAWFQQKPGKAPKSLIYAA SSLQSGVPSKFSGSGSGTDFTLTISSLQPEDFATYYCQQYNIYPITFGQGTRL EIK |
| | 142 | light | EVQLVQSGAEVKKPGESLKISCKGSGYRFTNYWIGWVRQMPGKGLEWM GIIYPGDSDTRYSPSFQGQVTISADKSVSTAYLQWSSLKASDSALYYCARLP HPVTGPLDYWGQGTLVTVSS |
| CCHFV-2B | 143 | heavy | QSALTQPASVSGSPGQSITISCTGTSNDVGSYNLVSWYQHPGKAPKLMI YEVSKRPSGVSNRFSGSKSGNTASLTVSGLQAEDEADYYCCSYAGSMTWV FGGGTKLTVL |
| | 144 | light | EVQLVESGGGLVKPGGSLRLSCAASGFTFRSYTMNWVRQAPGKGLEWVS SISTSSSYIYYADSVKGRFTISRDSAKSSLYLQMNSLRAEDTAVYYCASLRKD SGSFYNRALDYWGQGTLVTVSS |
| CCHFV-3B | 145 | heavy | QSALTQPASVSGSPGQSITISCTGTSSDVGGYNYVSWYQQHPGKAPKLMI YDVSNRPSGVSNRFSGSKSGNTASLTISGLQAEDEADYYCYSYTSNSTYVF GTGTKVTVL |
| | 146 | light | EVQLVESGGGLVQPGKSLRLSCAASGFTFDAYAMHWVRQAPGKGLEWV SGISWNGGNIGYADSVKGRFTFSRDNAKNSLYLQMNSLRADDTALYFCAK EDCPSTSCYFVRWGLNWLDPWGQGTLVTVSS |
| CCHFV-40A | 147 | heavy | QSVLTQPPSVSGAPGQRVTISCTGSSSNIGAGYDVHWYQQLPGTAPKLLIY DNNNRPSGVPDRFSGSKSGTSASLAITGLQAEDEADYYCQSFDSSLSRGVF GGGTKLTVL |
| | 148 | light | EVQLVESGGGLVQPGRSLRLSCSASGFTFADYAVSWVRQAPGKGLEWVG FIRSETYGGTTEYAASVKGRFTISRDDSKSIAYLQMHSLNTEDTAVFYCTRA RHDTRSWVLSDHWGQGTLVTVSS |
| CCHFV-4C | 149 | heavy | DAQMTQSPSTLSASVGDRVTITCRASQNINSWLAWYQHKPGKAPKLLIYK ASSLESEVPSRFSGSGSGTDFTLTISNLQPDDFATYYCQQYNSFHFGQGTKL EIK |
| | 150 | light | QLQLVQSGVEVKKPGASVKVSCKASGYTFTSYGIHWVRQAPGQGLEWM GWISGYNGNTNYAQKLQGRVTMTTDTSTRTAYMELRSLRSDDTAVYYCA RDPSMMTFGGVIVSRYFDYWGQGTLVTVSS |
| CCHFV-50B | 151 | heavy | QSVLTQPPSVSGAPGQRVTISCTGSSSNIGAGYDVHWYQQLPGTAPKLLIY NNSNRPSGVPDRFSGSKSGTSASLAITGLQAEDEADYYCQSYDSSVTVFG GGTKLTVL |
| | 152 | light | QLQLQESGPGLVKPSETLSLTCTLSGGFIRSSSYYWGWIRQPPGKGLEWIG SIYYTESTYYNPSLKSRVTISVDTSKNQFSLKLNSVTAADTAIYYCARHDYWT GARYSWFDPWGQGTLVTVSS |
| CCHFV-55B | 153 | heavy | QSVLTQPPSVSGAPGQRVTISCTGSSSNIGAGYDVHWYQQLPGTAPKLLIY GNSNRPSGVPDRFSGSKSGTSASLAITGLQAEDEADYYCQSYDTSLSGSGV FGGGTKLTVL |
| | 154 | light | QVQLVQSGAEVKKPGASVKLSCKASGYTFTSYYMHWVRQAPGQGLEWV GIMNPSGGSTMYAQKYQGRVTMTRDTSTSTVYMELSSLRSEDTAVYYCA RETVVQRLVGRDYYHGMDVWGQGTTVTVSS |
| CCHFV-59A | 155 | heavy | DIVMTQSPLSLPVTPGEPASISCRSSQSLLHSNGYNYLDWYLQKPGQSPQL LIYFGSNRASGVPDRFSGSGSGTDFTLKISRVEAEDVGVYYCMQALQTPLT FGGGTKVEIR |
| | 156 | light | EVQLVESGGVVVQPGGSLRLSCAASGFTFDDYAMHWVRQAPGKSLEWV SLISWDGGRTYYADSVKGRFTISRDNSKNSLYLQMNSLRPEDTALYYCATG HPPLVLWSLGYWGQGTLVTVSS |
| CCHFV-5A | 157 | heavy | DIQMTQSPSSLSASVGDRVTITCRASANINSYLNWYQQKPGKAPKFLIYAA SSLQGGVPSRFSGSGSGTVFTLTISSLQPEDFATYYCQQSYTTPITFGQGTR LEIK |
| | 158 | light | QVQLVQSGAEVKKPGSSVKVSCKASGGTFSTFAFSWVRQAPGRGLEWM GGIIPIFDRPAYAQRFQGRVTITADESTSTAYVELSSLRSEDTAVYYCARDRR YNYESSASQNNRWYFDLWGRGTLVTVSS |

TABLE 2-continued

PROTEIN SEQUENCES FOR ANTIBODY VARIABLE REGIONS

| Clone | SEQ ID NO: | Chain | Variable Sequence |
|-------|-----------|-------|-------------------|
| CCHFV-61 | 159 | heavy | DIVMTQSPDSLAVSLGERATINCKSSQSVLYTSNNKNYLAWYQQKPGQPP KLLVYWASIRESGVPDRFSGSGSGTDFTLTISSLQAEDVAVYYCQQYYTTPL TFGGGTKVEIK |
| | 160 | light | QVQLVESGGGVVQPGGSLRLSCAASGFTFSNYGIHWVRQAPGKGLEWV AFIRYDGSNQNYGDSVKGRFTISRDNSRNTLFLQMSSLRAEDTAVYYCAK DLAVLLMYGFGGFDAWGQGTLVTVSS |
| CCHFV-62B | 161 | heavy | DIQVTQSPSSLSASVGDRVSITCRASQSISHYLNWYQQKPGKAPKLLIYAAS TLQSGVPSRFSGSGSGTGFTLTISGLQPEDFATYYCQQSYSTPVSFGQGTK VEIK |
| | 162 | light | QVQLVQSGAEVKKPGSSVKVSCKASGGTFRSYAINWVRQAPGQGLEWM GGIIPIFGTANYAQNFQGRVTIIADESTSTAYMELSSLRSEDTAVYYCARYFF TTPHWTLPIDYGMDVWGQGTTVTVSS |
| CCHFV-64B | 163 | heavy | DIVMTQSPLSLPVTPGEPASISCRSSQSLLHSNGYNSLDWYLQKPGQSPQL LIYLGSYRASGVPDRFSGSGSGTDFTLKISRVEAEDVGVYYCMQALQTPYT FGQGTKLEIK |
| | 164 | light | QVQLQESGPGLVKPSGTLSLTCAVSGGSISSSNWWSWVRQPPGKGLEWI GQIYYSGTTNYNPSLKSRVSISVDKSKNQFALKLSSVTAADTAVYYCAGGTY FRRYFDYWGQGALVTVSP |
| CCHFV-65A | 165 | heavy | EIVMTQSPATLSVSPGERATLSCRASQSVSDNLAWYQQKPGQAPRLLIYG ASTRATGIPARFSGSGSGTEFTLTISSLQSEDFAVYYCQQYNNWPPLTFGG GTKVEIK |
| | 166 | light | QLQLQESGPGLVKPSETLSLICTVSGGSISSSYYWGWIRQPPGKGLEWIG SVFYSGNTYYNPSLKSRVTISVDTSKNQFSLNLSSVTAADTTVYYCARHQYS SSWNRIDAFDIWGQGTVVTVSA |
| CCHFV-71C | 167 | heavy | EVQLVESGGGLIQPGRSLRLSCTTSGFTFGNYVMSWVRQAPGKGLEWVG FIRSKAYGGTTEYAASVEGRFSISRDDSKSIAYLHMNSLKTEDTAVYYCLAA TVWTYFDFWGQGTLVTVSS |
| | 168 | light | QSALTQPRSVSGSPGQSVTISCTGTSSDVGAYNYVSWYQHHPGKAPKLMI FDVNSRPSGVPDRFSGSKSGNTASLTISGLQADDEADYYCCSYAGSFTWV FGGGTKLTVL |
| CCHFV-72B | 169 | heavy | QVQLVQSGAEVKKPGASVKVSCKASGYPFTNYGISWVRQAPGQGLEWM GWISAYNGNTNYAQKLQGRVTMTTDTSTSTAYMELRSLRSDDTAVYYCA RDYYDSSGSVWGQGTTVTVSS |
| | 170 | light | DIQMTQSPSSLSASVGDRVTITCRASQSISTYLNWYQQKPGKAPNLLIYGA SSLQSGVPSRFSGSGSGTDFTLTISSLQPEDFATYYCQQTYTTPRTFGQGTK VEIK |
| CCHFV-73C | 171 | heavy | QVQLVQSGAEVKKPGASVKVSCKTSGYTFISYTMHWVRQAPGQRLEWM GWINGGNGNTKYSQRFQGRVTITRDTSATTVYMELSSLTSEDTALYYCAR VKSDTLDFNWNPRFDYWGQGTLVTVSS |
| | 172 | light | EIVLTQSPGTLSLSPGERATLSCRASQSVSSSYLVWYQQKPGQAPRLLIYGA SSRATGIPDRFSGSGSGTDFTLTISRLEPEDFAVYYCQQCGSSPITFGQGTRL EIK |
| CCHFV-74A | 173 | heavy | QVQLQESGPGLVKPSETLSLTCDVSGYSISSGYYWGWIRQPPGKGLEWIG SIYHSGIIYYNPSLKSRVTISVDTSKNQFSLKLSSVTAADTAVYYCARLLPSNIY WGQGILVTVSS |
| | 174 | light | QSALTQPRSVSGSPGQSVTISCTGTSSDVGSYNYVSWYKQHPGKAPKLMI FDVSRRPSGVPDRFSGSKSGNTASLTISGLQAEDEADYFCCLYAGSYTFKFG GGTKVTVL |
| CCHFV-75A | 175 | heavy | EVQLVESGGGLVRPGRSLRLSCAASGFTFDDYAMHWVRQAPGKGLEWV SGISWHSGSIGYADSVQGRFTTSRDNAKNSLYLQMDSLRPEDTAFYYCAK SPLKIWQHLTPYDYWGQGTLVTVSS |
| | 176 | light | EIVMTQSPATLSVSPGERATLSCRASQSVSSNLAWYQQKRGQAPRLLMY GASTRATGIPARFSGSGSGTEFTLTISSLQSEDFAVYYCQQYNNWPPFFGG GTKVEIK |
| CCHFV-77A | 177 | heavy | QVQLQESGPGLVKPSQTLSLTCTVSDGSISSGDYYWSWVRQPPGKGLEWI GYIYYSGSTYYSPSLKSRVTISVNMSKNQFSLKLSSVTAADTAVYYCATAPA VGSYYMRWTGYHYYMDVWGKGTTVTVSS |
| | 178 | light | QSVLTQPPSVSAAPGQKVTISCSGSSSNIEYNYVSWYQQLPRTAPKLLIYD NNKRPSGIPDRFSGSKSGTSATLGITGLQTGDEADYYCGTWDSSLNAWVF GGGTKLTVL |
| CCHFV-77B | 179 | heavy | QVQLQESGPGLVKPSQTLSLTCTVSDGSISSGDYYWSWVRQPPGKGLEWI GYIYYSGSTYYSPSLKSRVTISVNMSKNQFSLKLSSVTAADTAVYYCATAPA VGSYYMRWTGYHYYMDVWGKGTTVTVSS |

TABLE 2-continued

PROTEIN SEQUENCES FOR ANTIBODY VARIABLE REGIONS

| Clone | SEQ ID NO: | Chain | Variable Sequence |
|---|---|---|---|
| | 180 | light | QSVLTQPPSVSAAPGQKVTISCSGSSSNIEYNYVSWYQQLPRTAPKLLIYD NNKRPSGIPDRFSGSKSGTSATLGITGLQTGDEADYYCGTWDSSLNAWVF GGGTKLTVL |
| CCHFV-79A | 181 | heavy | QMQLVQSGPEVKKPGTSVKVPCKASGLTFSRSAVQWVRQARGQRLEWI GWIVVGSGNTNYAQKFQDRVTITRDMSTSTAYMELSSLRSEDTAIYYCAA GPGVWARTERPNDAFNLWGQGTMVTVSS |
| | 182 | light | QSVLTQPPSVSAAPGQKVTISCSGSSSNIGNNYVSWYQQLPGAAPKVLIY DNNERPSGIPDRFSGSKSGRSATLGITGLQTGDEADYFCGTWDSSLSAWIF GGGTKLTVL |
| CCHFV-7C | 183 | heavy | EVQLLESGGGLVQPGGSLRLSCAASGFTFSSYAMIWVRQAPGRGLEWVS TITGSGGSTRFADSLKGRFAISRDNSKNTLYLQMNSLRVEDTAVYYCAKRY CSGTTSHLYCYYAMDVWGQGTAVTVSS |
| | 184 | light | QSALTQPASVSGSPGQSITISCTGTSSDVGGYNYVSWYQQHPGKAPKLMI YDVSNRPSGVSNRFSGSKSGNTASLTISGLQAEDEADYYCSSYTSSSTKLFG TGTKVTVL |
| CCHFV-82C | 185 | heavy | QVQLQESGPGLVKPSETLSLTCAVSDYSISSGYYWGWIRQPPGKGLEWIA SIYHGGSTDYNPSLKSRVTISLDTSKIQFSLKLSSVTAADTAVYYCASRHDRS GYDEYFEYWGQGTLVTVSS |
| | 186 | light | DIQMTQSPSSLSASVGDRVTIICRASHGISNSLAWYQQKPGKAPKLLLYAA SRLKSGVPSRFSGSGSGTDYTLTITSLQPEDFATYYCQQYYSTPLTFGPGTK VDLK |
| CCHFV-83A | 187 | heavy | EEQLVESGGGLIHPGGSLRLSCAASGFTVSSTYMNWVRQSPGKGLEWVSL IYSGGSTYYADSVKGRFTISRDNSKNTVYLQMNSLRAEDTAVYYCARIPLSF GPMYFDYWGQGTRVTVSS |
| | 188 | light | EEQLVESGGGLIHPGGSLRLSCAASGFTVSSTYMNWVRQSPGKGLEWVSL IYSGGSTYYADSVKGRFTISRDNSKNTVYLQMNSLRAEDTAVYYCARIPLSF GPMYFDYWGQGTRVTVSS |
| CCHFV-86C | 189 | heavy | QVQLVESGGGSVKPGGSLRLSCAASGFTFSDYYMTWIRQAPGKGLEWVS YISSSATTIYYADSVKGRFTISRDNAKNLLYLQMNSLRAEDTAVYYCARDHR YCTSTNCFAHWFDPWGQGILVTVSP |
| | 190 | light | QSVLTQPPSASGTPGQRVTISCSGSSSNIGSDTVKWYQQLPGTAPRLLIYS NNQRPSGVPDRFSGSKSGTSASLAISGLQSEDEADYYCAAWDDSLNGPVF GGGTKLTVL |
| CCHFV-88A | 191 | heavy | QVQLVQSGAEVKKPGASVKVSCKASGYTFSSYYIHWVRQAPGQGLEWM GIINPSVGATEYAHIFQGRVTLTRDTSTSTVYMDLSRLTSDDTAVYYCARW GLISESSPKYFDSWGQGTLVTVSS |
| | 192 | light | QSVLTQPPSVSGAPGQRVTISCTGSNSNIGAGYDVHWYQQLPGTAPKLLI YDNTNRPSGVPDRFSGSKSGTSASLAITGLQAEDEADYYCQSYDSSVSGFY VLFGGGTKLTVL |
| CCHFV-8B | 193 | heavy | QITLKESGPTLVKPTQTLTLTCTFSGFSLSNSGVGVGWIRQPPGKALEWLA LIYWDDDKRYRPSLKSRLTITKDTSKNQVVLKMTNMDPVDTATYYCAHSY FDFWSGYFSLDRRDRRAGRQSYFDYWGQGTLVTVSS |
| | 194 | light | QSALTQPASVSGSPGQSITISCTGTTSDVGGYDYVSWYQQHPGKAPKLMI FDVNHRPSGVSSRFSGSKSGNTASLTISGLQAEDEAAYYCSSYTTGTLFGG GTKLTVL |
| CCHFV-95A | 195 | heavy | QVLLQESGPGLVKPSGTLSLTCAVSGGSITTNNWWSWVRQPPGRGLEWI GEIFHGGKTNYNPSLKSRVTISVDKSKNQFSLKLTSLTAADTAVYYCARAGL YSTNWSPFDPWGQGTLVTVSS |
| | 196 | light | EVVLTQSPGTLSLSPGERATLSCRASQSVTSSYLAWYQQKPGQAPRLLIFD ASSRATGIPDRFSGSGSGTDFTLTIRRLEPEDFAVYYCQQYGGSPWTFGQG TKVEIK |
| CCHFV-lgG-BA | 197 | heavy | QVQLVQSGAEVKKPGASVKVSCKASGYTFSSYYIHWVRQAPGQGLEWM GIINPSVGATEYAHIFQGRVTLTRDTSTSTVYMDLSRLTSDDTAVYYCARW GLISESSPKYFDSWGQGTLVTVSS |
| | 198 | light | EIVLTQSPATLSLSPGERATLSCRASQSVSSYLAWYQQRPGQAPRLLIYDAS NRATGIPARFSGSGSGTDFTLTISSLEPEDFAVYYCQQRSNWPYTFGRGTK LEIK |
| CCHFV-lgG-BB | 199 | heavy | QVQLVQSGAEVKKPGSSVKVSCKASGGTFSSYSISWLRQAPGQGLEWM GQIIPMFGTANYAQKFQGRVTITADESTSTAYMELSSLRSEDTAVYYCARE ARAEGDVWGQGTTVTVSS |
| | 200 | light | EIVLTQSPATLSLSPGERATLSCRASQSVSSYLAWYQQRPGQAPRLLIYDAS NRATGIPARFSGSGSGTDFTLTISSLEPEDFAVYYCQQRSNWPYTFGRGTK LEIK |

TABLE 3

| | CDR HEAVY CHAIN SEQUENCES | | |
|---|---|---|---|
| Clone | CDRH1 (SEQ ID NO: ) | CDRH2 (SEQID NO: ) | CDRH3 (SEQ ID NO: ) |
| CCHFV-104A | GFTFSDYY 201 | ISSFGSNT 202 | ARSLRGIAVPSY 203 |
| CCHFV-104B | GFTFSDYY 204 | ISSFGSNT 205 | ARSLRGIAVPSY 206 |
| CCHFV-105B | GGSISSNIYY 207 | IYYSGNT 208 | ASQKMVYPIKRNNWFDP 209 |
| CCHFV-106A | GYSFTSYW 210 | IYPGDSDT 211 | ARHESEAFSIFGVVRYYYYYMDV 212 |
| CCHFV-108A | GGSISSSKW 213 | IYHSGST 214 | ARVGLGWHDGNGMDV 215 |
| CCHFV-114C | GGSISSGDYY 216 | IYYSGSA 217 | ARFRLGDAPTRDGYNLHYFDY 218 |
| CCHFV-115C | GFTFGDYA 219 | IRSKGYGGTT 220 | TRAHYDYVWGNYWSFAY 221 |
| CCHFV-116C | GFTFSTYG 222 | IWYDGSNK 223 | ARDPGGRRDGYILRPDAFDI 224 |
| CCHFV-117A | GYTFTSYG 225 | ISAYNGNT 226 | ARSGGYAIF 227 |
| CCHFV-128C | GFSISSSGVG 228 | LYWDDSK 229 | AHRRTTVFDY 230 |
| CCHFV-131A | GYRFTNYW 231 | IYPGDSNT 232 | ARHSETKDGYNWAQGNFYSYYYMDV 233 |
| CCHFV-132A | GGSINYYY 234 | IYYIEGSEST 235 | ARDSRRNRYSGYYFDF 236 |
| CCHFV-133A | GDSISGSFW 237 | IYHSGNT 238 | SRVLGLYQLLGSGYYAMDV 239 |
| CCHFV-135C | GYSLTELS 240 | FDPGDRKP 241 | ATDPGAVAGFLGF 242 |
| CCHFV-137B | GFTFGDYV 243 | IRTKPYGGTT 244 | LAGTDWSYFDY 245 |
| CCHFV-144B | GGSISSYY 246 | MYYSGST 247 | ARGAYYGSGSFHYYYYMDV 248 |
| CCHFV-14A | GFTFSSYS 249 | ISSSTFI 250 | ARGGNDYSDYENYYYYMDV 251 |
| CCHFV-19C | GFIFDDYA 252 | ITWDSGRI 253 | AKDRGPFGWLTLDY 254 |
| CCHFV-21B | GFTFGDYA 255 | IRSKAYGGTT 256 | TRATPVLLWFGSSGNFFDY 257 |
| CCHFV-23C | GDSINNNNYY 258 | IYYSGIT 259 | VRHGLDHKFDY 260 |
| CCHFV-29C | GFTFSSYS 261 | ISSSSGAI 262 | ARGNGATY 263 |
| CCHFV-2B | GYRFTNYW 264 | IYPGDSDT 265 | ARLPHPVTGPLDY 266 |
| CCHFV-3B | GFTFRSYT 267 | ISTSSSYI 268 | ASLRKDSGSFYNRALDY 269 |
| CCHFV-40A | GFTFDAYA 270 | ISWNGGNI 271 | AKEDCPSTSCYFVRWGLNWLDP 272 |
| CCHFV-4C | GFTFADYA 273 | IRSETYGGTT 274 | TRARHDTRSWVLSDH 275 |

TABLE 3-continued

| | CDR HEAVY CHAIN SEQUENCES | | |
|---|---|---|---|
| Clone | CDRH1 (SEQ ID NO: ) | CDRH2 (SEQID NO: ) | CDRH3 (SEQ ID NO: ) |
| CCHFV-50B | GYTFTSYG 276 | ISGYNGNT 277 | ARDPSMMTFGGVIVSRYFDY 278 |
| CCHFV-55B | GGFIRSSSYY 279 | IYYTEST 280 | ARHDYWTGARYSWFDP 281 |
| CCHFV-59A | GYTFTSYY 282 | MNPSGGST 283 | ARETVVQRLVGRDYYHGMDV 284 |
| CCHFV-5A | GFTFDDYA 285 | ISWDGGRT 286 | ATGHPPLVLWSLGY 287 |
| CCHFV-61 | GGTFSTFA 288 | IIPIFDRP 289 | ARDRRYNYESSASQNNRWYFDL 290 |
| CCHFV-62B | GFTFSNYG 291 | IRYDGSNQ 292 | AKDLAVLLMYGFGGFDA 293 |
| CCHFV-64B | GGTFRSYA 294 | IIPIFGTA 295 | ARYFFTTPHWTLPIDYGMDV 296 |
| CCHFV-65A | GGSISSSNW 297 | IYYSGTT 298 | AGGTYFRRYFDY 299 |
| CCHFV-69C | GGSISSSSYY 300 | VFYSGNT 301 | ARHQYSSSWNRIDAFDI 302 |
| CCHFV-71C | GFTFGNYV 303 | IRSKAYGGTT 304 | LAATVWTYFDF 305 |
| CCHFV-72B | GYPFTNYG 306 | ISAYNGNT 307 | ARDYYDSSGSV 308 |
| CCHFV-73C | GYTFISYT 309 | INGGNGNT 310 | ARVKSDTLDFNWNPRFDY 311 |
| CCHFV-74A | GYSISSGYY 312 | IYHSGII 313 | ARLLPSNIY 314 |
| CCHFV-75A | GFTFDDYA 315 | ISWHSGSI 316 | AKSPLKIWQHLTPYDY 317 |
| CCHFV-77A | DGSISSGDYY 318 | IYYSGST 319 | ATAPAVGSYYMRWTGYHYYMDV 320 |
| CCHFV-77B | DGSISSGDYY 321 | IYYSGST 322 | ATAPAVGSYYMRWTGYHYYMDV 323 |
| CCHFV-79A | GLTFSRSA 324 | IVVGSGNT 325 | AAGPGVWARTERPNDAFNL 326 |
| CCHFV-7C | GFTFSSYA 327 | ITGSGGST 328 | AKRYCSGTTSHLYCYYAMDV 329 |
| CCHFV-82C | DYSISSGYY 330 | IYHGGST 331 | ASRHDRSGYDEYFEY 332 |
| CCHFV-83A | GFTVSSTY 333 | IYSGGST 334 | ARIPLSFGPMYFDY 335 |
| CCHFV-83B | GFTVSSTY 336 | IYSGGST 337 | ARIPLSFGPMYFDY 338 |
| CCHFV-86C | GFTFSDYY 339 | ISSSATTI 340 | ARDHRYCTSTNCFAHWFDP 341 |
| CCHFV-88A | GYTFSSYY 342 | INPSVGAT 343 | ARWGLISESSPKYFDS 344 |
| CCHFV-8B | GFSLSNSGVG 345 | IYWDDDK 346 | AHSYFDFWSGYFSLDRRDRRAGRQSYFDY 347 |
| CCHFV-95A | GGSITTNNW 348 | IFHGGKT 349 | ARAGLYSTNWSPFDP 350 |

TABLE 3-continued

CDR HEAVY CHAIN SEQUENCES

| Clone | CDRH1 (SEQ ID NO: ) | CDRH2 (SEQID NO: ) | CDRH3 (SEQ ID NO: ) |
|---|---|---|---|
| CCHFV-IgG-BA | GYTFSSYY 351 | INPSVGAT 352 | ARWGLISESSPKYFDS 353 |
| CCHFV-IgG-BB | GGTFSSYS 354 | IIPMFGTA 355 | AREARAEGDV 356 |

TABLE 4

CDR LIGHT CHAIN SEQUENCES

| Clone | CDRL1 (SEQ ID NO: ) | CDRL2 (SEQ ID NO: ) | CDRL3 (SEQ ID NO: ) |
|---|---|---|---|
| CCHFV-104A | QSVSSD 357 | DAS 358 | QQYNNWPPWT 359 |
| CCHFV-104B | QSVSSD 360 | DAS 361 | QQYNNWPPWT 362 |
| CCHFV-105B | SSNIESNT 363 | GNN 364 | AAWDDGLNGWV 365 |
| CCHFV-106A | SSDVGGYNY 366 | DVT 367 | CSYAGTVV 368 |
| CCHFV-108A | LNIGSY 369 | DAS 370 | QQRSNWPPGYT 371 |
| CCHFV-114C | SSDVGSYNL 372 | EVS 373 | CSYGGFSTHVV 374 |
| CCHFV-115C | SSNIGNNY 375 | DDN 376 | GTWDSSLSVFV 377 |
| CCHFV-116C | QSITSW 378 | KAS 379 | QQYNTYTWT 380 |
| CCHFV-117A | QSLSSSY 381 | GAS 382 | QQYGSTPPYT 383 |
| CCHFV-128C | RGSIASNY 384 | EDN 385 | QSYDSYNHV 386 |
| CCHFV-131A | QSISSY 387 | AAS 388 | QQSYSISPLS 389 |
| CCHFV-132A | QSVRSN 390 | GAS 391 | HQYNNWPQT 392 |
| CCHFV-135C | QSVLYRSNNNNY 393 | WAS 394 | QQYYGTVT 395 |
| CCHFV-137B | SSDVGGYNY 396 | DVN 397 | CSYAGSYTWV 398 |
| CCHFV-144B | QSISNW 399 | KAS 400 | QQYNGYSYT 401 |
| CCHFV-14A | ELGDKY 402 | QDN 403 | QAWDSSTAYV 404 |
| CCHFV-19C | QSIRSY 405 | AGS 406 | QQSSTTPWT 407 |
| CCHFV-21B | SSDVGGYNY 408 | DVS 409 | SSYTTSNSYV 410 |
| CCHFV-23C | SSDVGTYNL 411 | EVS 412 | CSYAGGSNSVL 413 |

TABLE 4-continued

CDR LIGHT CHAIN SEQUENCES

| Clone | CDRL1 (SEQ ID NO: ) | CDRL2 (SEQ ID NO: ) | CDRL3 (SEQ ID NO: ) |
|---|---|---|---|
| CCHFV-29C | QDISSY 414 | AAS 415 | QQYNIYPIT 416 |
| CCHFV-2B | SNDVGSYNL 417 | EVS 418 | CSYAGSMTWV 419 |
| CCHFV-3B | SSDVGGYNY 420 | DVS 421 | YSYTSNSTYV 422 |
| CCHFV-40A | SSNIGAGYD 423 | DNN 424 | QSFDSSLSRGV 425 |
| CCHFV-4C | QNINSW 426 | KAS 427 | QQYNSFH 428 |
| CCHFV-50B | SSNIGAGYD 429 | NNS 430 | QSYDSSVTV 431 |
| CCHFV-55B | SSNIGAGYD 432 | GNS 433 | QSYDTSLSGSGV 434 |
| CCHFV-59A | QSLLHSNGYNY 435 | FGS 436 | MQALQTPLT 437 |
| CCHFV-5A | ANINSY 438 | AAS 439 | QQSYTTPIT 440 |
| CCHFV-61 | QSVLYTSNNKNY 441 | WAS 442 | QQYYTTPLT 443 |
| CCHFV-62B | QSISHY 444 | AAS 445 | QQSYSTPVS 446 |
| CCHFV-64B | QSLLHSNGYNS 447 | LGS 448 | MQALQTPYT 449 |
| CCHFV-65A | QSVSDN 450 | GAS 451 | QQYNNWPPLT 452 |
| CCHFV-71C | SSDVGAYNY 453 | DVN 454 | CSYAGSFTWV 455 |
| CCHFV-72B | QSISTY 456 | GAS 457 | QQTYTTPRT 458 |
| CCHFV-73C | QSVSSSY 459 | GAS 460 | QQCGSSPIT 461 |
| CCHFV-74A | SSDVGSYNY 462 | DVS 463 | CLYAGSYTFK 464 |
| CCHFV-75A | QSVSSN 465 | GAS 466 | QQYNNWPPF 467 |
| CCHFV-77A | SSNIEYNY 468 | DNN 469 | GTWDSSLNAWV 470 |

85

TABLE 4-continued

CDR LIGHT CHAIN SEQUENCES

| Clone | CDRL1 (SEQ ID NO: ) | CDRL2 (SEQ ID NO: ) | CDRL3 (SEQ ID NO: ) |
|---|---|---|---|
| CCHFV-77B | SSNIEYNY 471 | DNN 472 | GTWDSSLNAWV 473 |
| CCHFV-79A | SSNIGNNY 474 | DNN 475 | GTWDSSLSAWI 476 |
| CCHFV-7C | SSDVGGYNY 477 | DVS 478 | SSYTSSSTKL 479 |
| CCHFV-82C | HGISNS 480 | AAS 481 | QQYYSTPLT 482 |
| CCHFV-86C | SSNIGSDT 483 | SNN 484 | AAWDDSLNGPV 485 |
| CCHFV-88A | NSNIGAGYD 486 | DNT 487 | QSYDSSVSGFYVL 488 |
| CCHFV-8B | TSDVGGYDY 489 | DVN 490 | SSYTTGTL 491 |
| CCHFV-95A | QSVTSSY 492 | DAS 493 | QQYGGSPWT 494 |
| CCHFV-IgG-BA | QSVSSY 495 | DAS 496 | QQRSNWPYT 497 |
| CCHFV-IgG-BB 498 | QSVSSY 499 | DAS 500 | QQRSNWPYT |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567

86

U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, N Y, 1988.
Abbondanzo et al., Am. J. Pediatr. Hematol. Oncol., 12(4), 480-489, 1990.
Allred et al., Arch. Surg., 125(1), 107-113, 1990.
Atherton et al., Biol. of Reproduction, 32, 155-171, 1985.
Barzon et al., Euro Surveill. 2016 Aug. 11; 21(32).
Beltramello et al., Cell Host Microbe 8, 271-283, 2010.
Brown et al., J. Immunol. Meth., 12; 130(1), 111-121, 1990.
Campbell, In: Monoclonal Antibody Technology, Laboratory Techniques in Biochemistry and Molecular Biology, Vol. 13, Burden and Von Knippenberg, Eds. pp. 75-83, Amsterdam, Elsevier, 1984.
Capaldi et al., Biochem. Biophys. Res. Comm., 74(2):425-433, 1977.
De Jager et al., Semin. Nucl. Med. 23(2), 165-179, 1993.
Dholakia et al., J. Biol. Chem., 264, 20638-20642, 1989.
Diamond et al., J Virol 77, 2578-2586, 2003.
Doolittle and Ben-Zeev, Methods Mol. Biol., 109, 215-237, 1999.
Duffy et al., N. Engl. J. Med. 360, 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.
Gefter et al., Somatic Cell Genet., 3:231-236, 1977.
Gornet et al., Semin Reprod Med. 2016 September; 34(5): 285-292. Epub 2016 Sep. 14.
Gulbis and Galand, Hum. Pathol. 24(12), 1271-1285, 1993.
Halfon et al., PLoS ONE 2010; 5 (5) e10569
Hessell et al., Nature 449, 101-4, 2007.
Khatoon et al., Ann. of Neurology, 26, 210-219, 1989.
King et al., J. Biol. Chem., 269, 10210-10218, 1989.
Kohler and Milstein, Eur. J. Immunol., 6, 511-519, 1976.
Kohler and Milstein, Nature, 256, 495-497, 1975.
Kyte and Doolittle, J. Mol. Biol., 157(1):105-132, 1982.
Mansuy et al., Lancet Infect Dis. 2016 October; 16(10): 1106-7.
Nakamura et al., In: Enzyme Immunoassays: Heterogeneous and Homogeneous Systems, Chapter 27, 1987.
O'Shannessy et al., J. Immun. Meth., 99, 153-161, 1987.
Persic et al., Gene 187:1, 1997
Potter and Haley, Meth. Enzymol., 91, 613-633, 1983.
Purpura et al., Lancet Infect Dis. 2016 October; 16(10): 1107-8. Epub 2016 Sep. 19. Remington's Pharmaceutical Sciences, 15th Ed., 3:624-652, 1990.
Tang et al., J. Biol. Chem., 271:28324-28330, 1996.
Wawrzynczak & Thorpe, In: Immunoconjugates, Antibody Conjugates In Radioimaging And Therapy Of Cancer, Vogel (Ed.), NY, Oxford University Press, 28, 1987.
Yu et al., J Immunol Methods 336, 142-151, doi:10.1016/j.jim.2008.04.008, 2008.
Sidwell R W, and Smee D F. 2003. Viruses of the Bunya- and Togaviridae families: potential as bioterrorism agents and means of control. Antiviral Res. 57: 101-111.
Zhang, W. et al., 2002. Placement of the structural proteins in Sindbis virus. J. Virol. 76, 11645-58(2002).

Klasse P J. 2014. Neutralization of virus infectivity by antibodies: old problems in new perspectives. *Advances in Biology.* 2014: 157895.

Burton D R. 2002. Antibodies, viruses and vaccines. *Nature Reviews Immunology.* 2:706-713.

Jin et al., 2015. *Cell Rep.* 13(11):2553-2564.

Smith S A, and Crowe J E. 2015. Use of human hybridoma technology to isolate human monoclonal antibodies. *Microbiology Spectrum.* 3: 1-12.

Yu et al., 2008. An optimized electrofusion-based protocol for generating virus-specific human monoclonal antibodies. *J Immunol Methods.* 336(2): 142-151.

What is claimed is:

1. A method of detecting a Crimean Congo Hemorrhagic Fever Virus infection in a subject comprising:

(a) contacting a sample from said subject with an antibody or antigen binding fragment thereof comprising heavy and light chain CDR sequences comprising SEQ ID NOS: 330, 331, and 332, and SEQ ID NOS: 480, 481 and 482, respectively; and (b) detecting Crimean Congo Hemorrhagic Fever Virus in said sample by binding of said antibody or antibody fragment to a Crimean Congo Hemorrhagic Fever Virus antigen in said sample.

2. A method of treating a subject infected with Crimean Congo Hemorrhagic Fever Virus or reducing the likelihood of infection of a subject at risk of contracting Crimean Congo Hemorrhagic Fever Virus, comprising delivering to said subject an antibody or antigen binding fragment thereof comprising heavy and light chain CDR sequences comprising SEQ ID NOS: 330, 331, and 332, and SEQ ID NOS: 480, 481 and 482, respectively.

3. The method of claim 2, wherein the antibody or antigen binding fragment thereof is encoded by heavy and light chain variable regions comprising SEQ ID NOS: 85 and 86, respectively.

4. The method of claim 2, wherein the antibody or antigen binding fragment thereof is encoded by heavy and light chain variable regions having 95% identity to heavy and light chain variable sequences comprising SEQ ID NOS: 85 and 86, respectively, wherein the heavy and light chain CDRs comprise SEQ ID NOS: 330, 331, and 332, and SEQ ID NOS: 480, 481 and 482, respectively.

5. The method of claim 2, wherein said antibody or antigen binding fragment thereof is encoded by heavy and light chain variable regions having 90% identity to SEQ ID NOS: 85 and 86, respectively, wherein the heavy and light chain CDRs comprise SEQ ID NOS: 330, 331, and 332, and SEQ ID NOS: 480, 481 and 482, respectively.

6. The method of claim 2, wherein said antibody or antigen binding fragment thereof comprises heavy and light chain variable regions comprising SEQ ID NOS: 185 and 186, respectively.

7. The method of claim 2, wherein said antibody or antigen binding fragment thereof comprises heavy and light chain variable regions comprising 90% identity to SEQ ID NOS: 185 and 186, respectively, wherein the heavy and light chain CDRs comprise SEQ ID NOS: 330, 331, and 332, and SEQ ID NOS: 480, 481 and 482, respectively.

8. The method of claim 2, wherein said antibody or antigen binding fragment thereof comprises heavy and light chain variable regions comprising 95% identity to SEQ ID NOS: 185 and 186, respectively, wherein the heavy and light chain CDRs comprise SEQ ID NOS: 330, 331, and 332, and SEQ ID NOS: 480, 481 and 482, respectively.

9. The method of claim 2, wherein said antibody is a chimeric antibody or a bispecific antibody, or wherein the antigen binding fragment thereof is a recombinant scFv (single chain fragment variable) antibody, Fab fragment, F(ab')₂ fragment, or Fv fragment.

10. The method of claim 2, wherein said antibody is an IgG, or a recombinant IgG antibody or antigen binding fragment thereof comprising an Fc portion mutated to eliminate or enhance FcR interactions compared to wild-type, to increase half-life and/or increase therapeutic efficacy compared to wild-type, or glycan modified to eliminate or enhance FcR interactions compared to wild-type.

11. The method of claim 2, wherein said antibody or antigen binding fragment thereof is administered prior to infection.

12. The method of claim 2, wherein said antibody or antigen binding fragment thereof is administered after infection.

13. The method of claim 2, wherein said subject is a pregnant female, a sexually active female, or a female undergoing fertility treatments.

14. The method of claim 2, wherein delivering comprises antibody or antigen binding fragment thereof administration, or genetic delivery with an RNA or DNA sequence or vector encoding the antibody or antigen binding fragment thereof.

15. A monoclonal antibody or antigen binding fragment thereof, wherein the antibody or antigen binding fragment thereof comprises heavy and light chain CDR sequences comprising SEQ ID NOS: 330, 331, and 332, and SEQ ID NOS: 480, 481 and 482, respectively, wherein said antibody is a recombinant IgG antibody or antibody fragment comprising an Fc portion mutated to eliminate or enhance FcR interactions compared to wild-type, to increase half-life and/or increase therapeutic efficacy compared to wild-type, or glycan modified to eliminate or enhance FcR interactions compared to wild-type.

16. A hybridoma or engineered cell comprising one or more nucleic acid segments encoding an antibody or antigen binding fragment thereof wherein the antibody or antibody fragment comprises heavy and light chain CDR sequences comprising SEQ ID NOS: 330, 331, and 332, and SEQ ID NOS: 480, 481 and 482, respectively.

17. A vaccine formulation comprising antibodies or antigen binding fragments thereof comprising heavy and light chain CDR sequences comprising SEQ ID NOS: 330, 331, and 332, and SEQ ID NOS: 480, 481 and 482, respectively, wherein said antibodies are recombinant IgG antibodies or antibody fragments comprising an Fc portion mutated to eliminate or enhance FcR interactions compared to wild-type, to increase half-life and/or increase therapeutic efficacy compared to wild-type, or glycan modified to eliminate or enhance FcR interactions compared to wild-type.

18. A method of determining the antigenic integrity or correct conformation of a Crimean Congo Hemorrhagic Fever Virus antigen comprising:

(a) contacting a sample comprising said antigen with an antibody or antigen binding fragment thereof comprising heavy and light chain CDR sequences comprising SEQ ID NOS: 330, 331, and 332, and SEQ ID NOS: 480, 481 and 482, respectively; and (b) determining antigenic integrity or correct conformation of said antigen by detectable binding of said antibody or antibody fragment to said antigen.

19. The method of claim 10, wherein said Fc portion mutated to eliminate or enhance FcR interactions compared to wild-type, to increase half-life and/or increase therapeutic efficacy compared to wild-type is a LALA, LALA PG, N297, GASD/ALIE, DHS, YTE or LS mutation.

20. The method of claim 10, wherein the antibody is glycan modified by enzymatic or chemical addition or removal of glycans or expressed in a cell line engineered with a defined glycosylating pattern.

* * * * *